(12) United States Patent
Reeves et al.

(10) Patent No.: US 12,378,237 B2
(45) Date of Patent: *Aug. 5, 2025

(54) COMPOUNDS AS GLP-1R AGONISTS

(71) Applicant: Terns Pharmaceuticals, Inc., Foster City, CA (US)

(72) Inventors: Corey Reeves, Foster City, CA (US); F. Anthony Romero, Redwood City, CA (US); Christopher T. Jones, Foster City, CA (US); Martijn Fenaux, San Mateo, CA (US)

(73) Assignee: Terns Pharmaceuticals, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/018,773

(22) Filed: Jan. 13, 2025

(65) Prior Publication Data
US 2025/0145613 A1    May 8, 2025

Related U.S. Application Data

(63) Continuation of application No. 18/956,385, filed on Nov. 22, 2024, which is a continuation of application
(Continued)

(51) Int. Cl.
*C07D 417/14* (2006.01)
*A61P 3/04* (2006.01)
*A61P 3/10* (2006.01)

(52) U.S. Cl.
CPC ............. *C07D 417/14* (2013.01); *A61P 3/04* (2018.01); *A61P 3/10* (2018.01)

(58) Field of Classification Search
None
See application file for complete search history.

(56) References Cited

U.S. PATENT DOCUMENTS

| | | | |
|---|---|---|---|
| 5,665,732 | A | 9/1997 | Baker et al. |
| 5,714,498 | A | 2/1998 | Kulagowski et al. |
| (Continued) | | | |

FOREIGN PATENT DOCUMENTS

| | | |
|---|---|---|
| CN | 113480534 A | 10/2021 |
| CN | 113493447 A | 10/2021 |
| (Continued) | | |

OTHER PUBLICATIONS

Brown, Bioisosteres in Medicinal Chemistry, 2012 (Year: 2012).*
(Continued)

*Primary Examiner* — Jeffrey S Lundgren
*Assistant Examiner* — Anthony Joseph Seitz
(74) *Attorney, Agent, or Firm* — WILSON SONSINI GOODRICH & ROSATI

(57) ABSTRACT

The present application provides compounds that may be used as a glucagon-like peptide-1 receptors (GLP-1R) agonist, or pharmaceutically acceptable salts thereof. Also provided are pharmaceutical compositions containing such compounds, or pharmaceutically acceptable salts thereof. Methods of preparing these compounds and compositions, and methods of using these compounds and compositions to treat or prevent a disease or a condition mediated by GLP-1R, are also provided.

20 Claims, 12 Drawing Sheets

Related U.S. Application Data

No. 17/954,047, filed on Sep. 27, 2022, now abandoned.

(60) Provisional application No. 63/261,717, filed on Sep. 27, 2021.

(56) References Cited

U.S. PATENT DOCUMENTS

| | | | |
|---|---|---|---|
| 5,763,263 | A | 6/1998 | Dehlinger |
| 5,780,475 | A | 7/1998 | Baker et al. |
| 9,764,003 | B2 | 9/2017 | Jensen |
| 10,208,019 | B2 | 2/2019 | Aspnes et al. |
| 10,335,462 | B2 | 7/2019 | Jensen |
| 10,669,259 | B2 | 6/2020 | Aspnes et al. |
| 10,844,049 | B2 | 11/2020 | Zhong |
| 10,851,081 | B2 | 12/2020 | Aspnes et al. |
| 11,512,070 | B2 | 11/2022 | Aspnes et al. |
| 11,584,751 | B1 | 2/2023 | Ren et al. |
| 11,918,623 | B2 | 3/2024 | Corvari et al. |
| 12,024,507 | B2 * | 7/2024 | Reeves ............... C07D 413/14 |
| 2003/0162790 | A1 | 8/2003 | Cowart et al. |
| 2003/0176438 | A1 | 9/2003 | Arienti et al. |
| 2004/0127504 | A1 | 7/2004 | Cowart et al. |
| 2005/0004114 | A1 | 1/2005 | Whitehouse et al. |
| 2007/0244126 | A1 | 10/2007 | Edwards et al. |
| 2008/0280933 | A1 | 11/2008 | Efremov et al. |
| 2012/0028959 | A1 | 2/2012 | Thunuguntla et al. |
| 2018/0170908 | A1 | 6/2018 | Aspnes et al. |
| 2019/0119255 | A1 | 4/2019 | Aspnes et al. |
| 2020/0071306 | A1 | 3/2020 | Esler et al. |
| 2021/0047298 | A1 | 2/2021 | Aspnes et al. |
| 2022/0016136 | A1 | 1/2022 | Lian et al. |
| 2022/0089578 | A1 | 3/2022 | Romero et al. |
| 2022/0348564 | A1 | 11/2022 | Ren et al. |
| 2023/0124938 | A1 | 4/2023 | Aspnes et al. |
| 2023/0150998 | A1 | 5/2023 | Reeves et al. |
| 2023/0159512 | A1 | 5/2023 | Reeves et al. |
| 2023/0322744 | A1 | 10/2023 | Romero et al. |
| 2023/0322758 | A1 | 10/2023 | Reeves et al. |
| 2024/0360122 | A1 | 10/2024 | Bian et al. |
| 2024/0368120 | A1 | 11/2024 | Luehr et al. |
| 2024/0391910 | A1 * | 11/2024 | Reeves ............... A61K 9/0019 |

FOREIGN PATENT DOCUMENTS

| | | |
|---|---|---|
| EP | 3555064 B1 | 11/2022 |
| JP | 2019099571 A | 6/2019 |
| TW | 202128659 A | 8/2021 |
| WO | WO-2010114957 A1 | 10/2010 |
| WO | WO-2011143365 A1 | 11/2011 |
| WO | WO-2015166398 A1 | 11/2015 |
| WO | WO-2018056453 A1 | 3/2018 |
| WO | WO-2018109607 A1 | 6/2018 |
| WO | WO-2019239319 A1 | 12/2019 |
| WO | WO-2019239371 A1 | 12/2019 |
| WO | WO-2020103815 A1 | 5/2020 |
| WO | WO-2020207474 A1 | 10/2020 |
| WO | WO-2020263695 A1 | 12/2020 |
| WO | WO-2021018023 A1 | 2/2021 |
| WO | WO-2021081207 A1 | 4/2021 |
| WO | WO-2021096284 A1 | 5/2021 |
| WO | WO-2021096304 A1 | 5/2021 |
| WO | WO-2021112538 A1 | 6/2021 |
| WO | WO-2021116874 A1 | 6/2021 |
| WO | WO-2021154796 A1 | 8/2021 |
| WO | WO-2021155841 A1 | 8/2021 |
| WO | WO-2021160127 A1 | 8/2021 |
| WO | WO-2021187886 A1 | 9/2021 |
| WO | WO-2021197464 A1 | 10/2021 |
| WO | WO-2021219019 A1 | 11/2021 |
| WO | WO-2021242817 A1 | 12/2021 |
| WO | WO-2021244391 A1 | 12/2021 |
| WO | WO-2021244645 A1 | 12/2021 |
| WO | WO-2021249492 A1 | 12/2021 |
| WO | WO-2021254470 A1 | 12/2021 |
| WO | WO-2021259309 A1 | 12/2021 |
| WO | WO-2022007979 A1 | 1/2022 |
| WO | WO-2022017338 A1 | 1/2022 |
| WO | WO-2022028572 A1 | 2/2022 |
| WO | WO-2022031994 A1 | 2/2022 |
| WO | WO-2022040600 A1 | 2/2022 |
| WO | WO-2022042691 A1 | 3/2022 |
| WO | WO-2022048665 A1 | 3/2022 |
| WO | WO-2022052958 A1 | 3/2022 |
| WO | WO-2022068772 A1 | 4/2022 |
| WO | WO-2022078152 A1 | 4/2022 |
| WO | WO-2022078352 A1 | 4/2022 |
| WO | WO-2022078380 A1 | 4/2022 |
| WO | WO-2022078407 A1 | 4/2022 |
| WO | WO-2022109182 A1 | 5/2022 |
| WO | WO-2022111624 A1 | 6/2022 |
| WO | WO-2022116693 A1 | 6/2022 |
| WO | WO-2022135572 A1 | 6/2022 |
| WO | WO-2022165076 A1 | 8/2022 |
| WO | WO-2022192428 A1 | 9/2022 |
| WO | WO-2022192430 A1 | 9/2022 |
| WO | WO-2022199458 A1 | 9/2022 |
| WO | WO-2022199661 A1 | 9/2022 |
| WO | WO-2022202864 A1 | 9/2022 |
| WO | WO-2022207950 A1 | 10/2022 |
| WO | WO-2022216094 A1 | 10/2022 |
| WO | WO-2022219495 A1 | 10/2022 |
| WO | WO-2022225941 A1 | 10/2022 |
| WO | WO-2022228490 A1 | 11/2022 |
| WO | WO-2022235717 A1 | 11/2022 |
| WO | WO-2022246019 A1 | 11/2022 |
| WO | WO-2022258805 A1 | 12/2022 |
| WO | WO-2022268152 A1 | 12/2022 |
| WO | WO-2023000834 A1 | 1/2023 |
| WO | WO-2023001237 A1 | 1/2023 |
| WO | WO-2023011539 A1 | 2/2023 |
| WO | WO-2023016546 A1 | 2/2023 |
| WO | WO-2023028606 A1 | 3/2023 |
| WO | WO-2023029380 A1 | 3/2023 |
| WO | WO-2023031741 A1 | 3/2023 |
| WO | WO-2023038039 A1 | 3/2023 |
| WO | WO-2023049518 A1 | 3/2023 |
| WO | WO-2023057414 A1 | 4/2023 |
| WO | WO-2023057427 A1 | 4/2023 |
| WO | WO-2023057429 A1 | 4/2023 |
| WO | WO-2023066356 A1 | 4/2023 |
| WO | WO-2023076237 A1 | 5/2023 |
| WO | WO-2023103310 A1 | 6/2023 |
| WO | WO-2023106310 A1 | 6/2023 |
| WO | WO-2023111144 A1 | 6/2023 |
| WO | WO-2023111145 A1 | 6/2023 |
| WO | WO-2023124824 A1 | 7/2023 |
| WO | WO-2023138684 A1 | 7/2023 |
| WO | WO-2023151574 A1 | 8/2023 |
| WO | WO-2023151575 A1 | 8/2023 |
| WO | WO-2023152698 A1 | 8/2023 |
| WO | WO-2023164050 A1 | 8/2023 |
| WO | WO-2023164358 A1 | 8/2023 |
| WO | WO-2023169456 A1 | 9/2023 |
| WO | WO-2023179542 A1 | 9/2023 |
| WO | WO-2023198140 A1 | 10/2023 |
| WO | WO-2023222084 A1 | 11/2023 |
| WO | WO-2023222124 A1 | 11/2023 |
| WO | WO-2024041609 A1 | 2/2024 |
| WO | WO-2024046342 A1 | 3/2024 |
| WO | WO-2024051700 A1 | 3/2024 |
| WO | WO-2024063140 A1 | 3/2024 |
| WO | WO-2024063143 A1 | 3/2024 |
| WO | WO-2024102625 A1 | 5/2024 |
| WO | WO-2024107781 A1 | 5/2024 |
| WO | WO-2024131869 A1 | 6/2024 |
| WO | WO-2024149080 A1 | 7/2024 |

(56) References Cited

FOREIGN PATENT DOCUMENTS

| WO | WO-2024206647 A1 | 10/2024 |
| WO | WO-2024206878 A1 | 10/2024 |

OTHER PUBLICATIONS

Ballatore, C., Huryn, D.M. and Smith, A.B., III (2013), Carboxylic Acid (Bio)Isosteres in Drug Design. ChemMedChem, 8: 385-395 (Year: 2013).*

1H-Benzimidazole-6-carboxylic acid, 2-[[4-[(2S)-2-(5-chloro-2-pyridinyl)-2-methyl-1,3-benzodioxol-4-yl]-1-piperidinyl]methyl]-1-[(2S)-2-oxetanylmethyl]—, Chemical Book, 2017, 2 pages.

Ahmad, I., et al., "Xanthine oxidase/tyrosinase inhibiting, antioxidant, and antifungal oxindole alkaloids from Isatis costata," Pharmaceutical Biology, 2010, 48(6), pp. 716-721.

Arshad, M. F., et al., "Thiazole: A Versatile Standalone Moiety Contributing to the Development of Various Drugs and Biologically Active Agents," Molecules 2022, 27, 3994, https://doi.org/10.3390/molecules27133994, 54 pages.

Balaban, A. T., et al., Aromaticity as a Cornerstone of Heterocyclic Chemistry, Chem. Rev. 2004, 104, 2777-2812.

Beker, W, et al., "Reactivity Patterns of Imidazole, Oxazole, and Thiazole as Reflected by the Polarization Justified Fukui Functions," J. Phys. Chem. A 2013, 117, 1596-1600.

Belaidi, S., et al., "Electronic Structure and Physico-Chemical Property Relationship for Thiazole Derivatives," Asian Journal of Chemistry, 2013, vol. 25, No. 16, 9241-9245.

Beulah, K., et al., "Design, Synthesis and Biological Evaluation of Benzimidazole-pyridine—Piperidine Hybrids as a New Class of Potent Antimicrobial Agents," Letters in Drug Design & Discovery, 2015, vol. 12, No. 1, pp. 38-45.

Bjerregaard, L. G., et al., "Change in Overweight from Childhood to Early Adulthood and Risk of Type 2 Diabetes," The New England Journal of Medicine, Apr. 5, 2018, 378(14):1302-1312, DOI: 10.1056/NEJMoa1713231 doi:10.1056/NEJMoa1713231.

Blanco, F. J., et al., "Effect of Antiinflammatory Drugs on COX-1 and COX-2 Activity in Human Articular Chondrocytes," The Journal of Rheumatology, 1999, 26:6, pp. 1366-1373.

Blanpied, T. A., et al., "Trapping Channel Block of NMDA-Activated Responses by Amantadine and Memantine," The American Physiological Society, 1997, pp. 309-323.

Buckeridge, C et al., "Once-daily oral small molecule GLP-1R agonist PF-07081532 robustly reduces glucose and body weight within 4-6 weeks in adults with type 2 diabetes and non-diabetic adults with obesity," EASD Presentation 2022, No. 114, Diabetologia 2022, 65 (Suppl 1):S1-S469, p. S60.

Chen, L., et al., "Discovery of Novel 5,6-Dihydro-1,2,4-triazine Derivatives as Efficacious Glucagon-Like Peptide-1 Receptor Agonists," Journal of Medicinal Chemistry 2023, 66, pp. 7988-8010.

Coll, B., et al., "A Phase 1b/2a Study of the Safety and Tolerability of GSBR-1290, a Novel Oral Small Molecule Glucagon-Like Peptide 1 Receptor Agonist (GLP-1RA), in Healthy Overweight/Obese Volunteers (HOV) and Participants with Type 2 Diabetes Mellitus (T2DM)," ADA Poster Presentation, Jun. 23, 2024, Abstract 767-P, 1 page.

Davies, D. T., Aromatic Heterocyclic Chemistry, Chapters 3 and 4, Oxford University Press 1992, 21 pages.

Dolomanov, O. V., et al., "OLEX2: a complete structure solution, refinement and analysis program," J. Appl. Cryst. 2009, 42, 339-341, doi:10.1107/S0021889808042726.

Dorwald, Side Reactions in Organic Synthesis. Wiley-VCH, pp. 1-16 (2005).

Escobar-Morreale, H. F., "Polycystic ovary syndrome: definition, aetiology, diagnosis and treatment," Nature Reviews Endocrinology, May 2018, vol. 14, pp. 270-284, doi:10.1038/nrendo.2018.24.

Extended European Search Report for European Application No. 21859247.5 mailed Nov. 27, 2024, 15 pages.

Farrugia, L. J., "WinGX and ORTEP for Windows: an update," Applied Crystallography 2012, 45, 849-854, doi:10.1107/S0021889812029111.

Flack, H. D., "On Enantiomorph-Polarity Estimation," Acta Cryst. 1983, A39, 876-881.

Flack, H. D., et al., "The Use of X-ray Crystallography to Determine Absolute Configuration," CHIRALITY 20:681-690, 2008, DOI: 10.1002/chir.20473.

Griffith, D. A., et al., "A Small-Molecule Oral Agonist of the Human Glucagon-like Peptide-1 Receptor," Journal of Medicinal Chemistry, 2022, 65, pp. 8208-8226.

Guerrero-Pepinosa, N. Y., et al., "Antiproliferative activity of thiazole and oxazole derivatives: A systematic review of in vitro and in vivo studies," Biomedicine & Pharmacotherapy 138 (2021) 111495, https://doi.org/10.1016/j.biopha.2021.111495, 15 pages.

Guidance for Industry: Estimating the Maximum Safe Starting Dose in Initial Clinical Trials for Therapeutics in Adult Healthy Volunteers. US Department of Health and Human Services, Food and Drug Administration (FDA), Center for Drug Evaluation and Research, Jul. 2005, 30 pages, https://www.fda.gov/media/72309/download.

Guidance for Industry: Toxicity Grading Scale for Healthy Adult and Adolescent Volunteers Enrolled in Preventive Vaccine Clinical Trials. U.S. Department of Health and Human Services, Food and Drug Administration, Center for Biologics Evaluation and Research, Sep. 2007, 10 pages.

Haake, P., et al., "A Comparison of Thiazoles and Oxazoles," Communications to the Editor, vol. 85, Dec. 20, 1963, pp. 4044-4045.

Haberhauer, G., et al., "Structural Investigation of Westiellamide Analogues," Tetrahedron 2008, 64, 1853-1859.

Hamdan, F., et al., "Synthesis of novel cyclopeptides containing heterocyclic skeletons," RSC Advances Aug. 2018, 33893-33926, DOI: 10.1039/c8ra03899f.

Hampp, C. et al., "Use of Antidiabetic Drugs in the U.S., 2003-2012," Diabetes Care, May 2014, vol. 37, pp. 1367-1374, DOI: 10.2337/dc13-2289.

Holst, J. J., et al., The Physiology of Glucagon-like Peptide 1, Physiological Reviews, 2007, vol. 87, pp. 1409-1439, doi: 10.1152/physrev.00034.2006.

Hooft, R. W. W., et al., "Determination of absolute structure using Bayesian statistics on Bijvoet differences," J. Appl. Cryst. 2008, 41, 96-103, doi:10.1107/S0021889807059870.

Horner, K. E., et al., "Shielding in and around Oxazole, Imidazole, and Thiazole: How Does the Second Heteroatom Affect Aromaticity and Bonding?," J. Org. Chem. 2015, 80, 7150-7157.

Huang, K.-P., et al., "Dissociable hindbrain GLP1R circuits for satiety and aversion," Nature, Aug. 15, 2024, vol. 632, pp. 585-593, including Methods, Extended Data & Reporting Summary, 25 pages, https://doi.org/10.1038/s41586-024-07685-6.

International Preliminary Report on Patentability for International Application No. PCT/US2022/047687, mailed May 10, 2024, 8 pages.

International Preliminary Report on Patentability for International Application No. PCT/US2023/013700 mailed Sep. 6, 2024 8 pages.

International Preliminary Report on Patentability, mailed Apr. 11, 2024, for International Application No. PCT/US2022/044915, 8 pages.

International Preliminary Report on Patentability, mailed Mar. 2, 2023, for International Application No. PCT/US2021/047015, 8 pages.

International Search Report and Written Opinion for International Application No. PCT/US2021/047015, mailed Jan. 13, 2022, 11 Pages.

International Search Report and Written Opinion for International Application No. PCT/US2022/047687, mailed Feb. 16, 2023, 13 pages.

International Search Report and Written Opinion for International Application No. PCT/US2024/021994 mailed Jul. 30, 2024, 16 pages.

International Search Report and Written Opinion for International Application No. PCT/US2024/022311 mailed Aug. 14, 2024, 19 pages.

(56) References Cited

OTHER PUBLICATIONS

International Search Report and Written Opinion, mailed Apr. 28, 2023, for International Application No. PCT/US2023/013700, 11 pages.
International Search Report and Written Opinion, mailed Dec. 5, 2022, for International Application No. PCT/US2022/044915 (13 total pages).
Invitation to Pay Additional Fees and, Where Applicable, Protest Fee for International Application No. PCT/US2024/022311, mailed Jun. 24, 2024, 14 pages.
Invitation to Pay Additional Fees and, Where Applicable, Protest Fee, mailed Oct. 25, 2021, for International Application No. PCT/US2021/047015 (2 total pages).
Kalra, S., et al., "Consensus Recommendations on GLP-1 RA Use in the Management of Type 2 Diabetes Mellitus: South Asian Task Force," Diabetes Ther Oct. 2019: 1645-1717, https://doi.org/10.1007/s13300-019-0669-4.
Kaspady, M., et al., "Synthesis, Antibacterial Activity of 2,4-Disubstituted Oxazoles and Thiazoles as Bioisosteres," Letters in Drug Design & Discovery, Jun. 2009, pp. 21-28.
Krieger, J.-P., "Intestinal glucagon-like peptide-1 effects on food intake: Physiological relevance and emerging mechanisms," Peptides 2020, 131:170342, 8 pages, https://doi.org/10.1016/j.peptides.2020.170342.
Lega, I. C., et al., "Review: Diabetes, Obesity, and Cancer-Pathophysiology and Clinical Implications," Endocrine Reviews, Feb. 2020, 41(1):35-52, doi:10.1210/endrev/bnz014.
Macrae, C. F., et al., "Mercury: visualization and analysis of crystal structures," J. Appl. Cryst. 2006, 39, 453-457, doi: 10.1107/S002188980600731X.
Meier, J. J., et al., "Glucagon-Like Peptide 1 and Gastric Inhibitory Polypeptide," Biodrugs 2003, 17(2), pp. 93-102.
Meier, J. J., "GLP-1 receptor agonists for individualized treatment of type 2 diabetes mellitus," Nature Reviews Endocrinology, Dec. 2012, vol. 8, p. 728-742, Published online Sep. 4, 2012, doi: 10.1038/nrendo.2012.140.
Muller, T.D., et al., "Anti-Obesity Therapy: from Rainbow Pills to Polyagonists," Pharmacological Reviews, Oct. 2018, 70: 712-746, doi:10.1124/pr.117.014803.
Nauck, M. A., et al., "Another milestone in the evolution of GLP-1-based diabetes therapies," Nature Medicine, vol. 27, Jun. 2021, pp. 949-953.
NCT01237119: "Liraglutide Efficacy and Action in Non-Alcoholic Steatohepatitis (LEAN)," Aug. 2010, Phase 2, 7 pages, Retrieved on Feb. 13, 2025, Retrieved from https://clinicaltrials.gov/study/NCT01237119.
NCT03590626. "Effect of Dulaglutide on Liver Fat in Patients With Type 2 Diabetes and Nonalcoholic Fatty Liver Disease (D-LIFT)," Jan. 1, 2019, 11 pages, Retrieved on Feb. 13, 2025, Retrieved from https://clinicaltrials.gov/study/NCT03590626.
Ognyaov, V. I., et al., "Design of Potent, Orally Available Antagonists of the Transient Receptor Potential Vanilloid 1. Structure-Activity Relationships of 2-Piperazin-1-yl-1H-benzimidazoles," J. Med Chem, 2006, vol. 49, No. 12, pp. 3719-3742, including Supplemental Information S1-S31.
Partial Supplementary European Search Report for European Application No. 21859247.5 dated Sep. 6, 2024, 16 pages.
Pathway: HSA04911, Insulin secretion—*Homo sapiens* (human), KEGG, Jun. 6, 2017, 6 pages.
Pfizer Press release—Pfizer Announces Topline Phase 2b Results of Oral GLP-1R Agonist, Danuglipron, in Adults with Obesity, Dec. 1, 2023, 4 pages, businesswire.com: https://www.businesswire.com/news/home/20231130108413/en/.
Plamboeck, A., et al., "The effect of exogenous GLP-1 on food intake is lost in male truncally vagotomized subjects with pyloroplasty," Am J Physiol Gastrointest Liver Physiol 304: G1117-G1127, 2013, https://doi.org/10.1152/ajpgi.00035.2013.
Polyzos, S. A., et al., "Obesity and nonalcoholic fatty liver disease: From pathophysiology to therapeutics," Metabolism Clinical and Experimental 2019, 92:82-97, doi:10.1016/j.metabol.2018.11.014.

Priner, M. et al., "94-LB: A Phase 1, Double-Blind, Placebo-Controlled Multiple Escalating Dose Study of RGT-075 Novel Small-Molecule Oral GLP-1 Receptor Agonist in Adults with Type 2 Diabetes," Diabetes 2022;71(Supplement_1):94-LB, 1 page, https://doi.org/10.2337/db22-94-LB.
PUBCHEM "Danuglipron," CID: 134611040, Created Jun. 23, 2018; Modified Feb. 8, 2025, 32 pages, Retrieved on Feb. 13, 2025, Retrieved from https://pubchem.ncbi.nlm.nih.gov/compound/134611040#section=Information-Sources.
Roche, Ad hoc announcement pursuant to Art. 53 LR, "Roche announces positive Phase I results of its oral GLP-1 receptor agonist CT-996 for the treatment of people with obesity," Jul. 17, 2024, 5 pages, https://www.roche.com/media/releases/med-cor-2024-07-17.
Saxena, A., et al., "Tolerability, safety and pharmacodynamics of oral, small-molecule glucagon-like peptide-1 receptor agonist danuglipron for type 2 diabetes: A 12-week, randomized, placebo-controlled, Phase 2 study comparing different dose-escalation schemes," Diabetes Obes Metab. 2023;25:2805-2814, DOI: 10.1111/dom.15168.
Saxena, A. R., et al., "Danuglipron (PF-06882961) in type 2 diabetes: a randomized, placebo-controlled, multiple ascending-dose phase 1 trial," Nature Medicine, vol. 27, Jun. 2021, pp. 1079-1087, doi: 10.1038/s41591-021-01391-w.
Saxena, A. R., et al., "Efficacy and Safety of Oral Small Molecule Glucagon-Like Peptide 1 Receptor Agonist Danuglipron for Glycemic Control Among Patients With Type 2 Diabetes: A Randomized Clinical Trial," JAMA Network Open, May 22, 2023, vol. 6(5), e2314493, 12 pages, doi:10.1001/jamanetworkopen.2023.14493.
SAXENDA® (liraglutide) injection, for subcutaneous use. United States Prescribing Information (USPI). 2022. Accessed: Feb. 2, 2023. 13 pages. https://www.novo-pi.com/saxenda.pdf.
Shaffer, A. A, et al., "Comparison of Computational Methods Applied to Oxazole, Thiazole, and Other Heterocyclic Compounds," Journal of Computational Chemistry, vol. 14, No. 1, pp. 75-88 (1993).
Sharma, M. C., "QSAR studies of novel 1-(4-methoxyphenethyl)-1H-benzimidazole-5-carboxylic acid derivatives and their precursors as antileukaemic agents," Journal of Taibah University for Science, 2016, vol. 10, pp. 122-130.
Sheldrick, G. M., "Crystal structure refinement with SHELXL," ActaCryst. 2015, C71, 3-8, doi:10.1107/S2053229614024218.
Sheldrick, G. M., "SHELXL—Integrated space-group and crystal-structure determination" ActaCryst. 2015, A71, 3-8, doi: 10.1107/S2053273314026370.
Sloop, K. W., et al., "Novel Small Molecules Glucagon-Like Peptide-1 Receptor Agonist Stimulates Isulin Secretion in Rodents and From Human Islets," Diabetes, vol. 59, Dec. 2010, p. 3099-3107.
Stas, M., et al., "Thiazole-amino acids: influence of thiazole ring on conformational properties of amino acid residues," Amino Acids 2021, 53: 673-686, https://doi.org/10.1007/s00726-021-02974-0.
Stemmer, K., et al., "CNS-targeting pharmacological interventions for the metabolic syndrome," The Journal of Clinical Investigation, Oct. 2019, 129(10), pp. 4058-4071, https://www.jci.org/articles/view/129195/pdf.
Stevens, E., Medicinal Chemistry: The Modern Drug Discovery Process, 2013, Chapter 10, Lead Discovery, pp. 247-272.
Structure Therapeutics Corporate Presentation, GSBR-1290 Phase 1b MAD Results. Sep. 29, 2023, 24 pages.
Teague, S. J., et al., "The Design of Leadlike Combinatorial Libraries," Communications, Angew. Chem. Int. Ed., 1999, 38, No. 24, pp. 3743-3748.
Terns Pharmaceuticals Announces Positive Phase 1 Clinical Trial Results with TERN-601 Once-Daily Oral GLP-1R Agonist for the Treatment of Obesity, Sep. 9, 2024, 3 pages, retrieved on Feb. 12, 2025, retrieved from URL: https://ir.ternspharma.com/news-releases/news-release-details/terns-pharmaceuticals-announces-positive-phase-1-clinical-trial.
Twig, G., et al., "Body-Mass Index in 2.3 Million Adolescents and Cardiovascular Death in Adulthood," The New England Journal of Medicine, Jun. 23, 2016, 374;25:2430-2440, DOI: 10.1056/NEJMoa1503840.

(56) References Cited

OTHER PUBLICATIONS

U.S. Appl. No. 18/956,385, filed Nov. 22, 2024, by Reeves et al.
U.S. Appl. No. 19/018,754, filed Jan. 13, 2025, by Reeves et al.
U.S. Appl. No. 19/018,788, filed Jan. 13, 2025, by Reeves et al.
U.S. Appl. No. 19/018,805, filed Jan. 13, 2025, by Reeves et al.
U.S. Appl. No. 19/018,817, filed Jan. 13, 2025, by Reeves et al.
Vilsboll, T., et al., Reduced Postprandial Concentrations of Intact Biologically Active Glucagon-Like Peptide 1 in Type 2 Diabetic Patients, Diabetes, vol. 50, Mar. 2001, pp. 609-613.
Waise, T. M. Z., et al., The metabolic role of vagal afferent innervation, Nature Reviews Gastroenterology & Hepatology, vol. 15, Oct. 2018, pp. 625-636, https://doi.org/10.1038/s41575-018-0062-1.
WEGOVY® (semaglutide) injection, for subcutaneous use. United States Prescribing Information (USPI). 2023. Accessed: Feb. 2, 2023. 15 pages. https://www.novo-pi.com/wegovy.pdf.
Zhang, X. et al., "Differential GLP-1R Binding and Activation by Peptide and Non-peptide Agonists," Molecular Cell 80, Nov. 5, 2020; pp. 485-500 & 485-500.e1-e7, doi: 10.1016/j.molcel.2020.09.020.
GenBank Accession No. NM_002062.5. Version No. NM_002062.5. *Homo sapiens* glucagon like peptide 1 receptor (GLP1R), transcript variant 1, mRNA: pp. 1-6. Record created Nov. 22, 2018. Retrieved May 6, 2025. Retrieved from: https://www.ncbi.nlm.nih.gov/nuccore/NM_002062.5/.
Pfizer. Pfizer Provides Update on Oral GLP-1 Receptor Agonist Danuglipron. Apr. 14, 2025. [retrieved on May 7, 2025] Available at: https://www.pfizer.com/news/press-release/press-release-detail/pfizer-provides-update-oral-glp-1-receptor-agonist. pp. 5.
Remington: The Science and Practice of Pharmacy, 21st Edition. Lippincott Williams & Wilkins (2005).
Russak, Edward M., and Edward M Bednarczyk. Impact of Deuterium Substitution on the Pharmacokinetics of Pharmaceuticals. Annals of Pharmacotherapy 53(2):211-216 (2019). Published Online Aug. 23, 2018.
Terns. Terns Pharmaceuticals Announces Positive Phase 1 Clinical Trial Results with Tern-601 Once-Daily Oral GLP-1R Agonist for the Treatment of Obesity. Sep. 9, 2024. [retrieved on May 7, 2025] Available at: https://ir.ternspharma.com/news-releases/news-release-details/terns- pharmaceuticals-announces-positive-phase-1-clinical-trial. pp. 7.
Terns. Terns Pharmaceuticals. Our Programs. [retrieved May 7, 2025] Available at: https://www.ternspharma.com/our-programs. pp. 6.
Wuts, Peter G M, and Theodora W. Greene. Greene's Protective Groups in Organic Synthesis, 4th Edition. Wiley (2006).

\* cited by examiner

COMPOUNDS AS GLP-1R AGONISTS

CROSS REFERENCE TO RELATED APPLICATIONS

This application is a continuation of U.S. application Ser. No. 18/956,385, filed on Nov. 22, 2024, which is a continuation of U.S. application Ser. No. 17/954,047, filed on Sep. 27, 2022, which claims priority to, and the benefit of, U.S. Provisional Patent Application No. 63/261,717 filed Sep. 27, 2021, the entire contents of each of which are hereby incorporated by reference for all purposes.

BACKGROUND

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2. Type 1 diabetes (T1D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (T2DM) usually begins with either insulin resistance or when there is insufficient production of insulin to maintain an acceptable glucose level.

Currently, various pharmacological approaches are available for treating hyperglycemia and subsequently, T2DM (Hampp, C. et al. Use of Antidiabetic Drugs in the U.S., 2003-2012, Diabetes Care 2014, 37, 1367-1374). One of them is glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Marketed GLP-1R agonists are peptides administered by subcutaneous injection. Liraglutide is additionally approved for the treatment of obesity.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier et al. Biodrugs. 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll T, et al. Diabetes. 2001. 50; 609-613).

Holst (Physiol. Rev. 2007, 87, 1409) and Meier (Nat. Rev. Endocrinol. 2012, 8, 728) describe that GLP-1 receptor agonists, such as liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

There remains a need of developing GLP-1 receptor agonists for an easily-administered prevention and/or treatment for cardiometabolic and associated diseases.

SUMMARY

Disclosed are compounds that can be used as glucagon-like peptide-1 receptor (GLP-1R) agonists, compositions containing these compounds and methods for treating diseases and/or conditions mediated by GLP-1R.

In one aspect, provides is a compound of Formula (I), including compounds of Formulae (II)-(VIII), or selected from the group consisting of a compound listed in Table 1, or a pharmaceutically acceptable salt thereof, as detailed herein.

Further provided is a pharmaceutical composition comprising is a compound of Formula (I), including compounds of Formulae (II)-(VIII), or selected from the group consisting of a compound listed in Table 1, or a pharmaceutically acceptable salt thereof, and a pharmaceutically acceptable carrier or excipient.

In another aspect, provided is a method of treating a disease or a condition mediated by GLP-1R in a subject in need thereof comprises administering to the subject a therapeutically effective amount of a compound of Formula (I), including compounds of Formulae (II)-(VIII), or selected from the group consisting of compounds listed in Table 1, or a pharmaceutically acceptable salt thereof. In some embodiments, the disease or the condition is a cardiometabolic disease. In some embodiments, the disease or the condition is diabetes. In some embodiments, the disease or the condition is a liver disease.

Also provided is a compound of Formula (I), including compounds of Formulae (II)-(VIII), or selected from the group consisting of a compound listed in Table 1, or a pharmaceutically acceptable salt thereof, as detailed herein, for the treatment.

Also provided is use of a compound of Formula (I), including compounds of Formulae (II)-(VIII), or selected from the group consisting of a compound listed in Table 1, or a pharmaceutically acceptable salt thereof, as detailed herein, in the manufacture of a medicament for the treatment.

Further provided is a kit comprising a compound of Formula (I), including compounds of Formulae (II)-(VIII), or selected from the group consisting of a compound listed in Table 1, or a pharmaceutically acceptable salt thereof. In some embodiments, the kit comprises instructions for use according to a method described herein.

In yet another aspect, provided is a method of making a compound of Formula (I), including compounds of Formulae (II)-(VIII), or selected from the group consisting of a compound listed in Table 1, or a pharmaceutically acceptable salt thereof. Also provided are compound intermediates useful in synthesis of a compound of Formula (I), including compounds of Formulae (II)-(VIII), or selected from the group consisting of a compound listed in Table 1, or a pharmaceutically acceptable salt thereof.

In an aspect, the present disclosure provides a compound of Formula (I):

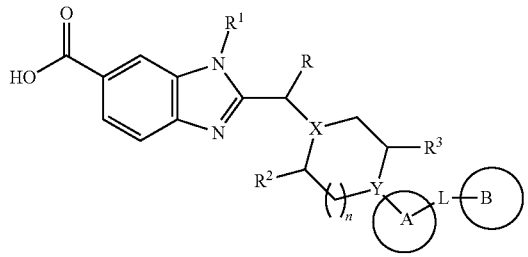

(I)

or a pharmaceutically acceptable salt thereof, wherein:
X is N or CH;
Y is N or CR$^4$;
n is 0 or 1;
R is hydrogen;
R$^1$ is —C$_1$-C$_6$ alkylene-R$^5$;
R$^2$ is hydrogen, oxo, or C$_1$-C$_6$ alkyl;
R$^3$ is hydrogen, oxo, or C$_1$-C$_6$ alkyl and R$^4$ is hydrogen, OH, or C$_1$-C$_6$ alkyl;
or R$^3$ and R$^4$ are taken together with the carbon atoms to which they are attached to form C$_3$-C$_6$ cycloalkyl optionally substituted by halo or C$_1$-C$_3$ alkyl;
R$^5$ is 5-membered heterocyclyl or 5-membered heteroaryl, each of which comprises 1, 2, or 3 heteroatoms independently selected from O, N, and S, wherein at least one heteroatom of R$^5$ is S, and further wherein R$^5$ is optionally substituted by halo, —O—C$_{1-6}$ alkyl, C$_{1-6}$ alkyl, C$_{1-6}$ alkenyl, or C$_1$-C$_6$ haloalkyl;
Ring A is 5- to 12-membered heterocyclyl or 5- to 12-membered heteroaryl, each of which is independently optionally substituted by halo, CN, C$_3$-C$_6$ cycloalkyl, or C$_1$-C$_6$ alkyl optionally substituted by halo or OH;
L is a bond, —O—, C$_1$-C$_6$ alkylene, *—O—C$_1$-C$_6$ alkylene-**, *—C$_1$-C$_6$ alkylene-O—**, or *—NR$^6$—C$_1$-C$_6$ alkylene-**, wherein
* represents the point of attachment to ring A and ** represents the point of attachment to ring B;
when L is *—O—C$_1$-C$_6$ alkylene-**, the C$_1$-C$_6$ alkylene of L is optionally substituted by R$^L$, wherein each R$^L$ is independently C$_1$-C$_6$ alkyl or halo, or two R$^L$ are taken together with the carbon atom or atoms to which they are attached to form C$_3$-C$_6$ cycloalkyl or 3- to 6-membered heterocyclyl; and
when L is C$_1$-C$_6$ alkylene, the C$_1$-C$_6$ alkylene is optionally substituted by R$^{L1}$, wherein each R$^{L1}$ is independently halo, OH, oxo, or C$_1$-C$_6$ alkyl, or two R$^{L1}$ are taken together with the carbon atom or atoms to which they are attached to form C$_3$-C$_6$ cycloalkyl or 3- to 6-membered heterocyclyl;
R$^6$ is hydrogen or C$_1$-C$_6$ alkyl; and
Ring B is C$_3$-C$_{10}$ cycloalkyl, C$_6$-C$_{14}$ aryl, 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl.

In some embodiments, X is N. In some embodiments, X is CH.
In some embodiments, Y is N. In some embodiments, Y is CR$^4$. In some embodiments, Y is CR$^4$, and R$^3$ and R$^4$ are taken together with the carbon atoms to which they are attached to form a cyclopropyl group.

In some embodiments, n is 0. In some embodiments, n is 1.

In some embodiments, R$^1$ is —CH$_2$—R$^5$. In some embodiments, R$^5$ is 5-membered heteroaryl comprising 1, 2, or 3 heteroatoms independently selected from O, N, and S, wherein at least one heteroatom of R$^5$ is S, and further wherein R$^5$ is optionally substituted by halo, —O—C$_{1-6}$ alkyl, C$_{1-6}$ alkyl, C$_{1-6}$ alkenyl, or C$_1$-C$_6$ haloalkyl. In some embodiments, R$^5$ is 5-membered heteroaryl comprising 1 or 2 heteroatoms selected from S and N, wherein one heteroatom of R$^5$ is S, and further wherein R$^5$ is optionally substituted by halo, —O—C$_{1-6}$ alkyl, C$_{1-6}$ alkyl, C$_{1-6}$ alkenyl, or C$_1$-C$_6$ haloalkyl. In some embodiments, R$^5$ is thiazolyl or isothiazolyl, each optionally substituted by halo, —O—C$_{1-6}$ alkyl, C$_1$-C$_6$ alkyl, C$_{1-6}$ alkenyl, or C$_1$-C$_6$ haloalkyl. In some embodiments, R$^5$ is thiazol-2-yl or thiazol-5-yl, each optionally substituted by C$_1$-C$_6$ alkyl. In some embodiments, R$^5$ is

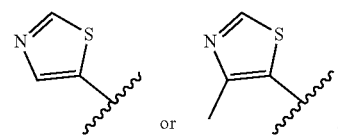

In some embodiments, R$^5$ is

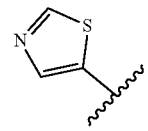

In some embodiments, Ring A is 5- to 6-membered heteroaryl optionally substituted by halo, CN, C$_3$-C$_6$ cycloalkyl, or C$_1$-C$_6$ alkyl optionally substituted by halo or OH. In some embodiments, Ring A is 6-membered heteroaryl optionally substituted by halo, CN, C$_3$-C$_6$ cycloalkyl, or C$_1$-C$_6$ alkyl optionally substituted by halo or OH. IN some embodiments, Ring A is benzodioxolyl, pyridyl, pyrimidinyl, or pyrazinyl, each of which is optionally substituted by halo, CN, C$_3$-C$_6$ cycloalkyl, or C$_1$-C$_6$ alkyl optionally substituted by halo or OH. In some embodiments, wherein Ring A is benzodioxolyl, pyridyl, pyrimidinyl, or pyrazinyl. In some embodiments, Ring A is

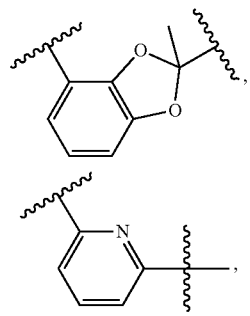

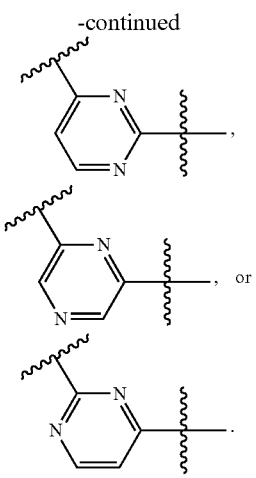

In some embodiments, Ring A is

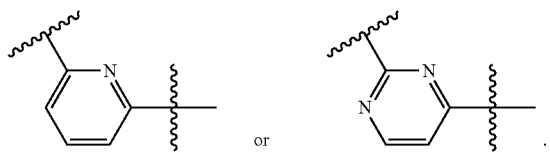 [SMILES: *c1cccc(*)n1 ; *c1ccnc(*)n1]

In some embodiments, L is *—O—$C_1$-$C_6$ alkylene-** optionally substituted by $R^L$. In some embodiments, L is *—O—$CH_2$—** or *—O—$CD_2$—**. In some embodiments, L is —O—. In some embodiments, L is a bond. In some embodiments, L is *—C(O)—$CH_2$—**.

In some embodiments, Ring B is $C_6$-$C_{14}$ aryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some embodiments, Ring B is phenyl optionally substituted by one to three substituents each independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some embodiments, Ring B is phenyl optionally substituted by one to three substituents each independently selected from the group consisting of halo, CN, and —$CONH_2$. In some embodiments, Ring B is

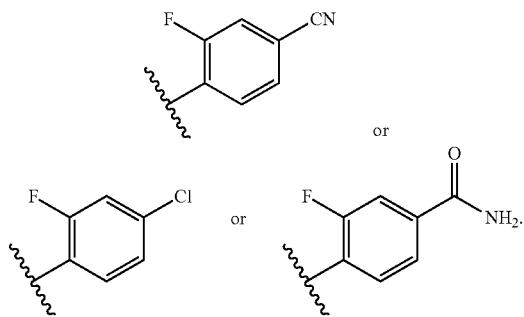

In some embodiments, Ring B is 4- to 12-membered heterocyclyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some embodiments, Ring B is tetrahydroisoquinolinyl optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some embodiments, Ring B is

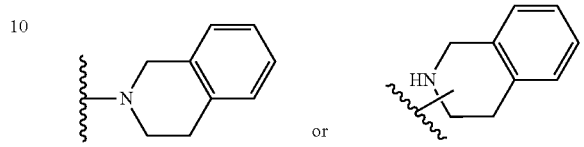

or optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some embodiments, Ring B is

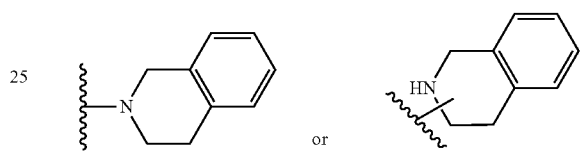

optionally substituted by one to three substituents independently selected from the group consisting of halo, and CN. In some embodiments, Ring B is

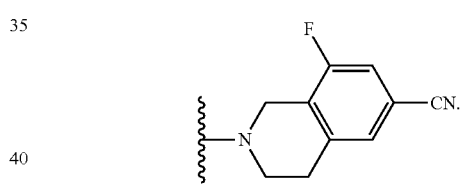

In some embodiments, Ring B is a 5- to 12-membered heteroaryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some embodiments, Ring B is a 9-membered heteroaryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some embodiments, Ring B is 9-membered heteroaryl, which is optionally substituted by one to two substituents independently selected from the group consisting of halo and CN. In some embodiments, Ring B is

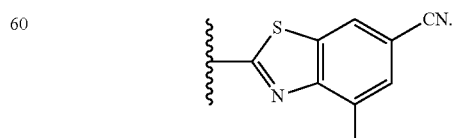

In some embodiments, the compound is of Formula VIII:

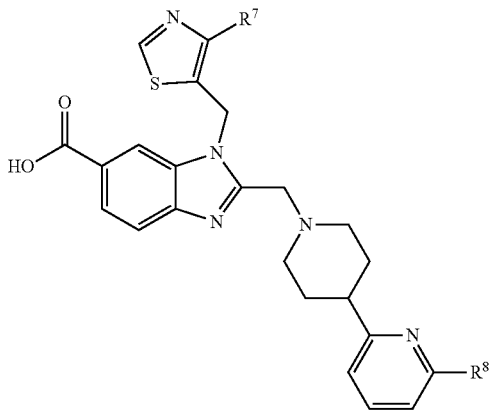

(VIII)

wherein $R^7$ is hydrogen, chloro, bromo, fluoro, methyl, or vinyl; and $R^8$ is

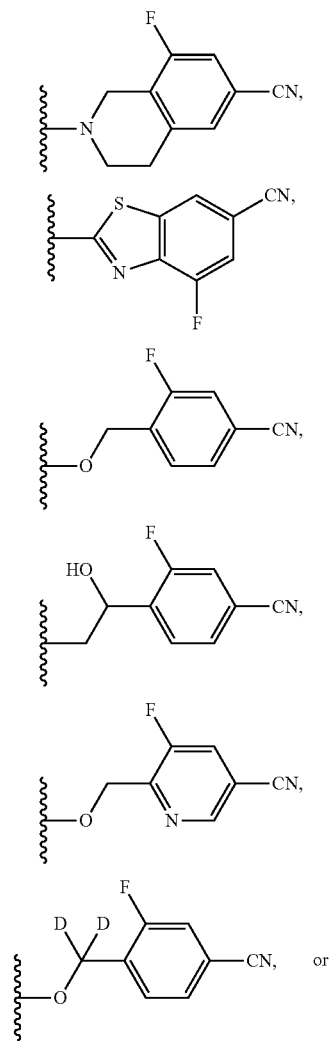

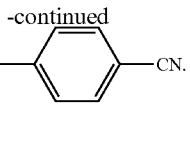

In some embodiments, $R^7$ is hydrogen.

In some embodiments, the compound is a meglumine salt.

In an aspect, the present disclosure provides a compound, or pharmaceutically acceptable salt thereof, wherein the compound is selected any one of the compounds in Table 1 other than Reference Compound A.

In some embodiments, the compound selected from any one of the compounds in Table 1 other than Reference Compound A is a meglumine salt.

In some embodiments, the present disclosure provides a pharmaceutical composition comprising the compound of Formula I-VIII or Compound 1-31, or a pharmaceutically acceptable salt thereof, and a pharmaceutically acceptable excipient.

In some embodiments, the present disclosure provides a method of treating a disease mediated by glucagon-like peptide-1 receptor (GLP-1R) in an individual in need thereof, comprising administering to the individual any one of the compounds disclosed herein, or a pharmaceutically acceptable salt thereof, or any pharmaceutical composition disclosed herein. In some embodiments, the disease is a liver disease. In some embodiments, the liver disease is primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, or oti-antitrypsin deficiency. In some embodiments, the disease is diabetes.

In some embodiments, the disease is a cardiometabolic disease. In some embodiments, the disease is obesity.

In some embodiments, the present disclosure provides the use of any one of the compounds disclosed herein, or a pharmaceutically acceptable salt thereof, in the manufacture of a medicament for treating a disease mediated by GLP-1R.

In some embodiments, the present disclosure provides a method of decreasing food intake in an individual in need thereof, comprising administering to the individual any one of the compounds, or pharmaceutically acceptable salts thereof, or pharmaceutical compositions disclosed herein.

In some embodiments, the present disclosure provides a method of increasing glucose tolerance in an individual in need thereof, comprising administering to the individual any one of the compounds, or pharmaceutically acceptable salts thereof, or pharmaceutical compositions disclosed herein.

DETAILED DESCRIPTION

Figure 1:
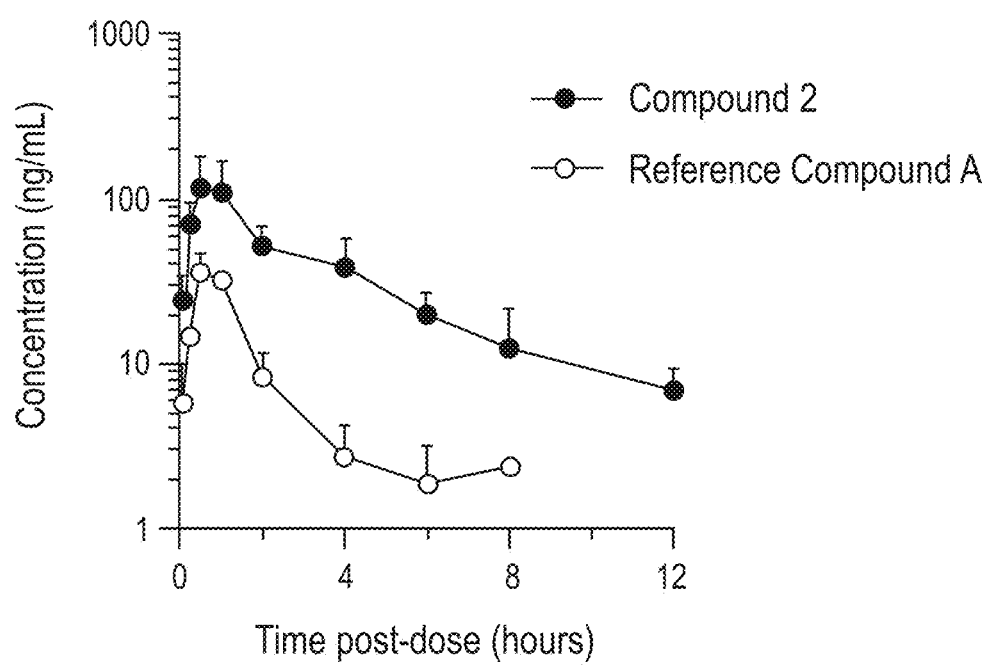
FIG. 1 shows plasma concentrations of Compound 2 and Reference Compound A after oral (PO) administration to rats (3 mg/kg).

In an aspect, this disclosure relates to compounds that the present inventors have discovered agonize GLP-1R. For example, the present inventors have discovered new GLP-1R agonists that have superior pharmacokinetic properties (e.g., Cmax, $AUC_{0-last}$) relative to alternative GLP-1R agonists, are potent agonists of GLP-1R, and, in humanized animal models, effectuate the improvement of disease-relevant phenotypes such as food intake and glucose tolerance. Significantly, the benefits of the presently-disclosed compounds could not have been predicted apriori. This disclosure also relates to compositions comprising the GLP-1R agonists disclosed herein and the use of the GLP-1R agonists in treating diseases.

Definitions

As used herein, the following definitions shall apply unless otherwise indicated. Further, if any term or symbol used herein is not defined as set forth below, it shall have its ordinary meaning in the art.

As used herein and in the appended claims, the singular forms "a", "an" and "the" include plural forms, unless the context clearly dictates otherwise.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in connection with a value, contemplate a variation within +10% of the specified value. Reference to "about" a value or parameter herein includes (and describes) embodiments that are directed to that value or parameter per se. For example, description referring to "about X" includes description of "X".

"Comprising" is intended to mean that the compositions and methods include the recited elements, but not exclude others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of, e.g., other ingredients and substantial method steps recited. Embodiments defined by each of these transition terms are within the scope of this invention.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Pharmaceutically acceptable" refers to safe and non-toxic, preferably for in vivo, more preferably, for human administration.

"Pharmaceutically acceptable salt" refers to a salt that is pharmaceutically acceptable. A compound described herein may be administered as a pharmaceutically acceptable salt.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, NH4, Ca, Ba, imidazolium, and ammonium cations based on naturally occurring amino acids, and ammonium cations that are not based on naturally occurring amino acids, e.g., meglumine. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, fumarate, propionate, succinate, tartrate, chloride, sulfate, bisulfate, mono-, di-, and tribasic phosphate, mesylate, tosylate, and the likes.

"Stereoisomer" or "stereoisomers" refers to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

As used herein, the term "subject" refers to an animal, including, but are not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

As used herein, "treatment" or "treating" is an approach for obtaining beneficial or desired results including clinical results. For purposes of this disclosure, beneficial or desired results include, but are not limited to, one or more of the following: decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delaying or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of this disclosure contemplate any one or more of these aspects of treatment.

In some embodiments, the term "glucose tolerance" refers to the ability of a subject to dispose of a glucose load or a subject's glycemic control.

"Therapeutically effective amount" or dose of a compound or a composition refers to that amount of the compound or the composition that results in reduction or inhibition of symptoms or a prolongation of survival in a patient. The results may require multiple doses of the compound or the composition.

"Alkyl" refers to monovalent saturated aliphatic hydrocarbyl groups having from 1 to 12 carbon atoms, preferably from 1 to 10 carbon atoms, and more preferably from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). Cx alkyl refers to an alkyl group having x number of carbon atoms.

"Alkylene" refers to a divalent saturated aliphatic hydrocarbyl group having from 1 to 12 carbon atoms, preferably from 1 to 10 carbon atoms, and more preferably from 1 to 6 carbon atoms. This term includes, by way of example, linear and branched hydrocarbyl groups such as methylene (—$CH_2$—), ethylene (—$CH_2CH_2$— or —CH(Me)—), propylene (—$CH_2CH_2CH_2$— or —CH(Me)$CH_2$—, or —CH(Et)—) and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Cyano" refers to the group —C≡N.

"Cycloalkyl" refers to saturated or unsaturated but non-aromatic cyclic alkyl groups of from 3 to 10 carbon atoms, preferably from 3 to 8 carbon atoms, and more preferably from 3 to 6 carbon atoms, having single or multiple cyclic rings including fused, bridged, and spiro ring systems. Cx cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, thiophenyl, thiazole, and furanyl. Other preferred heteroaryls include 9 or 10 membered heteroaryls, such as indolyl, quinolinyl, quinolonyl, isoquinolinyl, and isoquinolonyl.

"Heterocycle" or "heterocyclic" or "heterocycloalkyl" or "heterocyclyl" refers to a saturated or partially saturated, but not aromatic, group having from 1 to 10 ring carbon atoms, preferably from 1 to 8 carbon atoms, and more preferably from 1 to 6 carbon atoms, and from 1 to 4 ring heteroatoms, preferably from 1 to 3 heteroatoms, and more preferably from 1 to 2 heteroatoms selected from the group consisting of nitrogen, sulfur, or oxygen. Cx heterocycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl (S(O)), sulfonyl (S(O)$_2$) moieties.

Examples of heterocyclyl and heteroaryl include, but are not limited to, azetidinyl, pyrrolyl, imidazolyl, pyrazolyl, pyridyl, pyrazyl, pyrimidyl, pyridazyl, indolizyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]thiophenyl, thiazolyl, thiazolidinyl, thiophenyl, benzo[b]thiophenyl, morpholinyl, thiomorpholinyl (also referred to as thiamorpholinyl), 1,1-dioxothiomorpholinyl, piperidinyl, pyrrolidinyl, and tetrahydrofuranyl.

"Oxo" refers to the atom (=O) or (O).

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

It is understood that an optionally substituted moiety can be substituted with more than five substituents, if permitted by the number of valences available for substitution on the moiety. For example, a propyl group can be substituted with seven halogen atoms to provide a perhalopropyl group. The substituents may be the same or different.

Compounds

In one aspect, provided is a compound of Formula (I):

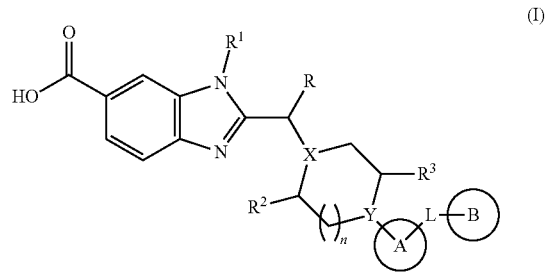

or a pharmaceutically acceptable salt thereof, wherein:
X is N or CH;
Y is N or CR$^4$;
n is 0 or 1;
R is hydrogen;
R$^1$ is —C$_1$-C$_6$ alkylene-R$^5$;
R$^2$ is hydrogen, oxo, or C$_1$-C$_6$ alkyl;
R$^3$ is hydrogen, oxo, or C$_1$-C$_6$ alkyl, and R$^4$ is hydrogen, OH, or C$_1$-C$_6$ alkyl;
or R$^3$ and R$^4$ are taken together with the carbon atoms to which they are attached to form C$_3$-C$_6$ cycloalkyl optionally substituted by halo or C$_1$-C$_3$ alkyl;
R$^5$ is 5-membered heterocyclyl or 5-membered heteroaryl, each of which comprises 1, 2, or 3 heteroatoms independently selected from O, N, and S, wherein at least one heteroatom of R$^5$ is S, and further wherein R$^5$ is optionally substituted by halo, —O—C$_{1-6}$ alkyl, C$_{1-6}$ alkyl, C$_{1-6}$ alkenyl, or C$_1$-C$_6$ haloalkyl;
Ring A is 5- to 12-membered heterocyclyl or 5- to 12-membered heteroaryl, each of which is independently optionally substituted by halo, CN, C$_3$-C$_6$ cycloalkyl, or C$_1$-C$_6$ alkyl optionally substituted by halo or OH;
L is a bond, —O—, C$_1$-C$_6$ alkylene, *—O—C$_1$-C$_6$ alkylene-**, *—C$_1$-C$_6$ alkylene-O—**, or *—NR$^6$—C$_1$-C$_6$ alkylene-**, wherein
* represents the point of attachment to ring A and ** represents the point of attachment to ring B;
when L is *—O—C$_1$-C$_6$ alkylene-**, the C$_1$-C$_6$ alkylene of L is optionally substituted by R$^L$, wherein each R$^L$ is independently C$_1$-C$_6$ alkyl or halo, or two R$^L$ are taken together with the carbon atom or atoms to which they are attached to form C$_3$-C$_6$ cycloalkyl or 3- to 6-membered heterocyclyl; and
when L is C$_1$-C$_6$ alkylene, the C$_1$-C$_6$ alkylene is optionally substituted by R$^{L1}$, wherein each R$^{L1}$ is independently halo, OH, oxo, or C$_1$-C$_6$ alkyl, or two R$^{L1}$ are taken together with the carbon atom or atoms to which they are attached to form C$_3$-C$_6$ cycloalkyl or 3- to 6-membered heterocyclyl;
R$^6$ is hydrogen or C$_1$-C$_6$ alkyl; and
Ring B is C$_3$-C$_{10}$ cycloalkyl, C$_6$-C$_{14}$ aryl, 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl.

In the descriptions herein, it is understood that every description, variation, embodiment or aspect of a moiety/variable may be combined with every description, variation, embodiment or aspect of other moieties/variables the same as if each and every combination of descriptions is specifically and individually listed. For example, every description, variation, embodiment or aspect provided herein with respect to $R^1$ of Formula (I) may be combined with every description, variation, embodiment or aspect of Ring A the same as if each and every combination were specifically and individually listed.

In some embodiments of formula (I), X and Y are each N. In some embodiments, X is N and Y is $CR^4$. In some embodiments, X is N, Y is $CR^4$, and $R^4$ is H, OH, or $C_1$-$C_6$ alkyl. In some embodiments, X is N, Y is $CR^4$, and $R^4$ is H, OH, or $C_1$-$C_3$ alkyl. In some embodiments, X is N, Y is $CR^4$, and $R^4$ is H or $C_1$-$C_3$ alkyl. In some such embodiments, X is N, Y is $CR^4$, and $R^4$ is H or OH. In some embodiments, X is N, Y is $CR^4$, and $R^4$ is H. In some embodiments, X is N, Y is $CR^4$, and $R^3$ and $R^4$ are taken together with the carbon atoms to which they are attached to form a cyclopropyl group optionally substituted by halo or $C_1$-$C_3$ alkyl In some embodiments, X is N, Y is $CR^4$, and $R^3$ and $R^4$ are taken together with the carbon atoms to which they are attached to form a cyclopropyl group optionally substituted by fluoro or methyl.

In some embodiments of Formula (I), provided is a compound of Formula (II):

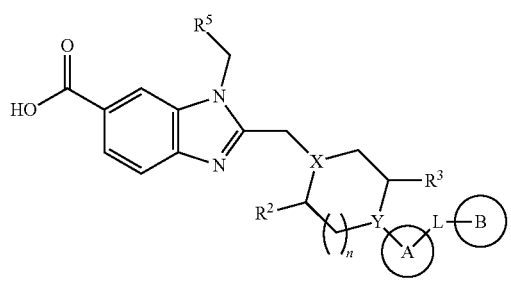

(II)

or a pharmaceutically acceptable salt thereof, wherein X, Y, n, $R^2$, $R^3$, $R^5$, Ring A, L, and Ring B are as defined for Formula (I).

In some embodiments of Formula (I) or (II), X is N and Y is $CR^4$. In some embodiments, the compound is of Formula (II-a):

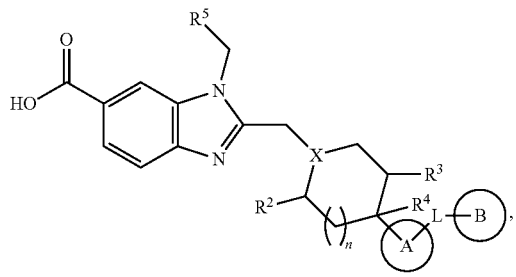

(II-a)

or a pharmaceutically acceptable salt thereof, wherein n, $R^2$, $R^3$, $R^4$, $R^5$, Ring A, L, and Ring B are as defined for Formula (I).

In some embodiments of Formula (I) or (II), X is N, Y is $CR^4$, and $R^3$ and $R^4$ are taken together with the carbon atoms to which they are attached to form a cyclopropyl group optionally substituted by halo or $C_1$-$C_3$ alkyl. In some embodiments, the compound is of Formula (II-b), (II-b1), or (II-b2):

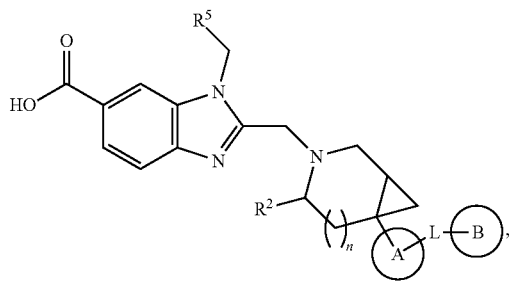

(II-b)

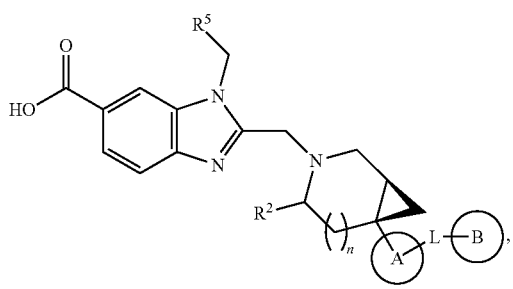

(II-b1)

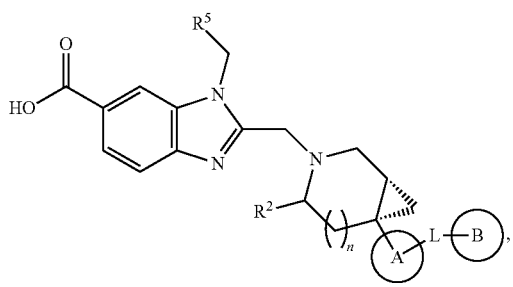

(II-b2)

wherein n, $R^2$, $R^5$, Ring A, L, and Ring B are as defined for Formula (I).

In some embodiments of Formula (II), X and Y are each N. In some embodiments, the compound is of Formula (II-c):

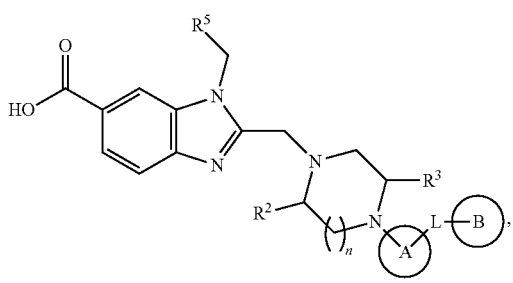

(II-c)

wherein n, $R^2$, $R^3$, $R^5$, Ring A, L, and Ring B are as defined for Formula (I).

In some embodiments of Formula (II), Ring A is a 6-membered heteroaryl comprising 1, 2, or 3 heteroatoms. In some embodiments, the compound is of formula (III):

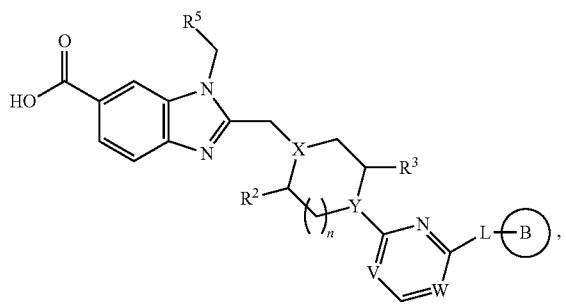

(III)

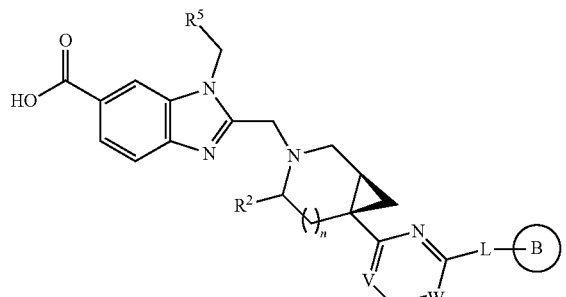

(III-b1)

wherein V and W are independently N or CR$^A$, wherein each R$^A$ is H, halo, CN, C$_3$-C$_6$ cycloalkyl, or C$_1$-C$_6$ alkyl optionally substituted by halo or OH. In some embodiments, V is N and W is CR$^A$. In some embodiments, V is CR$^A$ and W is N. In some embodiments, V and W are each CR$^A$. In some embodiments, V and W are each N. In some embodiments, V is N and W is CH. In some embodiments, V is CH and W is N. In some embodiments, V and W are each CH. In some embodiments of Formula (III), X is N and Y is CR$^4$. In some embodiments, the compound is of formula (III-a):

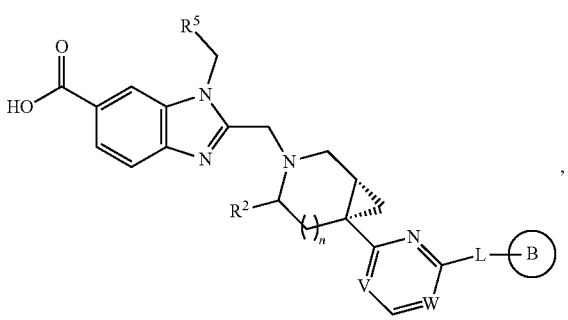

(III-b2)

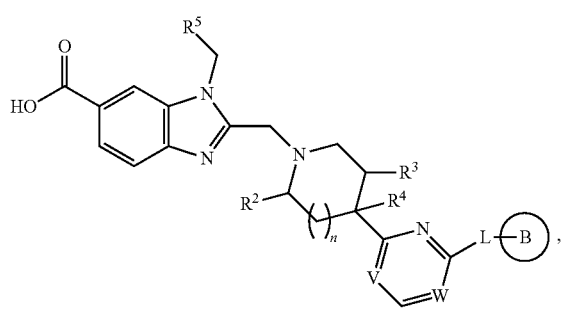

(III-a)

wherein n, R$^2$, R$^3$, R$^4$, R$^5$, L, and Ring B are as defined for Formula (I), and V and W are as defined for formula (III).

In some embodiments of Formula (III), X is N, Y is CR$^4$, and R$^3$ and R$^4$ are taken together with the carbon atoms to which they are attached to form a cyclopropyl group optionally substituted by halo or C$_1$-C$_3$ alkyl. In some embodiments, the compound is of Formula (III-b), (III-b1), or (III-b2):

wherein n, R$^2$, R$^5$, L, and Ring B are as defined for Formula (I), and V and W are as defined for formula (III). In some embodiments, the compound is of formula (III-b-3):

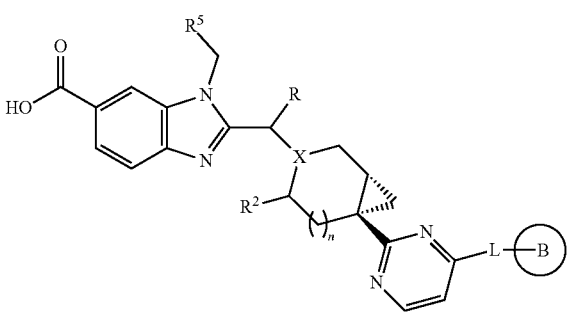

(III-b-3)

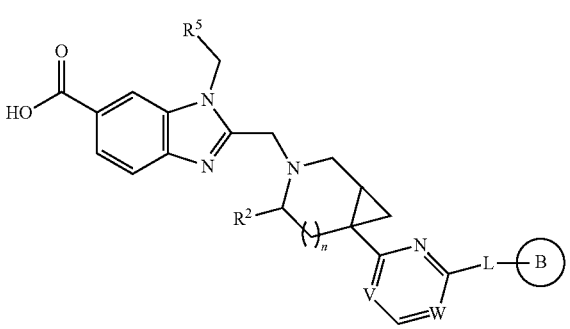

(III-b)

wherein n, R$^2$, R$^5$, L, and Ring B are as defined for Formula (I).

In some embodiments of Formula (III), X and Y are each N. In some embodiments, the compound is of Formula (III-c):

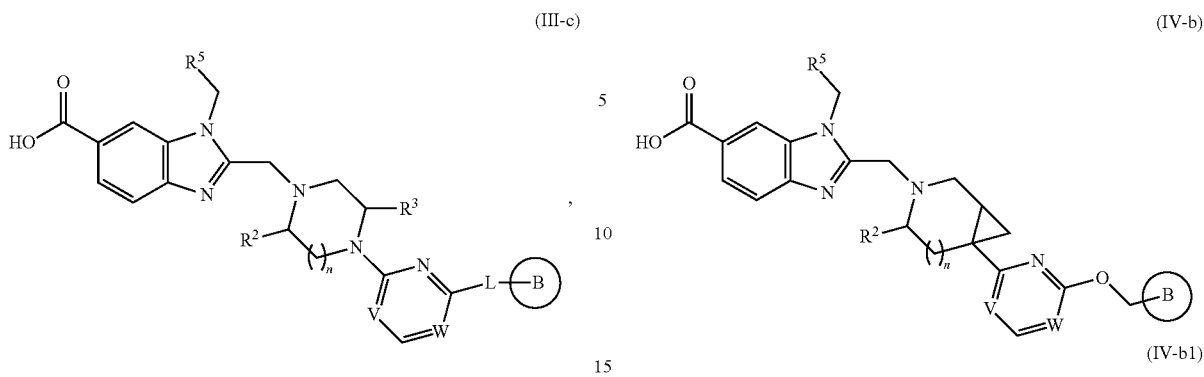

wherein n, $R^2$, $R^3$, $R^5$, L, and Ring B are as defined for Formula (I), and V and W are as defined for formula (III).

In some embodiments of Formula (III), L is *—O—$C_1$-$C_6$ alkylene-**, optionally substituted by $R^L$ as described for Formula (I). In some embodiments, L is *—O—$CH_2$—**. In some embodiments, the compound is of Formula (IV):

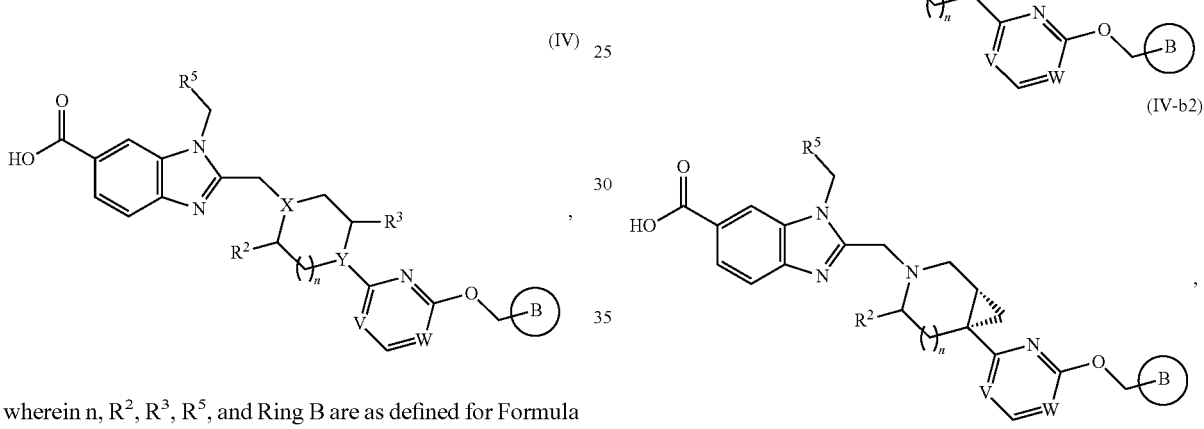

wherein n, $R^2$, $R^3$, $R^5$, and Ring B are as defined for Formula (I), and V and W are as defined for formula (III).

In some embodiments of Formula (IV), X is N and Y is $CR^4$. In some embodiments, the compound is of formula (IV-a):

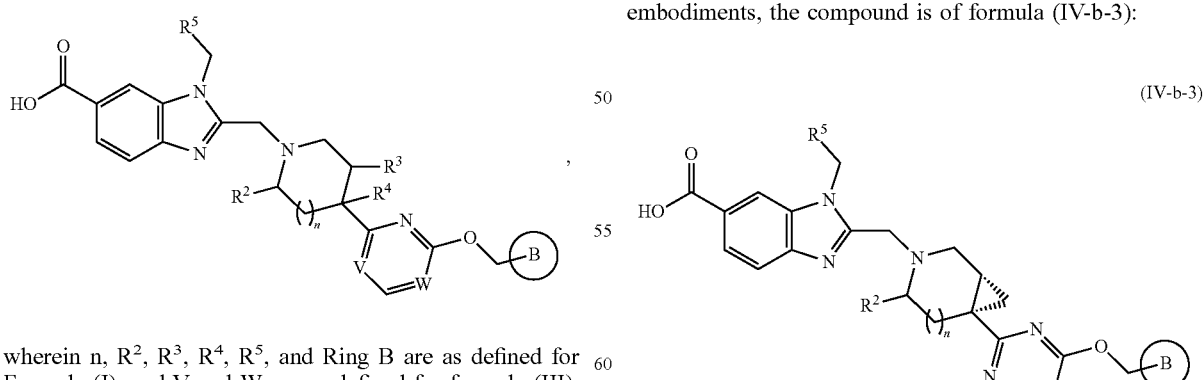

wherein n, $R^2$, $R^3$, $R^4$, $R^5$, and Ring B are as defined for Formula (I), and V and W are as defined for formula (III).

In some embodiments of Formula (IV), X is N, Y is $CR^4$, and $R^3$ and $R^4$ are taken together with the carbon atoms to which they are attached to form a cyclopropyl group optionally substituted by halo or $C_1$-$C_3$ alkyl. In some embodiments, the compound is of Formula (IV-b), (IV-b1), or (IV-b2):

wherein n, $R^2$, $R^5$, and Ring B are as defined for Formula (I), and V and W are as defined for formula (III). In some embodiments, the compound is of formula (IV-b-3):

wherein n, $R^2$, $R^5$, L, and Ring B are as defined for Formula (I).

In some embodiments of Formula (III), L is —O—. In some embodiments, the compound is of Formula (V):

(V)

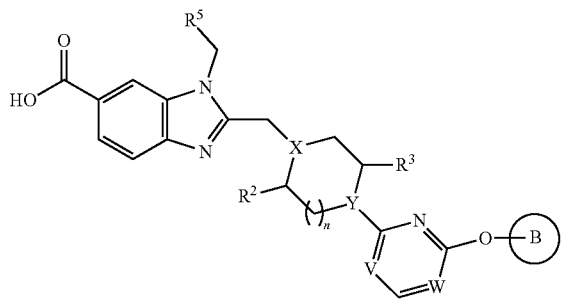

wherein n, $R^2$, $R^3$, $R^5$, and Ring B are as defined for Formula (I), and V and W are as defined for formula (III).

In some embodiments of Formula (V), X is N and Y is $CR^4$. In some embodiments, the compound is of formula (V-a):

(V-a)

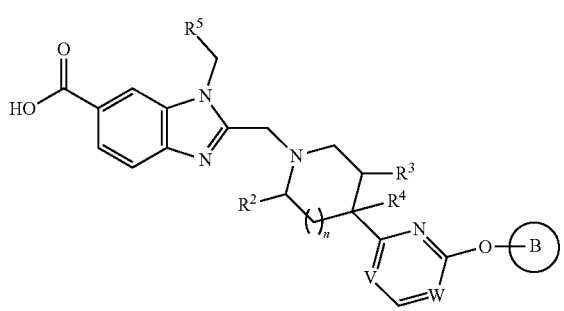

wherein n, $R^2$, $R^3$, $R^4$, $R^5$, and Ring B are as defined for Formula (I), and V and W are as defined for formula (III).

In some embodiments of Formula (I) or (V), X is N, Y is $CR^4$, and $R^3$ and $R^4$ are taken together with the carbon atoms to which they are attached to form a cyclopropyl group optionally substituted by halo or $C_1$-$C_3$ alkyl. In some embodiments, the compound is of Formula (V-b), (V-b1), or (V-b2):

(V-b)

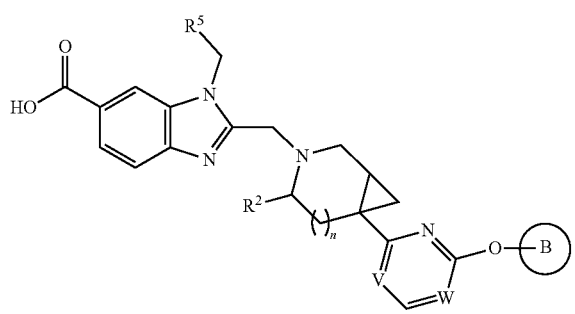

(V-b1)

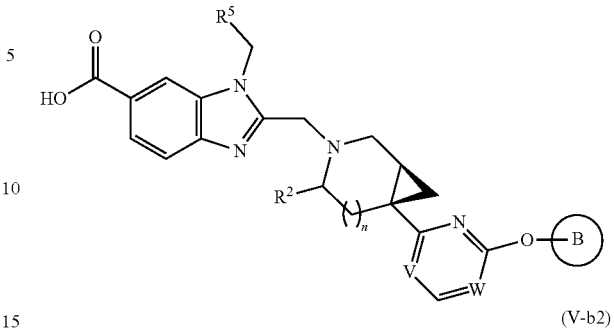

(V-b2)

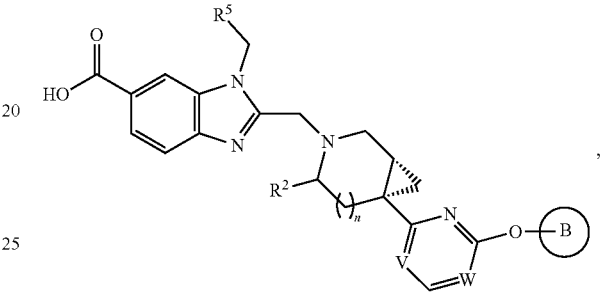

wherein n, $R^2$, $R^5$, and Ring B are as defined for Formula (I), and V and W are as defined for formula (III). In some embodiments, the compound is of formula (V-b3):

(V-b3)

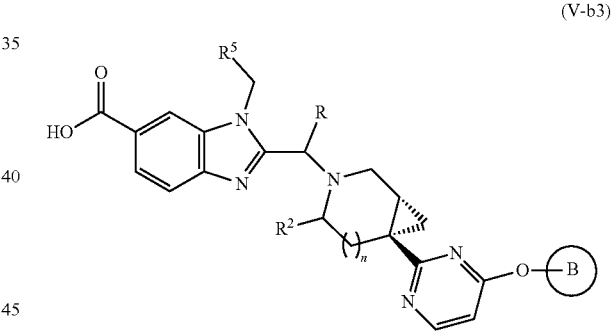

wherein n, $R^2$, $R^5$, L, and Ring B are as defined for Formula (I).

In some embodiments of Formula (I) (including compounds of Formulae (II)-(V), and subformulae thereof, if applicable), X is N, Y is $CR^4$; $R^3$ and $R^4$ are taken together with the carbon atoms to which they are attached to form a $C_3$-$C_6$ cycloalkyl; and n, $R^2$, Ring A, and Ring B are as detailed herein for Formula (I). In some embodiments of Formula (I) (including compounds of Formulae (II)-(V), and subformulae thereof, if applicable), Y is $CR^4$; $R^3$ and $R^4$ are taken together with the carbon atoms to which they are attached to form a $C_3$-$C_6$ cycloalkyl; Ring B is optionally substituted phenyl; and X, n, $R^2$, and Ring A are as detailed herein for Formula (I). In some embodiments of the foregoing, $R^3$ and $R^4$ are taken together with the carbon atoms to which they are attached to form a $C_3$ cycloalkyl. In some embodiments of the foregoing, X is N. In some embodiments of the foregoing, n is 1. In some embodiments of the foregoing, $R^2$ is H. In some embodiments of the foregoing, Ring A is pyridinyl. In some embodiments of the foregoing, X is N, n is 1, and $R^2$ is H.

In some embodiments of Formula (I) (including compounds of Formulae (II)-(V), and subformulae thereof, if applicable), X is N; Y is CR$^4$; R$^4$ is H; and n, R$^2$, R$^3$, Ring A, and Ring B are as detailed herein for Formula (I). In some embodiments of Formula (I) (including compounds of Formulae (II)-(V), and subformulae thereof, if applicable), X is N; Y is CR$^4$; R$^4$ is H; Ring B is C$_3$-C$_{10}$ cycloalkyl, 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl; and n, R$^2$, R$^3$, and Ring A are as detailed herein for Formula (I). In some embodiments of Formula (I) (including compounds of Formulae (II)-(V), and subformulae thereof, if applicable), X is N; Y is CR$^4$; R$^4$ is H; Ring B is 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl; and n, R$^2$, R$^3$, and Ring A are as detailed herein for Formula (I). In some embodiments of Formula (I) (including compounds of Formulae (II)-(V), and subformulae thereof, if applicable), X is N; Y is CR$^4$; R$^4$ is H; n is 1; R$^2$ and R$^3$ are each H; Ring A is pyridyl; Ring B is 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl.

In some embodiments of Formula (I) (including compounds of Formulae (II)-(V), and subformulae thereof, if applicable), X and Y are each N; Ring B is C$_3$-C$_{10}$ cycloalkyl, 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl; and n, R$^2$, R$^3$, and Ring A are as detailed herein for Formula (I). In some embodiments of Formula (I) (including compounds of Formulae (II)-(V), and subformulae thereof, if applicable), X and Y are each N; Ring B is C$_3$-C$_{10}$ cycloalkyl, 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl; n is 1; R$^2$ and R$^3$ are each H; and Ring A is as detailed herein for Formula (I). In some embodiments of Formula (I) (including compounds of Formulae (II)-(V), and subformulae thereof, if applicable), X and Y are each N; Ring B is 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl; n is 1; R$^2$ and R$^3$ are each H; and Ring A is as detailed herein for Formula (I). In some embodiments of Formula (I) (including compounds of Formulae (II)-(V), and subformulae thereof, if applicable), X and Y are each N; Ring B is C$_3$-C$_{10}$ cycloalkyl, 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl; n is 1; R$^2$ and R$^3$ are each H; and Ring A is pyrazolyl or pyridyl, each of which is optionally substituted by halo, CN, C$_3$-C$_6$ cycloalkyl, or C$_1$-C$_6$ alkyl optionally substituted by halo or OH.

In some embodiments of Formula (I) (including compounds of Formulae (II)-(V), and subformulae thereof, if applicable), X is N, Y is CH, n is 1, both R$^2$ and R$^3$ are hydrogen, and Ring A is

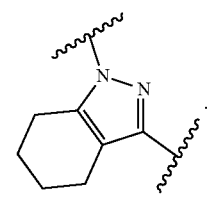 [SMILES: *c1nn(*)c2c1CCCC2]

In some embodiments of Formula (I) (including compounds of Formulae (II)-(V), and subformulae thereof, if applicable), X is N, Y is CH, n is 1, both R$^2$ and R$^3$ are hydrogen, Ring A is pyridinyl, and Ring B is 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —COCH$_3$, —CONH$_2$, —S(O)$_2$CH$_3$, and phenyl.

In some embodiments of a compound of Formula (I) (including compounds of Formulae (II)-(V), and subformulae thereof, if applicable), R$^1$ is —C$_1$-C$_3$ alkylene-R$^5$. In some embodiments, R$^1$ is —CH$_2$—R$^5$. In some embodiments of a compound of Formula (I) (including compounds of Formulae (II)-(V), and subformulae thereof, if applicable), R$^5$ is 5-membered heterocyclyl comprising 1, 2, or 3 heteroatoms independently selected from O, N, and S, wherein at least one heteroatom of R$^5$ is S, and wherein R$^5$ is optionally substituted by halo, —O—C$_{1-6}$ alkyl, C$_{1-6}$ alkyl, C$_{1-6}$ alkenyl, or C$_1$-C$_6$ haloalkyl. In some embodiments, R$^5$ is 5-membered heteroaryl comprising 1, 2, or 3 heteroatoms independently selected from O, N, and S, wherein at least one heteroatom of R$^5$ is S, and wherein R$^5$ is optionally substituted by by halo, —O—C$_{1-6}$ alkyl, C$_{1-6}$ alkyl, C$_{1-6}$ alkenyl, or C$_1$-C$_6$ haloalkyl. In some embodiments of a compound of Formula (I) (including compounds of Formulae (II)-(V), and subformulae thereof, if applicable), R$^5$ is 5-membered heterocyclyl or 5-membered heteroaryl, each of which comprises 1 or 2 heteroatoms independently selected from N and S, wherein at least one heteroatom of R$^5$ is S, and wherein R$^5$ is optionally substituted by halo, —O—C$_{1-6}$ alkyl, C$_{1-6}$ alkyl, C$_{1-6}$ alkenyl, or C$_1$-C$_6$ haloalkyl. In some embodiments of a compound of Formula (I) (including compounds of Formulae (II)-(V), and subformulae thereof, if applicable), R$^5$ is 5-membered heterocyclyl or 5-membered heteroaryl, each of which comprises 1 or 2 heteroatoms selected from N or S, wherein one heteroatom of R$^5$ is S, and wherein R$^5$ is optionally substituted by halo, —O—C$_{1-6}$ alkyl, C$_{1-6}$ alkyl, C$_{1-6}$ alkenyl, or C$_1$-C$_6$ haloalkyl. In some embodiments, R$^5$ is thiazolyl, isothiazolyl, or thiophenyl, each of which is optionally substituted by halo, —O—C$_{1-6}$ alkyl, C$_{1-6}$ alkyl, C$_{1-6}$ alkenyl, or C$_1$-C$_6$ haloalkyl. In some embodiments, R$^5$ is

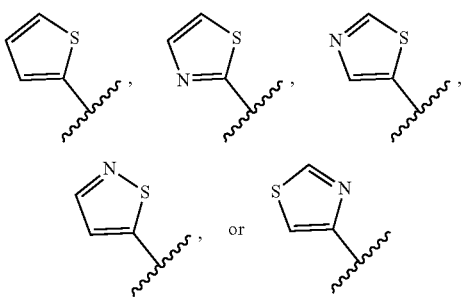

each of which is optionally substituted by halo, —O—$C_{1-6}$ alkyl, $C_{1-6}$ alkyl, $C_{1-6}$ alkenyl, or $C_1$-$C_6$ haloalkyl. In some embodiments, $R^5$ is

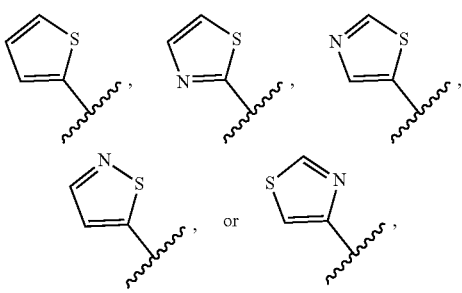

each of which is optionally substituted by halo, —O—$C_{1-3}$ alkyl, $C_{1-3}$ alkyl, $C_{2-6}$ alkenyl, or $C_1$-$C_3$ haloalkyl. In some embodiments, $R^5$ is

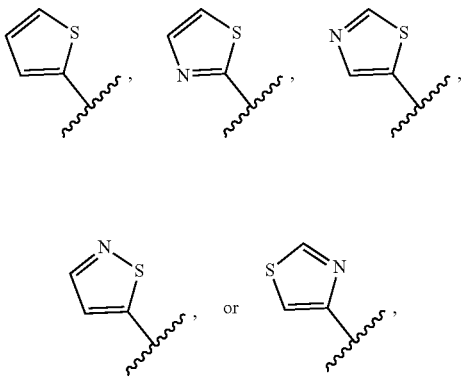

each of which is optionally substituted by bromo, —O—$CH_3$, methyl, ethyl, or vinyl. In some embodiments, $R^5$ is

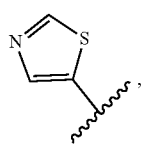

optionally substituted by halo, —O—$C_{1-3}$ alkyl, $C_{1-3}$ alkyl, $C_{2-6}$ alkenyl, or $C_1$-$C_3$ haloalkyl. In some embodiments, $R^5$ is unsubstituted

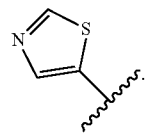

In some embodiments, $R^5$ is thiazole optionally substituted by methyl, bromo, vinyl, ethyl, methoxy, chloro, or fluoro. In some embodiments, $R^5$ is

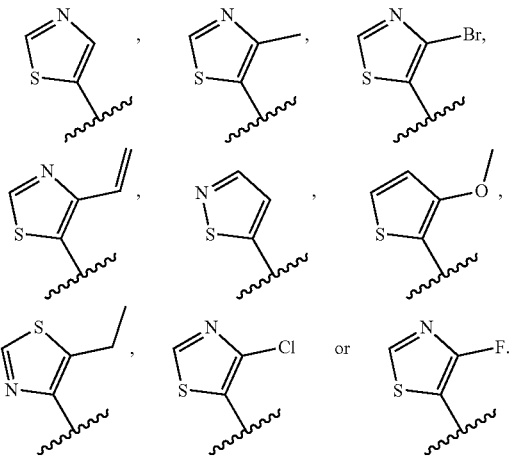

In some embodiments of a compound of Formula (I) (including compounds of Formulae (II)-(V), and subformulae thereof, if applicable), X is N. In other embodiments, X is CH.

In some embodiments of a compound of Formula (I) (including compounds of Formulae (II)-(V), and subformulae thereof, if applicable), n is 0. In other embodiments, n is 1.

In some embodiments of a compound of Formula (I) (including compounds of Formulae (II)-(V), and subformulae thereof, if applicable), Y is N. In other embodiments, Y is $CR^4$, wherein $R^4$ is hydrogen, OH or $C_1$-$C_6$ alkyl. In other embodiments, Y is $CR^4$, and $R^3$ and $R^4$ are optionally taken together with the carbon atoms to which they are attached to form $C_3$-$C_6$ cycloalkyl optionally substituted by halo or $C_1$-$C_3$ alkyl. For example, the $C_3$-$C_6$ cycloalkyl can be cyclopropyl optionally substituted by halo, such as fluoro, or $C_1$-$C_3$ alkyl, such as methyl.

In some embodiments of a compound of Formula (I) (including compounds of Formulae (II)-(V), and subformulae thereof, if applicable), $R^2$ and $R^3$ are independently hydrogen, oxo, or $C_1$-$C_6$ alkyl. In some embodiments, $R^2$ and $R^3$ are hydrogen. In some embodiments, $R^2$ and $R^3$ are oxo. In some embodiments, $R^2$ and $R^3$ are methyl.

In some embodiments of a compound of Formula (I) Formula (I) (including compounds of Formulae (II)-(V), and subformulae thereof, if applicable), the moiety

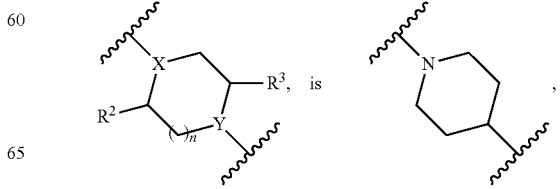

-continued

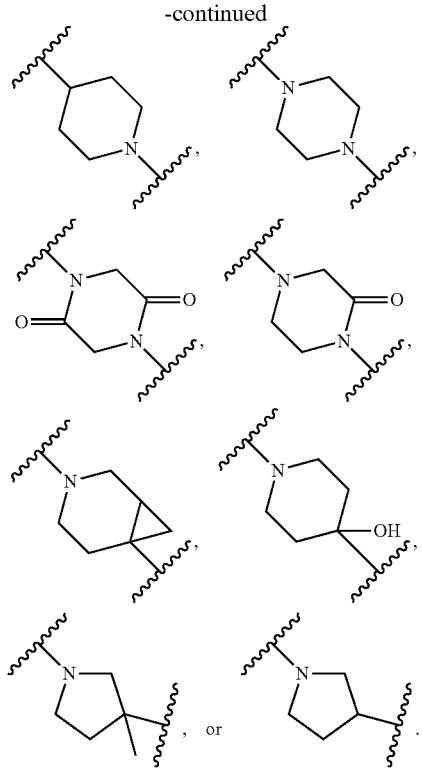

In some embodiments of a compound of Formula (I) (including compounds of Formulae (II)-(V), and subformulae thereof, if applicable), the moiety

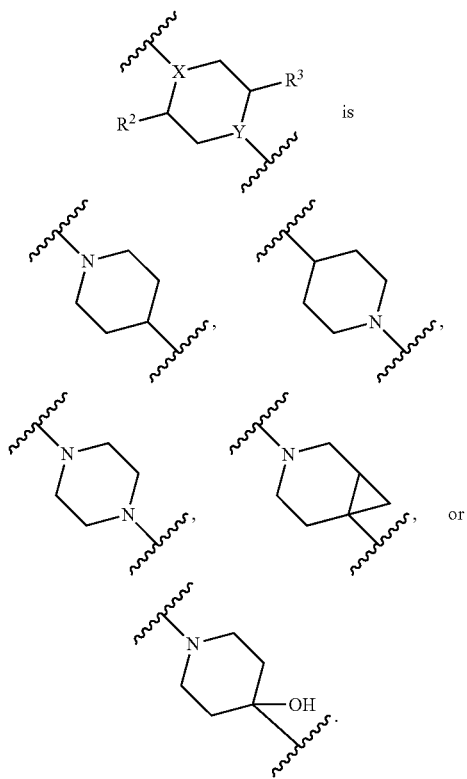

In some embodiments of a compound of Formula (I) (including compounds of Formulae (II)-(V), and subformulae thereof, if applicable), Ring A is 5- to 12-membered heterocyclyl, which is optionally substituted by halo, CN, $C_3$-$C_6$ cycloalkyl, or $C_1$-$C_6$ alkyl optionally substituted by halo or OH. In some embodiments, Ring A is

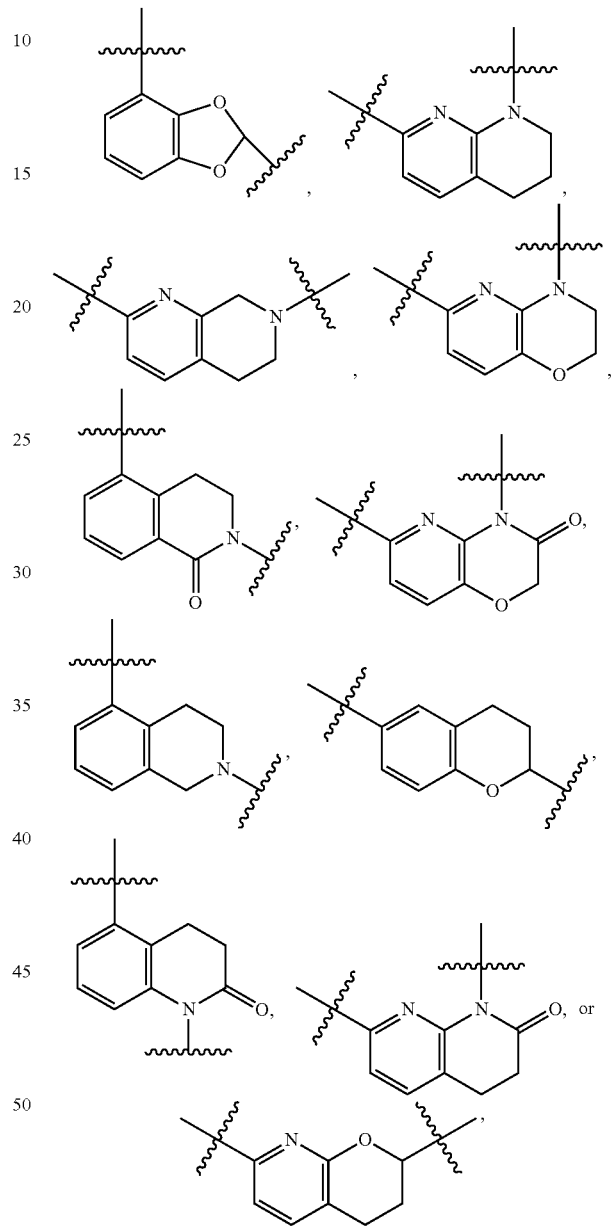

each of which is optionally substituted by halo, CN, $C_3$-$C_6$ cycloalkyl, or $C_1$-$C_6$ alkyl optionally substituted by halo or OH. In some embodiments, Ring A is 5- to 12-membered heteroaryl, which is optionally substituted by halo, CN, $C_3$-$C_6$ cycloalkyl, or $C_1$-$C_6$ alkyl optionally substituted by halo or OH. Exemplary Ring A include, but are not limited to,

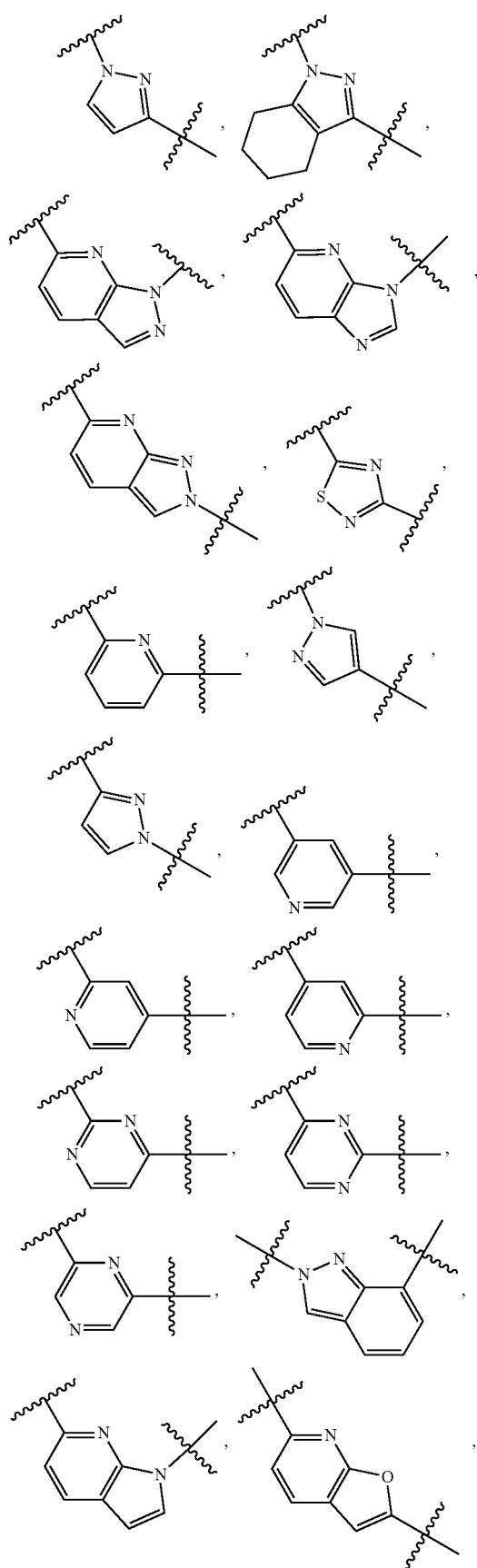

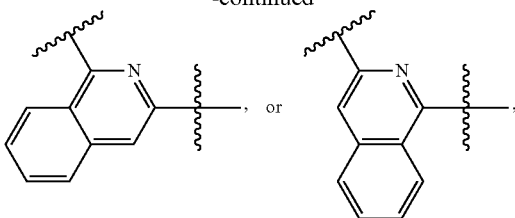

, or , each of which is independently optionally substituted by halo, CN, $C_3$-$C_6$ cycloalkyl, or $C_1$-$C_6$ alkyl optionally substituted by halo or OH. In some embodiments, Ring A is

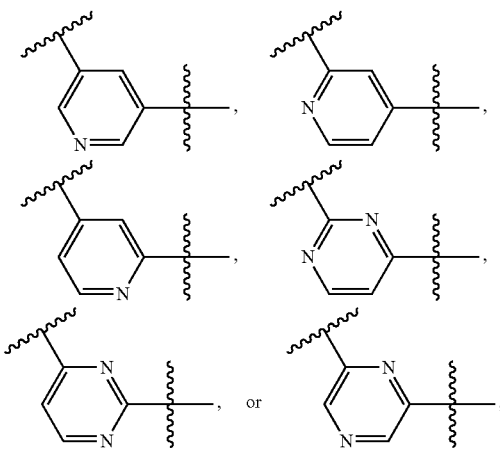

each of which is independently optionally substituted by halo, CN, $C_3$-$C_6$ cycloalkyl, or $C_1$-$C_6$ alkyl optionally substituted by halo or OH. In some embodiments, Ring A is benzodioxolyl, pyridyl, pyrimidinyl, or pyrazinyl. In some embodiments, Ring A is

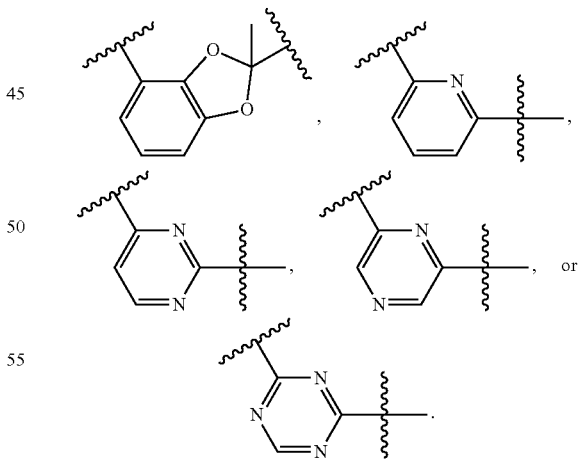

In some embodiments of a compound of Formula (I) (including compounds of Formulae (II)-(V), and subformulae thereof, if applicable), L is a bond. In some embodiments, L is —O—. In some embodiments, L is $C_1$-$C_6$ alkylene. In some embodiments, L is unsubstituted $C_1$-$C_6$ alkylene. In some embodiments, L is $C_1$-$C_6$ alkylene optionally substituted by $R^L$, wherein each $R^{L1}$ is independently halo, OH, oxo, or $C_1$-$C_6$ alkyl, or two $R^{L1}$ are taken together with the carbon atom or atoms to which they are attached to form $C_3$-$C_6$ cycloalkyl or 3- to 6-membered heterocyclyl. In some embodiments, L is unsubstituted $C_1$-$C_2$ alkylene. In some embodiments, L is $C_1$-$C_2$ alkylene optionally substituted by $R^{L1}$, wherein each $R^{L1}$ is independently halo, OH, oxo, or $C_1$-$C_6$ alkyl. In some embodiments, L is unsubstituted $C_2$ alkylene. In some embodiments, L is $C_2$ alkylene optionally substituted by $R^{L1}$, wherein each $R^{L1}$ is independently halo, OH, oxo, or $C_1$-$C_6$ alkyl. In some such embodiments, L is

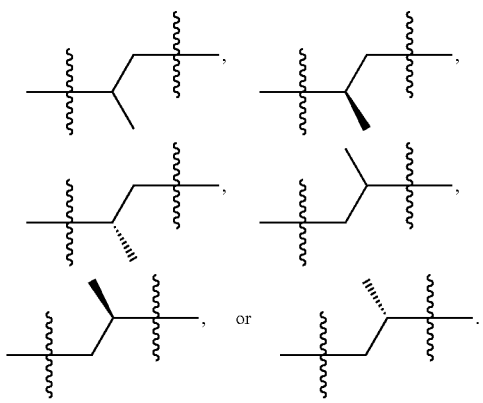

In some embodiments, L is *—O—$C_1$-$C_6$ alkylene-**, wherein * represents the point of attachment to ring A and ** represents the point of attachment to ring B. For example, L can be *—OCH$_2$—**. In some embodiments, when L is *—O—$C_1$-$C_6$ alkylene-**, the $C_1$-$C_6$ alkylene of L is substituted by $R^L$, wherein each $R^L$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl. In some embodiments, when L is *—O—$C_1$-$C_6$ alkylene-**, the $C_1$-$C_6$ alkylene is substituted by $R^L$, wherein each $R^L$ is independently $C_1$-$C_6$ alkyl or two $R^L$ are taken together with the carbon atom or atoms to which they are attached to form $C_3$-$C_6$ cycloalkyl or 3- to 6-membered heterocyclyl. To give a specific example, when L is *—OC($R^L$)$_2$—**, two $R^L$ can be taken together with the carbon atom or atoms to which they are attached to form $C_3$-$C_6$ cycloalkyl or 3- to 6-membered heterocyclyl. In some embodiments, L is *—$C_1$-$C_6$ alkylene-O—**. In some embodiments, L is *—$NR^6$—$C_1$-$C_6$ alkylene-**, wherein $R^6$ is hydrogen or $C_1$-$C_6$ alkyl. In some embodiments, L comprises an isotope of hydrogen, e.g., deuterium. In some embodiments, L is *—O—CH$_2$—** or *—O—CD$_2$—**. In some embodiments, L is *—O—CD$_2$—**. In some embodiments, L comprises an oxo group. In some embodiments, L is *—C(O)—CH$_2$—**.

In some embodiments of a compound of Formula (I) (including compounds of Formulae (II)-(V), and subformulae thereof, if applicable), Ring B is $C_3$-$C_{10}$ cycloalkyl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl. Exemplary $C_3$-$C_{10}$ cycloalkyl include, but are not limited to,

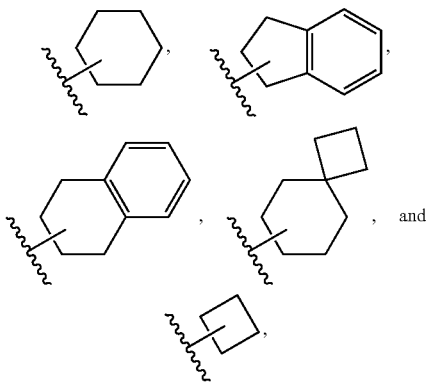

each of which is independently optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl. In some embodiments, Ring B is $C_6$-$C_{14}$ aryl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl. For example, the $C_6$-$C_{14}$ aryl can be

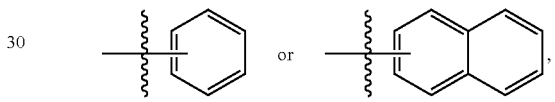

each of which is independently optionally substituted by one to three substituents each independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl. In some embodiments, Ring B is 4- to 12-membered heterocyclyl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl. Exemplary 4- to 12-membered heterocyclyl include, but are not limited to,

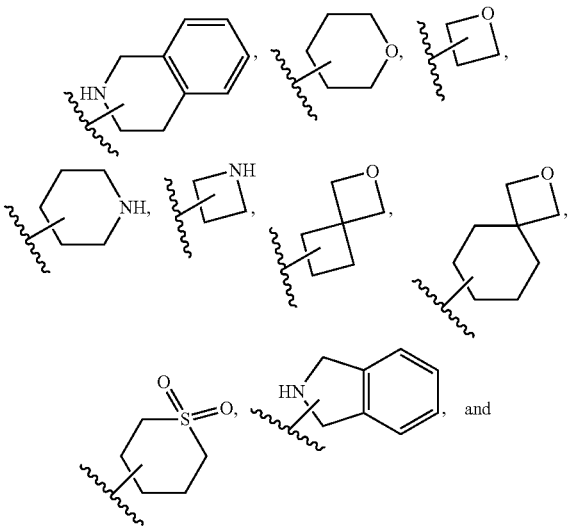

33

-continued

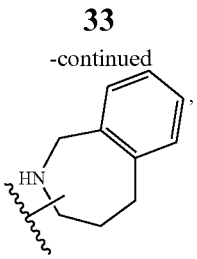

each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some embodiments, Ring B is 5- to 12-membered heteroaryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. Exemplary 5- to 12-membered heteroaryl include, but are not limited to,

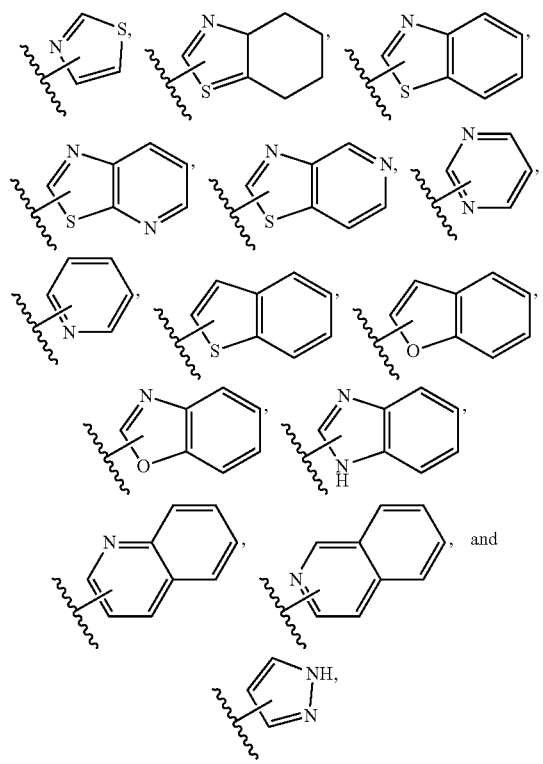

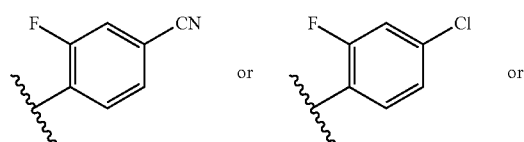

each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some embodiments, Ring B is phenyl optionally substituted by one to three substituents each independently selected from the group consisting of halo, CN, and —$CONH_2$. In some embodiments, Ring B is

34

-continued

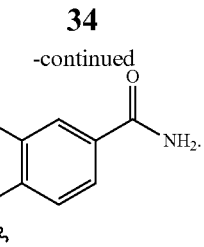

In some embodiments, Ring B is

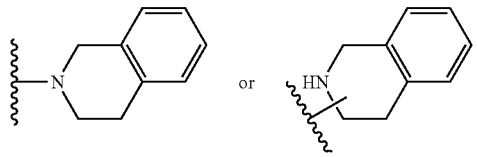

or optionally substituted by one to three substituents independently selected from the group consisting of halo, and CN. In some embodiments, Ring B is

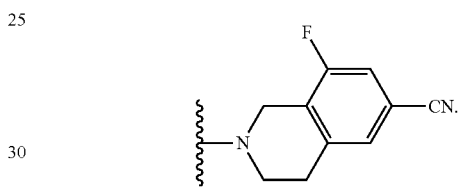

In some embodiments, Ring B is a 9-membered heteroaryl, which is optionally substituted by one to two substituents independently selected from the group consisting of halo and CN. In some embodiments, Ring B is

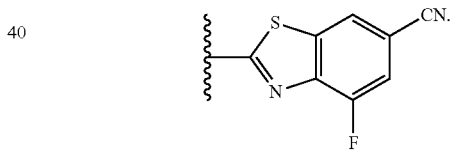

In some embodiments of Formula (I) (including compounds of Formulae (II)-(V), and subformulae thereof, if applicable), X, n, R, $R^1$, $R^2$, Ring A, and L are as described for Formula (I), and Ring B is $C_3$-$C_{10}$ cycloalkyl optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

In some embodiments of Formula (I) (including compounds of Formulae (II)-(V), and subformulae thereof, if applicable), X, n, R, $R^1$, $R^2$, Ring A, and L are as described for Formula (I), and Ring B is $C_6$-$C_{14}$ aryl optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

In some embodiments of Formula (I) (including compounds of Formulae (II)-(V), and subformulae thereof, if applicable), X, n, R, $R^1$, $R^2$, Ring A, and L are as described for Formula (I), and Ring B is $C_6$ aryl optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

In some embodiments of Formula (I) (including compounds of Formulae (II)-(V), and subformulae thereof, if applicable), X, n, R, $R^1$, $R^2$, Ring A, and L are as described for Formula (I), L is *—$OCH_2$—**, and Ring B is $C_6$ aryl optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

In some embodiments of Formula (I) (including compounds of Formulae (II)-(V), and subformulae thereof, if applicable), X, n, R, $R^1$, $R^2$, Ring A, and L are as described for Formula (I), and Ring B is 4- to 12-membered heterocyclyl optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

In some embodiments of Formula (I) (including compounds of Formulae (II)-(V), and subformulae thereof, if applicable), X, n, R, $R^1$, $R^2$, Ring A, and L are as described for Formula (I), and Ring B is 5- to 12-membered heteroaryl optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

In some embodiments of Formula (I) (including compounds of Formulae (II)-(V), and subformulae thereof, if applicable), X is N, n is 1, Ring A is 9- to 10-membered heterocyclyl, which is optionally substituted by halo, CN, $C_3$-$C_6$ cycloalkyl, or $C_1$-$C_6$ alkyl optionally substituted by halo or OH; and R, $R^1$, $R^2$, L, and Ring B is as described for Formula (I).

In some embodiments Formula (I) (including compounds of Formulae (II)-(V), and subformulae thereof, if applicable), X is N, n is 1, Ring A is 5- to 12-membered heteroaryl, which is optionally substituted by halo, CN, $C_3$-$C_6$ cycloalkyl, or $C_1$-$C_6$ alkyl optionally substituted by halo or OH; and R, $R^2$, L, and Ring B are as described for Formula (I). In some such embodiments, Ring A is 5- to 6-membered heteroaryl. In some such embodiments, Ring A is 6-membered heteroaryl, which is optionally substituted by halo, CN, $C_3$-$C_6$ cycloalkyl, or $C_1$-$C_6$ alkyl optionally substituted by halo or OH. In some such embodiments, Ring A is

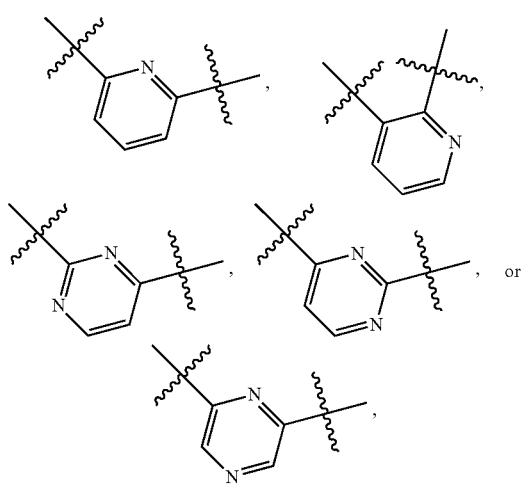

each of which is optionally substituted by halo, CN, $C_3$-$C_6$ cycloalkyl, or $C_1$-$C_6$ alkyl optionally substituted by halo or OH. In some such embodiments, Ring A is

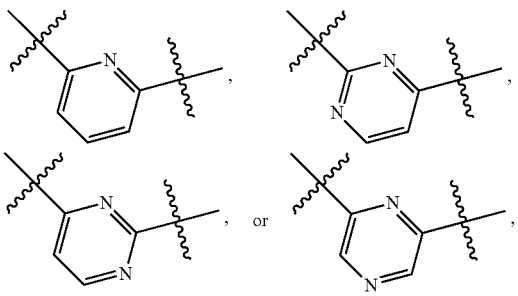

each of which is optionally substituted by halo, CN, $C_3$-$C_6$ cycloalkyl, or $C_1$-$C_6$ alkyl optionally substituted by halo or OH.

In some embodiments of Formula (I) (including compounds of Formulae (II)-(V), and subformulae thereof, if applicable), X is N, n is 1, Ring B is $C_3$-$C_{10}$ cycloalkyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R, $R^1$, $R^2$, Ring A, and L are as described for Formula (I).

In some embodiments of Formula (I), (V), (Va), or (Vb), Ring A is 5- to 6-membered heteroaryl, which is optionally substituted by halo, CN, $C_3$-$C_6$ cycloalkyl, or $C_1$-$C_6$ alkyl optionally substituted by halo or OH; Ring B is $C_3$-$C_{10}$ cycloalkyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R, $R^1$, $R^2$, and L are as described for Formula (I). In some such embodiments, Ring A is

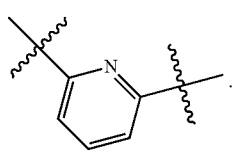 [SMILES: *c1cccc(*)n1]

In other such embodiments, Ring A is

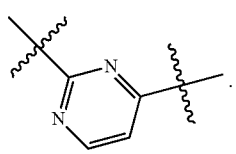

In still other such embodiments, Ring A is

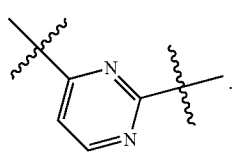

In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is *—O—$C_1$-$C_6$ alkylene-** optionally substituted by $R^L$ as described for Formula (I); Ring B is $C_3$-$C_{10}$ cycloalkyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R and $R^2$ are as described for Formula (I). In some such embodiments, L is *—O—$CH_2$—**. For example, in some embodiments

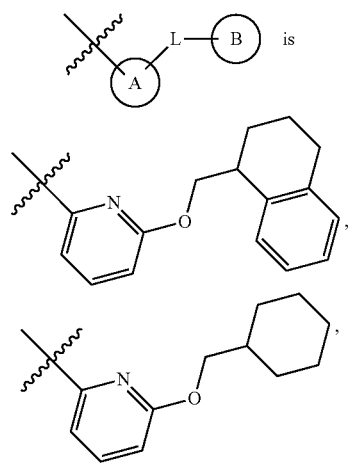

or the like, optionally substituted as described for Ring A, L, and Ring B herein. In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is a bond; Ring B is $C_3$-$C_{10}$ cycloalkyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R and $R^2$ are as described for Formula (I). For example, in some embodiments,

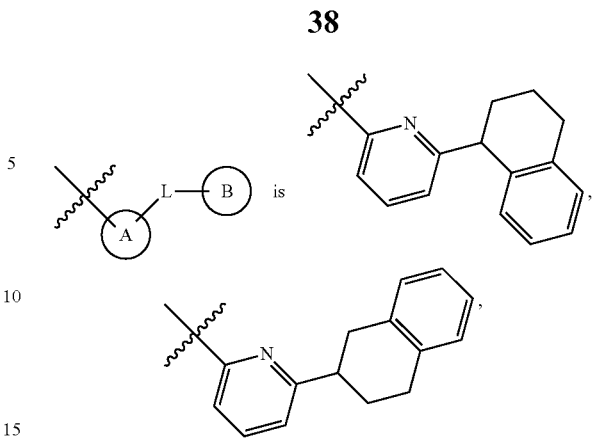

or the like, optionally substituted as described for Ring A and Ring B herein.

In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is —O—; Ring B is $C_3$-$C_{10}$ cycloalkyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R and $R^2$ are as described for Formula (I). For example, in some embodiments,

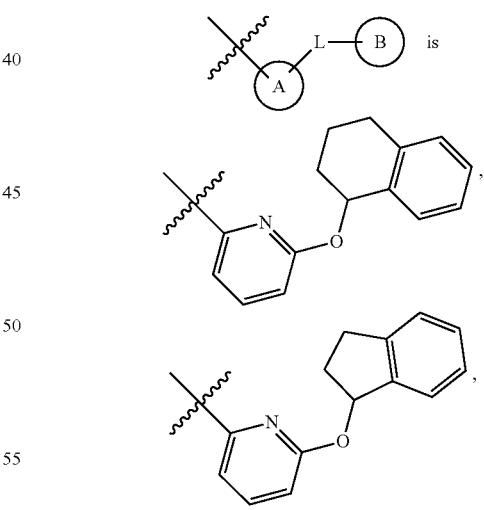

or the like, optionally substituted as described for Ring A and Ring B herein. In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring B is $C_6$-$C_{14}$ aryl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R, R$^2$, Ring A, and L are as described for Formula (I). In some embodiments of Formula (I) (including compounds of Formulae (II)-(V), and subformulae thereof, if applicable), X is N, n is 1, Ring B is $C_6$-$C_{14}$ aryl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R, R$^2$, Ring A, and L are as described for Formula (I). In some embodiments of Formula (I) (including compounds of Formulae (II)-(V), and subformulae thereof, if applicable), X is N, n is 1, Ring B is $C_6$ aryl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R, R$^2$, Ring A, and L are as described for Formula (I). In some embodiments of any of the foregoing, X is N, n is 1, R$^1$ is —CH$_2$—R$^5$, and R$^5$ is as described for Formula (I). In some embodiments of any of the foregoing, X is N, n is 1, R$^1$ is —CH$_2$—R$^5$, and R$^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; Ring B is $C_6$ aryl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R, R$^1$, R$^2$, and L are as described for Formula (I). In some such embodiments, Ring A is

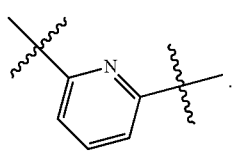 [SMILES: *c1ccnc(*)n1]

In other such embodiments, Ring A is

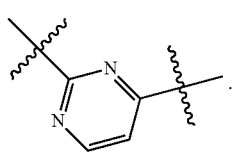

In still other such embodiments, Ring A is

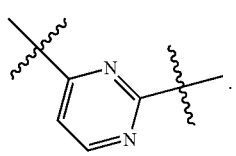

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is *—O—$C_1$-$C_6$ alkylene-** optionally substituted by R$^L$ as described for Formula (I); Ring B is $C_6$ aryl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R and R$^2$ are as described for Formula (I). In some such embodiments, L is *—O—CH$_2$—**. For example, in some embodiments,

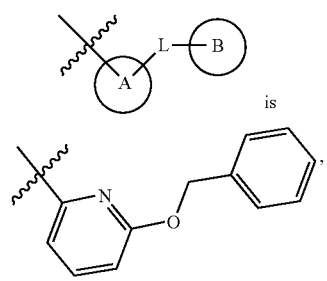

is

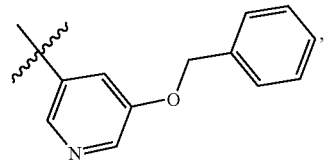

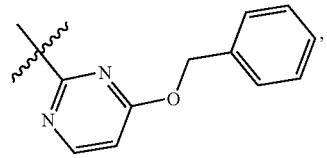

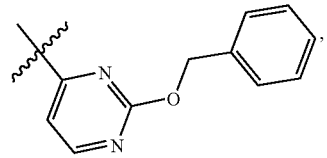

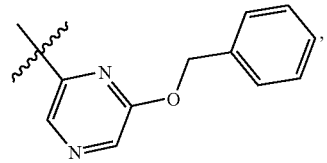

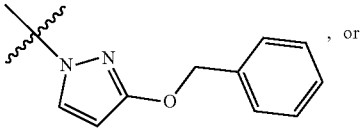

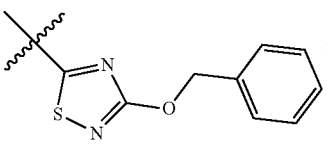

or N or the like, optionally substituted as described for Ring A, L and Ring B herein. For example, in some embodiments,

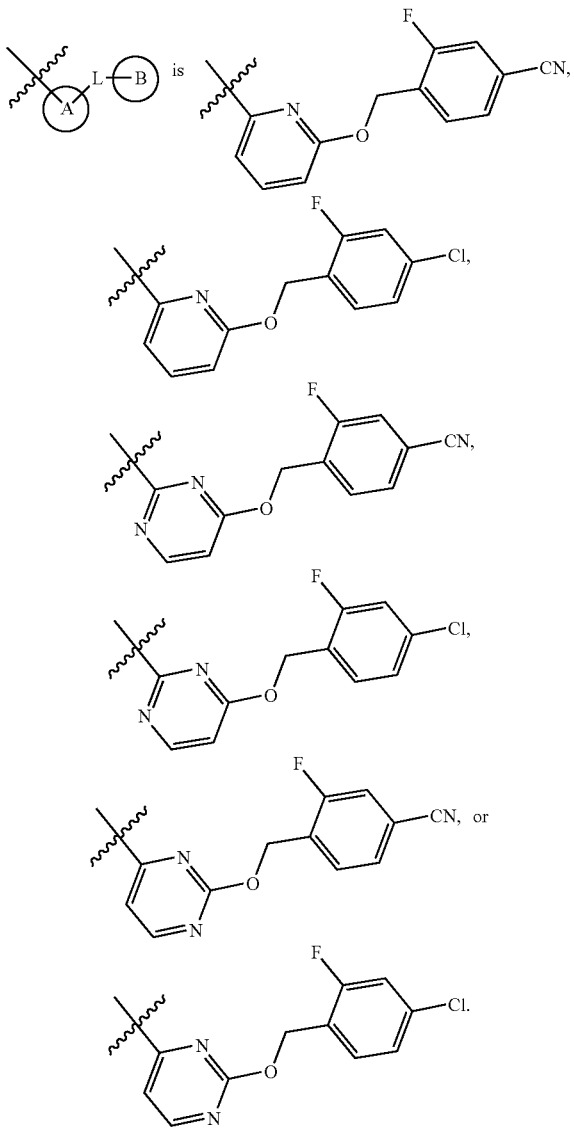

In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is a bond; Ring B is $C_6$ aryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R and $R^2$ are as described for Formula (I). In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is —O—; Ring B is $C_6$ aryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R and $R^2$ are as described for Formula (I). In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring B is 4- to 12-membered heterocyclyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R, $R^2$, Ring A, and L are as described for Formula (I). In some such embodiments, Ring A is

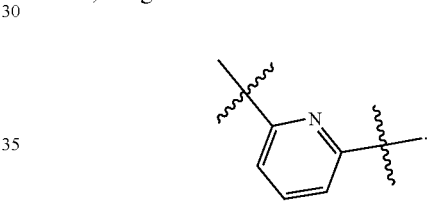

In other such embodiments, Ring A is

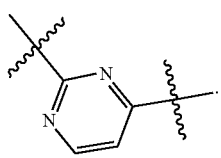

In still other such embodiments, Ring A is

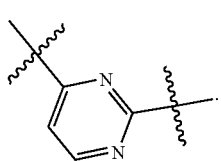

In some embodiments of any of the foregoing, X is N, n is 1, $R^1$ is —$CH_2$—$R^5$, $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_1$. 6 alkenyl, or $C_1$-$C_6$ haloalkyl.

In some embodiments of Formula (I) (including compounds of Formulae (II)-(V), and subformulae thereof, if applicable), Ring B is 4- to 12-membered heterocyclyl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R, R$^2$, Ring A, and L are as described for Formula (I). In some embodiments of Formula (I), (V), (Va), or (Vb), Ring B is 9- to 12-membered heterocyclyl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R, R$^2$, Ring A, and L are as described for Formula (I). In some embodiments of any of the foregoing, X is N, n is 1, R$^1$ is —CH$_2$—R$^5$, and R$^5$ is as described for Formula (I). In some embodiments of any of the foregoing, X is N, n is 1, R$^1$ is —CH$_2$—R$^5$, and R$^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; Ring B is 4- to 12-membered heterocyclyl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R, R$^2$, and L are as described for Formula (I). In some such embodiments, Ring A is

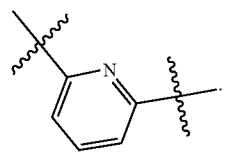

In other such embodiments, Ring A is

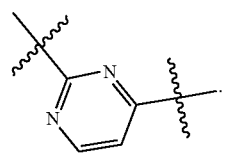

In still other such embodiments, Ring A is

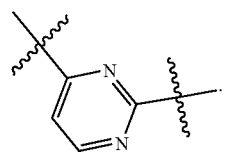

In some embodiments of any of the foregoing, X is N, n is 1, R$^1$ is —CH$_2$—R$^5$, and R$^5$ is as described for Formula (I). In some embodiments of any of the foregoing, X is N, n is 1, R$^1$ is —CH$_2$—R$^5$, and R$^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is *—O—$C_1$-$C_6$ alkylene-** optionally substituted by R$^L$ as described for Formula (I); Ring B is 4- to 12-membered heterocyclyl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R and R$^2$ are as described for Formula (I). In some such embodiments, L is *—O—CH$_2$—**. For example, in some embodiments of Formula (I), (V), (Va), or (Vb),

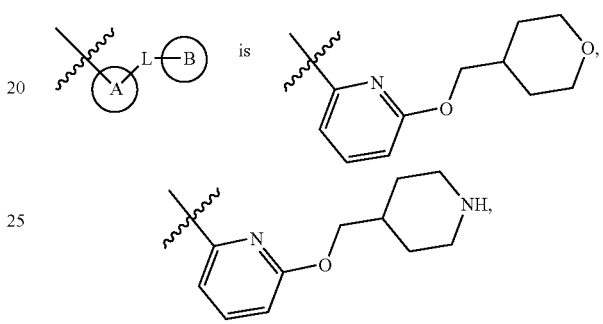

or the like, optionally substituted as described for Ring A and Ring B herein. In some embodiments of any of the foregoing, X is N, n is 1, R$^1$ is —CH$_2$—R$^5$, and R$^5$ is as described for Formula (I). In some embodiments of any of the foregoing, X is N, n is 1, R$^1$ is —CH$_2$—R$^5$, and R$^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is a bond; Ring B is 9- to 12-membered heterocyclyl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl; and R and R$^2$ are as described for Formula (I). For example, in some embodiments,

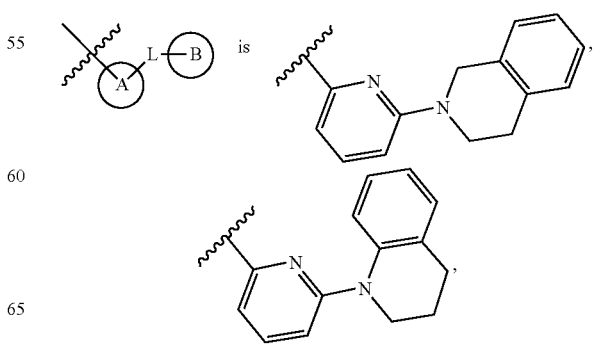

-continued

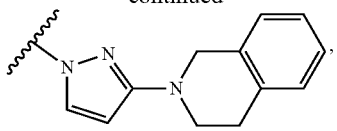

or the like, optionally substituted as described for Ring A and Ring B herein. In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is —O—; Ring B is 9- to 12-membered heterocyclyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R and $R^2$ are as described for Formula (I). In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring B is 5- to 12-membered heteroaryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R, $R^2$, Ring A, and L are as described for Formula (I). In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; Ring B is 5- to 12-membered heteroaryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R, $R^2$, and L are as described for Formula (I). In some such embodiments, Ring A is

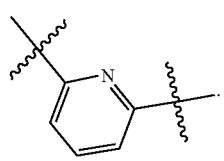

In other such embodiments, Ring A is

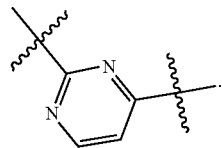

In still other such embodiments, Ring A is

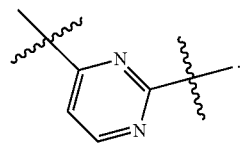 [SMILES: *c1ccnc(*)n1]

In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is *—O—$C_1$-$C_6$ alkylene-** optionally substituted by $R^L$ as described for Formula (I); Ring B is 5- to 12-membered heteroaryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and R and $R^2$ are as described for Formula (I). In some such embodiments, L is *—O—$CH_2$—**. For example, in some embodiments of Formula (I), (V), (Va), or (Vb),

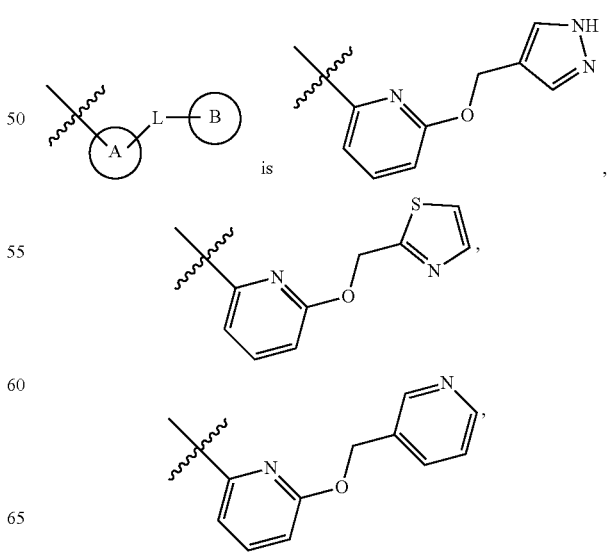

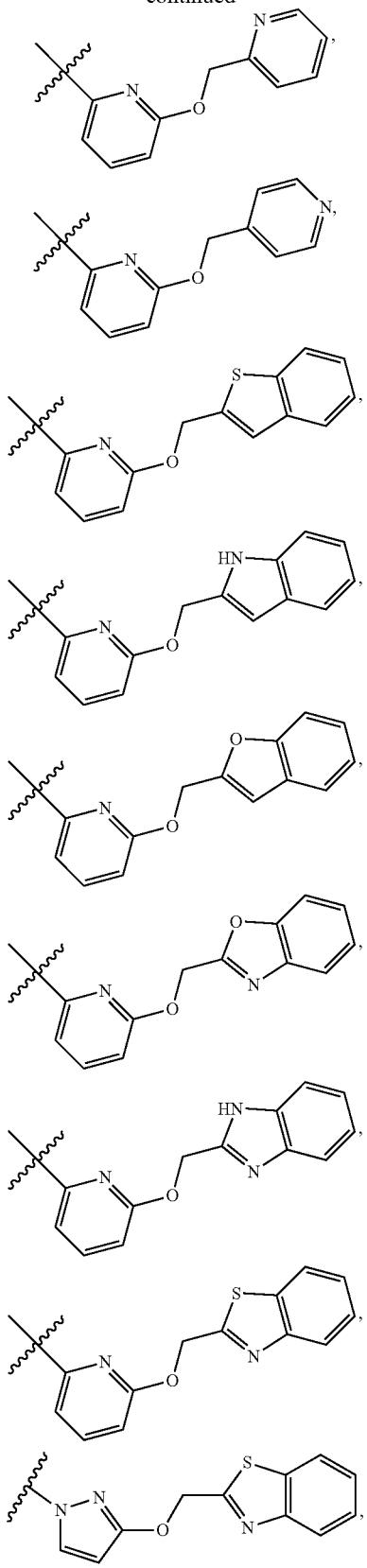

or the like, optionally substituted as described for Ring A, L, and Ring B herein. In some embodiments of any of the foregoing, X is N, n is 1, R¹ is —CH₂—R⁵, and R⁵ is as described for Formula (I). In some embodiments of any of the foregoing, X is N, n is 1, R¹ is —CH₂—R⁵, and R⁵ is 5-membered heteroaryl comprising one S heteroatom and one N heteroatom, optionally substituted by halo, —O—$C_{1-6}$ alkyl, $C_{1-6}$ alkyl, $C_1$. 6 alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is a bond; Ring B is 5- to 12-membered heteroaryl, which is optionally substituted by one to three substituents independently selected from the group consisting of halo, CN, oxo, $C_1$-$C_6$ alkyl, $C_1$-$C_6$ haloalkyl, —COCH₃, —CONH₂, —S(O)₂CH₃ and phenyl; and R and R² are as described for Formula (I). In some embodiments of any of the foregoing, X is N, n is 1, R¹ is —CH₂—R⁵, and R⁵ is as described for Formula (I). In some embodiments of any of the foregoing, X is N, n is 1, R¹ is —CH₂—R⁵, and R⁵ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I) (including compounds of Formulae (II)-(V), and subformulae thereof, if applicable), Ring A is 5- to 6-membered heteroaryl, which is optionally substituted by halo, CN, $C_3$-$C_6$ cycloalkyl, or $C_1$-$C_6$ alkyl optionally substituted by halo or OH; L is —O—; Ring B is 5- to 12-membered heteroaryl, which is optionally substituted by one to three substituents independently selected from the group consisting of halo, CN, oxo, $C_1$-$C_6$ alkyl, $C_1$-$C_6$ haloalkyl, —COCH₃, —CONH₂, —S(O)₂CH₃ and phenyl; and R and R² are as described for Formula (I). In some embodiments of any of the foregoing, X is N, n is 1, R¹ is —CH₂—R⁵, and R⁵ is as described for Formula (I). In some embodiments of any of the foregoing, X is N, n is 1, R¹ is —CH₂—R⁵, and R⁵ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I), Ring B is a fused bicyclic ring system comprising fused rings Ring C and Ring D. In some embodiments of Formula (I), provided is a compound of Formula (VI), (VI)

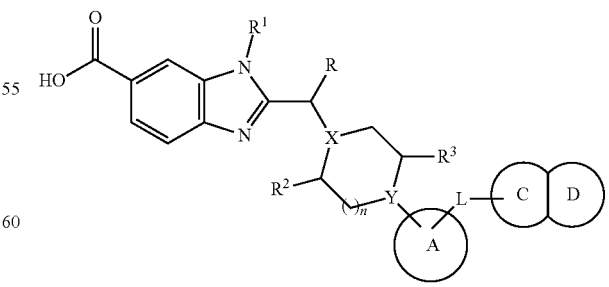

or a pharmaceutically acceptable salt thereof, wherein X, Y, n, R, R¹, R², R³, Ring A, and L are as described for Formula (I);

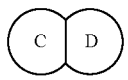

is a fused bicyclic ring system comprising fused rings Ring C and Ring D, wherein Ring C is $C_5$-$C_6$ cycloalkyl, 5- to 7-membered heterocyclyl, or 5- to 6-membered heteroaryl; and Ring D is $C_6$ cycloalkyl, $C_6$ aryl or 6-membered heteroaryl;

wherein Ring C and Ring D are optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

In some embodiments of Formula (VI), Ring D is $C_6$ aryl, and Ring C is $C_5$-$C_6$ cycloalkyl, 5- to 7-membered heterocyclyl, or 5- to 6-membered heteroaryl, wherein Ring C and Ring D are optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl. In some embodiments of any of the foregoing, Ring A is 5- to 6-membered heteroaryl, which is optionally substituted by halo, CN, $C_3$-$C_6$ cycloalkyl, or $C_1$-$C_6$ alkyl optionally substituted by halo or OH.

In some embodiments of Formula (VI), Ring D is $C_6$ aryl, and Ring C is $C_5$-$C_6$ cycloalkyl. In some such embodiments, Ring C and Ring D form

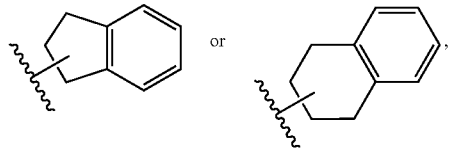

optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl. In some embodiments of any of the foregoing, X is N, n is 1, $R^1$ is —$CH_2$—$R^5$, and $R^5$ is 5- to 6-membered heteroaryl optionally substituted by $C_1$-$C_6$ alkyl. In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (VI), Ring D is $C_6$ aryl and Ring C is 5- to 7-membered heterocyclyl. In some such embodiments, Ring C and Ring D form

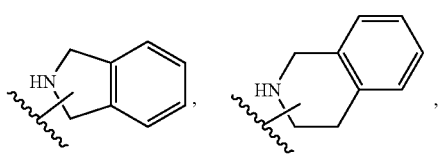

optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl. In some embodiments of any of the foregoing, X is N, n is 1, $R^1$ is —$CH_2$—$R^5$, and $R^5$ is 5- to 6-membered heteroaryl optionally substituted by $C_1$-$C_6$ alkyl. In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (VI), Ring D is $C_6$ aryl and Ring C is 5- to 6-membered heteroaryl. In some such embodiments, Ring C and Ring D form

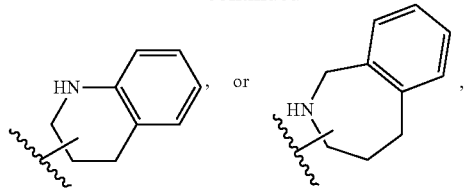

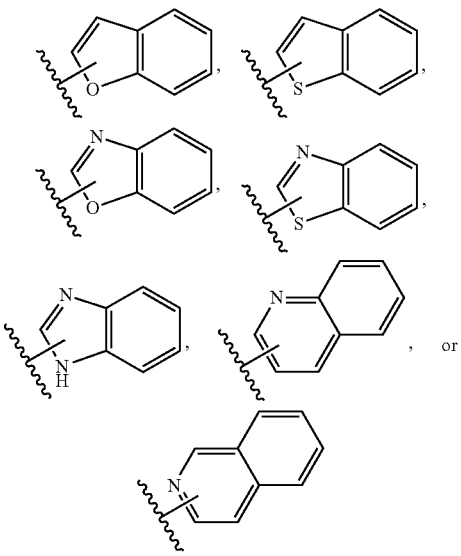

optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl. In some embodiments of any of the foregoing, X is N, n is 1, $R^1$ is —$CH_2$—$R^5$, and $R^5$ is 5- to 6-membered heteroaryl optionally substituted by $C_1$-$C_6$ alkyl. In some embodiments of any of the foregoing, X is N, n is 1, $R^1$ is —$CH_2$—$R^5$, and $R^5$ is as described for Formula (I). In some embodiments of any of the foregoing, X is N, n is 1, $R^1$ is —$CH_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (VI), Ring D is 6-membered heteroaryl and Ring C is $C_5$-$C_6$ cycloalkyl, 5- to 7-membered heterocyclyl, or 5- to 6-membered heteroaryl, wherein Ring C and Ring D are optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$, and phenyl. In some embodiments of any of the foregoing, X is N, n is 1, $R^1$ is —CH$_2$—$R^5$, and $R^5$ is as described for Formula (I). In some embodiments of any of the foregoing, X is N, n is 1, $R^1$ is —CH$_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_1$. 6 alkenyl, or $C_1$-$C_6$ haloalkyl.

In some embodiments of Formula (VI), Ring D is 6-membered heteroaryl and Ring C is $C_5$-$C_6$ cycloalkyl, wherein Ring C and Ring D are optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$, and phenyl. In some embodiments of any of the foregoing, X is N, n is 1, $R^1$ is —CH$_2$—$R^5$, and $R^5$ is as described for Formula (I). In some embodiments of any of the foregoing, X is N, n is 1, $R^1$ is —CH$_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (VI), Ring D is 6-membered heteroaryl and Ring C is 5- to 7-membered heterocyclyl, wherein Ring C and Ring D are optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$, and phenyl. In some embodiments of any of the foregoing, X is N, n is 1, $R^1$ is —CH$_2$—$R^5$, and $R^5$ is as described for Formula (I). In some embodiments of any of the foregoing, X is N, n is 1, $R^1$ is —CH$_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (VI), Ring D is 6-membered heteroaryl and Ring C is 5- to 6-membered heteroaryl. In some embodiments, Ring C and Ring D are

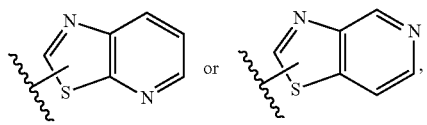

optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$, and phenyl. In some embodiments of any of the foregoing, X is N, n is 1, $R^1$ is —CH$_2$—$R^5$, and $R^5$ is as described for Formula (I). In some embodiments of any of the foregoing, X is N, n is 1, $R^1$ is —CH$_2$—$R^5$, and $R^5$ is 5-membered heteroaryl comprising one S heteroatom and one N heteroatom, optionally substituted by halo, —O—$C_{1-6}$ alkyl, $C_{1-6}$ alkyl, $C_{1-6}$ alkenyl, or $C_1$-$C_6$ haloalkyl.

In some embodiments of Formula (I), provided is a compound of Formula (VII)

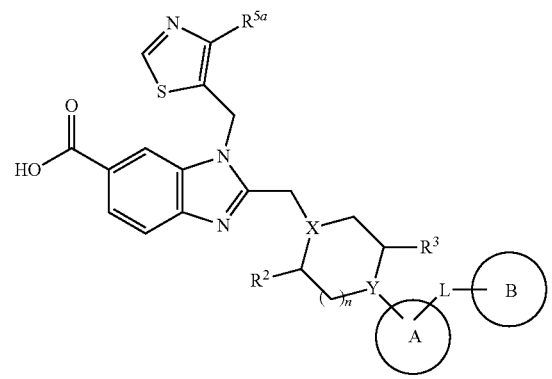

(VII)

wherein X, Y, n, $R^2$, $R^3$, Ring A, L, and Ring B are as described for Formula (I), and $R^{5a}$ is H, halo, —O—$C_{1-6}$ alkyl, $C_{1-6}$ alkyl, $C_{1-6}$ alkenyl, or $C_1$-$C_6$ haloalkyl. In some embodiments of Formula (VII), $R^{5a}$ is H or —CH$_3$.

In some embodiments of Formula (VII), X is N and Y is $CR^4$. In some embodiments, the compound is of Formula (VII-a):

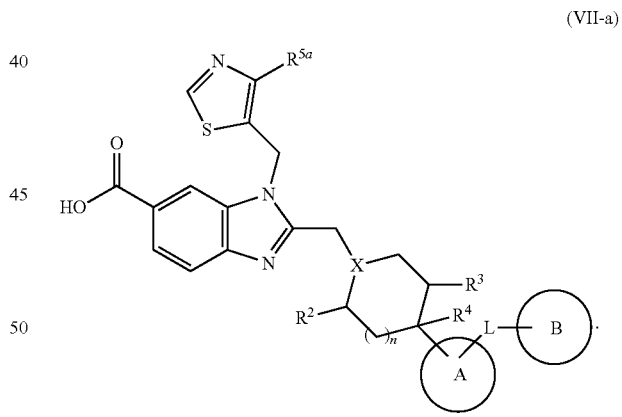

(VII-a)

wherein n, $R^2$, $R^3$, $R^4$, Ring A, L, and Ring B are as described for Formula (I), and $R^{5a}$ is as described for Formula (VII).

In some embodiments of Formula (VII), X is N, Y is $CR^4$, and $R^3$ and $R^4$ are taken together with the carbon atoms to which they are attached to form a cyclopropyl group optionally substituted by halo or $C_1$-$C_3$ alkyl. In some embodiments, the compound is of Formula (VII-b), (VII-b1), or (VII-b2):

(VII-b)

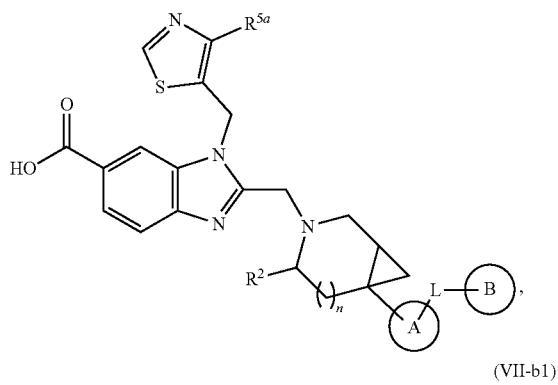

(VII-b1)

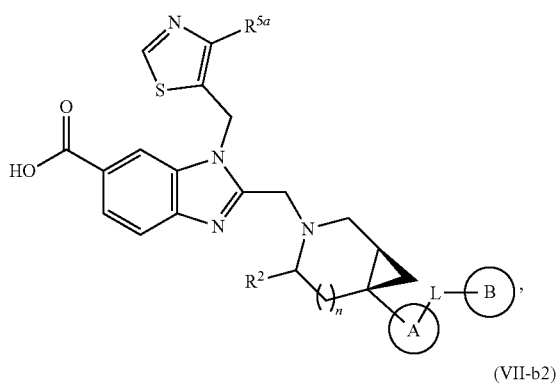

(VII-b2)

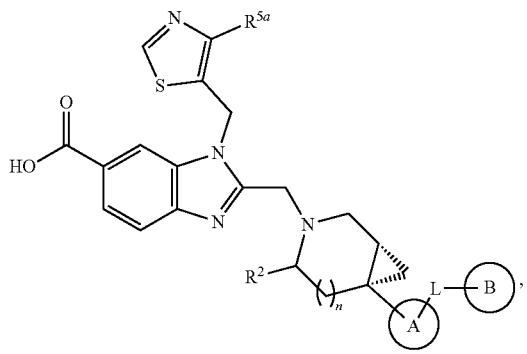

wherein n, R², R³, R⁴, Ring A, L, and Ring B are as described for Formula (I), and $R^{5a}$ is as described for Formula (VII).

In some embodiments of Formula (VII), including subformulae thereof, Ring B is C₆ aryl, which is optionally substituted by one to three substituents independently selected from the group consisting of halo, CN, oxo, C₁-C₆ alkyl, C₁-C₆ haloalkyl, —COCH₃, —CONH₂, —S(O)₂CH₃ and phenyl. In some embodiments of Formula (VII), Ring B is C₆ aryl, which is optionally substituted by one to two substituents independently selected from the group consisting of halo, CN, oxo, C₁-C₆ alkyl, C₁-C₆ haloalkyl, —COCH₃, —CONH₂, —S(O)₂CH₃ and phenyl. In some embodiments of Formula (VII), Ring B is C₆ aryl, which is optionally substituted by one to two substituents independently selected from the group consisting of halo and CN. In some embodiments of any of the foregoing, L is *—O—CH₂—**. In some embodiments, the compound is of Formula (VII-c):

(VII-c)

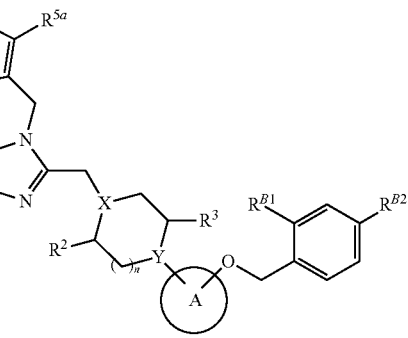

wherein X, Y, n, R², R³, and Ring A are as described for Formula (I), $R^{5a}$ is as described for Formula (VII), and $R^{B1}$ and $R^{B2}$ are independently selected from the group consisting of halo, CN, oxo, C₁-C₆ alkyl, C₁-C₆ haloalkyl, —COCH₃, —CONH₂, —S(O)₂CH₃ and phenyl. In some embodiments, $R^{B1}$ and $R^{B2}$ are independently selected from the group consisting of halo and CN.

In some embodiments of Formula (VII-c), X is N, Y is CR⁴, and R³ and R⁴ are taken together with the carbon atoms to which they are attached to form a cyclopropyl group optionally substituted by halo or C₁-C₃ alkyl. In some embodiments, the compound is of Formula (VII-d), (VII-d1), or (VII-d2):

(VII-d)

(VII-d1)

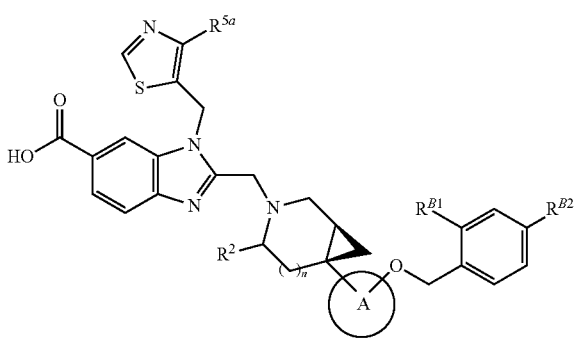

-continued (VII-d2)

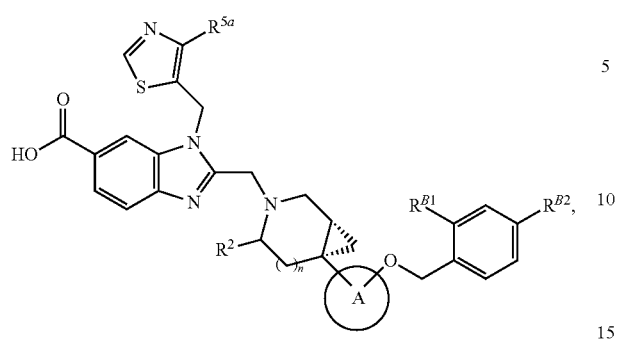

wherein R² and Ring A are as described for Formula (I), R^{5a} is as described for Formula (VII), and R^{B1} and R^{B2} are as described for Formula (VII-c).

In some embodiments, the compound of Formula VII is of Formula VII-e:

(VII-e)

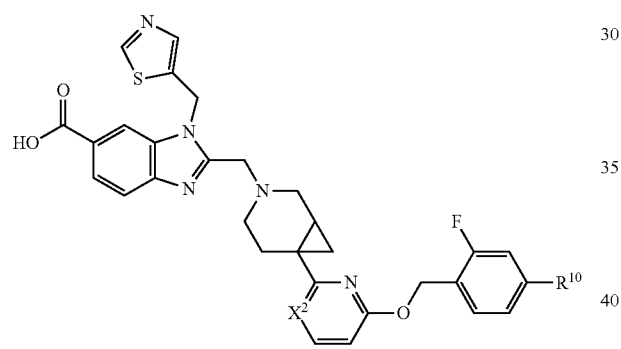

wherein $X^2$ is N or CH; and
$R^{10}$ is $C_1$ or CN.

In some embodiments, the compound of Formula VII-e is of Formula VII-ei (VII-ei)

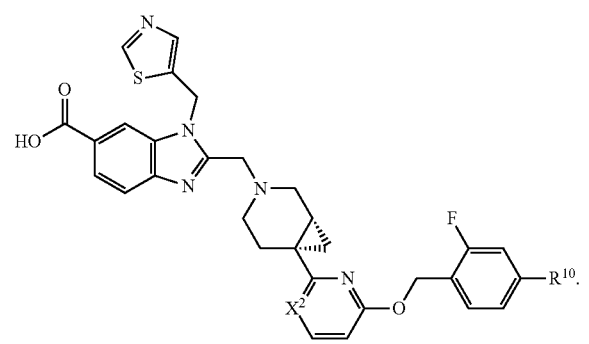

In some embodiments, the compound of Formula VII-e is of Formula VII-eii:

(VII-eii)

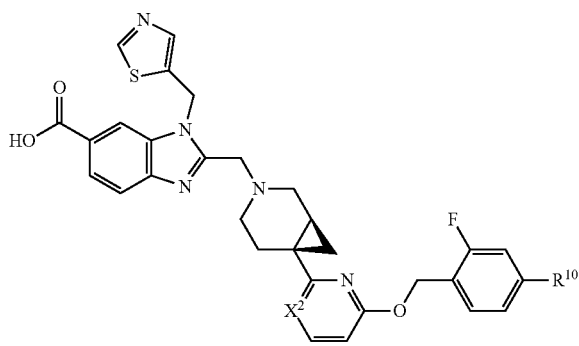

In some embodiments, the compound of Formula I is of Formula VIII (VIII)

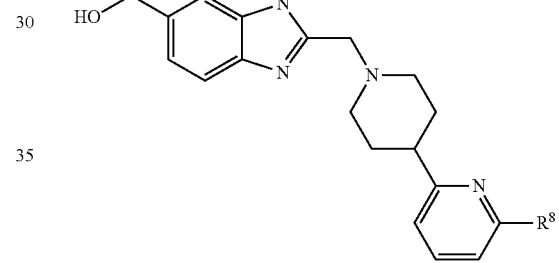

wherein $R^7$ is hydrogen, chloro, bromo, fluoro, methyl, or vinyl; and
$R^8$ is

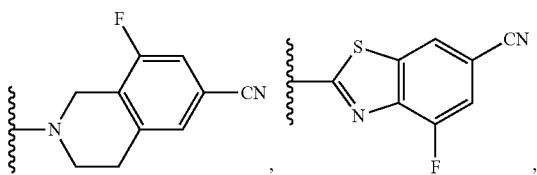

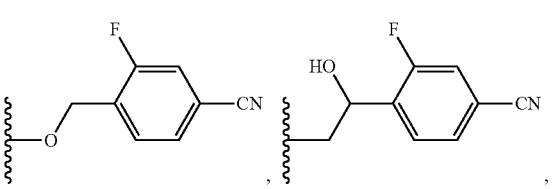

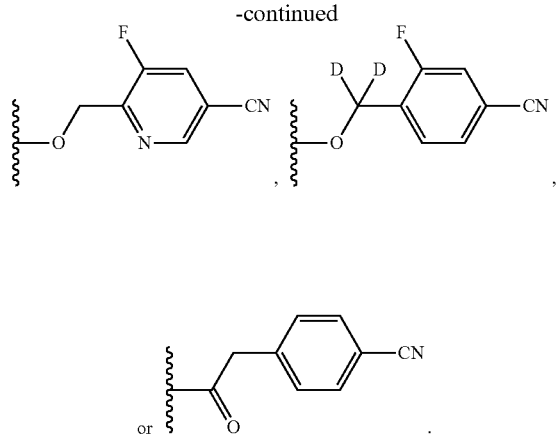

In some embodiments, the compound of Formula I is of Formula VIII-a:

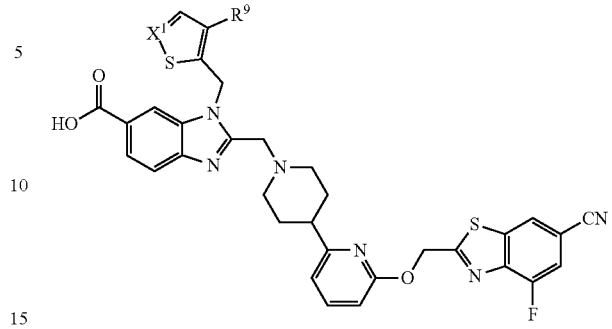

wherein $X^1$ is N or CH; and $R^9$ is H or —OCH$_3$.

Representative compounds are listed in Table 1 below. In some embodiments, provided is a compound, or a pharmaceutically acceptable salt thereof, as described in Table 1. In some embodiments, provided is a compound, or a pharmaceutically acceptable salt thereof, which is selected from Compound Nos. 1-16 in Table 1. In some embodiments, provided is a compound, or a pharmaceutically acceptable salt thereof, which is selected from Compound Nos. 1-31 in Table 1. Compounds were prepared as described in the General Procedures provided in the Examples.

TABLE 1

| Compound No. | Structure |
| --- | --- |
| Reference Compound A | 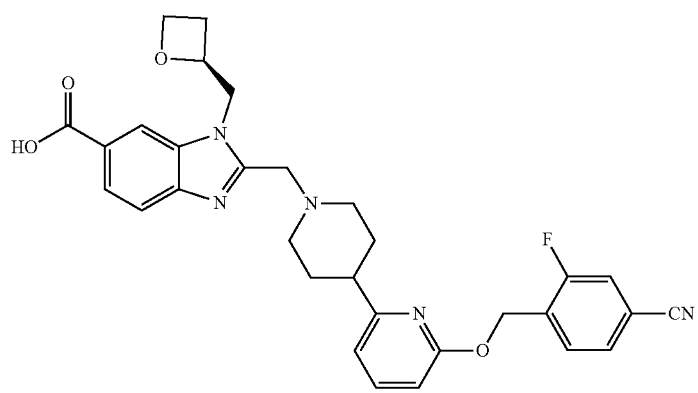 [SMILES: N#Cc1ccc(COc2cccc(C3CCN(Cc4nc5ccc(C(=O)O)cc5n4C[C@@H]4CCO4)CC3)n2)c(F)c1] |
| 1 | 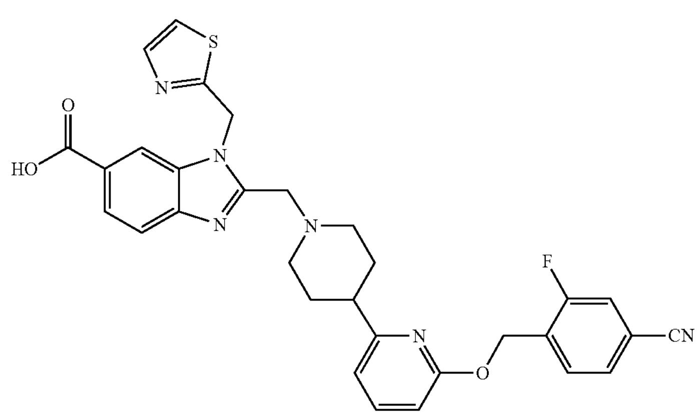 [SMILES: N#Cc1ccc(COc2cccc(C3CCN(Cc4nc5ccc(C(=O)O)cc5n4Cc4nccs4)CC3)n2)c(F)c1] |

TABLE 1-continued
| Compound No. | Structure |
|---|---|
| 2 | 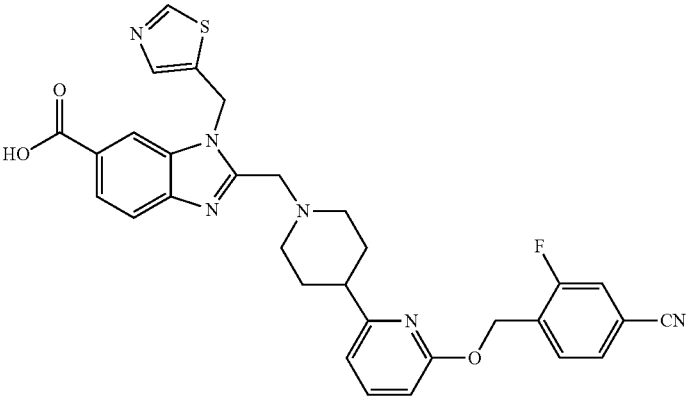 [SMILES: N#Cc1ccc(COc2cccc(C3CCN(Cc4nc5ccc(C(=O)O)cc5n4Cc4cncs4)CC3)n2)c(F)c1] |
| 3 | 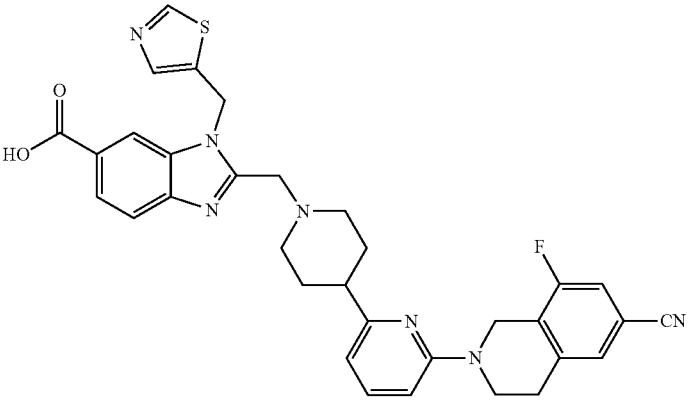 [SMILES: N#Cc1cc(F)c2c(c1)CCN(c1cccc(C3CCN(Cc4nc5ccc(C(=O)O)cc5n4Cc4cncs4)CC3)n1)C2] |
| 4 | 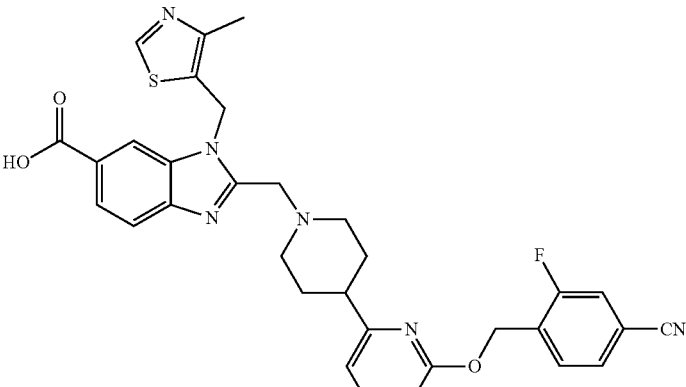 |

TABLE 1-continued
| Compound No. | Structure |
| --- | --- |
| 5 | 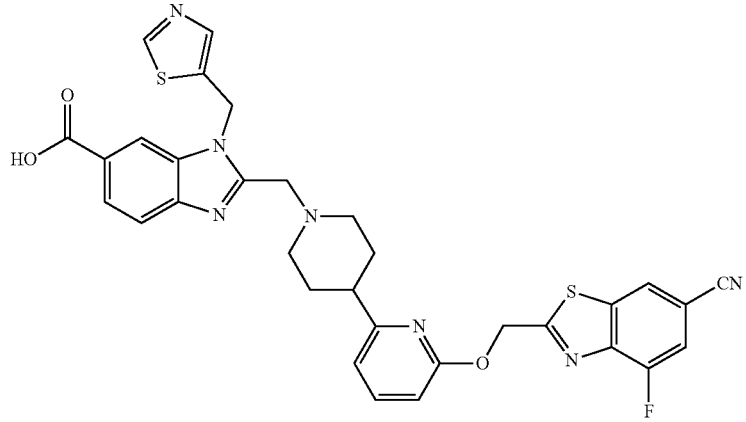 [SMILES: N#Cc1cc(F)c2nc(COc3cccc(C4CCN(Cc5nc6ccc(C(=O)O)cc6n5Cc5cncs5)CC4)n3)sc2c1] |
| 6 | 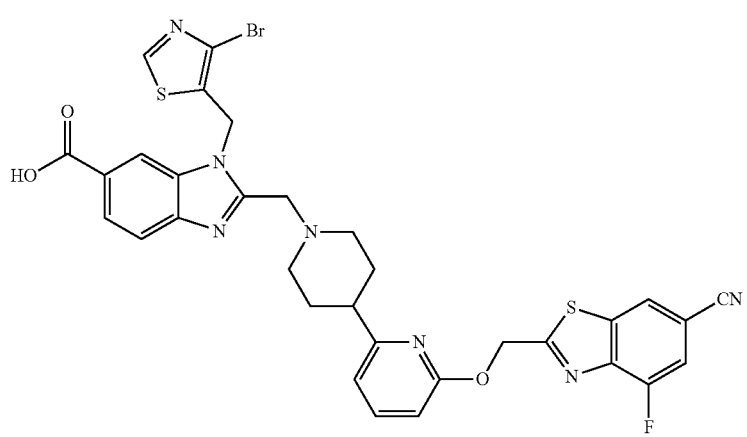 [SMILES: N#Cc1cc(F)c2nc(COc3cccc(C4CCN(Cc5nc6ccc(C(=O)O)cc6n5Cc5scnc5Br)CC4)n3)sc2c1] |
| 7 | 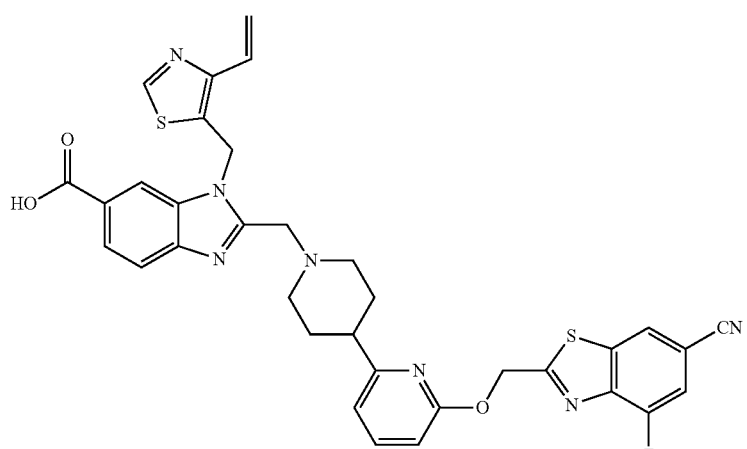 |

TABLE 1-continued
| Compound No. | Structure |
|---|---|
| 8 | 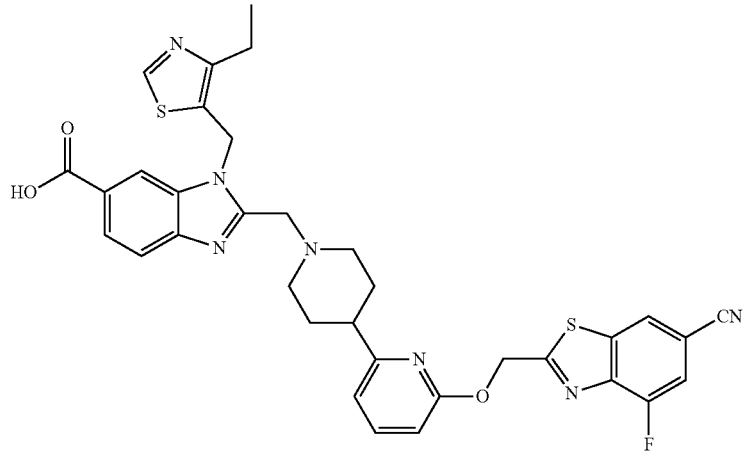 [SMILES: CCc1ncsc1Cn1c(CN2CCC(c3cccc(OCc4nc5c(F)cc(C#N)cc5s4)n3)CC2)nc2ccc(C(=O)O)cc21] |
| 9 | 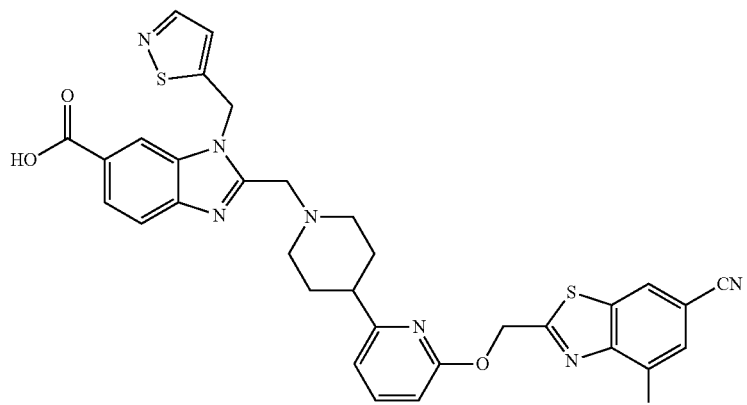 |
| 10 | 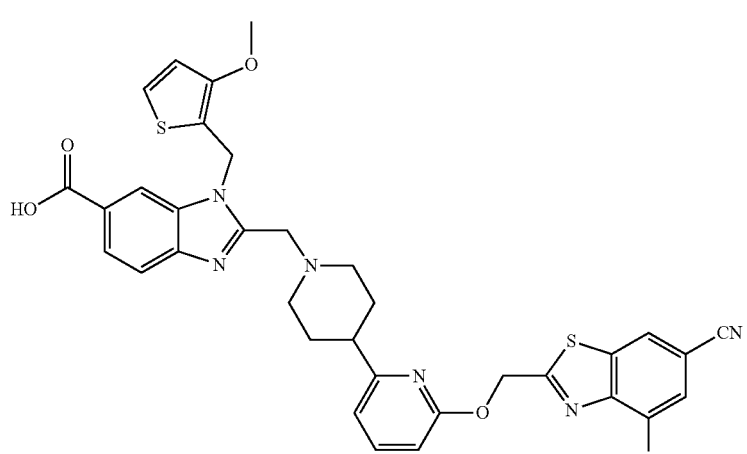 |

TABLE 1-continued

| Compound No. | Structure |
|---|---|
| 11 | (structure) |
| 12 | (structure) |
| 13 | (structure) |

TABLE 1-continued
| Compound No. | Structure |
|---|---|
| 14 | 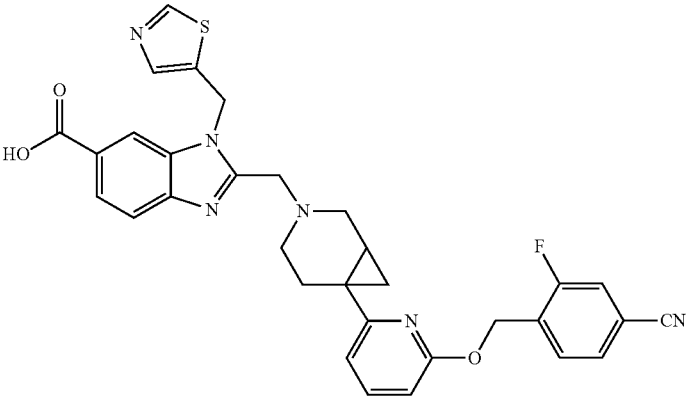 [SMILES: N#Cc1ccc(COc2cccc(C34CCN(Cc5nc6ccc(C(=O)O)cc6n5Cc5cncs5)CC3C4)n2)c(F)c1] |
| 15 | 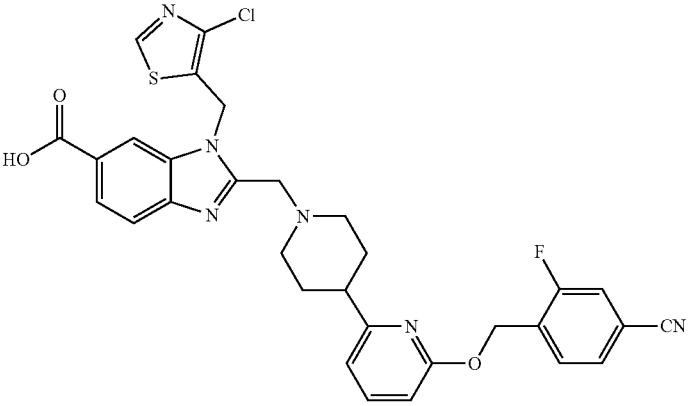 [SMILES: N#Cc1ccc(COc2cccc(C3CCN(Cc4nc5ccc(C(=O)O)cc5n4Cc4scnc4Cl)CC3)n2)c(F)c1] |
| 16 | 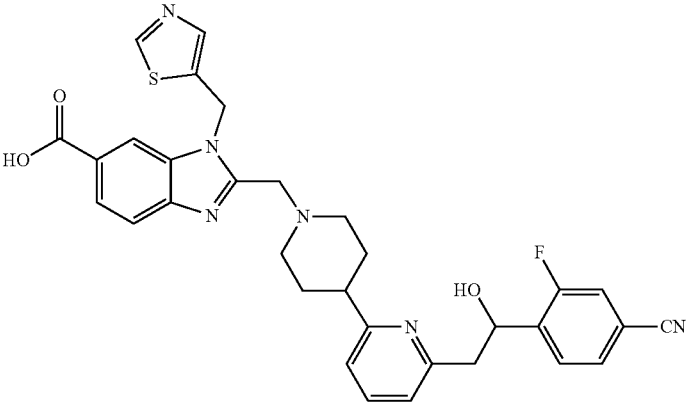 [SMILES: N#Cc1ccc(C(O)Cc2cccc(C3CCN(Cc4nc5ccc(C(=O)O)cc5n4Cc4cncs4)CC3)n2)c(F)c1] |

TABLE 1-continued
| Compound No. | Structure |
|---|---|
| 17 | 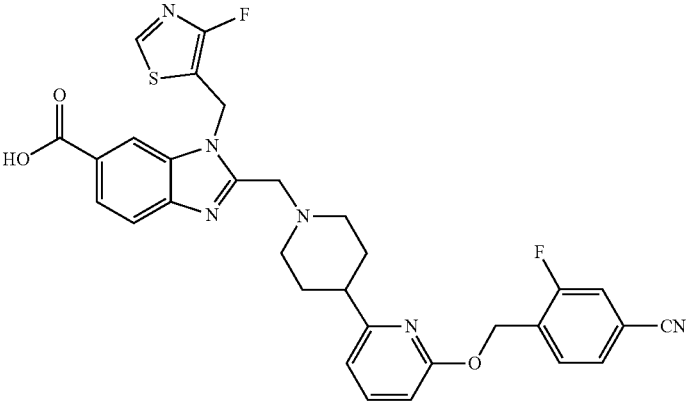 |
| 18 | 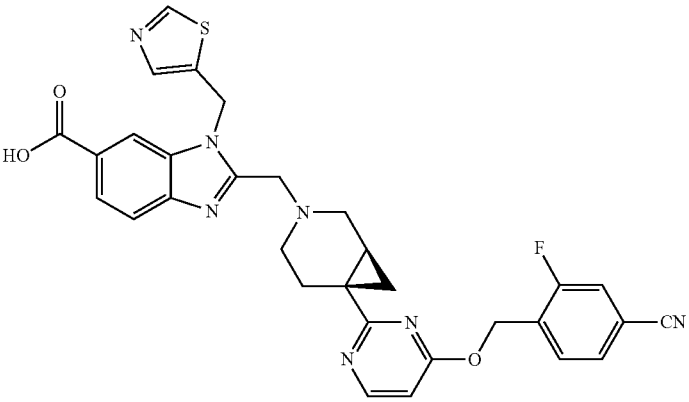 [SMILES: N#Cc1ccc(COc2ccnc([C@]34CCN(Cc5nc6ccc(C(=O)O)cc6n5Cc5cncs5)C[C@H]3C4)n2)c(F)c1] |
| 19 | 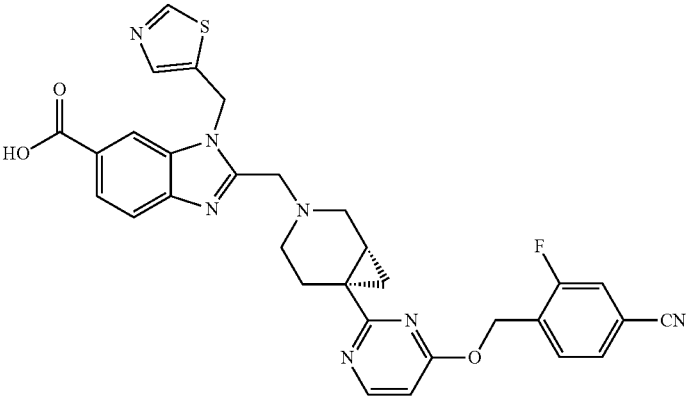 [SMILES: N#Cc1ccc(COc2ccnc([C@@]34CCN(Cc5nc6ccc(C(=O)O)cc6n5Cc5cncs5)C[C@@H]3C4)n2)c(F)c1] |

TABLE 1-continued
| Compound No. | Structure |
|---|---|
| 20 | 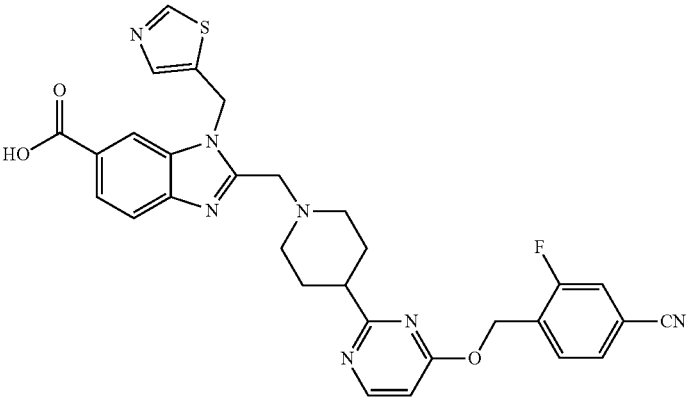 [SMILES: N#Cc1ccc(COc2ccnc(C3CCN(Cc4nc5ccc(C(=O)O)cc5n4Cc4cncs4)CC3)n2)c(F)c1] |
| 21 | 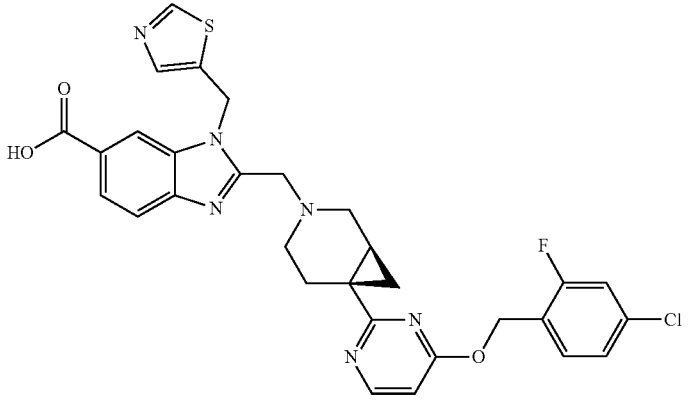 [SMILES: O=C(O)c1ccc2nc(CN3CC[C@]4(c5nccc(OCc6ccc(Cl)cc6F)n5)C[C@@H]4C3)n(Cc3cncs3)c2c1] |
| 22 | 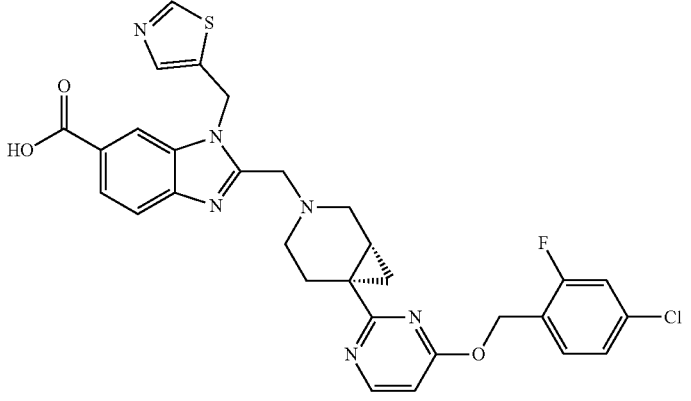 [SMILES: O=C(O)c1ccc2nc(CN3CC[C@@]4(c5nccc(OCc6ccc(Cl)cc6F)n5)C[C@H]4C3)n(Cc3cncs3)c2c1] |
| 23 | 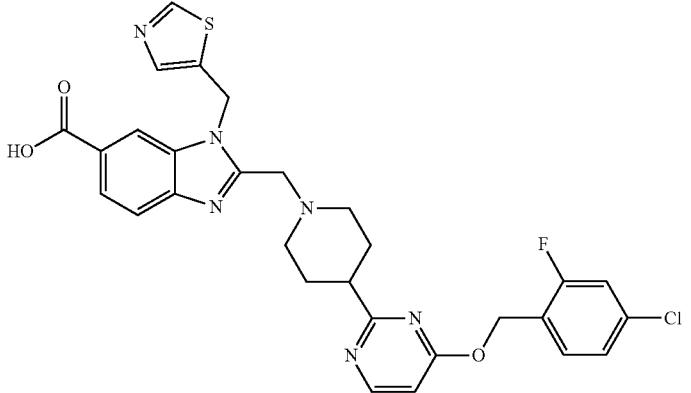 [SMILES: O=C(O)c1ccc2nc(CN3CCC(c4nccc(OCc5ccc(Cl)cc5F)n4)CC3)n(Cc3cncs3)c2c1] |

TABLE 1-continued
| Compound No. | Structure |
|---|---|
| 24 | 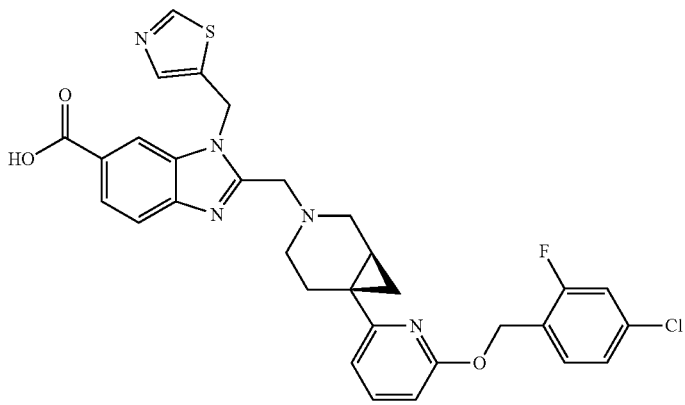 [SMILES: O=C(O)c1ccc2nc(CN3CC[C@]4(c5cccc(OCc6ccc(Cl)cc6F)n5)C[C@@H]4C3)n(Cc3cncs3)c2c1] |
| 25 | 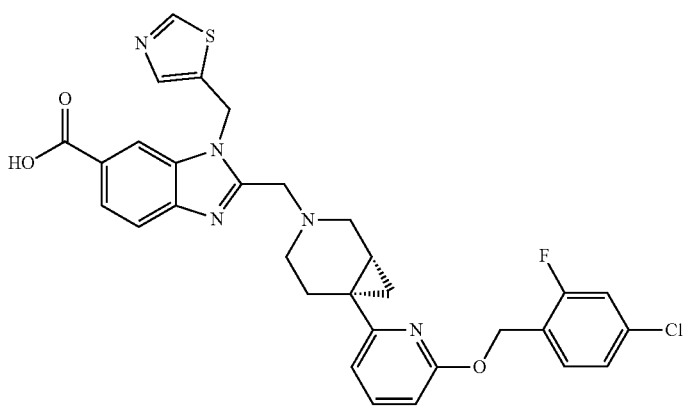 [SMILES: O=C(O)c1ccc2nc(CN3CC[C@@]4(c5cccc(OCc6ccc(Cl)cc6F)n5)C[C@H]4C3)n(Cc3cncs3)c2c1] |
| 26 | 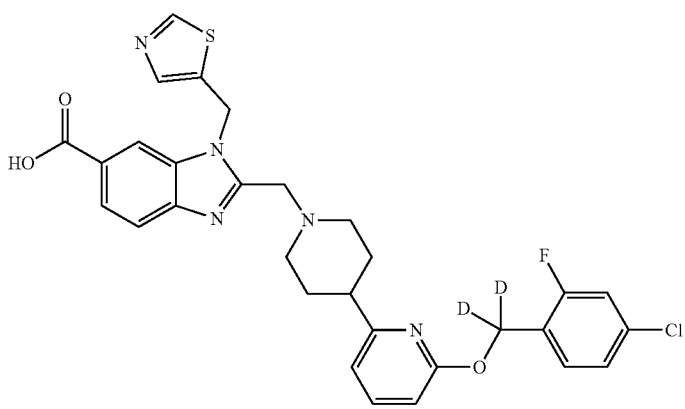 [SMILES: [2H]C([2H])(Oc1cccc(C2CCN(Cc3nc4ccc(C(=O)O)cc4n3Cc3cncs3)CC2)n1)c1ccc(Cl)cc1F] |

TABLE 1-continued
| Compound No. | Structure |
|---|---|
| 27 | 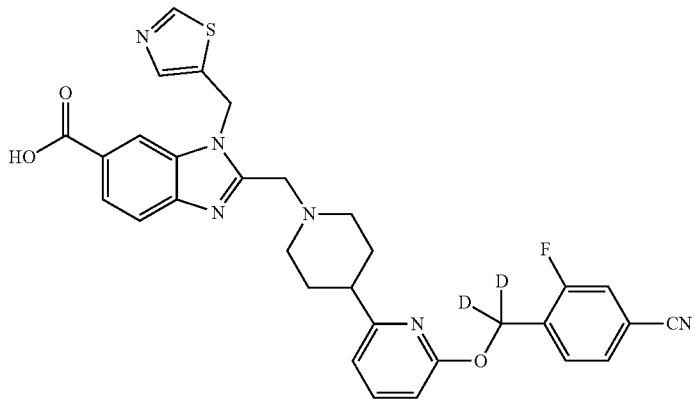 [SMILES: [2H]C([2H])(Oc1cccc(C2CCN(Cc3nc4ccc(C(=O)O)cc4n3Cc3cncs3)CC2)n1)c1ccc(C#N)cc1F] |
| 28 | 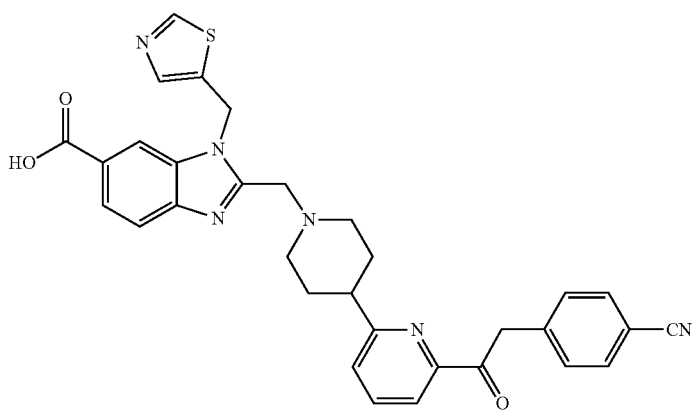 [SMILES: N#Cc1ccc(CC(=O)c2cccc(C3CCN(Cc4nc5ccc(C(=O)O)cc5n4Cc4cncs4)CC3)n2)cc1] |
| 29 | 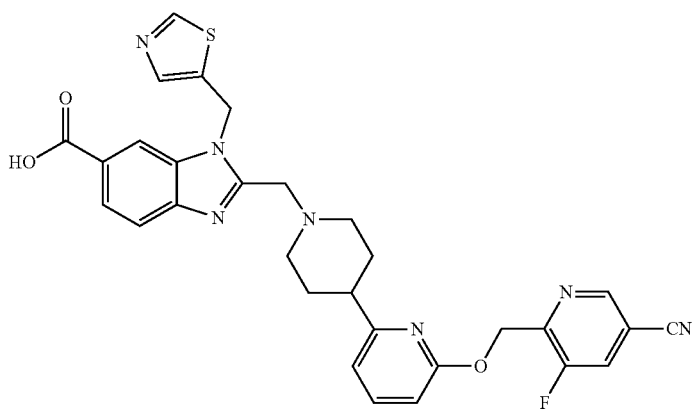 [SMILES: N#Cc1cnc(COc2cccc(C3CCN(Cc4nc5ccc(C(=O)O)cc5n4Cc4cncs4)CC3)n2)c(F)c1] |

TABLE 1-continued

| Compound No. | Structure |
|---|---|
| 30 | *[chemical structure: benzimidazole with carboxylic acid, N-thiazolylmethyl, 2-(piperazinylmethyl) linked to pyridine-O-CH2-(fluoro-cyanophenyl)]* |
| 31 | *[chemical structure: benzimidazole with carboxylic acid, N-thiazolylmethyl, 2-(piperidinylmethyl) where piperidine is attached to a benzodioxole bearing methyl and (fluoro-cyanophenyl) substituents]* |

In another aspect, provided is a method of making a compound of Formula (I), (including compounds of Formulae (II)-(V), (VI), (VII), (VIII) and subformulae thereof), or selected from the group consisting of a compound listed in Table 1, or a pharmaceutically acceptable salt of any of the foregoing. Compounds described herein may be prepared according to general schemes, as exemplified by the general procedures and examples. Minor variations in starting materials, temperatures, concentrations, reaction times, and other parameters can be made when following the general procedures, which do not substantially affect the results of the procedures.

Also provided are compound intermediates useful in synthesis of a compound of Formula (I), including compounds of Formulae (II)-(VIII), or selected from the group consisting of a compound listed in Table 1, or a stereoisomer, tautomer, or a pharmaceutically acceptable salt of any of the foregoing.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. Compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio, unless a specific stereochemistry is otherwise indicated. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is the enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2H$, $^3H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g., $^3H$ and $^{14}C$) are useful in compound or substrate tissue distribution study. Incorporation of heavier isotopes such as deuterium (2H) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

In some embodiments, the present disclosure also includes salts, e.g., pharmaceutically acceptable salts, of any of the compounds disclosed herein. In some embodiments, the present disclosure provides a meglumine salt of any one of the compounds disclosed herein, e.g., a 1:1 compound:meglumine salt, a 2:1 compound:meglumine salt, a 1:2 compound:meglumine salt.

Pharmaceutically Acceptable Compositions and Formulations

Pharmaceutically acceptable compositions or simply "pharmaceutical compositions" of any of the compounds detailed herein are embraced by this invention. Thus, the invention includes pharmaceutical compositions comprising a compound of Formula (I) (including compounds of Formulae (II)-(VIII)), or a pharmaceutically acceptable salt thereof, and a pharmaceutically acceptable carrier or excipient.

In some embodiments, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity.

In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compounds may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

Compounds described herein can be used in the preparation of a formulation, such as a pharmaceutical formulation, by combining the compounds as active ingredients with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington: The Science and Practice of Pharmacy, Lippincott Williams & Wilkins, 21st ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Compositions comprising two compounds utilized herein are described. Any of the compounds described herein can be formulated in a tablet in any dosage form described herein. In some embodiments, the composition comprises a compound of Formula (I) (including compounds of Formulae (II)-(VIII)), or a pharmaceutically acceptable salt thereof, as described herein. In some embodiments, provided herein is a dosage form comprises a therapeutically effective amount of a compound of Formula (I) (including compounds of Formulae (II)-(VIII)), or a pharmaceutically acceptable salt thereof. In some embodiments, the compound or a pharmaceutically acceptable salt thereof is selected from Compound Nos. 1-11 in Table 1. In some embodiments, the compound or a pharmaceutically acceptable salt thereof is selected from Compound Nos. 1-31 in Table 1

Methods of Use and Uses

Compounds and compositions described herein may in some aspects be used in treatment of diseases and/or conditions described herein, for example, diseases and/or conditions mediated by GLP-1R. In some embodiments, the method of treating a disease or condition in a subject in need thereof comprises administering to the subject a therapeutically effective amount of a compound of Formula (I) (including compounds of Formulae (II)-(VI)), or a pharmaceutically acceptable salt thereof. In some embodiments, the method of treating a disease or condition in a subject in need thereof comprises administering to the subject a therapeutically effective amount of a compound selected from any one of the compounds in Table 1, or a pharmaceutically acceptable salt thereof.

In some embodiments, the method of treating a disease or condition in a subject in need thereof comprises administering to the subject an effective amount of a compound of Formula (I) (including compounds of Formulae (II)-(VIII)), or a pharmaceutically acceptable salt thereof. In some embodiments, the method of treating a disease or condition in a subject in need thereof comprises administering to the subject an effective amount of a compound selected from any one of the compounds in Table 1, or a pharmaceutically acceptable salt thereof.

In accordance with the present application, a disease or condition to be treated and/or prevented is selected from the group consisting of cardiometabolic and associated diseases including diabetes (T1 D and/or T2DM, including pre-diabetes), idiopathic T1 D (Type 1 b), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), hyperinsulinemia, liver diseases such as NAFLD, steatosis, NASH, fibrosis, cirrhosis, and hepatocellular carcinoma, cardiovascular disease, atherosclerosis (including coronary artery disease), peripheral vascular disease, hypertension, endothelial dysfunction, impaired vascular compliance, congestive heart failure, myocardial infarction (e.g. necrosis and apoptosis), stroke, hemorrhagic stroke, ischemic stroke, traumatic brain injury, pulmonary hypertension, restenosis after angioplasty, intermittent claudication, postprandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, Polycystic Ovary Syndrome and addiction (e.g., alcohol and/or drug abuse), prevention or treatment of Polycystic Ovary Syndrome and treatment of addiction (e.g., alcohol and/or drug abuse).

In some embodiments, provided herein is a method of treating a cardiometabolic disease in a subject (e.g., a human patient) in need thereof, comprising administering to the subject a therapeutically effective amount of a compound described herein, or a pharmaceutically acceptable salt thereof.

In some embodiments, provided herein is a method of treating diabetes in a subject (e.g., a human patient) in need thereof, comprising administering to the subject a therapeutically effective amount of a compound described herein, or a pharmaceutically acceptable salt thereof. Exemplary diabetes include, but are not limited to, T1 D, T2DM, pre-diabetes, idiopathic T1 D, LADA, EOD, YOAD, MODY, malnutrition-related diabetes, and gestational diabetes.

In some embodiments, provided herein is a method of treating a liver disorder in a subject (e.g., a human patient) in need thereof, comprising administering to the subject a therapeutically effective amount of a compound described herein, or a pharmaceutically acceptable salt thereof. Exemplary liver disorders include, without limitation, liver inflammation, fibrosis, and steatohepatitis. In some embodiments, the liver disorder is selected from the list consisting of primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, and oti-antitrypsin deficiency. In some embodiments, the liver disorder is selected from the list consisting of liver inflammation, liver fibrosis, alcohol induced fibrosis, steatosis, alcoholic steatosis, primary sclerosing cholangitis (PSC), primary biliary cirrhosis (PBC), non-alcoholic fatty liver disease (NAFLD), and non-alcoholic steatohepatitis (NASH). In some embodiments, the liver disorder is selected from the group consisting of liver fibrosis, alcohol induced fibrosis, steatosis, alcoholic steatosis, NAFLD, and NASH. In one embodiment, the liver disorder is NASH. In another embodiment, the liver disorder is liver inflammation. In another embodiment, the liver disorder is liver fibrosis. In another embodiment, the liver disorder is alcohol induced fibrosis. In another embodiment, the liver disorder is steatosis. In another embodiment, the liver disorder is alcoholic steatosis. In another embodiment, the liver disorder is NAFLD. In one embodiment, the treatment methods provided herein impedes or slows the progression of NAFLD to NASH. In one embodiment, the treatment methods provided herein impedes or slows the progression of NASH. NASH can progress, e.g., to one or more of liver cirrhosis, hepatic cancer, etc. In some embodiments, the liver disorder is NASH. In some embodiments, the patient has had a liver biopsy. In some embodiments, the method further comprising obtaining the results of a liver biopsy.

In some embodiments, the present disclosure provides a method of decreasing food intake in a subject in need thereof, the method comprising administering an effective amount of any one of the compounds or pharmaceutical compositions disclosed herein to the subject. In some embodiments, administration of a compound disclosed herein causes the subject's food intake to be reduced at least 10%, e.g., at least 20%, at least 30%, at least 40%, at least 50%, at least 60%, at least 70%, at least 75%, at least 80%, at least 85%, at least 90%, or at least 95% relative to the subject's food intake in the absence of a compound disclosed herein. In some embodiments, the subject's food intake is reduced, e.g., reduced by at least 10%, at least 20%, at least 30%, at least 40%, at least 50%, at least 60%, at least 70%, at least 75%, at least 80%, at least 85%, at least 90%, or at least 95%, for at least 1 hour following administration, e.g., at least 1 hour, at least 2 hours, at least 3 hours, at least 4 hours, at least 5 hours, at least 6 hours, at least 12 hours, at least 1 day, or at least 2 days following administration.

In some embodiments, the present disclosure provides a method of improving glucose tolerance in a subject in need thereof. In some embodiments, following glucose intake, e.g., glucose intake caused by consuming food, and the administration of a compound disclosed herein, the concentration of glucose in the blood of a subject is lower, e.g., 10% lower, 20% lower, 30% lower, 40% lower, 50% lower, 60% lower, 70% lower, 80% lower, 90% lower, 100% lower, 200% lower, 500% lower, 1000% lower, than the blood glucose concentration would have been had the subject not been administered the compound disclosed herein.

In accordance with the present application, a compound described herein, or a pharmaceutically acceptable salt thereof, can be administered by any suitable route in the form of a pharmaceutical composition adapted to such a route, and in a dose effective for the treatment intended. In some embodiments, it is a compound of any embodiment of Formula (I) or selected from the compounds of Table 1, or a pharmaceutically acceptable salt thereof. The compounds and/or compositions described herein may be administered orally, rectally, vaginally, parenterally, or topically.

In some embodiments, the compounds and/or compositions may be administered orally. Oral administration may involve swallowing, so that the compound enters the gastrointestinal tract, or buccal or sublingual administration may be employed by which the compound enters the bloodstream directly from the mouth.

In some embodiments, the compounds and/or compositions may be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In some embodiments, the compounds and/or compositions may be administered topically to the skin or mucosa, that is, dermally or transdermally. In some embodiments, the compounds and/or compositions may be administered intranasally or by inhalation. In some embodiments, the compounds and/or compositions may be administered rectally or vaginally. In some embodiments, the compounds and/or compositions may be administered directly to the eye or ear.

The dosage regimen for the compounds and/or compositions described herein is based on a variety of factors, including the type, age, weight, sex and medical condition of the patient; the severity of the condition; the route of administration; and the activity of the particular compound employed. Thus, the dosage regimen may vary widely. In some embodiments, the total daily dose of the compounds of the present application is typically from about 0.001 to about 100 mg/kg (i.e., mg compound per kg body weight) for the treatment of the indicated conditions discussed herein. In one embodiment, total daily dose of the compounds of the present application is from about 0.01 to about 30 mg/kg, and in another embodiment, from about 0.03 to about 10 mg/kg, and in yet another embodiment, from about 0.1 to about 3. It is not uncommon that the administration of the compounds of the present application will be repeated a plurality of times in a day (typically no greater than 4 times). Multiple doses per day typically may be used to increase the total daily dose, if desired.

For oral administration, the compounds and/or compositions described herein may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

The compounds and/or compositions described herein can be used alone, or in combination with other therapeutic agents. The administration of two or more agents "in combination" means that all of the agents are administered closely enough in time that each may generate a biological effect in the same time frame. The presence of one agent may alter the biological effects of the other agent(s). The two or more agents may be administered simultaneously, concurrently or sequentially. Additionally, simultaneous administration may be carried out by mixing the agents prior to administration or by administering the compounds at the same point in time but as separate dosage forms at the same or different site of administration.

The present application provides any of the uses, methods or compositions as defined herein wherein a compound of any embodiment of Formula (I) or selected from the compounds of Table 1 as described herein, or a pharmaceutically acceptable salt thereof, is used in combination with one or more other therapeutic agent. This would include a pharmaceutical composition comprising a compound of any embodiment of Formula (I) or selected from the compounds of Table 1, or a pharmaceutically acceptable salt thereof, as defined in any of the embodiments described herein, in admixture with at least one pharmaceutically acceptable excipient and one or more other therapeutic agent.

In some embodiments, the one or more other therapeutic agent is an anti-diabetic agent including but not limited to a biguanide (e.g., metformin), a sulfonylurea (e.g., tolbutamide, glibenclamide, gliclazide, chlorpropamide, tolazamide, acetohexamide, glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLT1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In some embodiments, the one or more other therapeutic agent is an antiobesity agent including but not limited to peptide YY or an analogue thereof, a neuropeptide Y receptor type 2 (NPYR2) agonist, a NPYR1 or NPYR5 antagonist, a cannabinoid receptor type 1 (CB1 R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues therof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLT1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In some embodiments, the one or more other therapeutic agent is an agent to treat NASH including but not limited to PF-05221304, an FXR agonist (e.g., obeticholic acid), a PPAR α/δ agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor21 (FGF21) agonist (e.g., BMS-986036), a leukotriene D4 (LTD4) receptor antagonist (e.g., tipelukast), a niacin analogue (e.g., ARI 3037MO), an ASBT inhibitor (e.g., volixibat), an acetyl-CoA carboxylase (ACC) inhibitor (e.g., NDI 010976), a ketohexokinase (KHK) inhibitor, a diacylglyceryl acyltransferase 2 (DGAT2) inhibitor, a CB1 receptor antagonist, an anti-CB1 R antibody, or an apoptosis signal-regulating kinase 1 (ASK1) inhibitor, including the pharmaceutically acceptable salts of the specifically named agents and the pharmaceutically acceptable solvates of said agents and salts.

Articles of Manufacture and Kits

The present disclosure further provides articles of manufacture comprising a compound, or a pharmaceutically acceptable salt thereof in accordance with the present application, a composition described herein, or one or more unit dosages described herein in suitable packaging. In certain embodiments, the article of manufacture is for use in any of the methods described herein. Suitable packaging (e.g., containers) is known in the art and includes, for example, vials, vessels, ampules, bottles, jars, flexible packaging and the like. An article of manufacture may further be sterilized and/or sealed.

The kits may be in unit dosage forms, bulk packages (e.g., multi-dose packages) or sub-unit doses. For example, kits may be provided that contain sufficient dosages of a compound, or a pharmaceutically acceptable salt thereof in accordance with the present application, a composition described herein, and/or one or more other therapeutic agent useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds/compositions described herein and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively, an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively, an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) has been synthesized by any one of the processes defined herein, the processes may then further comprise the additional steps of: (i) removing any protecting groups present; (ii) converting the compound Formula (I) into another compound of Formula (I); (iii) forming a pharmaceutically acceptable salt, hydrate or solvate thereof, and/or (iv) forming a prodrug thereof.

The resultant compounds of Formula (I) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, N,N-dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilizing the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesized by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

Routes for the preparation of the compounds of the present disclosure are described in the Examples.

General routes for the preparation of the compounds of the present disclosure are described in General Schemes A-D herein.

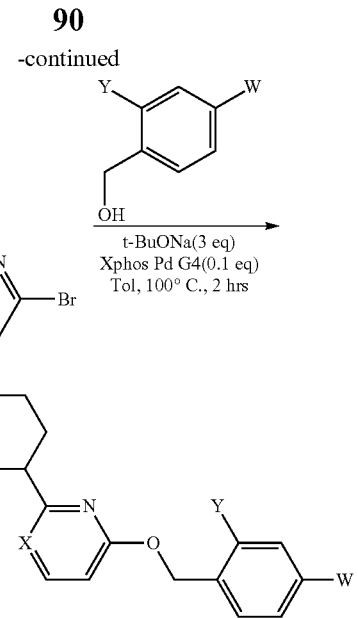

General scheme B shows general methods for the preparation of various compounds.

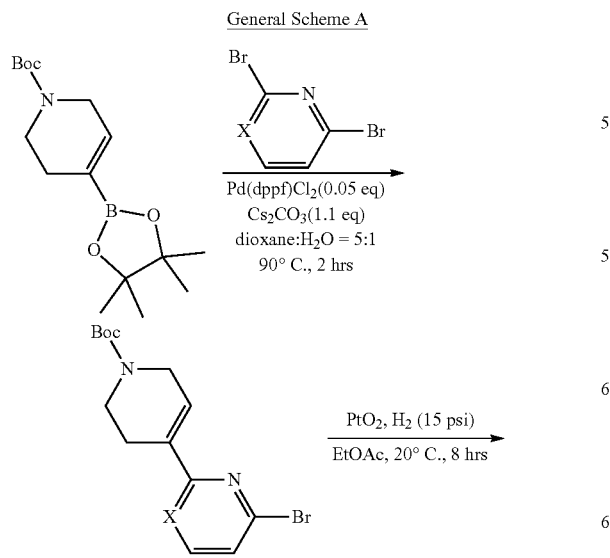

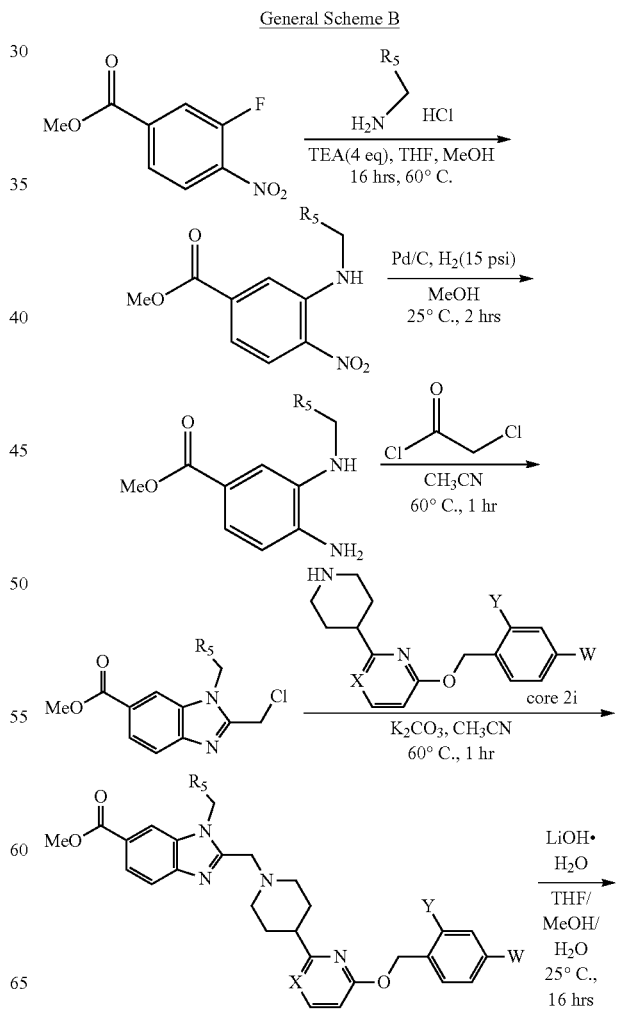

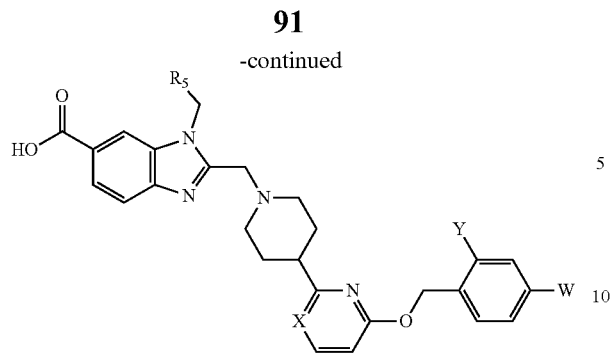

General Scheme C

General scheme C shows the preparation of compounds from Cores 1i, 2i, and 3i.

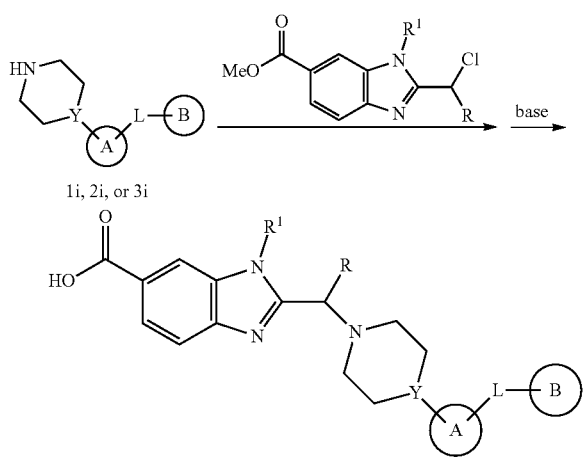

General scheme D shows general methods for the preparation of compounds with Core 4i.

General Scheme D

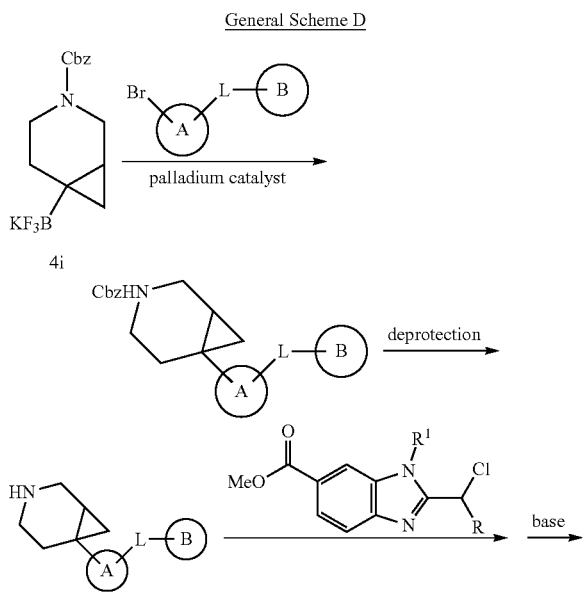

Biological Assays

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Various in vitro or in vivo biological assays may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

In some embodiments, the biological assays are described in the Examples herein.

GLP-1R Cell Assay

Stable cell lines expressing high and low GLP-1R surface expression were generated in CHO-K1 cells transfected (Fugene 6) with a puromycin selectable DNA plasmid encoding human GLP-1R receptor (accession number: NM_002062.5) under control of an EF1A promoter. Transfected cells were seeded into 24-well plates (9,000 cells/well) containing complete medium and incubated in a humidified incubator at 37° C. with 5% carbon dioxide. After overnight incubation, medium was replaced with complete medium supplemented with puromycin (6 μg/mL) and refreshed every 2-3 days to select for stably transfected cells. Individual pools of selected cells were expanded prior to analysis for responsiveness to GLP-1 control peptide using a TR-FRET assay to detect cAMP (LANCE Ultra cAMP Assay, Perkin Elmer). Briefly, cells were collected in Versene solution, plated in 384-well plates (1,000 cells/well) and combined with serially diluted GLP-1R control peptide (10 nL) using an acoustic dispenser (ECHO). Plates were incubated for 30 minutes at 25° C. prior to the addition of EU-cAMP tracer (5 μL) and Ulight-anti-cAMP (5 μL) reagents to each well, followed by 15 minutes incubation at 25° C. TR-FRET signal was detected using an EnVision Multimode Plate Reader (excitation=320 nm; emission=615 and 655 nm). Dose-response curves were used to generate $EC_{50}$ values as a measure of responsiveness to the GLP-1R control peptide. Selected cell lines were monitored for responsiveness over multiple passages to ensure stability. CHO-K1_hGLP-1Rhigh_clone16 and CHO-K1_hGLP-1Rlow_clone10 showed consistently high and low responsiveness to GLP-1R control peptide, respectively, and were chosen for further analysis to determine relative levels of GLP-1R surface expression. Briefly, GLP-1R expression was analyzed by flow cytometry using a fluorescein-labeled Exendin-4 peptide fluorescent probe (FLEX). Cells were harvested in Versene solution and washed 3-times with PBS+0.5% BSA before incubation with FLEX reagent (10 μM) for 2 hours at room temperature. After incubation, cells were washed 3-times in PBS+0.5% BSA before final resuspension in PBS prior to analysis by flow cytometry to measure FLEX mean fluorescence intensity (MFI) as a measure of GLP-1R expression on the cell surface. Both cell lines showed higher MFI values relative to control CHO-K1 cells, confirming GLP-1R surface expression; CHO-K1_hGLP-1Rhigh_clone16 cells showed significantly higher MFI levels relative to CHO-K1-hGLP-1low_clone10 cells.

For compound testing in the CHO-K1_hGLP-1Rlow_clone10 cell line, cells were seeded in 384-well plates (1,000 cells/well). Test compounds were serially diluted in DMSO (10-point, 3-fold dilution), added to wells using an ECHO dispenser (10 nL/well) and plates were centrifuged for 1 min and agitated for 2 min at room temperature prior to 30-minute incubation at 25° C. After incubation, Eu-cAMP (5 μL) and Ulight-anti-cAMP (5 μL) reagents were added to each well, followed by centrifugation for 1 minute, agitation for 2 minutes at room temperature, and final incubation of the plates at 25° C. for 15 minutes. Plates were read using an EnVision microplate reader (excitation=320 nm; emission=615 and 655 nm). Dose-response curves were generated from duplicate wells based on percent activation calculated relative to a control GLP-1 peptide agonist that was run in parallel. $EC_{50}$ values were determined by fitting percent activation as a function of compound concentration using the Hill equation (XLfit).

Hepatic Clearance

Hepatic clearance, or the ability of the liver to extract and metabolize a drug as it passes through the liver, is controlled by hepatic blood flow (Q), protein binding (fu) and the intrinsic ability of the liver enzymes to metabolize a drug (CLint). CLint is a measure of theoretical unrestricted maximum clearance of unbound drug by an eliminating organ, in absence of blood flow or plasma protein binding limitations. This term relates to the functional reserve of the organ. The CLint may be determined in vitro using enzyme kinetics. An in vitro hepatocyte stability assay can be conducted to determine the unrestricted maximum liver clearance of unbound test agents as compared to clearance of reference standard.

EXAMPLES

General Synthetic Procedures

Part I: Preparation of Compounds from Cores 1i, 2i, 3i, and 4i

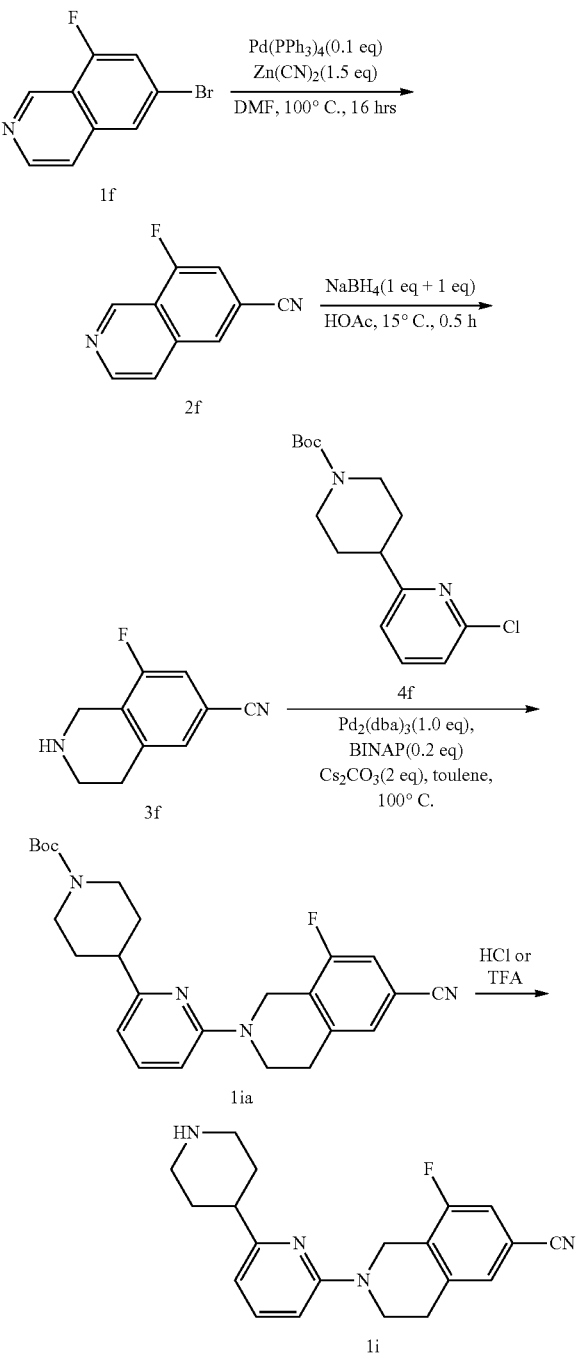

General Procedure for Preparation of Core 1i

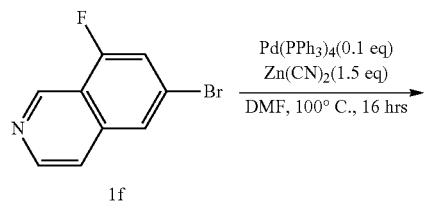

Step 1: A mixture of intermediate 1f (3.8 g, 16.81 mmol, 1 eq), Pd(PPh3)4 (1.94 g, 1.68 mmol, 0.1 eq), Zn(CN)2 (2.96 g, 25.22 mmol, 1.60 mL, 1.5 eq) in DMF (10 mL) was degassed and purged with N2 (3×), and then the mixture was stirred at 100° C. for 16 hrs under N2 atmosphere. TLC (Petroleum ether: Ethyl acetate=2:1, product Rf=0.45) showed intermediate if was consumed. The reaction was then quenched with H$_2$O (50 mL). The solution was extracted with ethyl acetate (2×50 mL) and the organic layers combined. The resulting mixture was washed with brine (2×50 mL), dried over anhydrous sodium sulfate, and concentrated under vacuum. The residue was purified by column chromatography (SiO$_2$, Petroleum ether/Ethyl acetate=100/1 to 10/1). Intermediate 2f (2.4 g, 13.94 mmol, 82.93% yield) was obtained as a white solid. LCMS: RT=0.409 min, MS cal.: 172.04, [M+H]$^+$=173.0. $^1$H NMR (400 MHz, chloroform-d) δ=9.64 (br s, 1H) 8.75-8.83 (m, 1H) 8.05 (br s, 1H) 7.70-7.81 (m, 1H) 7.43 (br d, J=9.29 Hz, 1H) 7.24-7.27 (m, 1H).

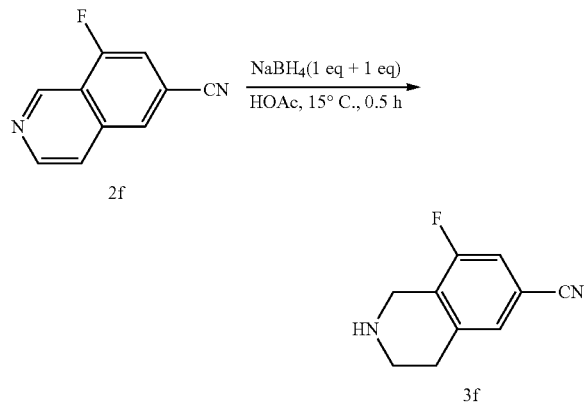

Step 2: NaBH$_4$ (417.53 mg, 11.04 mmol, 1 eq) was added to the solution of intermediate 2f (1.9 g, 11.04 mmol, 1 eq) in AcOH (10 mL) at 15° C. The solution was stirred at 15° C. for 15 min. Then NaBH$_4$ (417.53 mg, 11.04 mmol, 1 eq) was added to the solution at 15° C. The solution was stirred at 15° C. for 15 min. TLC (Petroleum ether/Ethyl acetate=2/1, product R$_f$=0.45) indicated intermediate 2f was consumed completely. The mixture was quenched with Na$_2$CO$_3$ to pH 8. The mixture was extracted with DCM (50 mL*3). The combined DCM was washed with brine (15 mL), dried over Na$_2$SO$_4$, filtered and concentrated. Intermediate 3f (1.6 g, 9.08 mmol, 82.28% yield) was obtained as a white solid. $^1$H NMR (400 MHz, chloroform-d) δ=7.24 (s, 1H) 7.15 (d, J=8.80 Hz, 1H) 4.05-4.12 (m, 2H) 3.15 (t, J=5.87 Hz, 2H) 2.85 (t, J=5.75 Hz, 2H) 1.94-1.99 (m, 1H).

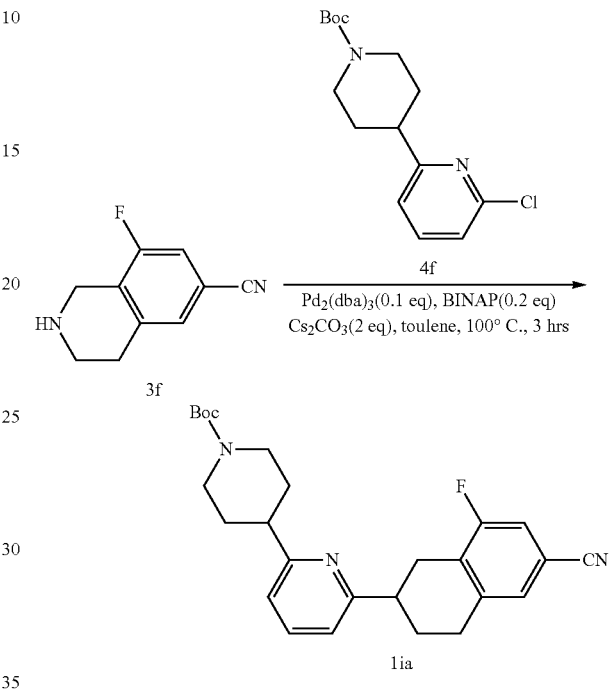

Step 3: A mixture of intermediate 3f (2 g, 6.74 mmol, 1 eq), intermediate 4f (1.42 g, 8.09 mmol, 1.2 eq), BINAP (839.20 mg, 1.35 mmol, 0.2 eq), Cs$_2$CO$_3$ (4.39 g, 13.48 mmol, 2 eq) and Pd$_2$(dba)$_3$ (617.08 mg, 673.87 mol, 0.1 eq) in toluene (80 mL) was degassed and purged with N$_2$ for 3 times, and then the mixture was stirred at 100° C. for 3 hrs under N$_2$ atmosphere. LC-MS showed intermediate 3f was consumed and one main peak with desired mass was detected. The residue was diluted with H$_2$O (20 mL) and extracted with EtOAc (50 mL*2). The combined organic layers were washed with brine (30 mL), dried over Na$_2$SO$_4$, filtered, and concentrated under reduced pressure to give a residue. The residue was purified by column chromatography (SiO$_2$, Petroleum ether/Ethyl acetate=100/1 to 0/1). The crude product was purified by reversed-phase HPLC (column: Welch Xtimate C18 250*70 mm #10 um; mobile phase: [water (10 mM NH$_4$HCO$_3$)-ACN]; B %: 55%-85%, 20 min). 1ia (7.3 g, 16.72 mmol, 82.72% yield) was obtained as a yellow solid. LCMS: RT=0.973 min, MS cal.:436.52, [M+H]$^+$=437.3 $^1$H NMR (400 MHz, chloroform-d) δ=7.44-7.53 (m, 1H) 7.29 (s, 1H) 7.21 (d, J=8.88 Hz, 1H) 6.56 (br dd, J=15.51, 7.75 Hz, 2H) 4.73 (s, 2H) 4.22 (brs, 2H) 3.93 (brd, J=5.50 Hz, 2H) 3.03-3.04 (m, 1H) 2.99 (brs, 2H) 2.85 (brt, J=11.57 Hz, 2H) 2.71 (br s, 1H) 1.90 (br d, J=12.51 Hz, 2H) 1.65-1.79 (m, 2H) 1.59 (s, 1H) 1.50 (s, 9H).

Deprotection of 1ia to secondary amine 1i was carried out immediately prior to use under acidic conditions similar to those described for the preparation of intermediate 3i.

General Scheme for Preparation of Core 2i

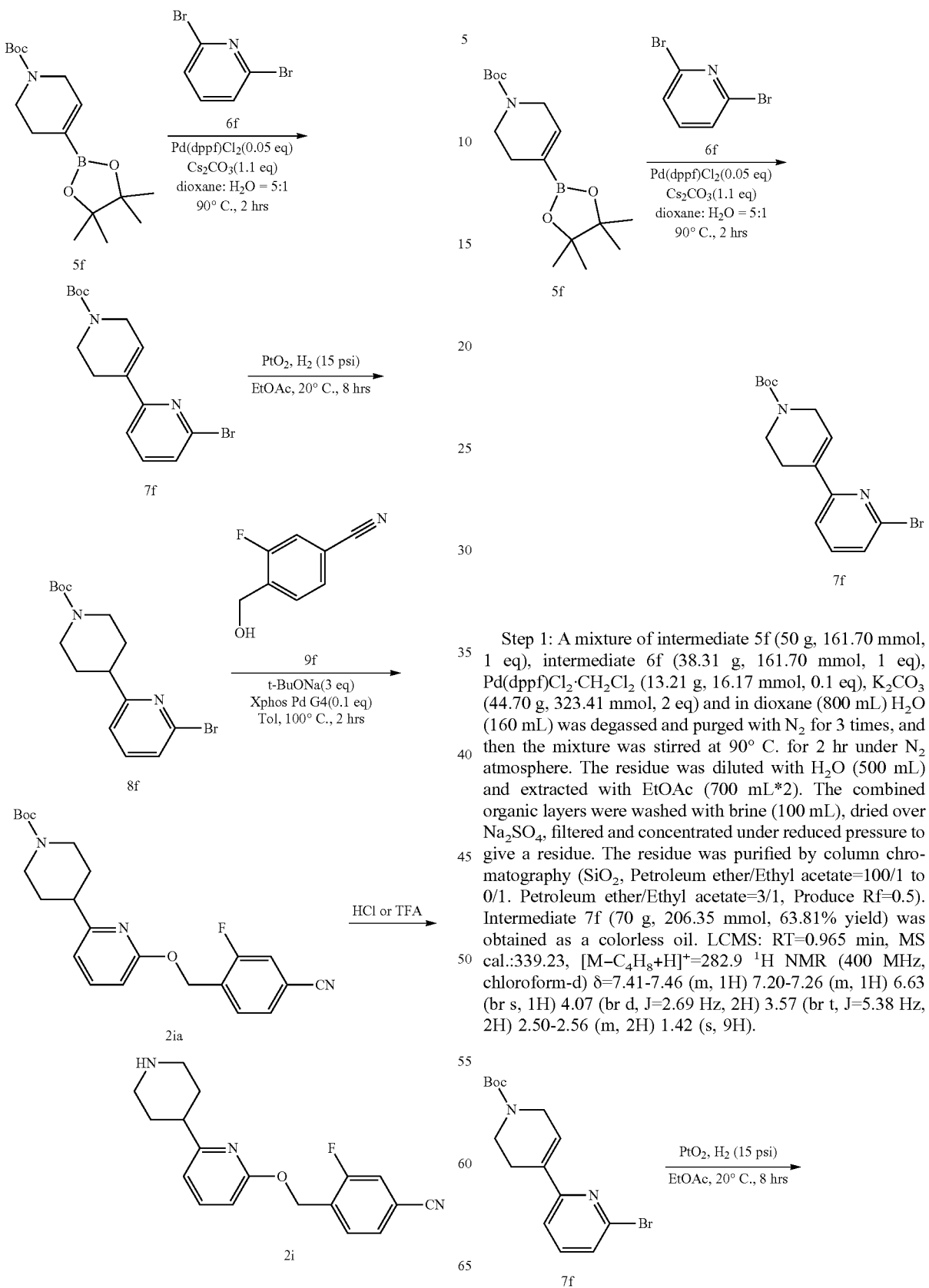

Step 1: A mixture of intermediate 5f (50 g, 161.70 mmol, 1 eq), intermediate 6f (38.31 g, 161.70 mmol, 1 eq), Pd(dppf)Cl$_2$·CH$_2$Cl$_2$ (13.21 g, 16.17 mmol, 0.1 eq), K$_2$CO$_3$ (44.70 g, 323.41 mmol, 2 eq) and in dioxane (800 mL) H$_2$O (160 mL) was degassed and purged with N$_2$ for 3 times, and then the mixture was stirred at 90° C. for 2 hr under N$_2$ atmosphere. The residue was diluted with H$_2$O (500 mL) and extracted with EtOAc (700 mL*2). The combined organic layers were washed with brine (100 mL), dried over Na$_2$SO$_4$, filtered and concentrated under reduced pressure to give a residue. The residue was purified by column chromatography (SiO$_2$, Petroleum ether/Ethyl acetate=100/1 to 0/1. Petroleum ether/Ethyl acetate=3/1, Produce Rf=0.5). Intermediate 7f (70 g, 206.35 mmol, 63.81% yield) was obtained as a colorless oil. LCMS: RT=0.965 min, MS cal.:339.23, [M−C$_4$H$_8$+H]$^+$=282.9 $^1$H NMR (400 MHz, chloroform-d) δ=7.41-7.46 (m, 1H) 7.20-7.26 (m, 1H) 6.63 (br s, 1H) 4.07 (br d, J=2.69 Hz, 2H) 3.57 (br t, J=5.38 Hz, 2H) 2.50-2.56 (m, 2H) 1.42 (s, 9H).

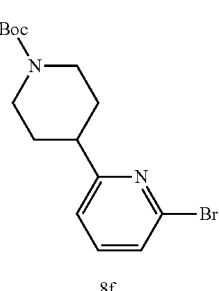

8f

Step 2: To a mixture of intermediate 7f (15 g, 44.22 mmol, 1 eq) in EtOAc (200 mL) was added PtO$_2$ (3.13 g, 13.76 mmol) under N$_2$. The suspension was degassed under vacuum and purged with H$_2$ several times. The mixture was stirred under H$_2$ (15 psi) at 20° C. for 8 hrs. LC-MS showed intermediate 7f was consumed completely and one main peak with desired mass was detected. The reaction mixture was filtered, and the filtrate was concentrated. The residue was purified by column chromatography (SiO$_2$, Petroleum ether/Ethyl acetate=100/1 to 0/1, TLC-Petroleum ether/Ethyl acetate=3/1, Produce R$_f$=0.5). Intermediate 8f (5 g, 14.65 mmol, 16.57% yield) was obtained as a yellow colorless oil. LCMS: RT=0.982 min, MS cal.:341.24, [M−C$_4$H$_8$+H]$^+$=285.0 $^1$H NMR (400 MHz, chloroform-d) δ=7.44-7.51 (m, 1H) 7.32 (d, J=7.88 Hz, 1H) 7.10 (d, J=7.63 Hz, 1H) 4.24 (br s, 2H) 2.74-2.89 (m, 3H) 1.92 (br d, J=12.88 Hz, 2H) 1.59-1.75 (m, 2H) 1.47 (s, 9H)

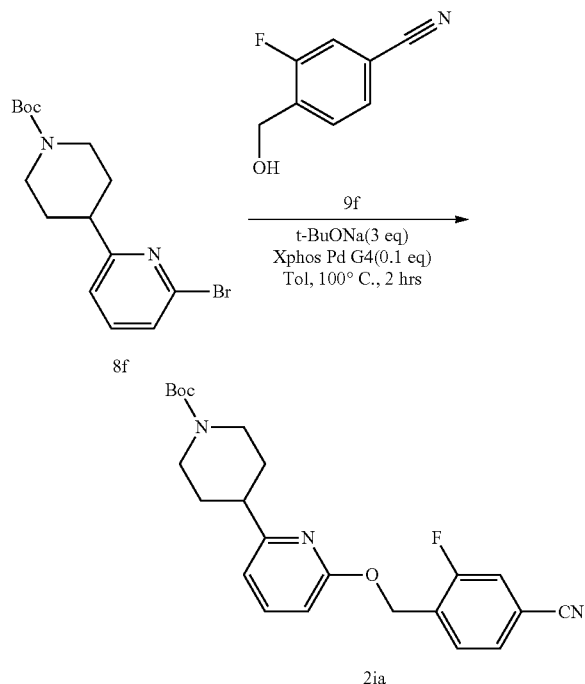

Step 3: A mixture of intermediate 8f (10 g, 29.30 mmol, 1 eq), intermediate 9f (5.31 g, 35.17 mmol, 1.2 eq), t-BuONa (8.45 g, 87.91 mmol, 3 eq), Xphos Pd G4 (2.52 g, 2.93 mmol, 0.1 eq) in toluene (100 mL) was degassed and purged with N$_2$ 3 times, and then the mixture was stirred at 100° C. for 2 hrs under N$_2$ atmosphere. LC-MS showed intermediate 8f was consumed completely and one main peak with desired mass was detected. The residue was diluted with H$_2$O (30 mL) and extracted with EtOAc (50 mL*2). The combined organic layers were washed with brine (10 mL), dried over Na$_2$SO$_4$, filtered and concentrated under reduced pressure to give a residue. The residue was purified by column chromatography (SiO$_2$, Petroleum ether/Ethyl acetate=100/1 to 10/1, TLC-Petroleum ether/Ethyl acetate=3/1, Produce R$_f$=0.5). Intermediate 2ia (6.8 g, 16.53 mmol, 56.39% yield) was obtained as a wine-red solid. LCMS: RT=1.049 min, MS cal.:411.47, [M−C$_4$H$_8$+H]$^+$=356.2 $^1$H NMR (400 MHz, chloroform-d) δ=7.62 (t, J=7.50 Hz, 1H) 7.54 (t, J=7.75 Hz, 1H) 7.45 (d, J=8.00 Hz, 1H) 7.38 (d, J=9.26 Hz, 1H) 6.75 (d, J=7.25 Hz, 1H) 6.66 (d, J=8.25 Hz, 1H) 5.50 (s, 2H) 4.21 (br s, 1H) 4.16-4.30 (m, 1H) 4.12 (q, J=7.13 Hz, 1H) 2.82 (br t, J=12.19 Hz, 1H) 2.71 (tt, J=11.79, 3.66 Hz, 1H) 2.65-2.88 (m, 1H) 2.05 (s, 1H) 1.83 (br d, J=12.51 Hz, 2H) 1.65-1.71 (m, 2H) 1.49 (s, 9H) 1.26 (t, J=7.19 Hz, 1H).

Deprotection of 2ia to secondary amine 2i was carried out immediately prior to use under acidic conditions similar to those described for the preparation of intermediate 3i.

Scheme 3: General scheme for preparation of core 3i

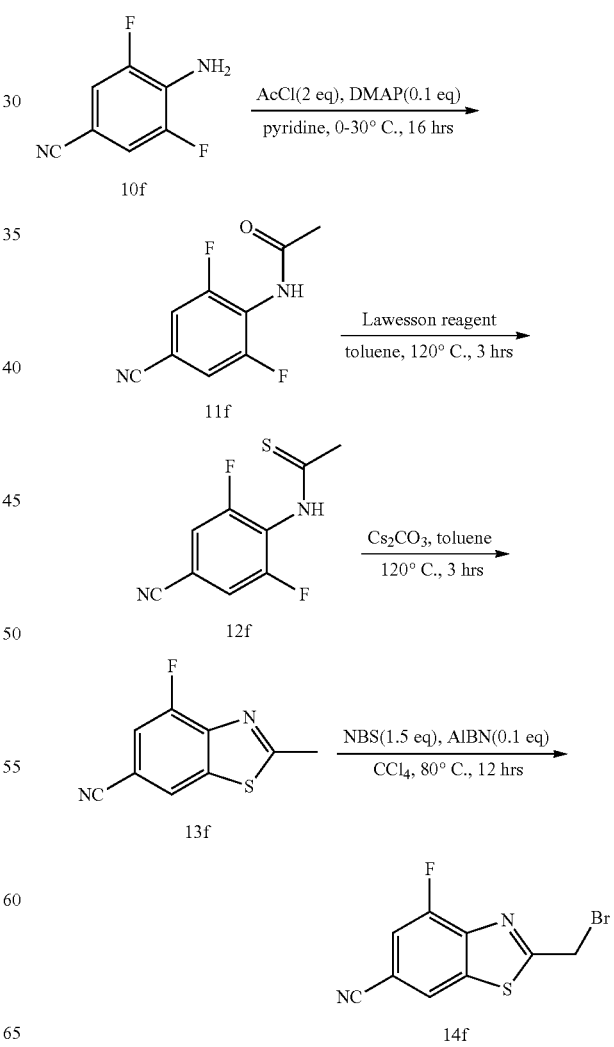

-continued

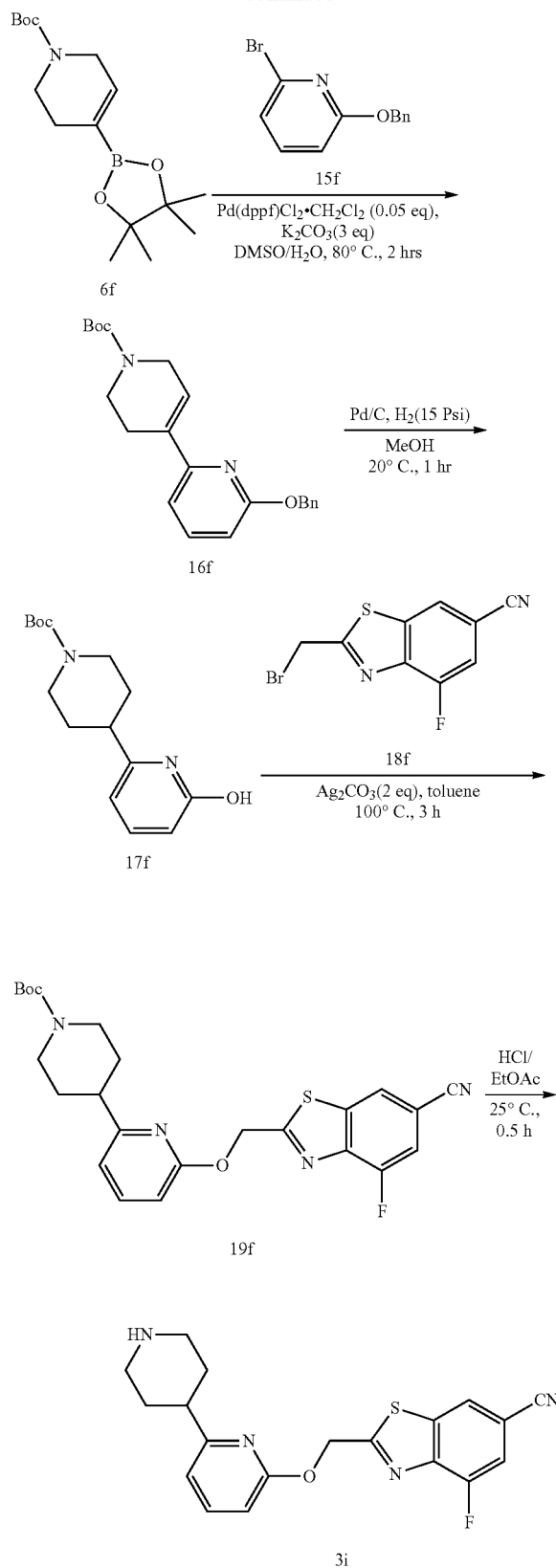

General Procedure for Preparation of Core 3i

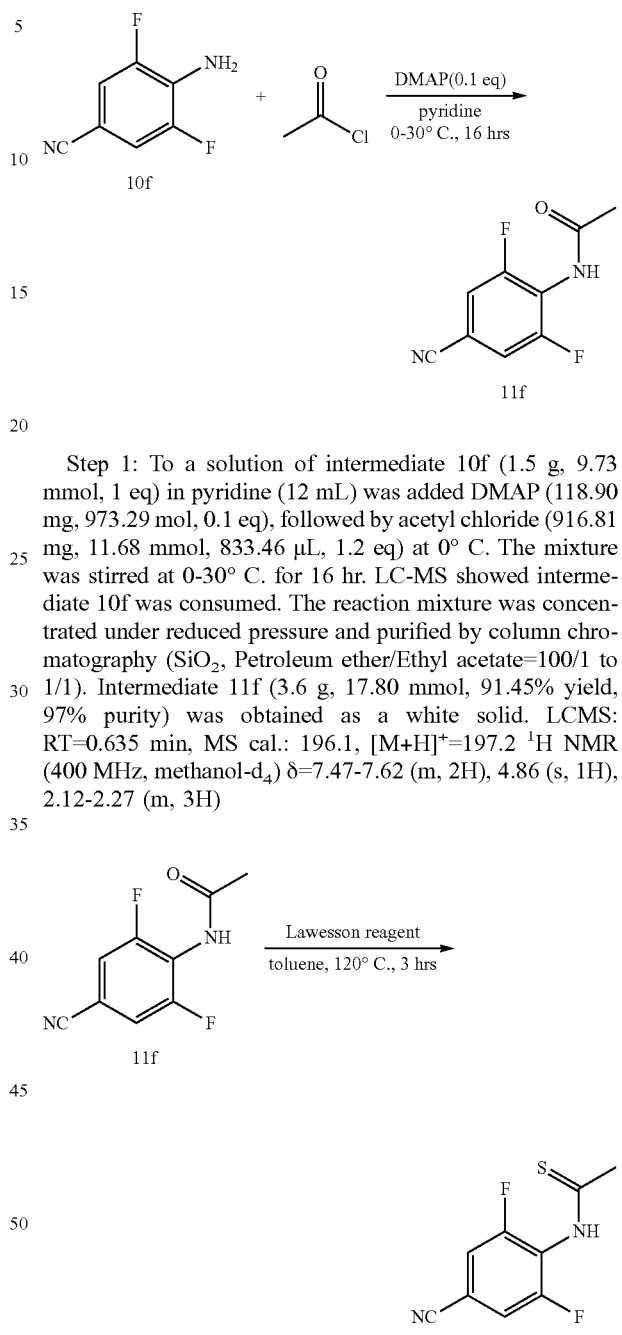

Step 1: To a solution of intermediate 10f (1.5 g, 9.73 mmol, 1 eq) in pyridine (12 mL) was added DMAP (118.90 mg, 973.29 mol, 0.1 eq), followed by acetyl chloride (916.81 mg, 11.68 mmol, 833.46 μL, 1.2 eq) at 0° C. The mixture was stirred at 0-30° C. for 16 hr. LC-MS showed intermediate 10f was consumed. The reaction mixture was concentrated under reduced pressure and purified by column chromatography (SiO$_2$, Petroleum ether/Ethyl acetate=100/1 to 1/1). Intermediate 11f (3.6 g, 17.80 mmol, 91.45% yield, 97% purity) was obtained as a white solid. LCMS: RT=0.635 min, MS cal.: 196.1, [M+H]$^+$=197.2 $^1$H NMR (400 MHz, methanol-d$_4$) δ=7.47-7.62 (m, 2H), 4.86 (s, 1H), 2.12-2.27 (m, 3H)

Step 2: A mixture of intermediate 11f (1.3 g, 6.63 mmol, 1 eq), Lawesson's reagent (1.61 g, 3.98 mmol, 0.6 eq) in toluene (20 mL) was degassed and purged with N$_2$ for 3 times, and then the mixture was stirred at 120° C. for 3 hr under N$_2$ atmosphere. TLC (Petroleum ether/EtOAc=5:1) indicated the clean consumption of intermediate 11f to a single new intermediate. The crude product was used without purification directly in the next step. Crude Intermediate 12f (2.81 g, 13.24 mmol, 100.00% yield) was obtained as a yellow liquid.

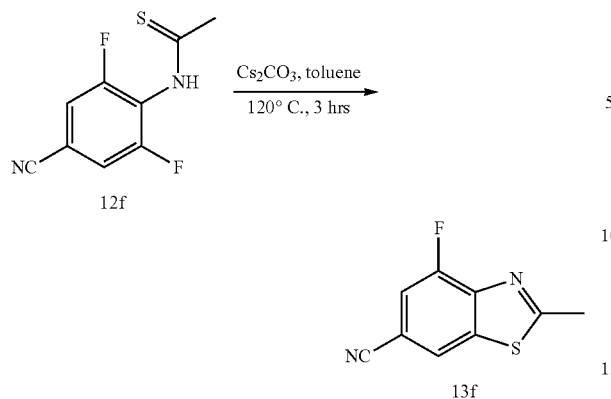

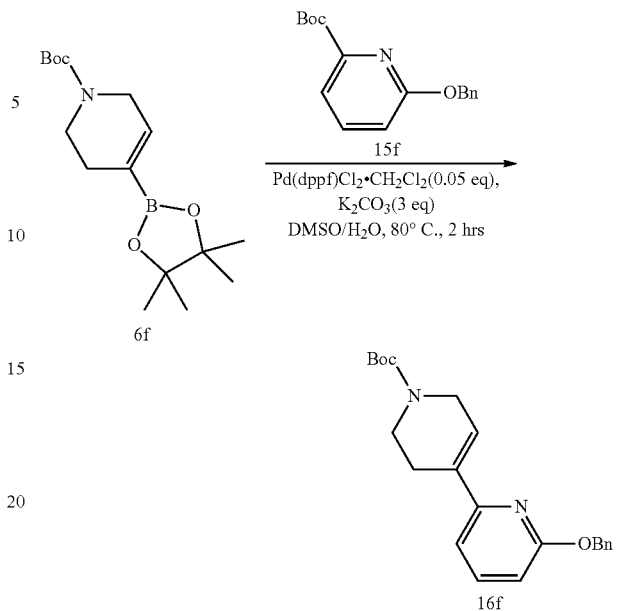

Step 2: To a solution of intermediate 12f (1.4 g, 6.60 mmol, 1 eq) in toluene (20 mL) was added Cs$_2$CO$_3$ (5.37 g, 16.49 mmol, 2.5 eq). The mixture was stirred at 120° C. for 3 hr. The residue was diluted with H$_2$O (10 mL) and extracted with EtOAc (15 mL*3). The reaction mixture was separated, dried over Na$_2$SO$_4$, filtered, and concentrated under reduced pressure to give a residue. The residue was purified by column chromatography (SiO$_2$, Petroleum ether/Ethyl acetate=100/1 to 1/1). Intermediate 13f (2 g, 10.41 mmol, 78.86% yield) was obtained as a white solid. LCMS: RT=0.789 min, MS cal.: 192.2, [M+H]$^+$=193.2. $^1$H NMR (400 MHz, chloroform-d) δ=7.97-7.99 (m, 1H), 7.44 (dd, J=1.38, 9.63 Hz, 1H), 2.94 (s, 3H).

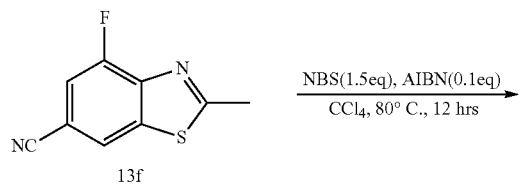

Step 4: A mixture of intermediate 6f (2.8 g, 9.06 mmol, 1 eq), intermediate 15f (2.63 g, 9.96 mmol, 1.1 eq), Pd(dppf)Cl$_2$·CH$_2$Cl$_2$ (369.75 mg, 452.77 mol, 0.05 eq), K$_2$CO$_3$ (3.75 g, 27.17 mmol, 3 eq) in DMSO (15 mL) and H$_2$O (1.5 mL) was degassed and purged with N$_2$ for 3 times, and then the mixture was stirred at 80° C. for 2 hr under N$_2$ atmosphere. The reaction mixture was diluted with H$_2$O 10 mL and extracted with EtOAc (10 mL*3). The combined organic layers were washed with NaCl (5 mL), dried over Na$_2$SO$_4$, filtered and concentrated under reduced pressure to give a residue. The residue was purified by column chromatography (SiO$_2$, Petroleum ether/Ethyl acetate=100/1 to 1/1). Intermediate 16f (2.7 g, 7.37 mmol, 81.37% yield, 100% purity) was obtained as a colorless oil. $^1$H NMR (400 MHz, chloroform-d) δ=7.56 (t, J=7.82 Hz, 1H), 7.47 (d, J=7.21 Hz, 2H), 7.39 (t, J=7.27 Hz, 2H), 7.29-7.35 (m, 1H), 6.95 (d, J=7.46 Hz, 1H), 6.67-6.76 (m, 2H), 5.43 (s, 2H), 4.15 (br d, J=1.83 Hz, 2H), 3.66 (br s, 2H), 2.62 (br s, 2H), 1.51 (s, 9H)

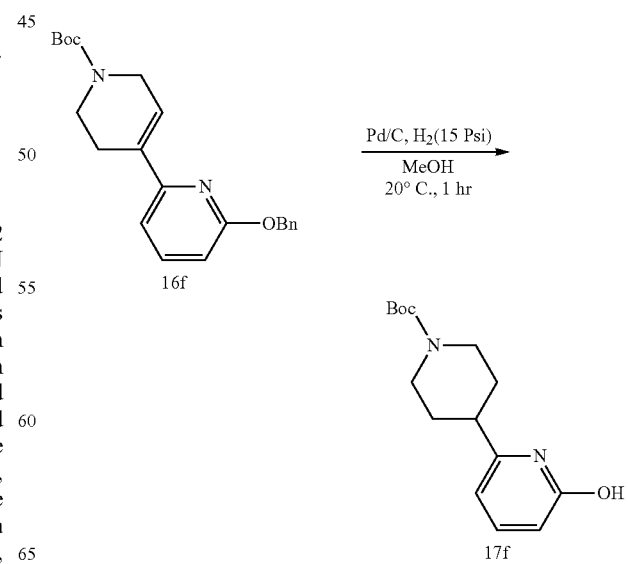

Step 3: A mixture of intermediate 13f (600 mg, 3.12 mmol, 1 eq), NBS (833.38 mg, 4.68 mmol, 1.5 eq), AIBN (51.26 mg, 312.15 mol, 0.1 eq) in CCl$_4$ (6 mL) was degassed and purged with N$_2$ for 3 times, and then the mixture was stirred at 80° C. for 12 hr under N$_2$ atmosphere. The reaction mixture was diluted with H$_2$O (30 mL) and extracted with DCM (30 mL*3). The combined organic layers were washed with NaCl a.q. (10 mL*3), dried over Na$_2$SO$_4$, filtered, and concentrated under reduced pressure to give a residue. The residue was purified by column chromatography (SiO$_2$, Petroleum ether/Ethyl acetate=100/1 to 1/1). Intermediate 14f (400 mg, 1.48 mmol, 16.68% yield) was obtained as a white solid. LCMS: RT=0.719 min, MS cal.: 271.1, [M+H]$^+$=272.1 $^1$H NMR (400 MHz, chloroform-d) δ=8.04 (s, 1H), 7.49 (dd, J=1.21, 9.54 Hz, 1H), 4.85 (s, 2H).

Step 5: To a solution of intermediate 16f (1.3 g, 3.55 mmol, 1 eq) in MeOH (15 mL) was added Pd/C (300 mg, 10% purity). The mixture was stirred under H₂ (15 psi) at 20° C. for 1 hr. LC-MS showed intermediate 16f was consumed completely and desired mass was detected. The reaction mixture was filtered, and the pad cake was washed with DCM (20 mL*3). The mixture was concentrated under reduced pressure to give a residue. Intermediate 17f (1.7 g, 6.11 mmol, 86.08% yield) was obtained as a white solid. LCMS: RT=0.857 min, MS cal.: 278.3, [M+H]⁺=279.4

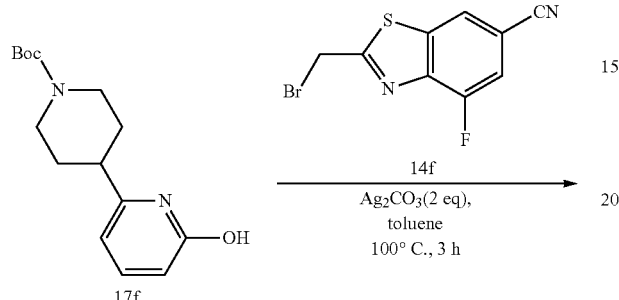

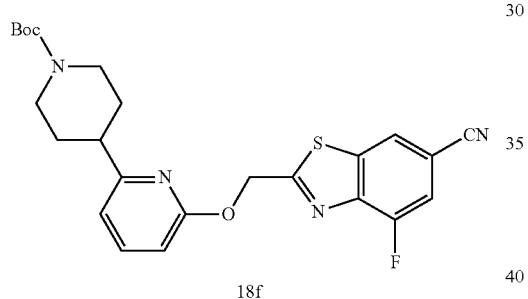

Step 6: A mixture of intermediate 17f (410 mg, 1.47 mmol, 1 eq), intermediate 14f (399.34 mg, 1.47 mmol, 1 eq), Ag₂CO₃ (812.34 mg, 2.95 mmol, 2 eq), in toluene (7 mL) was degassed and purged with N₂ for 3 times, and then the mixture was stirred at 100° C. for 3 hr under N₂ atmosphere. LC-MS showed intermediate 17f was consumed completely and one main peak with desired. The reaction mixture was diluted with H₂O (20 mL) and extracted with EtOAc (20 mL*3). The combined organic layers were washed with NaCl (10 mL*3), dried over Na₂SO₄, filtered and concentrated under reduced pressure to give a residue. The residue was purified by column chromatography (SiO₂, Petroleum ether/Ethyl acetate=100/1 to 1/1). Intermediate 18f (330 mg, 704.31 mol, 47.82% yield) was obtained as a yellow solid. LCMS: RT=1.056 min, MS cal.: 468.5, [M+H]⁺=469.5 ¹H NMR (400 MHz, chloroform-d) δ=8.02 (s, 1H), 7.62 (t, J=7.78 Hz, 1H), 7.47 (dd, J=1.21, 9.54 Hz, 1H), 6.74-6.87 (m, 2H), 5.88 (s, 2H), 4.20 (br d, J=12.28 Hz, 2H), 2.69-2.87 (m, 3H), 1.86 (br d, J=12.50 Hz, 2H), 1.67 (dq, J=4.28, 12.53 Hz, 2H), 1.48 (s, 9H).

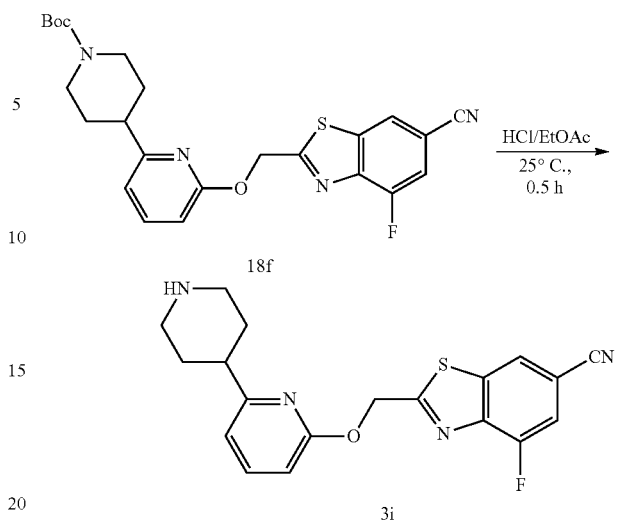

Step 7: A mixture of intermediate 18f (190 mg, 405.51 mol, 1 eq), HCl/EtOAc (4 M, 2.85 mL, 28.11 eq), in EtOAc (2 mL) was degassed and purged with N₂ 3 times, and then the mixture was stirred at 25° C. for 0.5 hr under N₂ atmosphere. LC-MS showed intermediate 18f was consumed completely and one main peak with desired. The reaction mixture was concentrated under reduced pressure. Core 3i (150 mg, 370.47 mol, 91.36% yield, as HCl salt) was obtained as a white solid. LCMS: RT=0.735 min, MS cal.: 368.1, [M+H]⁺=369.1H NMR (400 MHz, DMSO-d₆) δ=8.91 (br s, 1H), 8.69 (br s, 1H), 8.60 (d, J=1.10 Hz, 1H), 8.01 (dd, J=1.28, 10.57 Hz, 1H), 7.78 (t, J=7.82 Hz, 1H), 6.86-7.01 (m, 2H), 5.89 (s, 2H), 3.29 (br d, J=12.59 Hz, 2H), 2.88-3.02 (m, 3H), 1.97 (br d, J=14.79 Hz, 2H), 1.79-1.91 (m, 2H).

Scheme 4: General Scheme for preparation of intermediate core 4i

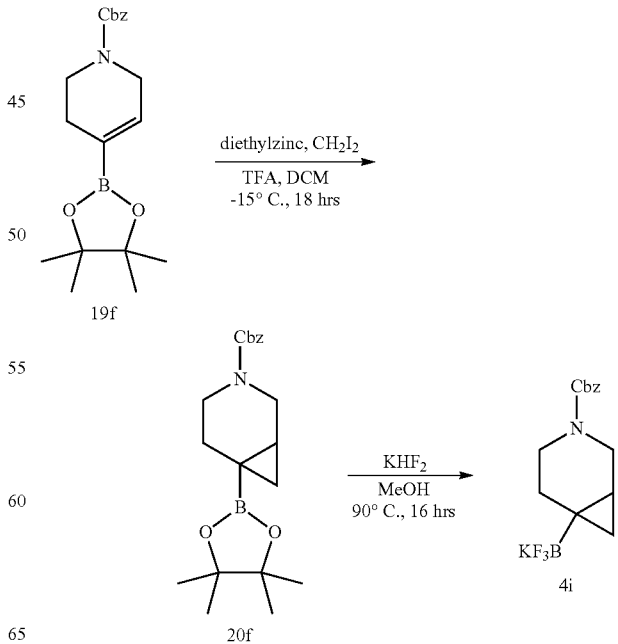

General Procedure for Preparation of Intermediate 20f

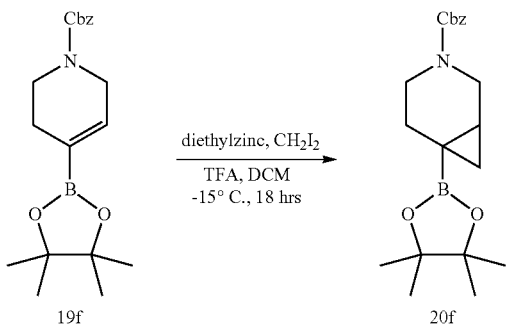

Step 1: To a solution of diethylzinc (1 M, 303.01 mL, 8 eq) in DCM (50 mL) was added TFA (34.55 g, 303.01 mmol, 22.44 mL, 8 eq) in DCM (50 mL) slowly at −15° C. and the mixture was stirred at −15° C. for 1 hour. $CH_2I_2$ (162.31 g, 606.02 mmol, 48.89 mL, 16 eq) in DCM (50 mL) was added to the mixture at −15° C. and the mixture was stirred at −15° C. for 1 hour. Then intermediate 19f (13 g, 37.88 mmol, 1 eq) in DCM (50 mL) was added to the reaction mixture slowly at −15° C. and the mixture was stirred at 25° C. for 16 hours. The mixture was quenched with $NaCO_3$ to pH 8. The reaction mixture was filtered, and the filter was extracted with DCM (300 mL*3). The combined DCM layers were washed with brine (500 mL), dried over $Na_2SO_4$, filtered and concentrated. The residue was purified by column chromatography ($SiO_2$, Petroleum ether/Ethyl acetate=100/1 to 0/1). Intermediate 20f (9 g, 25.19 mmol, 66.51% yield) was obtained as a yellow oil. $^1$H NMR (400 MHz, chloroform-d) δ ppm 7.28-7.40 (m, 5H) 5.11-5.16 (m, 2H) 3.83-3.96 (m, 1H) 3.43-3.67 (m, 2H) 2.87-3.05 (m, 1H) 2.07-2.17 (m, 1H) 1.49-1.61 (m, 1H) 1.21 (s, 13H) 0.91 (br s, 1H) 0.41-0.48 (m, 1H).

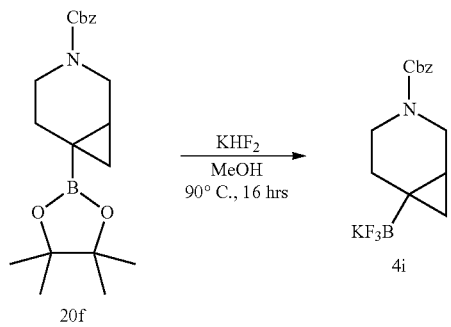

Step 2: To a solution of intermediate 20f (9 g, 25.19 mmol, 1 eq) in MeOH (90 mL) was added $KHF_2$ (13.77 g, 176.35 mmol, 5.81 mL, 7 eq) at 25° C. The mixture was stirred at 90° C. for 16 hours. The reaction mixture was concentrated under reduced pressure to remove MeOH. The solid was triturated with a solution of Petroleum ether: MTBE=5:1 (30 mL).

The mixture was filtered; the filter cake was dried in vacuum to give crude product as a white solid. The crude product was dissolved in hot MeCN (50 mL) and filtered. The filtrate was concentrated under reduced pressure to give a white solid. Core 4i (6.4 g, 18.98 mmol, 75.34% yield, K$^+$) was obtained as a white solid. LCMS: RT=0.779 min, MS cal.: 337.19, [M+H]$^+$=276.0 $^1$H NMR (400 MHz, DMSO-d$_6$) δ ppm 7.26-7.40 (m, 5H) 4.98-5.08 (m, 2H) 3.44-3.62 (m, 2H) 3.10-3.25 (m, 1H) 2.88-3.03 (m, 1H) 1.75-1.87 (m, 1H) 1.22-1.37 (m, 1H) 0.62 (br s, 1H) 0.25 (br d, J=5.50 Hz, 1H) −0.25 (br s, 1H).

Scheme 5: General scheme for the preparation of compounds from Cores 1i, 2i, and 3i.

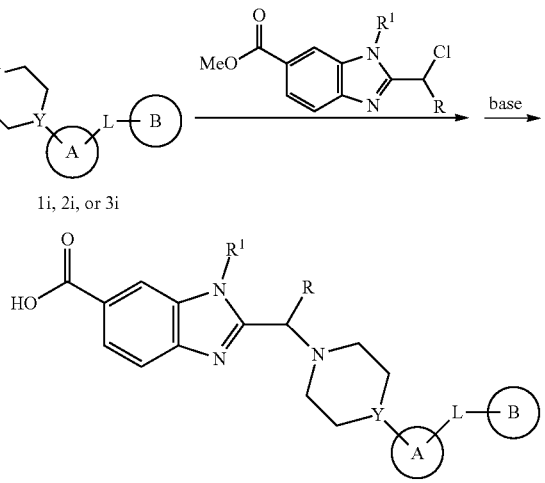

Scheme 6: General scheme for the preparation of compounds from Core 4i.

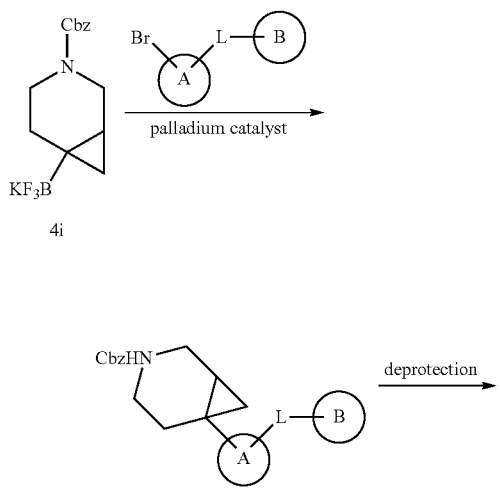

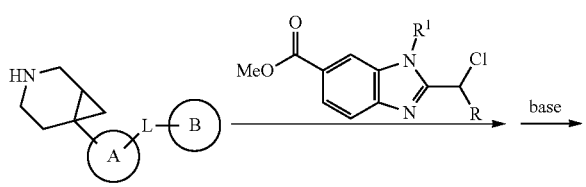

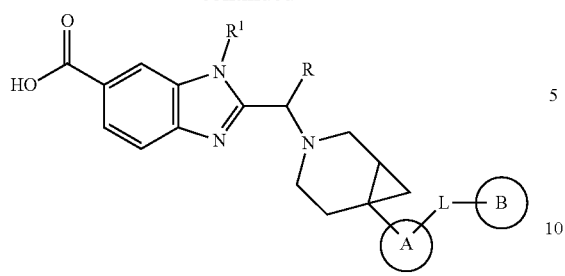
Part II: Synthetic Examples
Example 1: Preparation of Compound 2
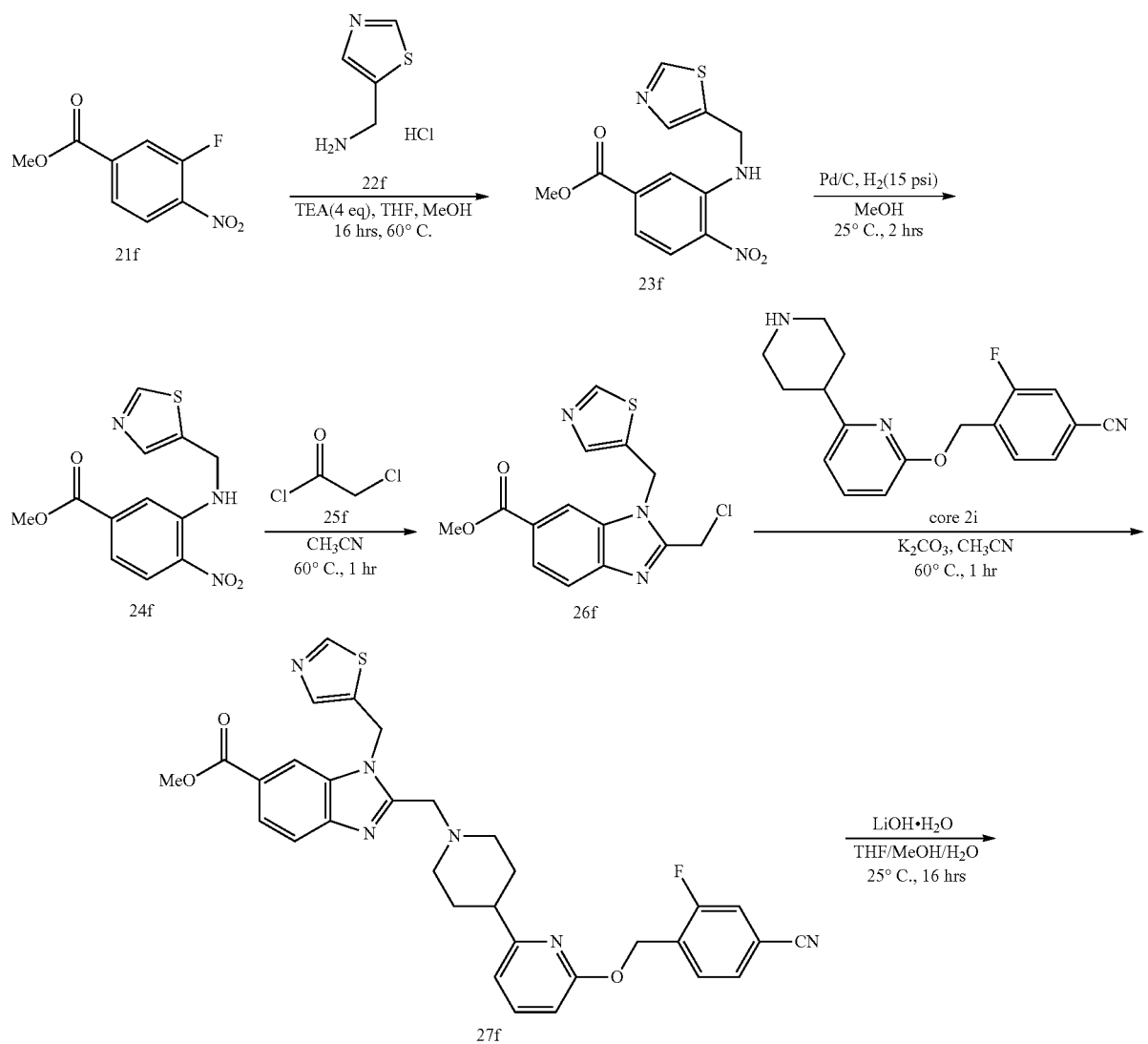

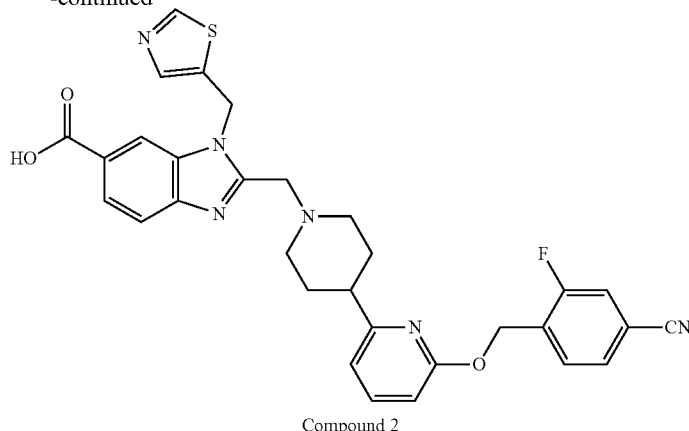

Compound 2

Step 1: Preparation of Intermediate 23f

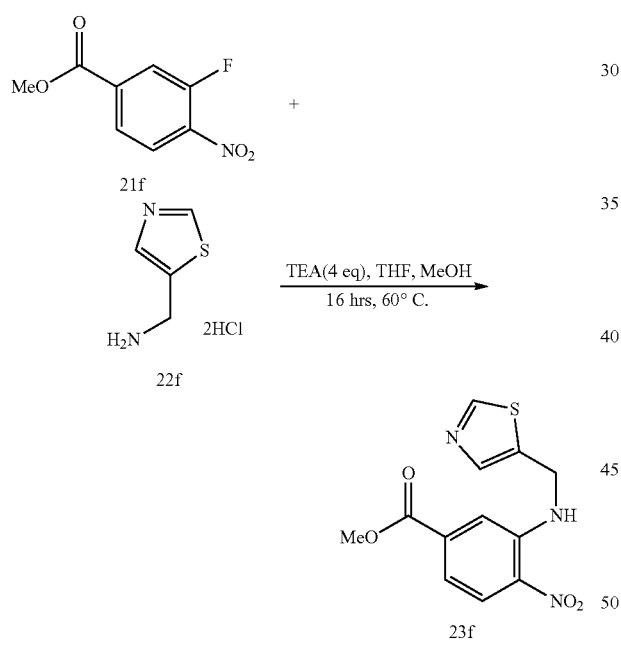

A mixture of intermediate 21f (1 g, 5.02 mmol, 1 eq), intermediate 22f (939.51 mg, 5.02 mmol, 1 e q, 2HCl), TEA (2.03 g, 20.09 mmol, 2.80 mL, 4 eq), in THF (10 mL) and MeOH (7.5 mL) was degassed and purged with N₂ for 3 times, and then the mixture was stirred at 60° C. for 16 h under N₂ atmosphere. The reaction mixture was diluted with H₂O (100 mL) and extracted with EtOAc (100 mL*3), dried over Na₂SO₄, filtered and concentrated under reduced pressure to give a residue. The residue was purified by column chromatography (SiO₂, Petroleum ether/Ethyl acetate=100/1 to 1/1). Intermediate 23f (2.68 g, 9.14 mmol, 90.98% yield) was obtained as a yellow solid. LCMS: RT=0.694 min, MS cal.: 293.1, [M+H]⁺=294.1 ¹H NMR (400 MHz, chloroform-d) δ=8.81 (s, 1H), 8.24-8.34 (m, 2H), 7.92 (s, 1H), 7.64 (d, J=1.59 Hz, 1H), 7.35 (dd, J=1.65, 8.86 Hz, 1H), 7.27 (s, 1H), 4.86 (d, J=5.26 Hz, 2H), 3.95 (s, 3H), 2.19 (br s, 1H).

Step 2: Preparation of Intermediate 24f

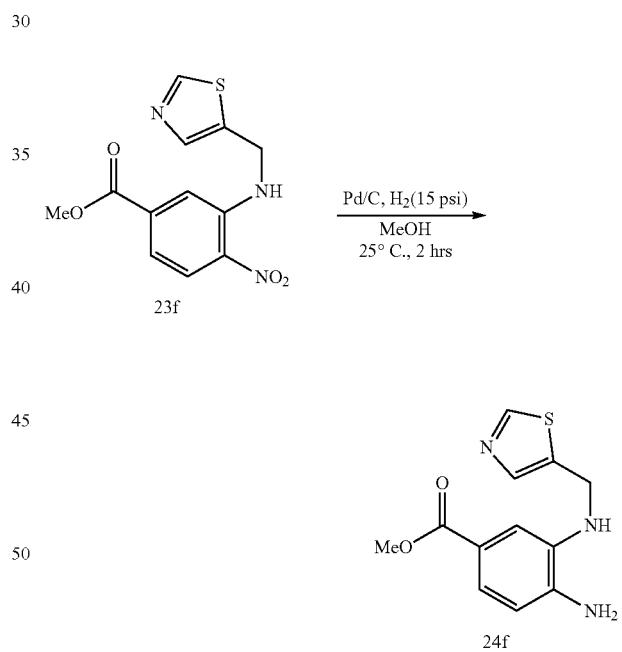

A mixture of intermediate 23f (500 mg, 1.70 mmol, 1 eq), Pd/C (125 mg, 1.70 mmol, 10 wt %, 1 eq), in MeOH (5 mL) was degassed and purged with H₂ for 3 times, and then the mixture was stirred at 25° C. for 2 h under H₂ atmosphere. The reaction mixture was filtered, and the filtrate was concentrated under reduced pressure to give a residue. Intermediate 24f (860 mg, 3.27 mmol, 95.79% yield) was obtained as a green solid. LCMS: RT=0.614 min, MS cal.: 263.1, [M+H]⁺=264.0 ¹H NMR (400 MHz, chloroform-d) δ=8.77 (s, 1H), 7.87 (s, 1H), 7.54 (td, J=0.86, 8.07 Hz, 1H), 7.46 (s, 1H), 6.73 (d, J=8.19 Hz, 1H), 4.60 (s, 2H), 3.87 (s, 3H).

Step 3: Preparation of Intermediate 26f

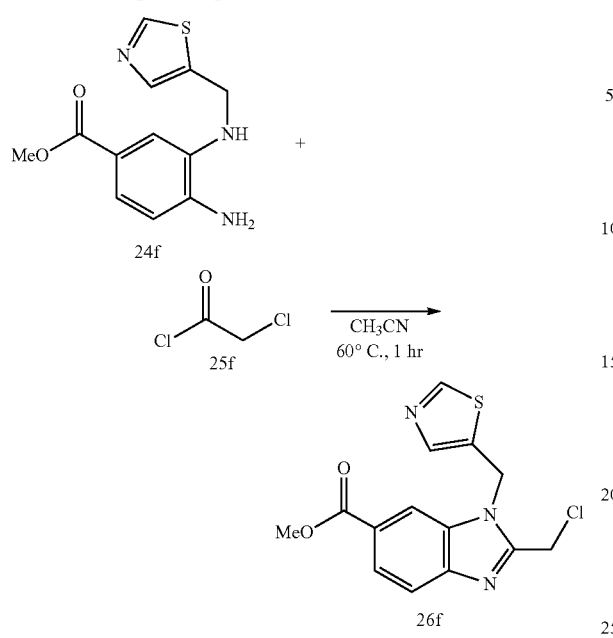

A mixture of intermediate 24f (160 mg, 607.64 mol, 1 eq), intermediate 25f (54.90 mg, 486.11 mol, 38.66 µL, 0.8 eq), p-TsOH (20.93 mg, 121.53 mol, 0.2 eq), in $CH_3CN$ (3 mL) was degassed and purged with $N_2$ for 3 times, and then the mixture was stirred at 60° C. for 1 h under $N_2$ atmosphere. The reaction mixture was concentrated under reduced pressure to give a residue. Intermediate 26f (192 mg, 596.68 mol, 98.20% yield) was obtained as a white solid. LCMS: RT=0.633 min, MS cal.: 321.0, [M+H]$^+$=322.1

Step 4: Preparation of Intermediate 27f

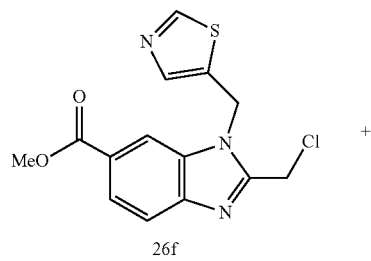

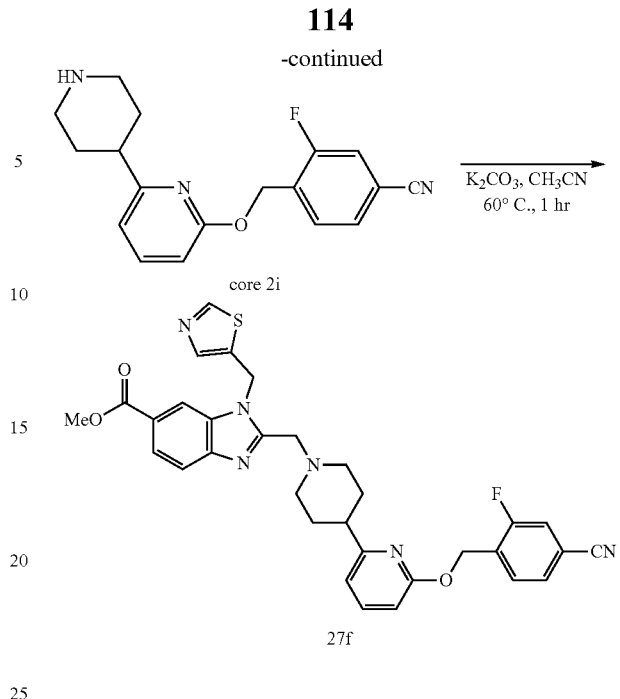

A mixture of intermediate 26f (200 mg, 642.36 mol, 1 eq), core 2i (190 mg, 590.46 mol, 9.19e-1 eq), and $K_2CO_3$ (266.33 mg, 1.93 mmol, 3 eq), in $CH_3CN$ (4 mL) was degassed and purged with $N_2$ for 3 times, and then the mixture was stirred at 60° C. for 1 h under $N_2$ atmosphere. The reaction mixture was diluted with $H_2O$ (80 mL) and extracted with EtOAc (40 mL*3), dried over $Na_2SO_4$, filtered and concentrated under reduced pressure to give a residue. The residue was purified by column chromatography ($SiO_2$, Petroleum ether/Ethyl acetate=100/1 to 1/1). Intermediate 27f (260 mg, 435.75 mol, 67.84% yield) was obtained as a green solid. LCMS: RT=0.790 min, MS cal.: 596.2, [M+H]$^+$=597.2 $^1$H NMR (400 MHz, chloroform-d) δ=8.75 (s, 1H), 8.15 (s, 1H), 8.01 (br d, J=8.51 Hz, 1H), 7.87 (s, 1H), 7.78 (d, J=8.51 Hz, 1H), 7.64 (br t, J=7.44 Hz, 1H), 7.52-7.57 (m, 1H), 7.45 (d, J=8.25 Hz, 1H), 7.37 (dd, J=1.31, 9.32 Hz, 1H), 6.76 (d, J=7.38 Hz, 1H), 6.66 (d, J=8.13 Hz, 1H), 5.51 (s, 2H), 3.96 (s, 4H), 3.86-3.92 (m, 1H), 2.89-3.07 (m, 2H), 2.63 (br s, 1H), 2.24-2.38 (m, 2H), 2.03-2.14 (m, 1H), 1.68-1.94 (m, 3H), 1.22-1.32 (m, 1H).

Step 5: Preparation of Compound 2

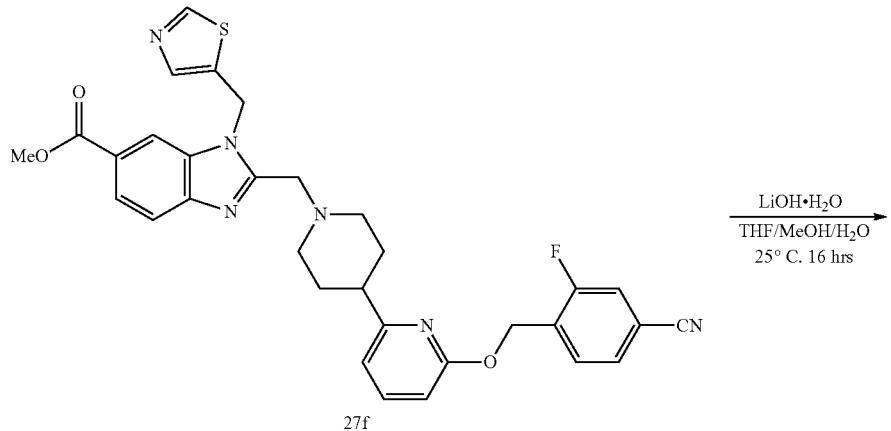

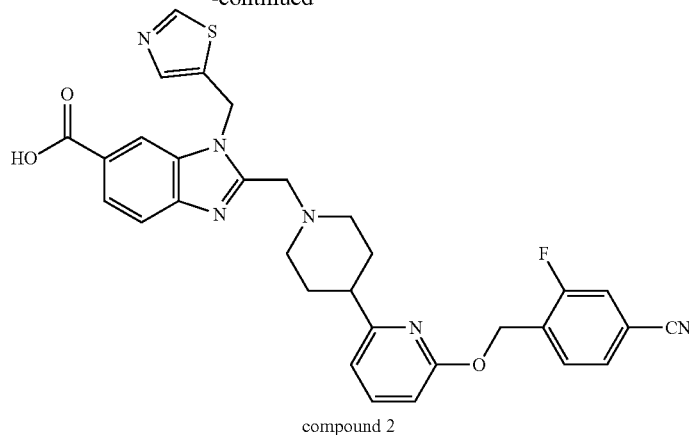

compound 2

A mixture of intermediate 27f (120 mg, 201.12 mol, 1 eq), LiOH H$_2$O (25.32 mg, 603.35 mol, 3 eq) and MeOH/H$_2$O (0.3 mL), in THF (0.7 mL) was degassed and purged with N$_2$ for 3 times, and then the mixture was stirred at 25° C. for 16 h under N$_2$ atmosphere. The reaction solution was adjusted with citric acid to a pH of 7, The reaction mixture was concentrated under reduced pressure. The residue was purified by prep-HPLC (TFA condition column: Waters Xbridge BEH C18 100*30 mm*10 um; mobile phase: [water (10 mM NH$_4$HCO$_3$)-ACN]; B %: 20%-50%, 8 min). Compound 2 (36.22 mg, 62.16 mol, 30.91% yield) was obtained as a white solid. LCMS: RT=1.573 min, MS cal.: 582.2, [M+H]$^+$=583.2 $^1$H NMR (400 MHz, methanol-d$_4$) δ=8.92 (s, 1H), 8.18 (s, 1H), 7.95-7.99 (m, 2H), 7.62-7.69 (m, 2H), 7.53-7.61 (m, 3H), 6.81 (d, J=7.21 Hz, 1H), 6.67 (d, J=8.19 Hz, 1H), 6.00 (s, 2H), 5.51 (s, 2H), 3.91 (s, 2H), 3.00 (br d, J=11.49 Hz, 2H), 2.57-2.66 (m, 1H), 2.28 (dt, J=3.55, 11.13 Hz, 2H), 1.74-1.82 (m, 4H).

Example 2: Preparation of Compound 3

General Scheme for Preparation of Compound 3

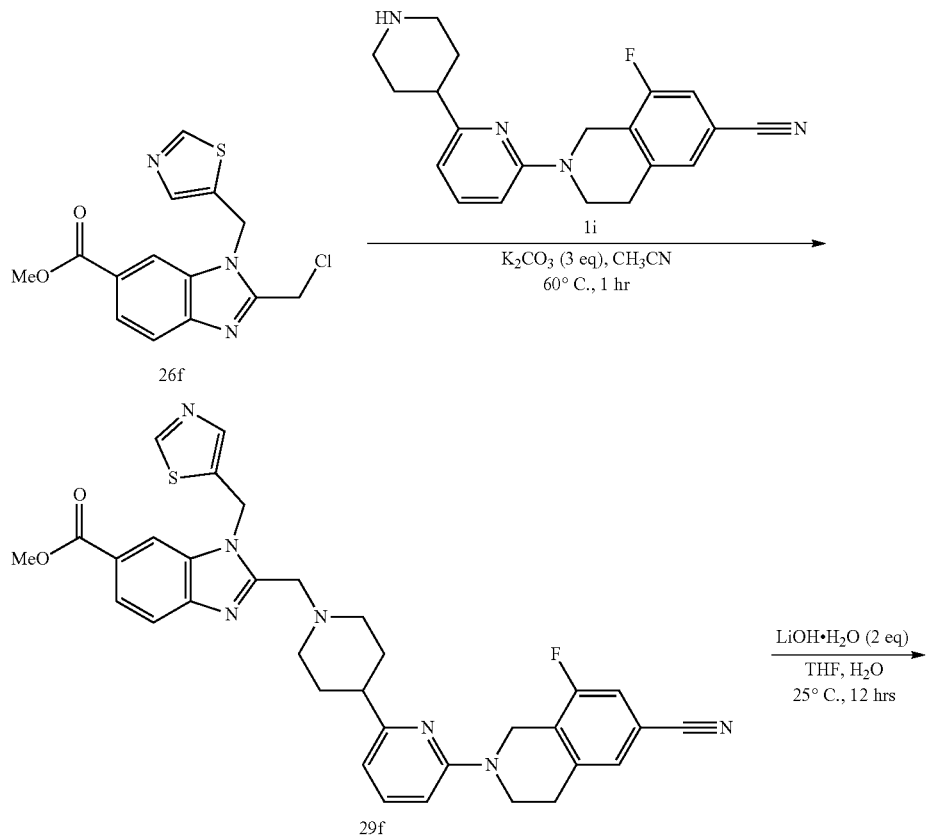

-continued

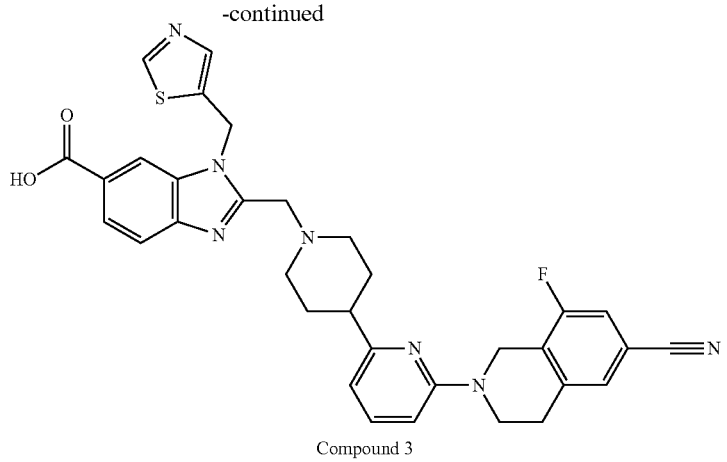

Compound 3

Step 1: Preparation of Intermediate 29f

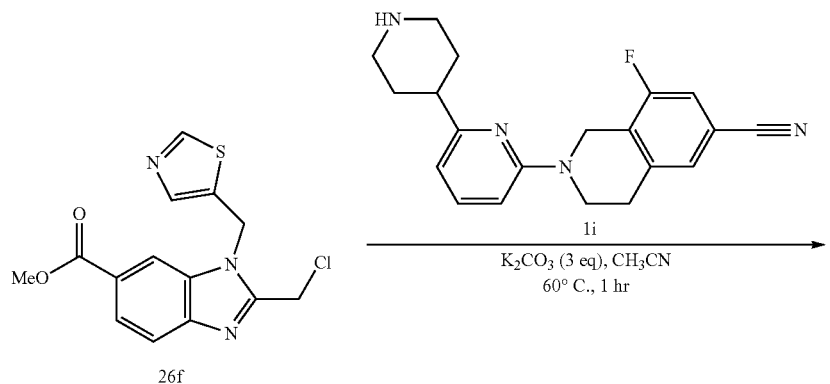

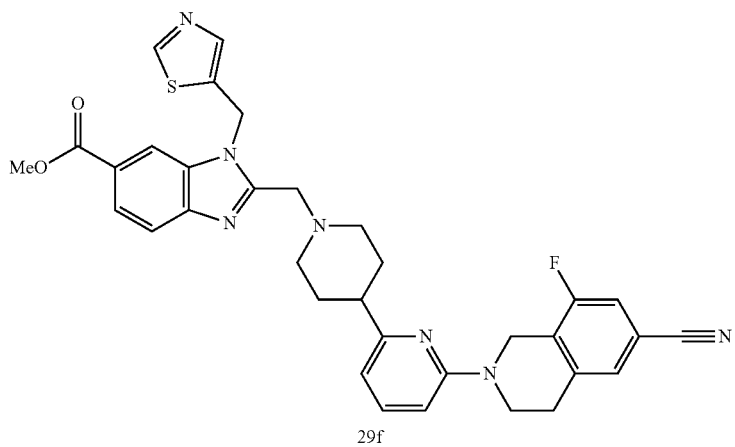

To a solution of intermediate 26f (300 mg, 932.31 mol, 1 eq) in CH₃CN (10 mL) was added K$_2$CO$_3$ (386.55 mg, 2.80 mmol, 3 eq), then freshly prepared core 1i (313.63 mg, 932.31 mol, 1 eq) was added under N$_2$. The mixture was stirred at 60° C. for 1 hr. The reaction mixture was filtered, the filtrate was purified by prep-HPLC (column: Waters Xbridge Prep OBD C18 150*40 mm*10 um; mobile phase: [water (NH$_4$HCO$_3$)-ACN]; B %:55%-85%, 8 min). Intermediate 29f (150 mg, 241.26 mol, 25.88% yield) was obtained as a white solid. LCMS: RT=0.964 min, MS cal.:621.2, [M+H]$^+$=622.4 $^1$H NMR (400 MHz, methanol-d$_4$) δ=8.96 (s, 1H), 8.23 (s, 1H), 8.04-7.92 (m, 2H), 7.71 (d, J=8.6 Hz, 1H), 7.55-7.28 (m, 3H), 6.79-6.44 (m, 2H), 6.03 (s, 2H), 4.78 (s, 2H), 3.94-3.91 (m, 5H), 3.88 (t, J=5.8 Hz, 2H), 3.09-2.94 (m, 4H), 2.68-2.52 (m, 1H), 2.39-2.24 (m, 2H), 1.90-1.78 (m, 4H)

Step 2: Preparation of Compound 3

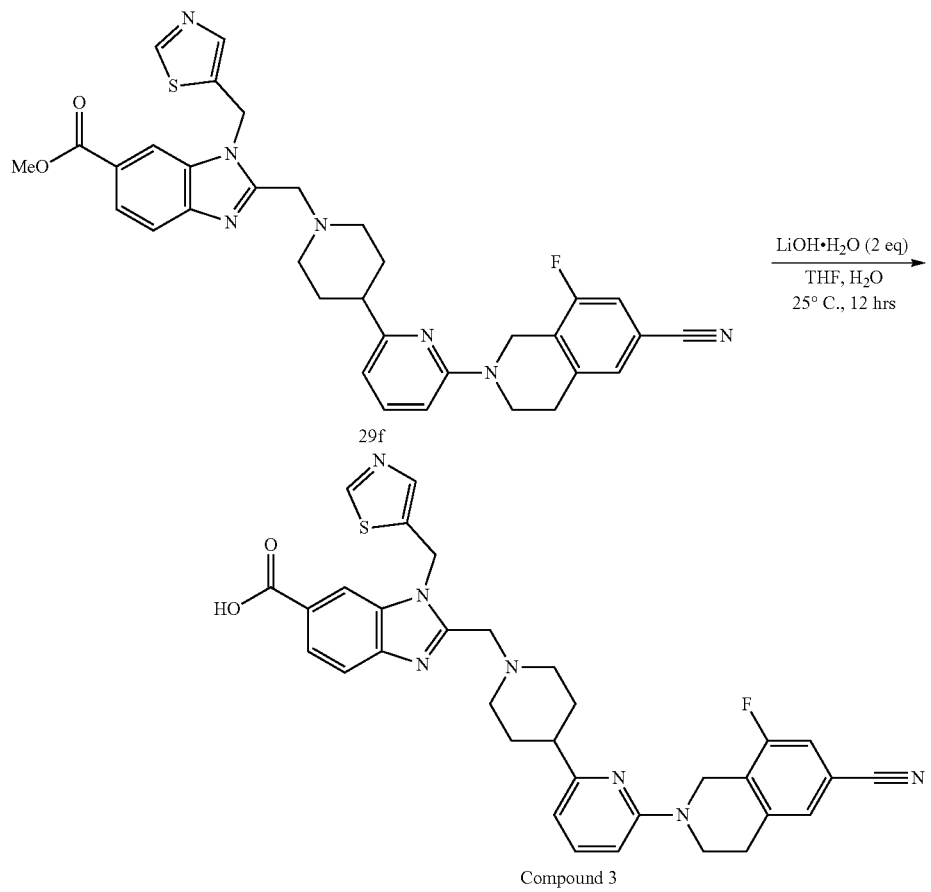

To a solution of Intermediate 29f (100 mg, 160.84 mol, 1 eq) in THF (1.5 mL) and H$_2$O (0.6 mL) was added LiOH·H$_2$O (13.50 mg, 321.69 mol, 2 eq). The mixture was stirred at 25° C. for 12 hr. The reaction mixture was filtered. The filtrate was purified by prep-HPLC (column: Waters Xbridge BEH C18 100*30 mm*10 um; mobile phase: [water (NH$_4$HCO$_3$)-ACN]; B %: 40%-60%, 8 min) to give Compound 3 as an off white solid. LCMS: RT=0.781 min, MS cal.:607.2, [M+H]=608.4. LCMS: RT=2.004 min, MS cal.:607.2, [M+H]$^+$=608.1. HPLC: RT=7.611 min $^1$H NMR (400 MHz, methanol-d$_4$) δ=8.94 (s, 1H), 8.18 (s, 1H), 8.01-7.92 (m, 2H), 7.64 (d, J=8.3 Hz, 1H), 7.51-7.45 (m, 1H), 7.42-7.34 (m, 2H), 6.69 (d, J=8.3 Hz, 1H), 6.55 (d, J=7.2 Hz, 1H), 6.00 (s, 2H), 4.78 (s, 2H), 3.92 (s, 2H), 3.88 (t, J=5.7 Hz, 2H), 3.06-2.94 (m, 4H), 2.68-2.52 (m, 1H), 2.35-2.23 (m, 2H), 1.88-1.77 (m, 4H).

Example 3: Preparation of Compound 4

General Scheme for Preparation of Compound 4

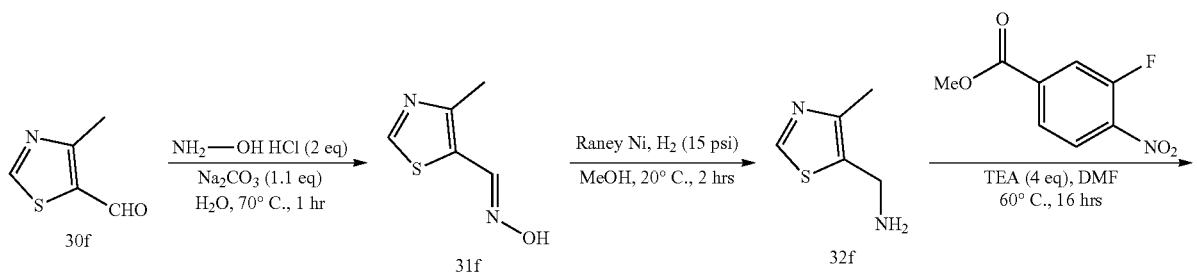

121                                                                                     122
-continued
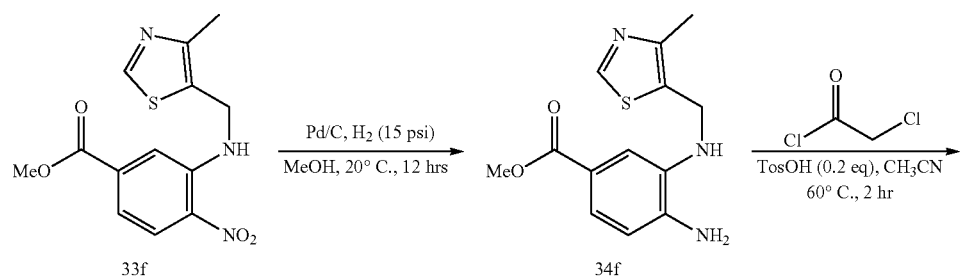
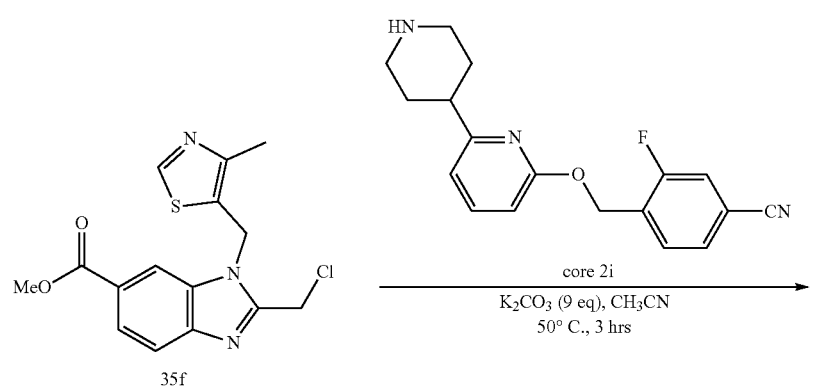
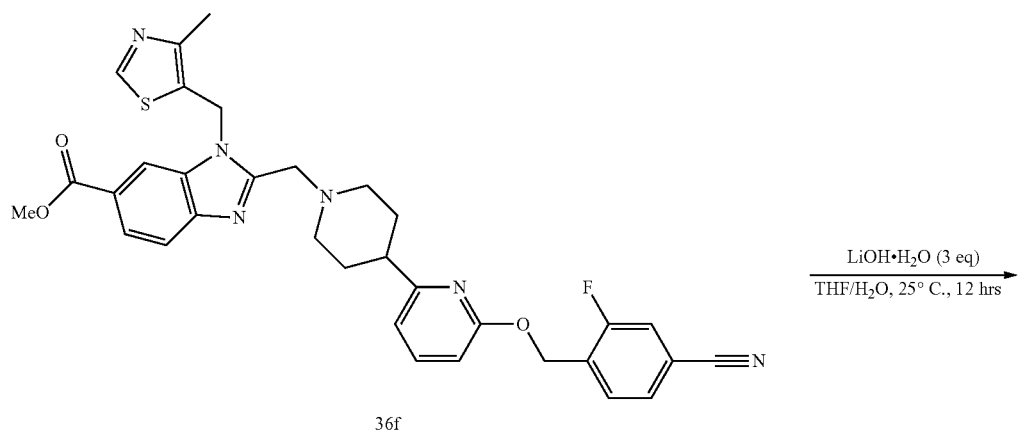
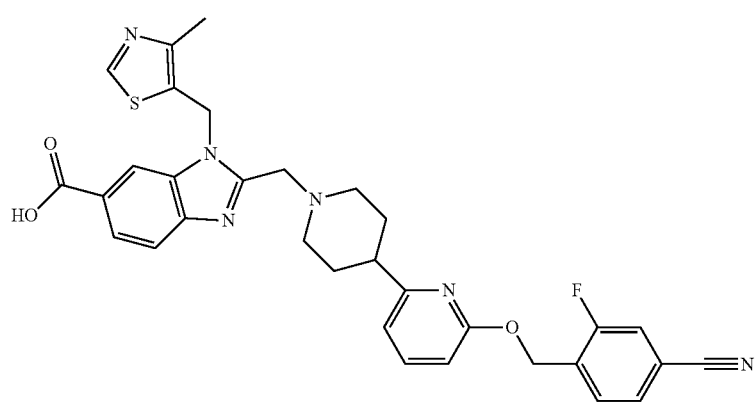
compound 4

Step 1: Preparation of Intermediate 31f

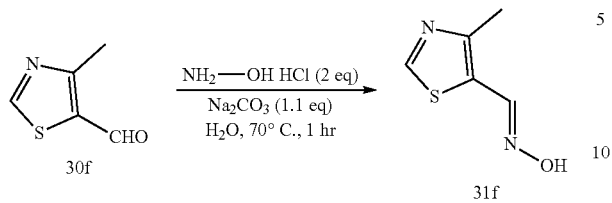

A mixture of Intermediate 30f (5 g, 39.32 mmol, 1 eq), hydroxylamine hydrochloride (5.46 g, 78.64 mmol, 2 eq) and $Na_2CO_3$ (3.59 g, 43.25 mmol, 1.1 eq) in $H_2O$ (50 mL) was degassed and purged with $N_2$ for 3 times, and then the mixture was stirred at 70° C. for 1 hour under $N_2$ atmosphere. LCMS showed the reaction was complete. The mixture was extracted with DCM (50 mL*3). The combined organic layer was dried over $Na_2SO_4$, filtered and the filtrate was concentrated to give Intermediate 31f (4.9 g, 34.46 mmol, 87.65% yield) as a yellow oil. LCMS: RT=0.479 min, MS cal.: 142.0, $[M+H]^+$=143.0

Step 2: Preparation of Compound 32f

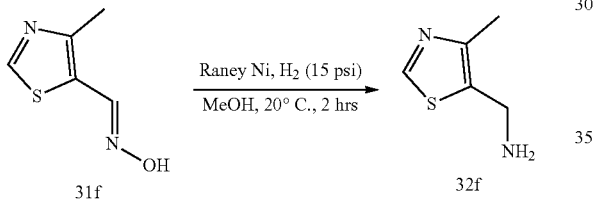

To a solution of Intermediate 31f (4.9 g, 34.46 mmol, 1 eq) in MeOH (50 mL) was added Raney-Ni (980.00 mg, 11.44 mmol, 3.32e-1 eq) under $N_2$. The suspension was degassed under vacuum and purged with $H_2$ several times. The mixture was stirred under $H_2$ (15 psi) at 20° C. for 2 hours. The reaction was complete detected by LCMS. The suspension was filtered and the wet cake was washed with MeOH (50 mL×2). The combined filtrates were concentrated to dryness to give Intermediate 32f (1.5 g, 11.70 mmol, 33.95% yield) as a yellow oil. LCMS: RT=0.127 min, MS cal.: 128.1, $[M+H]^+$=129.1 $^1$H NMR (400 MHz, chloroform-d) δ=8.62 (s, 1H), 4.03 (s, 2H), 2.42 (s, 3H).

Step 3: Preparation of Intermediate 33f

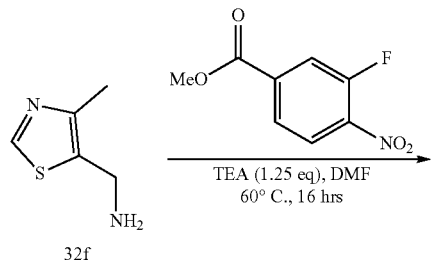

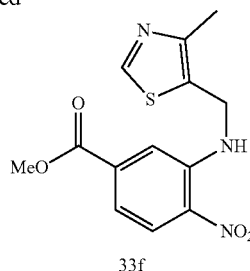

A mixture of Intermediate 32f (400 mg, 3.12 mmol, 1 eq), aryl ester (621.35 mg, 3.12 mmol, 1 eq) and TEA (394.67 mg, 3.90 mmol, 542.87 μL, 1.25 eq) in DMF (4 mL) was degassed and purged with $N_2$ for 3 times, and then the mixture was stirred at 60° C. for 16 hours under $N_2$ atmosphere. LCMS showed the reaction was complete. The mixture was diluted with $H_2O$ (10 mL), extracted with EtOAc (50 mL*3). The combined organic layer was dried over $Na_2SO_4$, filtered and the filtrate was concentrated to give a crude product. The residue was purified by column chromatography ($SiO_2$, Petroleum ether/Ethyl acetate=50/1 to 2/1) to give Intermediate 33f (650 mg, 2.12 mmol, 67.78% yield) as a yellow solid. LCMS: RT=0.826 min, MS cal.: 307.1, $[M+H]^+$=308.1 $^1$H NMR (400 MHz, chloroform-d) δ=8.72 (s, 1H), 8.26 (d, J=8.9 Hz, 1H), 8.19 (br s, 1H), 7.60 (d, J=1.5 Hz, 1H), 7.35 (dd, J=1.6, 8.9 Hz, 1H), 4.72 (d, J=5.3 Hz, 2H), 3.95 (s, 3H), 2.59 (s, 3H).

Step 4: Preparation of Intermediate 34f

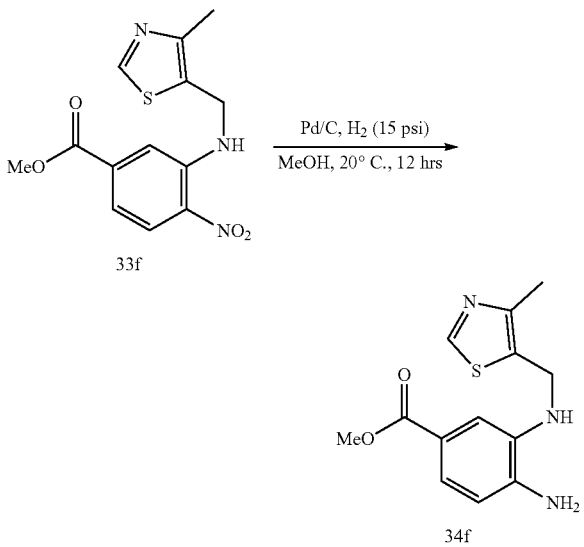

To a solution of Intermediate 33f (650 mg, 2.12 mmol, 1 eq) in MeOH (12 mL) was added Pd/C (120 mg, 10 wt %) under $N_2$. The suspension was degassed under vacuum and purged with $H_2$ several times. The mixture was stirred under $H_2$ (15 psi) at 20° C. for 12 hours. LCMS showed the reaction was complete. The suspension was filtered and the wet cake was washed with MeOH (5 mL×2). The combined filtrates were concentrated to dryness to give Intermediate 34f (500 mg, 1.80 mmol, 85.24% yield) as a yellow solid. LCMS: RT=0.671 min, MS cal.: 277.1, $[M+H]^+$=278.1 $^1$H NMR (400 MHz, chloroform-d) δ=8.68 (s, 1H), 7.54 (dd, J=1.8, 8.1 Hz, 1H), 7.44 (d, J=1.8 Hz, 1H), 6.73 (d, J=8.1 Hz, 1H), 4.48 (s, 2H), 3.87 (s, 3H), 2.50 (s, 3H).

Step 5: Preparation of Intermediate 35f

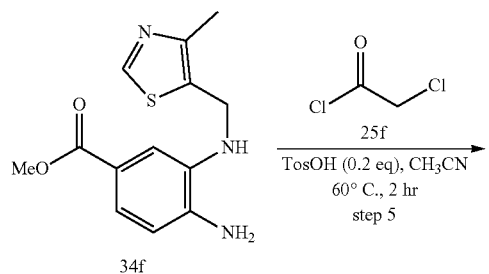

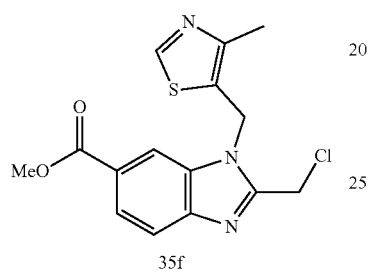

A mixture of Intermediate 34f (300 mg, 1.08 mmol, 1 eq), 25f (122.17 mg, 1.08 mmol, 86.04 μL, 1 eq) and p-TsOH (37.25 mg, 216.34 mol, 0.2 eq) in CH$_3$CN (3 mL) was degassed and purged with N$_2$ for 3 times, and then the mixture was stirred at 60° C. for 2 hour under N$_2$ atmosphere. LCMS showed the reaction was complete. The reaction mixture was concentrated to dryness to give Intermediate 35f (350 mg, 1.04 mmol, 96.35% yield) as a yellow solid. LCMS: RT=0.752 min, MS cal.: 335.1, [M+H]$^+$=336.1 $^1$H NMR (400 MHz, DMSO-d$_6$) δ=8.16 (d, J=1.0 Hz, 1H), 7.89 (dd, J=1.5, 8.5 Hz, 1H), 7.47 (d, J=8.1 Hz, 1H), 7.11 (d, J=7.9 Hz, 1H), 5.93 (s, 2H), 5.16 (s, 2H), 3.86 (s, 3H), 2.55 (s, 3H).

Step 6: Preparation of Intermediate 36f

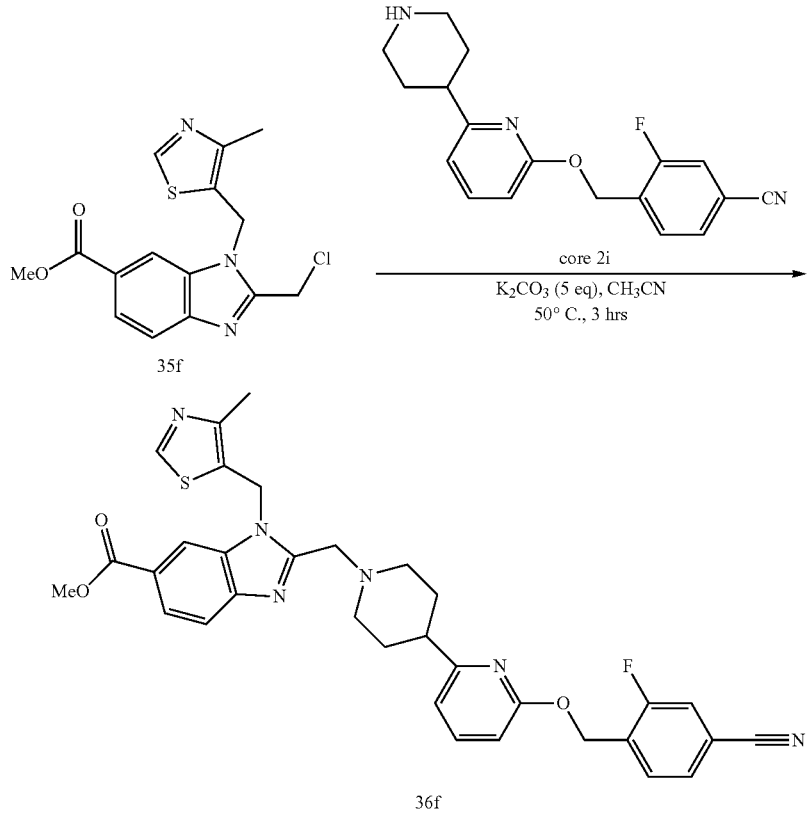 [SMILES: COC(=O)c1ccc2nc(CCl)n(Cc3scnc3C)c2c1 ; N#Cc1ccc(COc2cccc(C3CCNCC3)n2)c(F)c1 ; COC(=O)c1ccc2nc(CN3CCC(c4cccc(OCc5ccc(C#N)cc5F)n4)CC3)n(Cc3scnc3C)c2c1]

A mixture of Intermediate 35f (300 mg, 893.37 mol, 1 eq), core 2i (278.15 mg, 893.37 mol, 1 eq) and $K_2CO_3$ (617.34 mg, 4.47 mmol, 5 eq) in $CH_3CN$ (3 mL) was degassed and purged with $N_2$ for 3 times, and then the mixture was stirred at 50° C. for 3 hours under $N_2$ atmosphere. LCMS showed the reaction was complete. The mixture was diluted with $H_2O$ (10 mL), extracted with EtOAc (10 mL×3). The combined organic layer was dried over $Na_2SO_4$, filtered and the filtrate was concentrated to give a crude product. The residue was purified by prep-HPLC ($NH_4HCO_3$) to give Intermediate 36f (150 mg, 245.62 mol, 27.49% yield) as a white solid. LCMS: RT=0.806 min, MS cal.: 610.1, $[M+H]^+$=611.2 $^1H$ NMR (400 MHz, chloroform-d) δ=8.62 (s, 1H), 8.08 (d, J=1.1 Hz, 1H), 8.00 (dd, J=1.5, 8.5 Hz, 1H), 7.77 (d, J=8.5 Hz, 1H), 7.63 (t, J=7.5 Hz, 1H), 7.54 (dd, J=7.4, 8.1 Hz, 1H), 7.44 (dd, J=1.3, 7.9 Hz, 1H), 7.36 (dd, J=1.4, 9.3 Hz, 1H), 6.75 (d, J=7.3 Hz, 1H), 6.66 (d, J=8.1 Hz, 1H), 5.84 (s, 2H), 5.51 (s, 2H), 3.95 (s, 3H), 3.87 (s, 2H), 2.95 (br d, J=11.6 Hz, 2H), 2.65 (s, 3H), 2.28 (dt, J=2.1, 11.7 Hz, 2H), 1.90-1.83 (m, 2H), 1.82-1.70 (m, 2H).

Step 7: Preparation of Compound 4

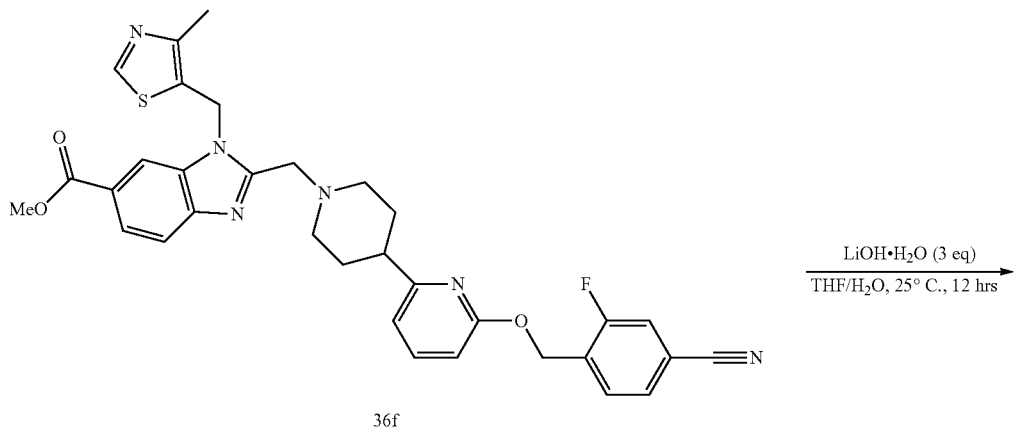

36f

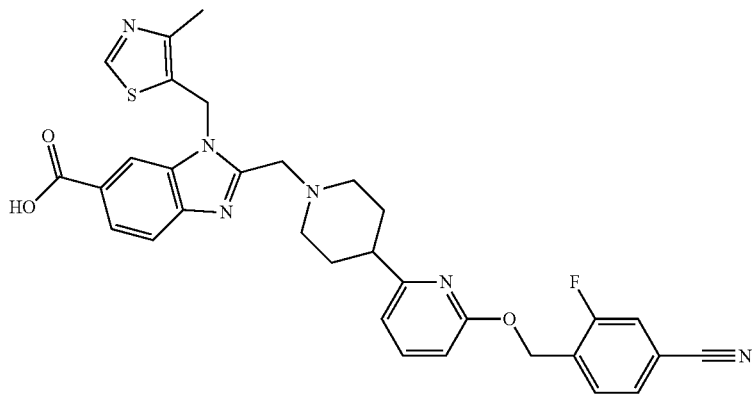

Compound 4

A mixture of Intermediate 36f (120 mg, 196.50 mol, 1 eq) and LiOH $H_2O$ (24.74 mg, 589.49 mol, 3 eq) in THF (1.5 mL) and $H_2O$ (0.3 mL) was degassed and purged with $N_2$ for 3 times, and then the mixture was stirred at 25° C. for 12 hrs under $N_2$ atmosphere. LCMS showed the reaction was complete. The reaction mixture was dried under $N_2$. The crude product was pre-purified by prep-HPLC ($NH_4HCO_3$) to give Compound 4 (38.48 mg, 64.49 mol, 32.82% yield) as a white solid. LCMS: RT=0.826 min, MS cal.: 596.1, $[M+H]^+$=597.1 HPLC: RT=7.829 min $^1H$ NMR (400 MHz, chloroform-d) δ=8.64 (s, 1H), 8.13 (s, 1H), 8.05 (br s, 1H), 7.81 (br d, J=8.4 Hz, 1H), 7.63 (br s, 1H), 7.54 (br t, J=7.8 Hz, 1H), 7.44 (br d, J=7.9 Hz, 1H), 7.36 (br d, J=9.0 Hz, 1H), 6.76 (br d, J=6.8 Hz, 1H), 6.66 (br d, J=7.9 Hz, 1H), 5.86 (br s, 2H), 5.51 (s, 2H), 3.91 (br s, 2H), 2.98 (br s, 2H), 2.68 (s, 3H), 2.32 (br s, 2H), 1.93-1.76 (m, 5H).

Example 4: Preparation of Compound 5
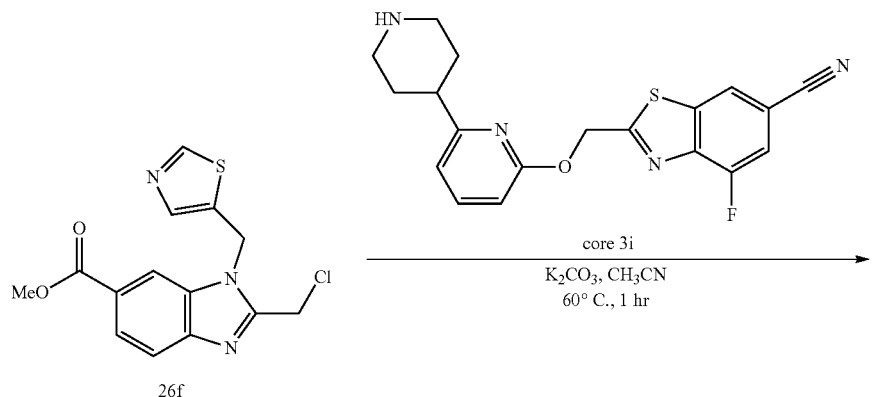
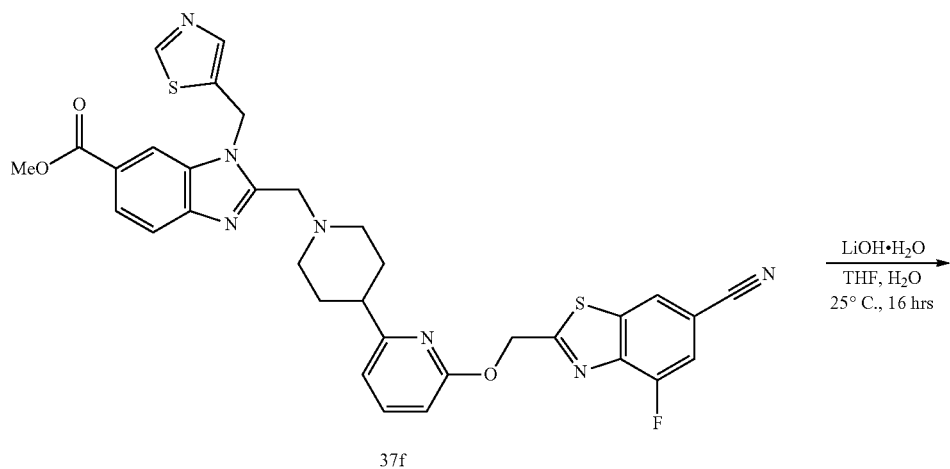
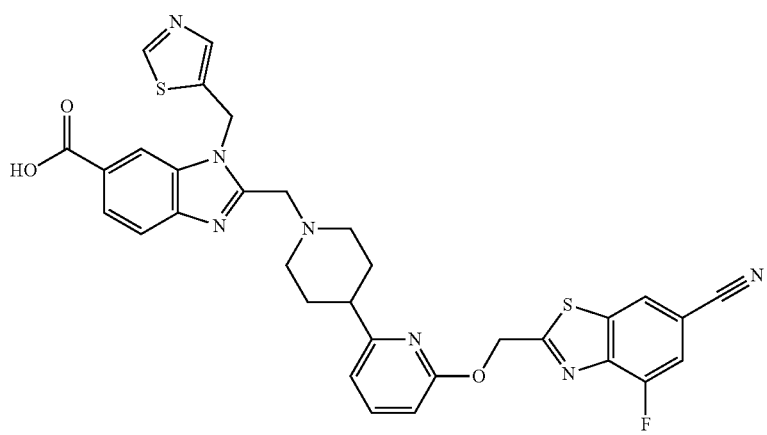

Step 1: Preparation of Intermediate 37f

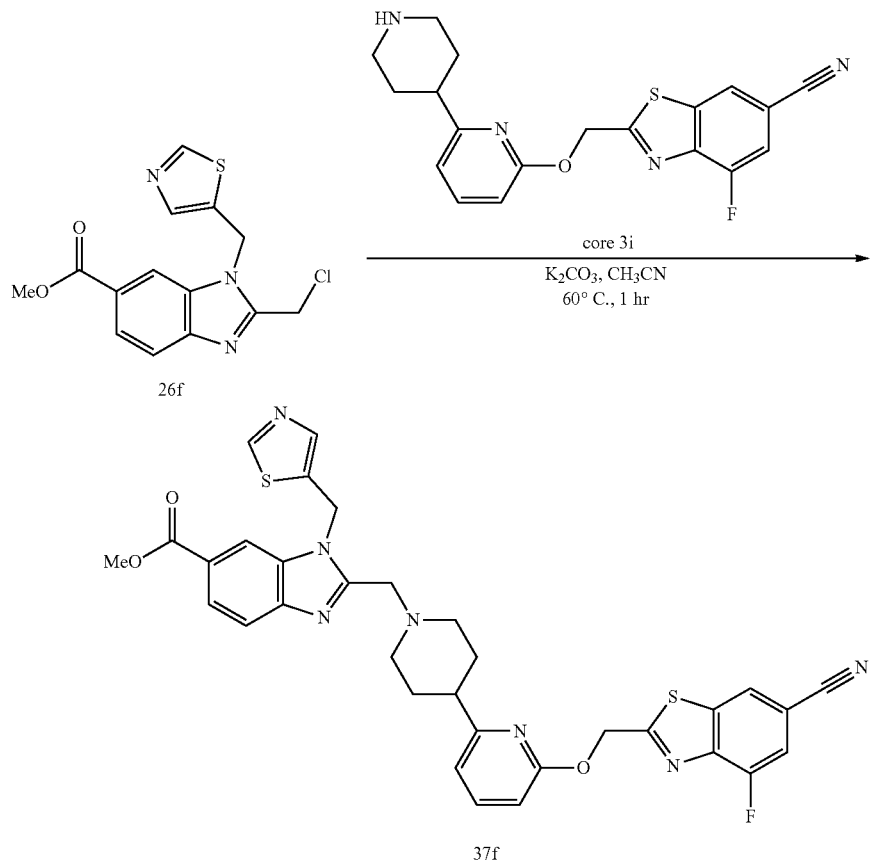 [SMILES: COC(=O)c1ccc2nc(CCl)n(Cc3cncs3)c2c1 ; N#Cc1cc(F)c2nc(COc3cccc(C4CCNCC4)n3)sc2c1 ; COC(=O)c1ccc2nc(CN3CCC(c4cccc(OCc5nc6c(F)cc(C#N)cc6s5)n4)CC3)n(Cc3cncs3)c2c1]

A mixture of compound 26f (130 mg, 404.00 μmol, 1 eq), core 3i (148.84 mg, 404.00 μmol, 1 eq), K$_2$CO$_3$ (167.51 mg, 1.21 mmol, 3 eq) in CH$_3$CN (2 mL) was degassed and purged with N$_2$ for 3 times, and then the mixture was stirred at 60° C. for 1 hr under N$_2$ atmosphere. LC-MS showed compound 26f was consumed completely and one main peak with desired. The reaction mixture was diluted with H$_2$O (60 mL) and extracted with EtOAc (30 mL*3), dried over Na$_2$SO$_4$, filtered and concentrated under reduced pressure to give a residue. The residue was purified by column chromatography (SiO$_2$, Petroleum ether/Ethyl acetate=100/1 to 1/1). Compound 37f (180 mg, 275.34 mol, 68.15% yield) was obtained as a white solid. LCMS: RT=2.542 min, MS cal.:653.75, [M+H]$^+$=654.1 $^1$H NMR (400 MHz, DMSO-d$_6$) δ =ppm 1.17 (dd, J=6.25, 2.88 Hz, 2H) 1.59-1.76 (m, 4H) 1.96 (d, J=2.88 Hz, 1H) 2.17 (br t, J=11.19 Hz, 2H) 3.81-3.89 (m, 5H) 5.83-5.99 (m, 4H) 6.83 (br d, J=8.00 Hz, 1H) 6.93 (br d, J=5.00 Hz, 1H) 7.67-7.76 (m, 2H) 7.83 (br d, J=8.25 Hz, 1H) 7.94 (br d, J=10.13 Hz, 1H) 8.01 (s, 1H) 8.22 (s, 1H) 8.54 (s, 1H) 8.98 (d, J=2.13 Hz, 1H).

Step 2: Preparation of Compound 5

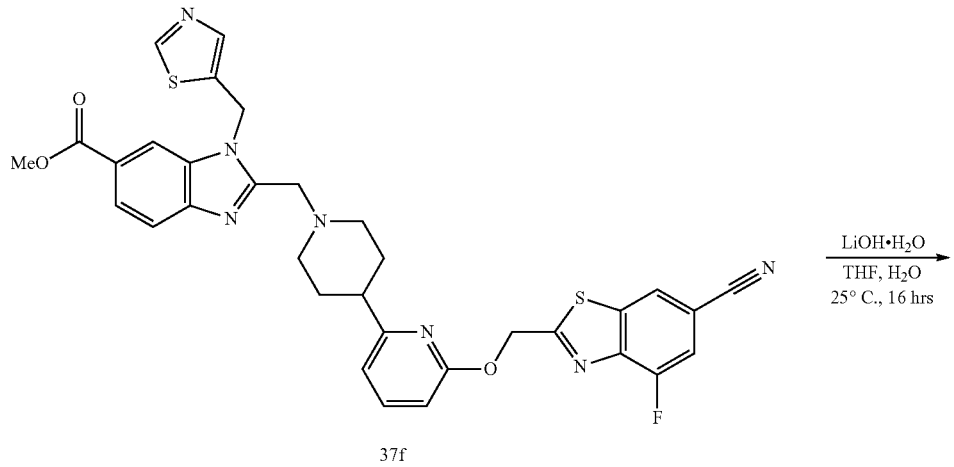

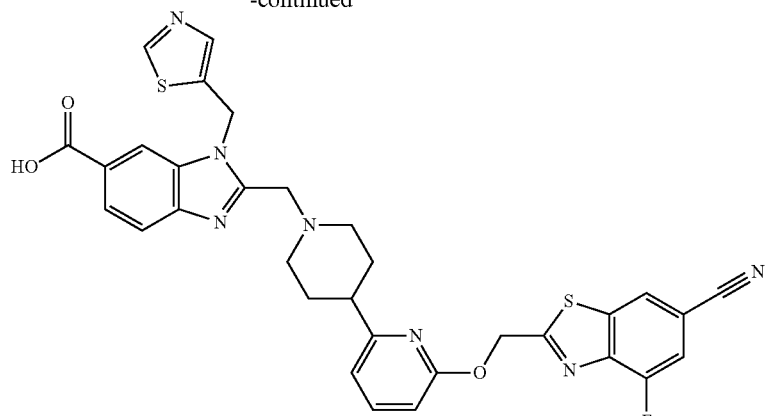

compound 5

A mixture of compound 37f (70 mg, 107.07 mol, 1 eq), LiOH H$_2$O (4.94 mg, 117.78 mol, 1.1 eq) in THF (0.7 mL) and H$_2$O (0.4 mL) was degassed and purged with N$_2$ for 3 times, and then the mixture was stirred at 25° C. for 16 hr under N$_2$ atmosphere. LC-MS showed compound 37f was consumed completely and one main peak with desired. The reaction mixture was concentrated under reduced pressure to remove solvent. The residue was purified by prep-HPLC (neutral condition column: Waters Xbridge BEH C18 100*30 mm*10 um; mobile phase: [water (NH$_4$HCO$_3$)-ACN]; B %: 10%-50%, 8 min). Compound 5 (15.4 mg, 24.07 mol, 22.48% yield) was obtained as a white solid. LCMS: RT=1.918 min, MS cal.: 639.1, [M+H]$^+$=640.1 $^1$H NMR (400 MHz, DMSO-d$_6$) δ=ppm 1.14 (s, 2H) 1.23 (s, 1H) 1.38 (s, 1H) 1.68 (br d, J=14.66 Hz, 4H) 1.72-1.75 (m, 1H) 2.17 (br s, 2H) 2.89 (br s, 2H) 3.86 (brd, J=11.80 Hz, 2H) 5.88 (s, 2H) 5.86-5.90 (m, 1H) 5.93 (s, 1H) 6.84 (brd, J=8.23 Hz, 1H) 6.93 (br d, J=6.91 Hz, 1H) 7.67 (br d, J=8.58 Hz, 1H) 7.72 (br t, J=7.57 Hz, 1H) 7.81 (br d, J=7.75 Hz, 1H) 7.95 (d, J=11.44 Hz, 1H) 8.02 (s, 1H) 8.18 (s, 1H) 8.14-8.23 (m, 1H) 8.55 (s, 1H) 8.98 (s, 1H) 12.70-12.90 (m, 1H) 12.70-12.90 (m, 1H).

Example 5: Preparation of Compound 6

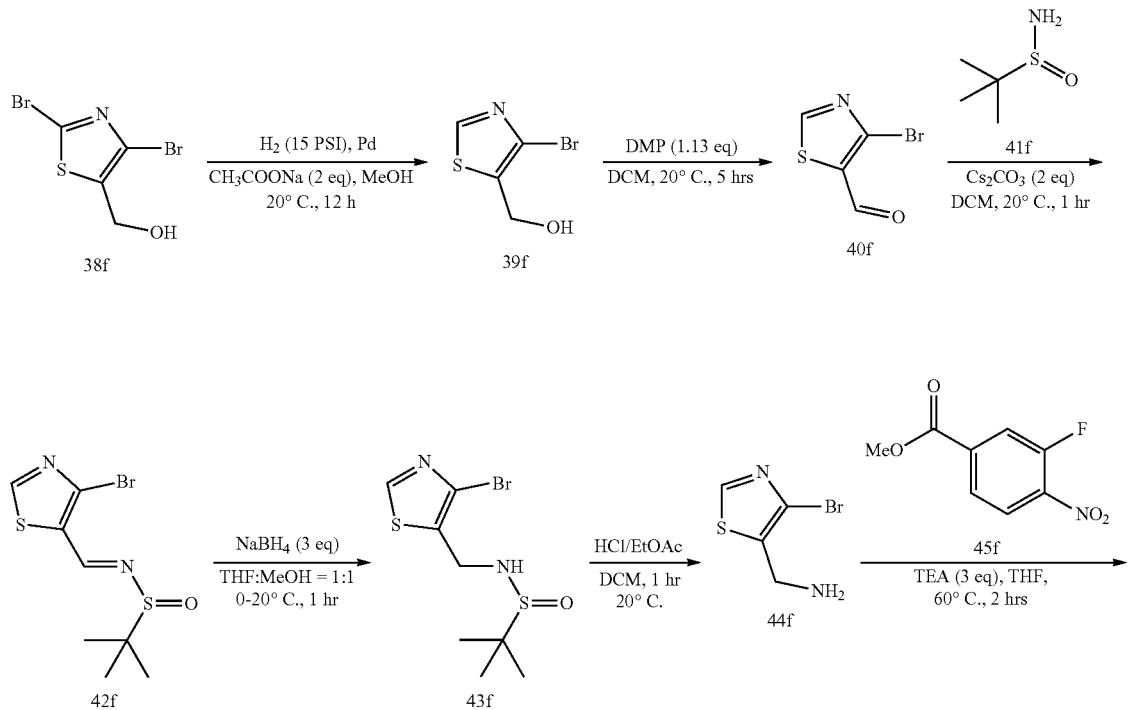

-continued
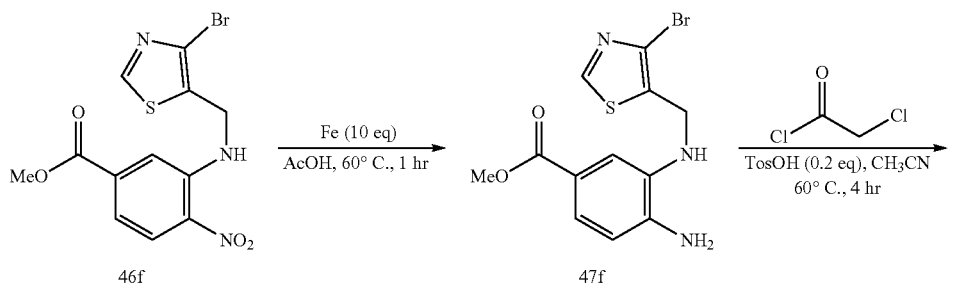
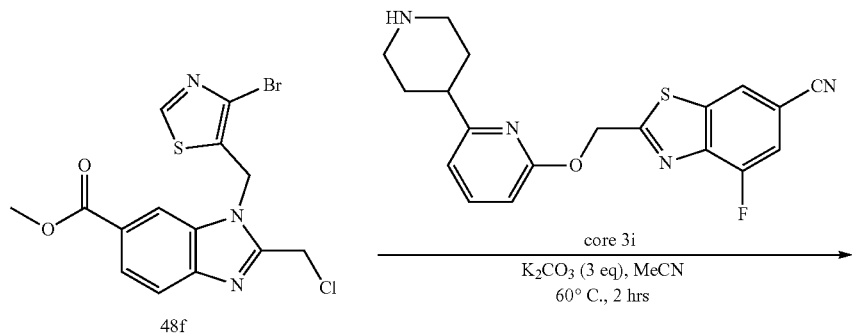
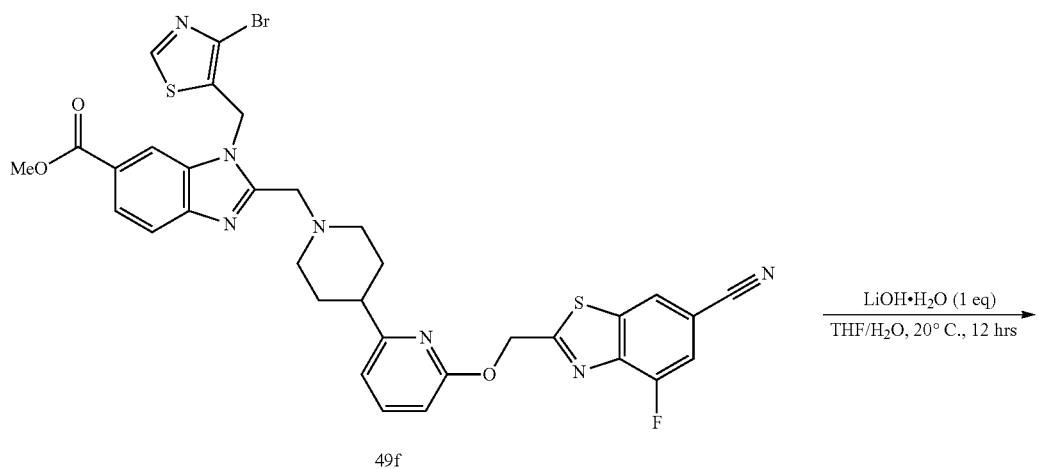
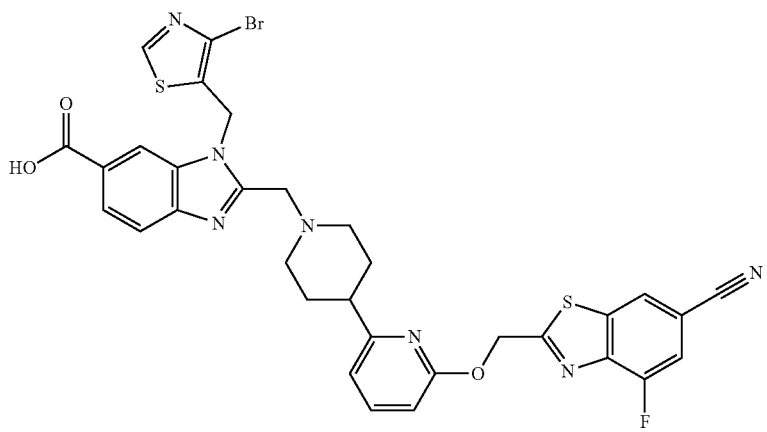
compound 6

Step 1: Preparation of Intermediate 39f

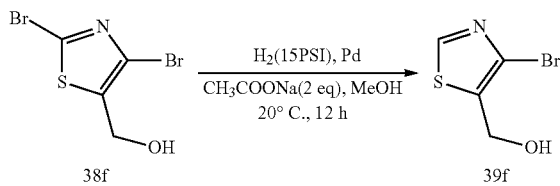 [SMILES: OCc1sc(Br)nc1Br ; OCc1scnc1Br]

To a solution of Intermediate 38f (5 g, 18.32 mmol, 1 eq) in MeOH (50 mL) was added Pd (1 g, 9.40 mmol, 5.13e-1 eq) and sodium acetate (3.01 g, 36.64 mmol, 2 eq) under $N_2$. The suspension was degassed under vacuum and purged with $H_2$ several times. The reaction mixture was stirred under $H_2$ at 20° C. for 12 hr and filtered, and the filtrate was concentrated. Intermediate 39f (3.5 g, crude) was obtained as a yellow oil. LCMS: RT=0.227 min, MS cal.: 192.9, [M+H]$^+$=193.8, 195.8 $^1$H NMR (400 MHz, chloroform-d) δ=8.65-8.78 (1H, m) 4.77-4.91 (2H, m) 4.02 (2H, br s) 2.07 (1H, br s).

Step 2: Preparation of Intermediate 40f

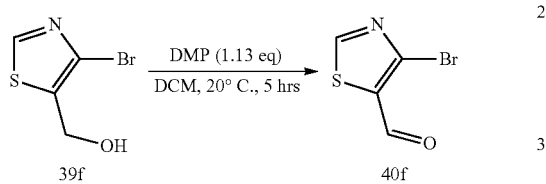

A mixture of Intermediate 39f (14 g, 72.15 mmol, 1 eq), DMP (34.72 g, 81.86 mmol, 25.34 mL, 1.13 eq) in DCM (300 mL) was degassed and purged with $N_2$ 3 times, and then the mixture was stirred at 20° C. for 5 hrs under Ar atmosphere. The mixture was basified to pH 8 using aqueous $NaHCO_3$, then residue was diluted with $H_2O$ (10 mL) and extracted with DCM (20 mL*2). The reaction mixture was poured into separatory funnel, separated, and the combined organic layers were washed with brine (10 mL), dried over $Na_2SO_4$, filtered and concentrated under reduced pressure to give a residue. The residue was purified by column chromatography (SiO$_2$, Petroleum ether/Ethyl acetate=100/1 to 92/1). Intermediate 40f (11 g, 57.28 mmol, 79.40% yield) was obtained as a white solid. LCMS: RT=0.646 min, MS cal.: 190.9, [M+H]$^+$=192.8, 194.0 $^1$H NMR (400 MHz, chloroform-d) δ=10.05 (1H, d, J=1.07 Hz) 9.03 (1H, d, J=0.83 Hz).

Step 3: Preparation of Intermediate 42f

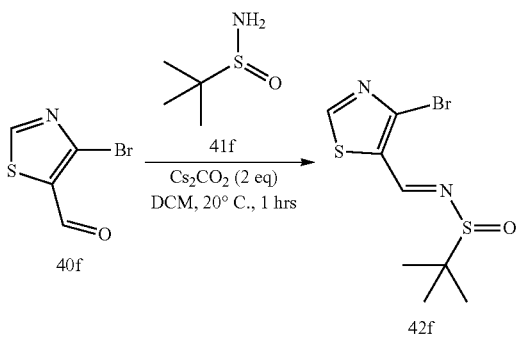

To a solution of Intermediate 40f (4.3 g, 22.39 mmol, 1 eq) in DCM (43 mL) was added $Cs_2CO_3$ (14.59 g, 44.78 mmol, 2 eq) and Intermediate 41f (5.43 g, 44.78 mmol, 2 eq). The mixture was stirred at 20° C. for 1 hr. LC-MS showed Intermediate 40f was consumed completely and one main peak with desired mass was detected. The mixture was filtered and concentrated in vacuum. Intermediate 42f (9 g, crude) was obtained as a brown solid. LCMS: RT=0.646 min, MS cal.: 294.0, [M+H]$^+$=295.0 $^1$H NMR (400 MHz, DMSO-d$_6$) δ=9.25-9.55 (1H, m) 8.41-8.66 (1H, m) 1.17 (9H, s).

Step 3: Preparation of Intermediate 43f

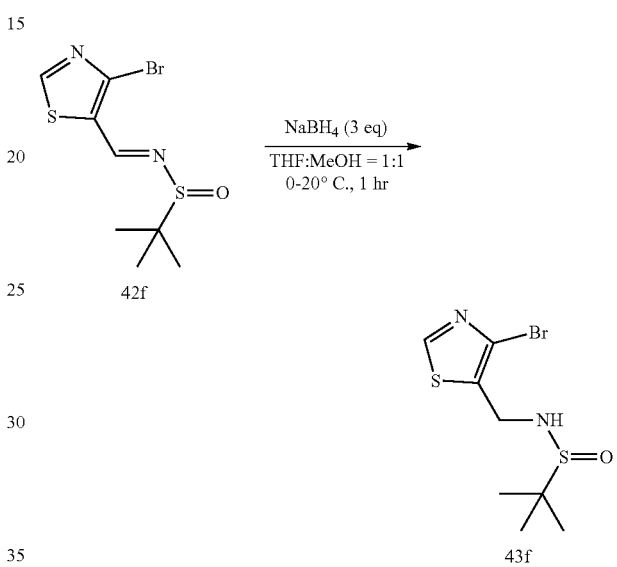

To a solution of Intermediate 42f (9 g, 30.49 mmol, 1 eq) in THF (50 mL) and MeOH (50 mL) was added NaBH$_4$ (3.52 g, 93.04 mmol, 3.05 eq) at 0° C. The mixture was stirred at 0-20° C. for 1 hr and then poured into sat. NH$_4$Cl solution (200 mL) and extracted with ethyl acetate (50 mL*3). The combined organic phase was washed with brine (50 mL*2), dried with anhydrous Na$_2$SO$_4$, filtered and concentrated under vacuum. The residue was purified by column chromatography (SiO$_2$, Petroleum ether/Ethyl acetate=I/O to 0/1). Intermediate 43f (4.6 g, 15.48 mmol, 50.76% yield) was obtained as a white solid. LCMS: RT=0.607 min, MS cal.: 296.0, [M+H]$^+$=296.9, 298.9 $^1$H NMR (400 MHz, DMSO-d$_6$) δ=9.08 (1H, s) 6.13 (1H, t, J=5.71 Hz) 4.23-4.39 (2H, m) 1.14 (9H, s).

Step 4: Preparation of Intermediate 44f

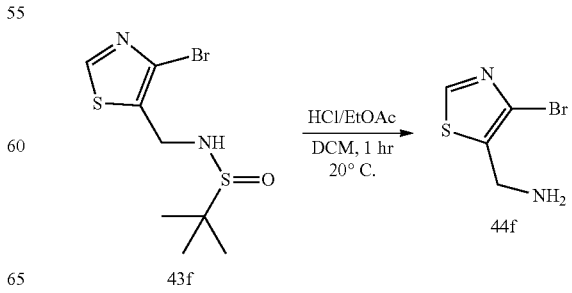

To a solution of Intermediate 43f (3.2 g, 10.77 mmol, 1 eq) in DCM (5 mL) was added HCl/EtOAc (20 mL). The mixture was stirred at 20° C. for 1 hr and then concentrated under vacuum. Intermediate 44f (2.5 g, crude) was obtained as a white solid. LCMS: RT=0.130 min, MS cal.: 191.9, [M+H]$^+$=192.8, 194.8 $^1$H NMR (400 MHz, DMSO-d$_6$) δ=9.16-9.36 (1H, m) 8.76 (3H, br s) 6.62 (3H, br s) 4.22 (2H, q, J=5.58 Hz).

Step 5: Preparation of Intermediate 46f

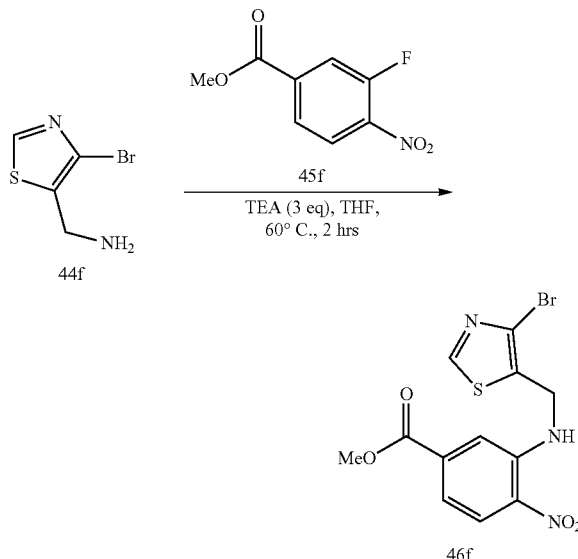

To a solution of Intermediate 44f (2.5 g, 12.95 mmol, 1 eq) and Intermediate 45f (2.58 g, 12.95 mmol, 1 eq) in THF (30 mL) was added TEA (3.93 g, 38.85 mmol, 5.41 mL, 3 eq). The mixture was stirred at 60° C. for 2 hrs under N$_2$. The residue was poured into water (50 mL). The aqueous phase was extracted with ethyl acetate (30 mL*3). The combined organic phase was washed with brine (30 mL*2), dried with anhydrous Na$_2$SO$_4$, filtered and concentrated under vacuum. The residue was purified by column chromatography (SiO$_2$, Petroleum ether/Ethyl acetate=10/1 to 0/1). Intermediate 46f (1 g, 2.69 mmol, 20.75% yield) was obtained as a white solid. LCMS: RT=0.769 min, MS cal.: 371.0, [M+H]$^+$=371.8, 373.8 $^1$H NMR (400 MHz, DMSO-d$_6$) δ=9.04-9.10 (1H, m) 8.74-8.82 (1H, m) 8.19-8.26 (1H, m) 7.45-7.51 (1H, m) 7.18-7.27 (1H, m) 4.76-4.84 (2H, m) 3.83-3.89 (3H, m).

Step 6: Preparation of Intermediate 47f

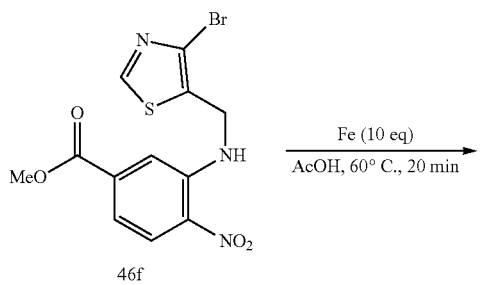

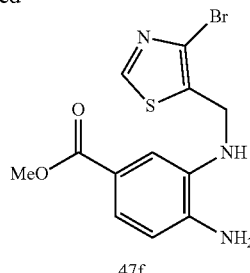

To the mixture of Intermediate 46f (950 mg, 2.55 mmol, 1 eq) in AcOH (10 mL) was added Fe (1.43 g, 25.52 mmol, 10 eq) at 0° C., and then the mixture was stirred at 60° C. for 20 min under N$_2$ atmosphere. The mixture was filtered and the filtrate was poured into 1M Na$_2$CO$_3$ solution (210 mL) and stirred for 60 min. The aqueous phase was extracted with DCM (50 mL*3). The combined organic phase was washed with brine (50 mL*3), dried with anhydrous Na$_2$SO$_4$, filtered and concentrated under vacuum. Intermediate 47f (900 mg, crude) was obtained as a white solid. LCMS: RT=0.522 min, MS cal.: 341.0, [M+H]$^+$=342.0, 343.9 $^1$H NMR (400 MHz, DMSO-d$_6$) δ=9.02-9.15 (1H, m) 7.18-7.30 (1H, m) 7.01-7.11 (1H, m) 6.61-6.67 (1H, m) 5.47-5.68 (3H, m) 4.49-4.58 (2H, m) 3.74-3.78 (3H, m).

Step 7: Preparation of Intermediate 48f

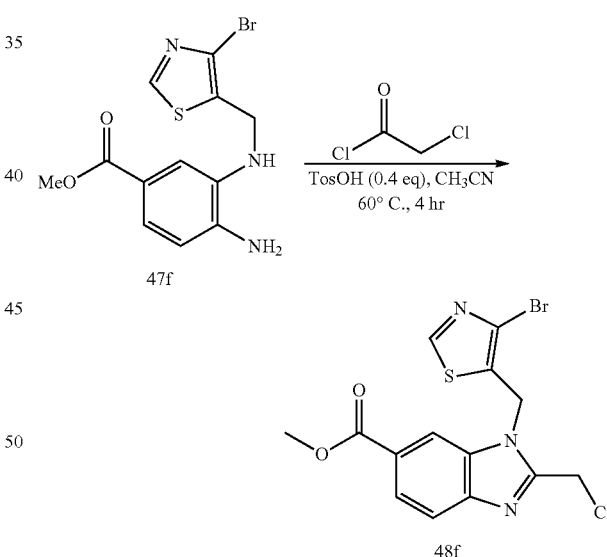

To a solution of Intermediate 47f (270 mg, 788.99 mol, 1 eq) in MeCN (4 mL) was added p-TsOH (54.35 mg, 315.59 mol, 0.4 eq), then 2-chloroacetyl chloride (106.93 mg, 946.78 mol, 75.30 μL, 1.2 eq) was added at 20° C., then the mixture was stirred at 60° C. for 4 hr. The mixture was concentrated under vacuum. Intermediate 48f (350 mg, crude) was obtained as a yellow solid. LCMS: RT=0.715 min, MS cal.: 398.9, [M+H]$^+$=399.9, 401.9 $^1$H NMR (400 MHz, DMSO-d$_6$) δ=9.12-9.16 (1H, m) 8.29-8.31 (1H, m) 7.84-7.88 (1H, m) 7.51-7.58 (1H, m) 5.96-5.99 (2H, m) 5.19-5.24 (2H, m) 3.93 (3H, s).

Step 8: Preparation of Intermediate 49f

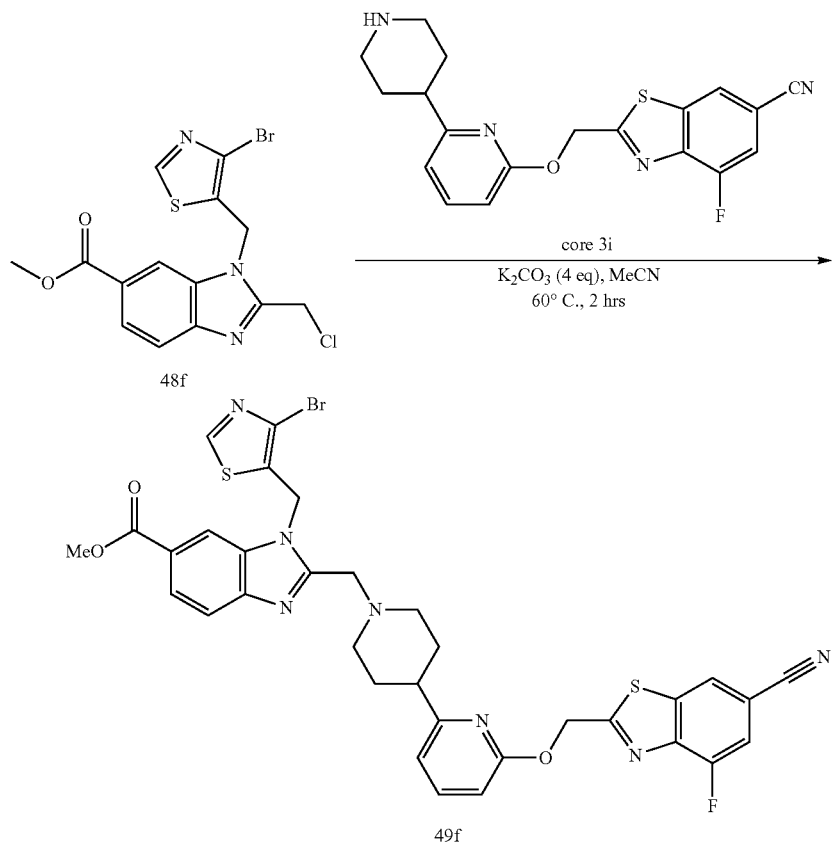

To a solution of Intermediate 48f (310 mg, 773.69 mol, 1 eq) and core 3i (373.27 mg, 773.69 mol, 1 eq, TFA) in MeCN (4 mL) was added K$_2$CO$_3$ (427.71 mg, 3.09 mmol, 4 eq). The mixture was stirred at 60° C. for 2 hrs. The mixture was filtrated and the cake reserved. Intermediate 49f (350 mg, 477.72 mol, 61.75% yield) was obtained as a white solid. LCMS: RT=2.816 min, MS cal.: 731.1, [M+H]$^+$=732.1, 734.1 $^1$H NMR (400 MHz, chloroform-d) δ=8.68-8.80 (1H, m) 8.18-8.23 (1H, m) 8.02-8.08 (2H, m) 7.78-7.85 (1H, m) 7.57-7.68 (1H, m) 7.42-7.52 (1H, m) 6.75-6.89 (2H, m) 5.92 (2H, s) 5.86 (2H, s) 3.98 (3H, s) 3.91 (2H, s) 2.94-3.04 (2H, m) 2.59-2.69 (1H, m) 2.25-2.35 (2H, m) 1.80-1.88 (2H, m) 1.68-1.80 (2H, m).

Step 9: Preparation of Compound 6

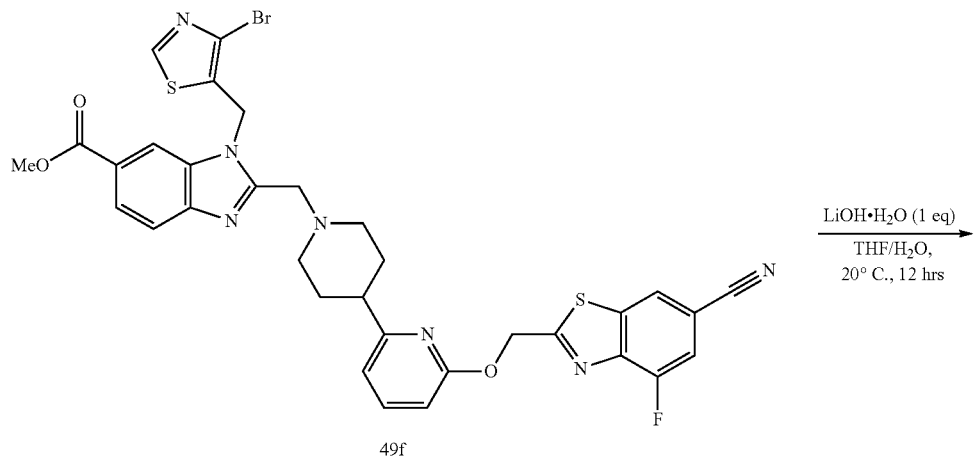

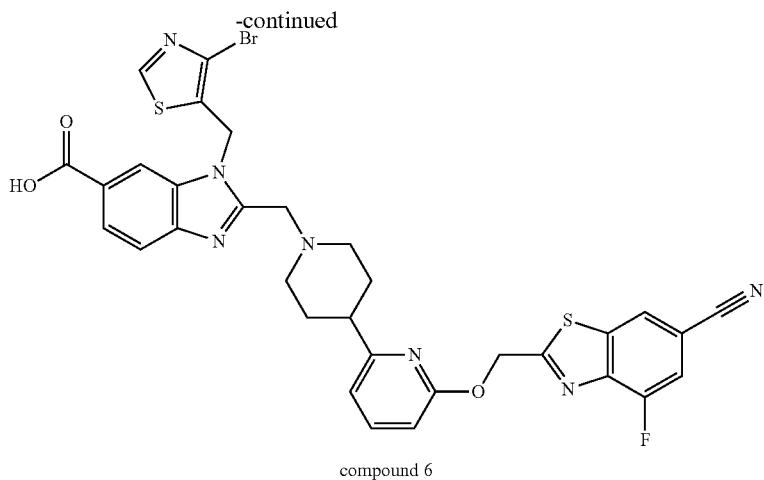

compound 6

To a solution of Intermediate 49f (150 mg, 204.74 mol, 1 eq) in THF (5 mL) and H₂O (2.1 mL) was added LiOH H₂O (10.31 mg, 245.69 mol, 1.2 eq). The mixture was stirred at 20° C. for 12 hrs, then adjusted to pH 7 using 1M citric acid, and then concentrated under reduced pressure to give a residue. The residue was purified by prep-HPLC (neutral condition: column: Phenomenex C18 80*40 mm*3 um; mobile phase: [water (NH₄HCO₃)-ACN]; B %: 30%-60%, 8 min). Compound 6 (15.09 mg, 21.00 mol, 10.26% yield) was obtained as a white solid. LCMS: Rt=0.715 min, MS cal.: 717.1, [M+H]$^+$=717.9, 719.9 $^1$H NMR (400 MHz, chloroform-d) δ=8.74-8.78 (1H, m) 8.23 (1H, s) 8.06-8.11 (1H, m) 8.00-8.04 (1H, m) 7.79-7.86 (1H, m) 7.55-7.63 (1H, m) 7.40-7.47 (1H, m) 6.71-6.84 (2H, m) 5.88-5.91 (2H, m) 5.85 (2H, s) 3.88-3.94 (2H, m) 2.92-3.01 (2H, m) 2.58-2.69 (2H, m) 2.24-2.34 (3H, m) 1.68-1.87 (17H, m).

Example 6: Preparation of Compound 7

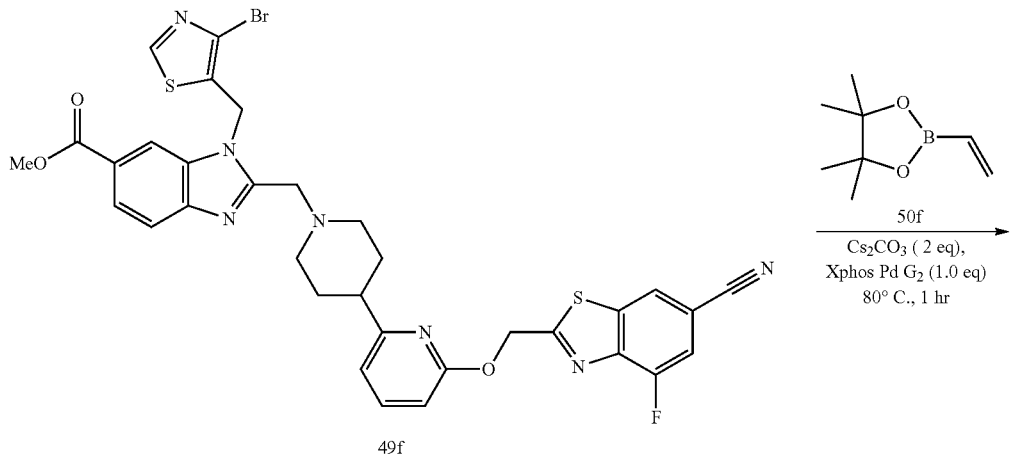

-continued
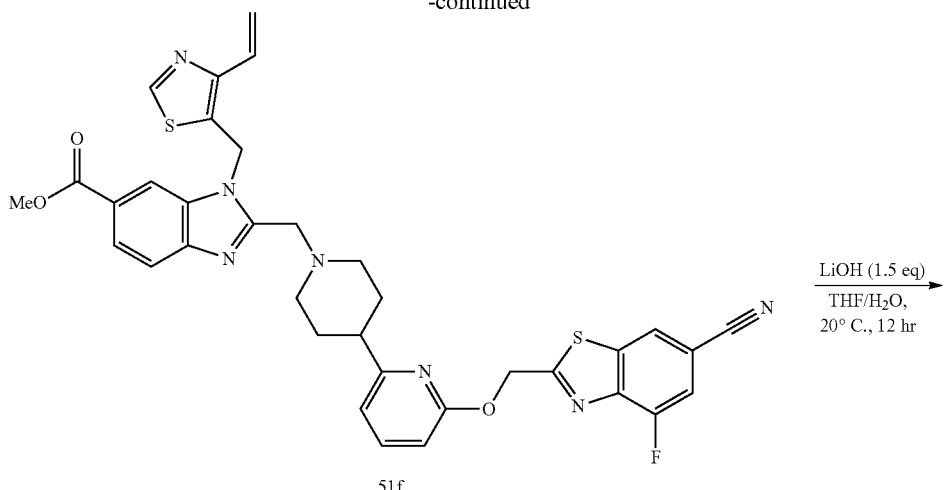
51f
compound 7
40
Step 1: Preparation of Intermediate 51f
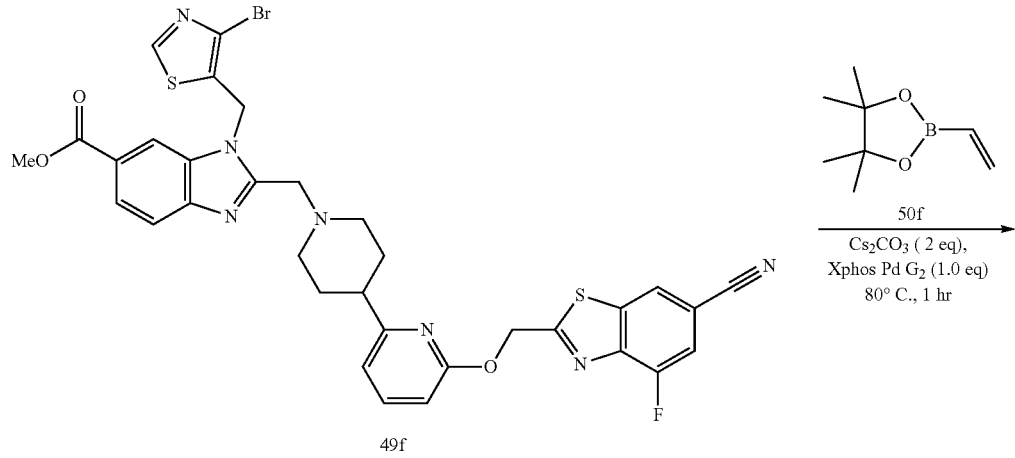
49f -continued

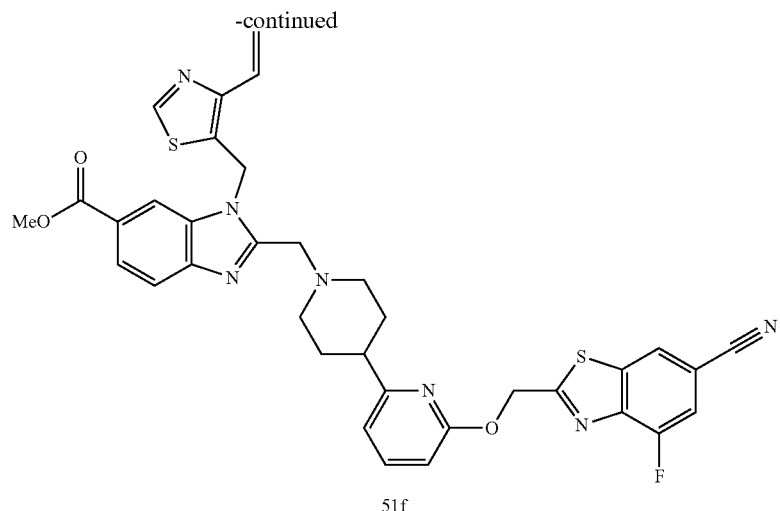

51f

A mixture of Intermediate 49f (300 mg, 409.48 mol, 1 eq), Intermediate 50f (126.13 mg, 818.95 mol, 138.91 μL, 2 eq), Cs$_2$CO$_3$ (266.83 mg, 818.95 mol, 2 eq), XPHOS-PD-G$_2$ (32.22 mg, 40.95 mol, 0.1 eq) in dioxane (3 mL) and H$_2$O (1.5 mL) was degassed and purged with N$_2$ for 3 times, and then the mixture was stirred at 80° C. for 1 hr under N$_2$ atmosphere. The residue was poured into water (10 mL). The aqueous phase was extracted with ethyl acetate (5 mL*3). The combined organic phase was washed with brine (5 mL*2), dried with anhydrous Na$_2$SO$_4$, filtered and concentrated in vacuum. The residue was purified by column chromatography (SiO$_2$, Petroleum ether/Ethyl acetate=10/1 to 0/1). Intermediate 51f (150 mg, 220.66 mol, 53.89% yield) was obtained as a white solid. LCMS: Rt=2.215 min, MS cal.: 679.2, [M+H]$^+$=680.2, 681.6 $^1$H NMR (400 MHz, chloroform-d) δ=8.60 (1H, s) 8.04 (1H, s) 7.91-7.95 (2H, m) 7.69 (1H, d, J=8.53 Hz) 7.53 (1H, t, J=7.72 Hz) 7.35 (1H, d, J=9.45 Hz) 6.88-6.97 (1H, m) 6.75 (1H, d, J=7.28 Hz) 6.68 (1H, d, J=8.28 Hz) 6.21 (1H, dd, J=17.00, 1.57 Hz) 5.86 (2H, s) 5.81 (2H, s) 5.50-5.54 (1H, m) 3.87 (3H, s) 3.70-3.79 (2H, m) 2.81-2.89 (2H, m) 2.56 (1H, br d, J=3.64 Hz) 2.12-2.23 (2H, m) 1.66-1.81 (4H, m).

Step 2: Preparation of Compound 7

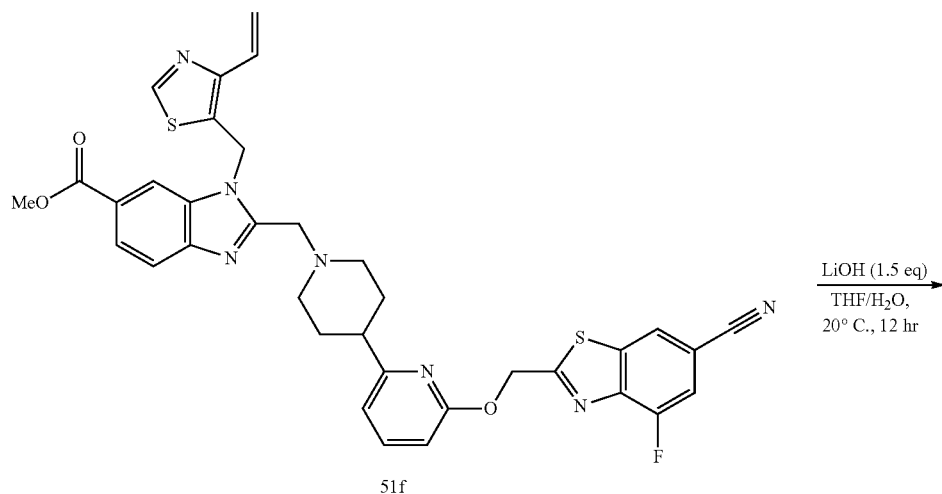

51f

LiOH (1.5 eq)
———————→
THF/H$_2$O,
20° C., 12 hr

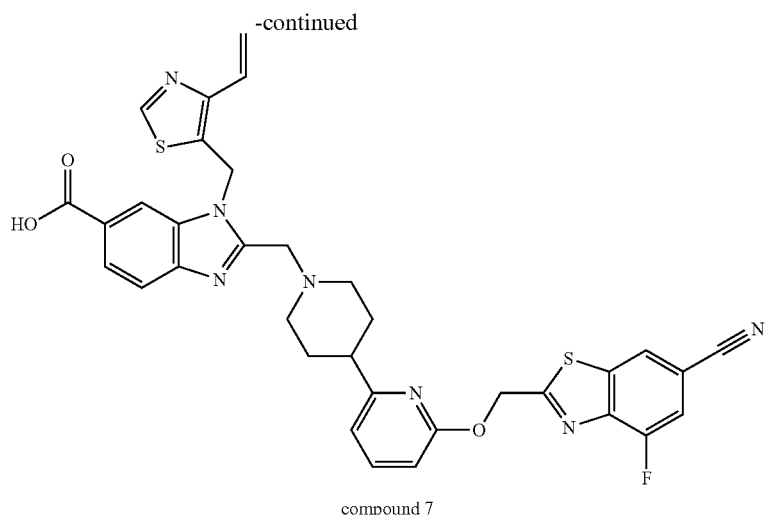

compound 7

To a solution of Intermediate 51f (140 mg, 205.95 mol, 1 eq) in THF (4.9 mL) and H₂O (2.1 mL) was added LiOH H₂O (12.96 mg, 308.92 mol, 1.5 eq). The mixture was stirred at 20° C. for 12 hrs, then adjusted to pH 7 using 1M citric acid, and then concentrated under reduced pressure to give a residue. The residue was purified by prep-HPLC (neutral condition: column: Phenomenex C18 80*40 mm*3 um; mobile phase: [water (NH₄HCO₃)-ACN]; B %: 50%-60%, 8 min). LCMS: Rt=1.771 min, MS cal.: 665.2, [M+H]⁺=666.3 ¹H NMR (400 MHz, chloroform-d) δ=8.68-8.71 (1H, m) 8.17-8.21 (1H, m) 8.04-8.10 (1H, m) 7.99-8.02 (1H, m) 7.79-7.85 (1H, m) 7.58-7.64 (1H, m) 7.40-7.46 (1H, m) 6.95-7.05 (1H, m) 6.75-6.75 (1H, m) 6.73-6.85 (1H, m) 6.29 (1H, dd, J=17.05, 1.31 Hz) 5.93-6.01 (2H, m) 5.84-5.92 (2H, m) 5.57-5.63 (1H, m) 3.85 (2H, s) 2.96 (1H, br s) 2.91-3.00 (1H, m) 2.60-2.69 (1H, m) 2.24-2.32 (2H, m) 1.75-1.90 (4H, m).

Example 7: Preparation of Compound 14

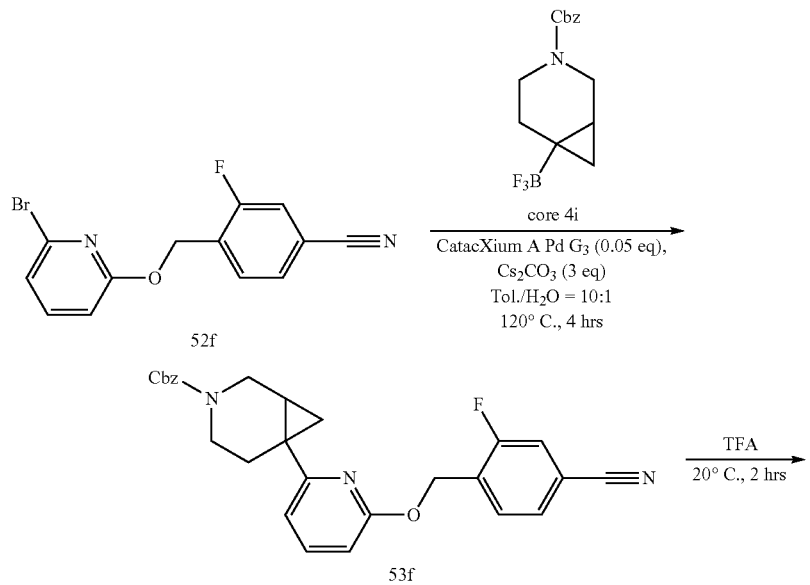

151 / 152

-continued

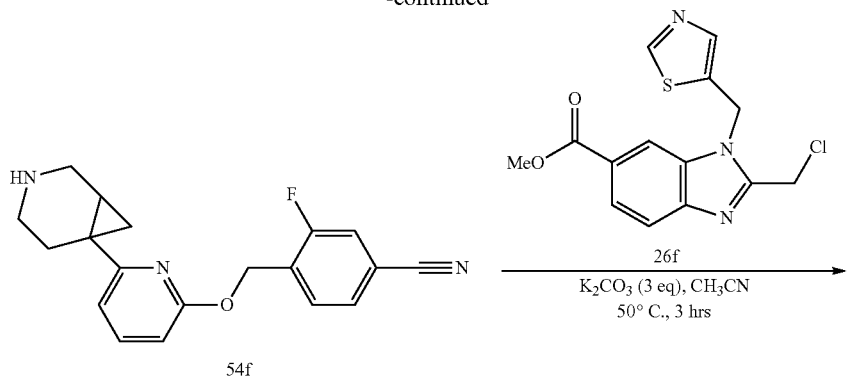

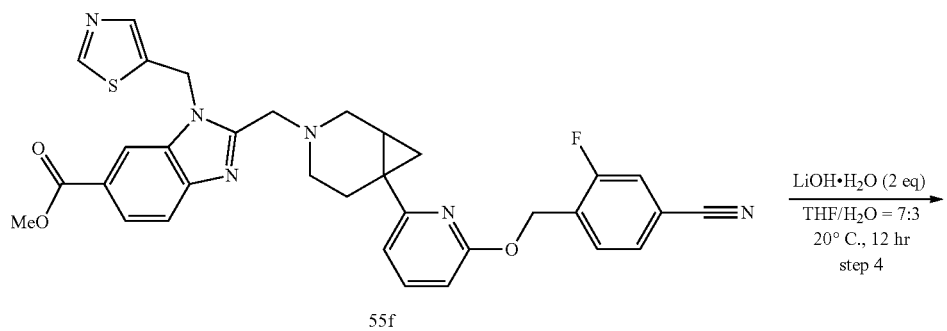

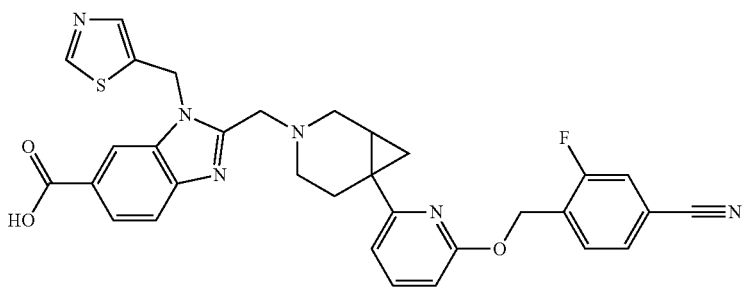

compound 14

Step 1: Preparation of Intermediate 53f

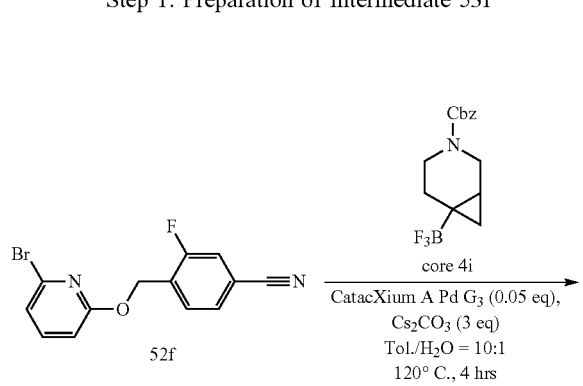

-continued

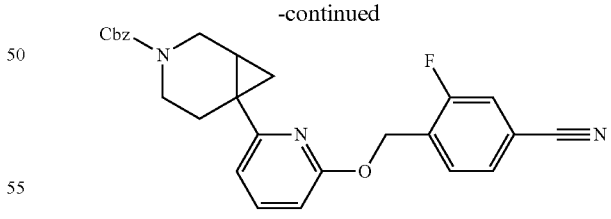

53f

A mixture of intermediate 52f (100 mg, 325.61 mol, 1 eq), core 4i (165.18 mg, 488.41 mol, 1.5 eq, K⁺), Cs₂CO₃ (318.27 mg, 976.82 mol, 3 eq), CatacXium A Pd G₃ (11.86 mg, 16.28 mol, 0.05 eq) in toluene (5 mL) H₂O (0.5 mL) was degassed and purged with N₂ for 3 times, and then the mixture was stirred at 120° C. for 4 hrs under N₂ atmosphere. The residue was diluted with H₂O (10 mL) and extracted with EtOAc (20 mL*2). The reaction mixture was poured into separatory funnel and separated. The combined organic layers were washed with brine (10 mL), dried over Na$_2$SO$_4$, filtered and concentrated under reduced pressure to give a residue. The residue was purified by column chromatography (SiO$_2$, Petroleum ether/Ethyl acetate=100/1 to 0/1, TLC-Petroleum ether/Ethyl acetate=10/1, Produce Rf=0.6). Intermediate 53f (200 mg, 437.16 mol, 67.13% yield) was obtained as a yellow oil. LCMS: RT=1.049 min, MS cal.:457.50, [M+H]$^+$=458.2 $^1$H NMR (400 MHz, chloroform-d) δ=ppm 7.55 (dt, J=17.79, 7.67 Hz, 2H) 7.29-7.47 (m, 7H) 6.78-6.87 (m, 1H) 6.62 (d, J=8.32 Hz, 1H) 5.45 (d, J=3.22 Hz, 2H) 5.31 (s, 1H) 5.15 (s, 2H) 3.74-3.88 (m, 2H) 3.50-3.65 (m, 1H) 3.30 (br s, 1H) 2.41-2.51 (m, 1H) 2.02-2.18 (m, 1H) 1.69 (br s, 1H) 1.20-1.31 (m, 2H) 0.83-0.97 (m, 2H).

Step 2: Preparation of Intermediate 54f

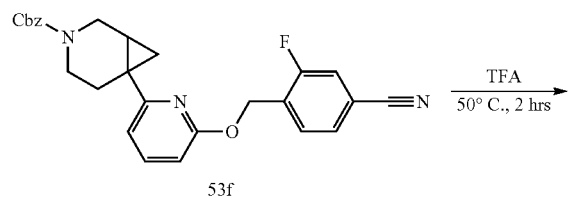

53f

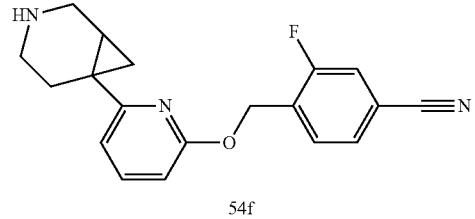

54f

A mixture of intermediate 53f (15 mg, 32.79 mol, 1 eq) in TFA (32.79 mol, 1.00 eq) was degassed and purged with N$_2$ for 3 times, and then the mixture was stirred at 50° C. for 2 hrs under N$_2$ atmosphere. The reaction mixture was filtered and the filtrate was concentrated. Intermediate 54f (14 mg, crude, TFA) was obtained as a yellow oil. LCMS: RT=0.735 min, MS cal.:323.36, [M+H]$^+$=324.2 $^1$H NMR (400 MHz, chloroform-d) δ=ppm 7.72 (t, J=7.88 Hz, 1H) 7.62 (t, J=7.50 Hz, 1H) 7.48 (br d, J=8.00 Hz, 1H) 7.37-7.43 (m, 2H) 6.96 (d, J=7.50 Hz, 1H) 6.80 (d, J=8.25 Hz, 1H) 5.39-5.53 (m, 2H) 4.58 (br s, 16H) 3.76-3.86 (m, 2H) 3.26-3.43 (m, 2H) 2.95 (br d, J=9.26 Hz, 1H) 2.69-2.79 (m, 1H) 2.31-2.39 (m, 1H) 1.79-1.88 (m, 1H) 1.49 (dd, J=9.26, 5.63 Hz, 1H) 1.46-1.53 (m, 1H) 1.26 (s, 1H) 1.08 (t, J=5.75 Hz, 1H)

Step 3: Preparation of Intermediate 55f

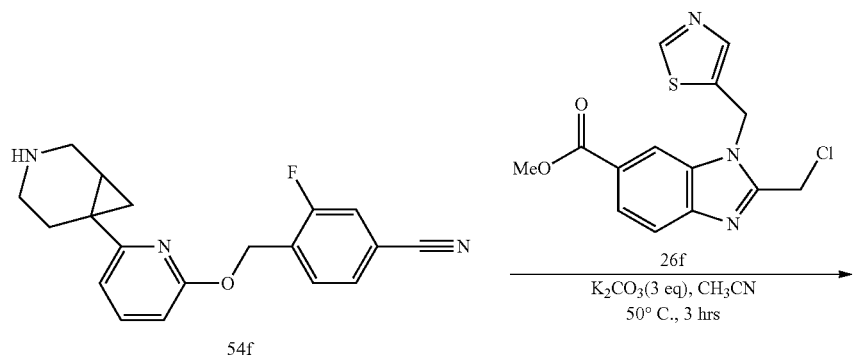

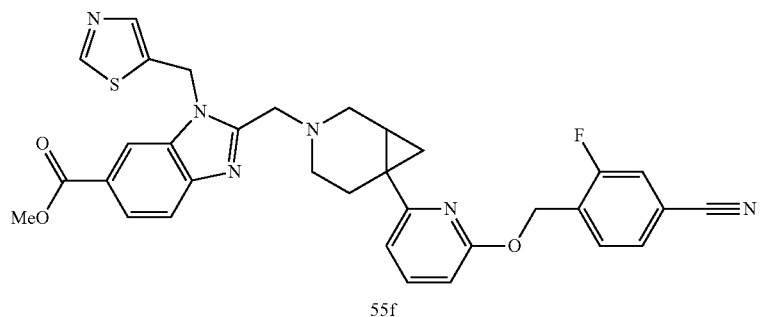

55f

A mixture of intermediate 54f (241.18 mg, 745.85 mol, 1 eq), 26f (240 mg, 745.85 mol, 1 eq), $K_2CO_3$ (309.24 mg, 2.24 mmol, 3 eq) in ACN (5 mL) was degassed and purged with $N_2$ for 3 times, and then the mixture was stirred at 50° C. for 3 hrs under $N_2$ atmosphere. The residue was diluted with $H_2O$ (30 mL) and extracted with EtOAc (50 mL*2). The reaction mixture was poured into separatory funnel and separated. The combined organic layers were washed with brine (10 mL), dried over $Na_2SO_4$, filtered and concentrated under reduced pressure to give a residue. The residue was purified by column chromatography ($SiO_2$, Petroleum ether/ Ethyl acetate=100/1 to 30/1, TLC-Dichloromethane/Methanol=10/1, Produce Rf=0.6). Intermediate 55f (300 mg, crude) was obtained as a yellow oil. LCMS: RT=0.807 min, MS cal.:608.69, [M+H]$^+$=609.3 $^1$H NMR (400 MHz, DMSO-$d_6$) δ=ppm 9.03 (s, 1H) 8.91 (s, 1H) 8.89-8.92 (m, 1H) 8.29 (d, J=1.25 Hz, 1H) 8.19 (d, J=1.00 Hz, 1H) 8.04 (s, 1H) 7.95 (s, 1H) 7.82-7.92 (m, 2H) 7.77 (d, J=8.50 Hz, 1H) 7.60-7.74 (m, 4H) 7.31-7.38 (m, 1H) 6.90-6.95 (m, 1H) 6.66 (d, J=8.13 Hz, 1H) 6.02 (s, 1H) 5.96 (s, 1H) 5.38-5.47 (m, 2H) 5.19 (s, 1H) 3.90 (br s, 1H) 3.88 (d, J=6.75 Hz, 5H) 2.68-2.90 (m, 2H) 2.32-2.43 (m, 2H) 1.84-1.97 (m, 1H) 1.84-1.97 (m, 1H) 1.61-1.73 (m, 1H) 1.01-1.09 (m, 1H) 0.78 (dd, J=5.88, 3.50 Hz, 1H).

Step 4: Preparation of Compound 14

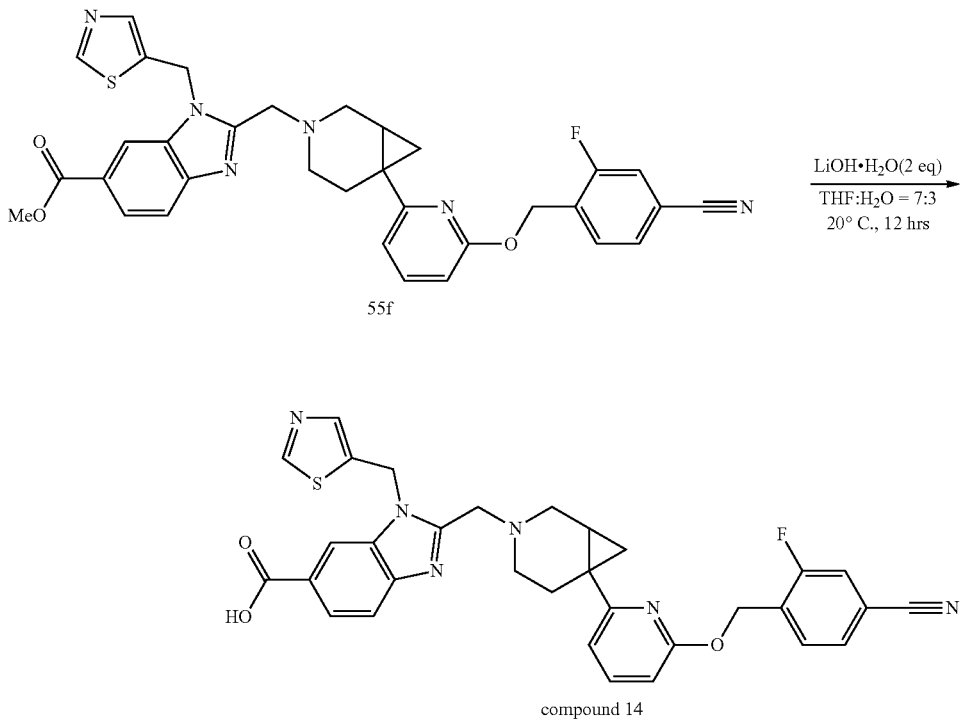

A mixture of intermediate 55f (150 mg, 246.43 mol, 1 eq), LiOH $H_2O$ (20.68 mg, 492.87 mol, 2 eq) in THF (2.1 mL) and $H_2O$ (0.9 mL) was degassed and purged with $N_2$ for 3 times, and then the mixture was stirred at 20° C. for 12 hrs under $N_2$ atmosphere. The reaction mixture was filtered and the filtrate was concentrated. The crude product was purified by reversed-phase HPLC (column: Waters Xbridge BEH C18 100*30 mm*10 um; mobile phase: [water ($NH_4HCO_3$)-ACN]; B %: 15%-45%, 8 min). Intermediate 14 (26.73 mg, 43.93 mol, 17.83% yield, 97.74% purity) was obtained as a white solid. LCMS: RT=2.647 min, MS cal.:594.66, [M+H]$^+$=595.3 $^1$H NMR (400 MHz, DMSO-$d_6$) δ=ppm 8.91 (d, J=0.63 Hz, 1H) 8.13 (s, 1H) 7.95 (s, 1H) 7.89 (dd, J=10.01, 1.25 Hz, 1H) 7.82 (dd, J=8.38, 1.50 Hz, 1H) 7.68-7.71 (m, 1H) 7.60-7.66 (m, 3H) 6.92 (d, J=7.63 Hz, 1H) 6.66 (d, J=8.13 Hz, 1H) 5.93 (s, 2H) 5.42 (d, J=3.00 Hz, 2H) 3.87 (d, J=13.63 Hz, 1H) 3.75 (d, J=13.63 Hz, 1H) 2.81-2.85 (m, 1H) 2.76 (br d, J=10.38 Hz, 2H) 2.38-2.46 (m, 2H) 1.86-1.94 (m, 1H) 1.86-1.94 (m, 1H) 1.62-1.70 (m, 1H) 1.04 (dd, J=9.13, 3.13 Hz, 1H) 0.80 (dd, J=5.94, 3.56 Hz, 1H).

Example 8: Preparation of Compound 16
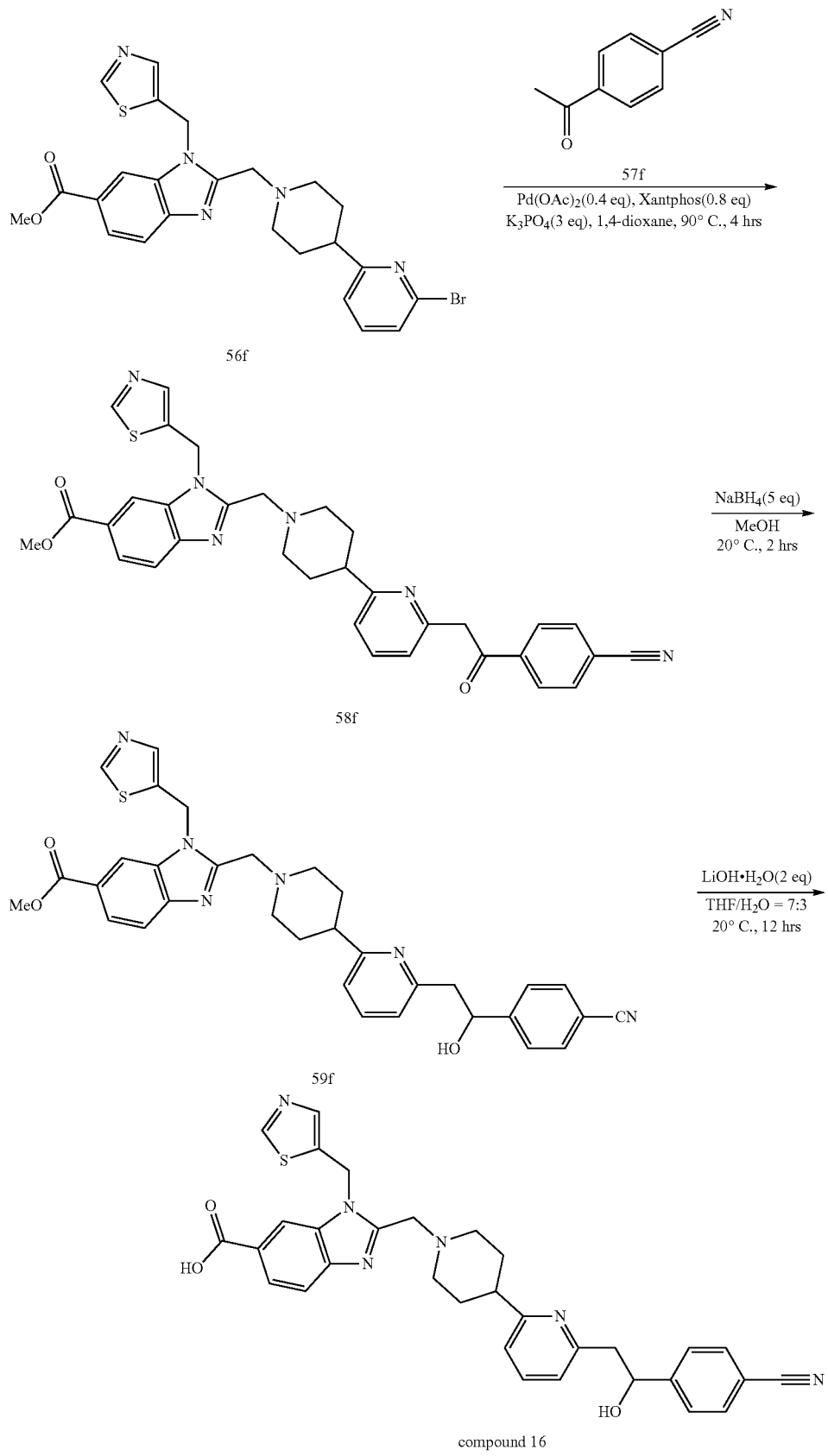

Step 1: Preparation of Intermediate 58f

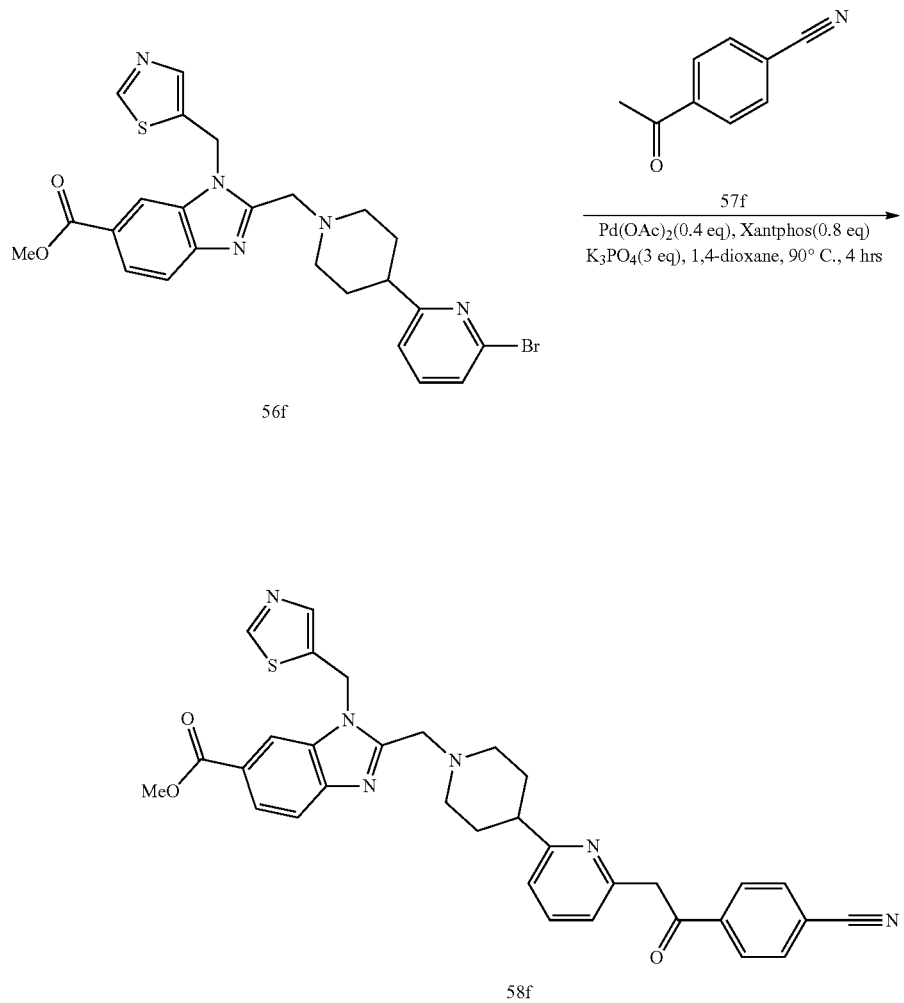

A mixture of intermediate 56f (27.57 mg, 189.95 mol, 2 eq), intermediate 57f (50 mg, 94.98 mol, 1 eq), K$_3$PO$_4$ (60.48 mg, 284.93 mol, 3 eq), Xantphos (43.96 mg, 75.98 mol, 0.8 eq) and Pd(OAc)$_2$ (8.53 mg, 37.99 mol, 0.4 eq) in dioxane (2 mL) was degassed and purged with N$_2$ for 3 times, and then the mixture was stirred at 90° C. for 4 hrs under N$_2$ atmosphere. The residue was diluted with H$_2$O (5 mL) and extracted with EtOAc (4 mL*2). The reaction mixture was poured into separatory funnel and separated. The combined organic layers were washed with brine (2 mL), dried over Na$_2$SO$_4$, filtered and concentrated under reduced pressure to give a residue. The residue was purified by prep-TLC (SiO$_2$, Petroleum ether: Ethyl acetate=0:1, produce Rf=0.5). Intermediate 58f (10 mg, 16.93 mol, 17.82% yield) was obtained as a yellow solid. LCMS: RT=0.574 min, MS cal.:590.69, [M+H]$^+$=591.4 $^1$H NMR (400 MHz, chloroform-d) δ=ppm 8.77 (d, J=0.63 Hz, 1H) 8.14 (d, J=1.50 Hz, 1H) 7.98-8.02 (m, 1H) 7.88-7.94 (m, 3H) 7.76-7.79 (m, 1H) 7.68-7.72 (m, 2H) 7.62 (t, J=7.82 Hz, 1H) 7.26 (s, 4H) 6.92-7.01 (m, 2H) 6.15 (s, 1H) 5.89 (s, 2H) 3.95 (s, 3H) 3.92 (s, 2H) 3.06 (br d, J=11.63 Hz, 2H) 2.73-2.82 (m, 1H) 2.73-2.82 (m, 1H) 2.32-2.41 (m, 2H) 1.89-2.03 (m, 5H) 1.35-1.35 (m, 1H) 0.75-0.93 (m, 7H).

Step 2: Preparation of Intermediate 59f

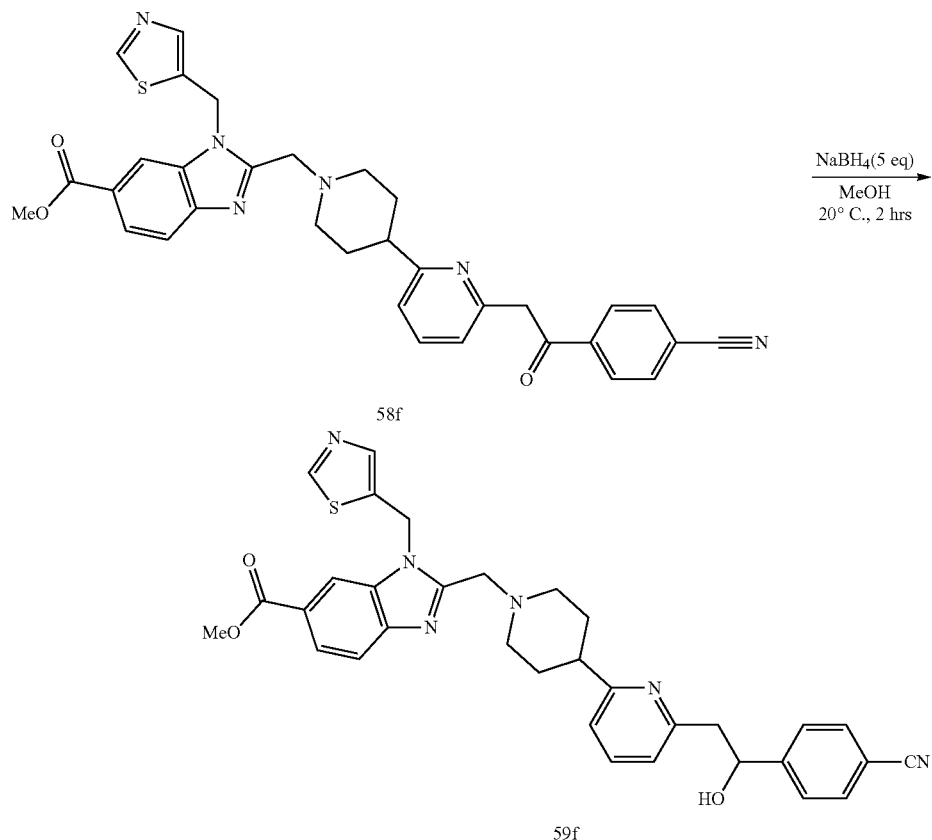

A mixture of intermediate 58f (90 mg, 152.36 mol, 1 eq), NaBH$_4$ (28.82 mg, 761.82 mol, 5 eq) in MeOH (5 mL) was degassed and purged with N$_2$ for 3 times, and then the mixture was stirred at 20° C. for 2 hrs under N$_2$ atmosphere. The residue was diluted with sat. NH$_4$Cl (1 mL) (0° C.) and extracted with DCM (2 mL*2). The reaction mixture was poured into separatory funnel and separated. The combined organic layers were washed with brine (1 mL), dried over Na$_2$SO$_4$, filtered and concentrated under reduced pressure to give a residue. Intermediate 59f (80 mg, crude) was obtained as a yellow solid. LCMS: RT=0.616 min, MS cal.:592.71, [M+H]$^+$=593.3 $^1$H NMR (400 MHz, chloroform-d) δ=ppm 8.78 (s, 1H) 8.14 (s, 1H) 8.01 (d, J=8.50 Hz, 1H) 7.88 (s, 1H) 7.77 (d, J=8.50 Hz, 1H) 7.64 (d, J=8.13 Hz, 2H) 7.50-7.60 (m, 3H) 7.08 (d, J=7.75 Hz, 1H) 6.94 (d, J=7.63 Hz, 1H) 5.88 (s, 2H) 5.31 (s, 2H) 5.23 (dd, J=8.50, 2.63 Hz, 1H) 3.95 (s, 3H) 3.90 (s, 2H) 3.01-3.18 (m, 4H) 2.75 (br t, J=11.76 Hz, 1H) 2.30-2.40 (m, 2H) 1.84-1.98 (m, 3H).

Step 3: Preparation of Compound 16

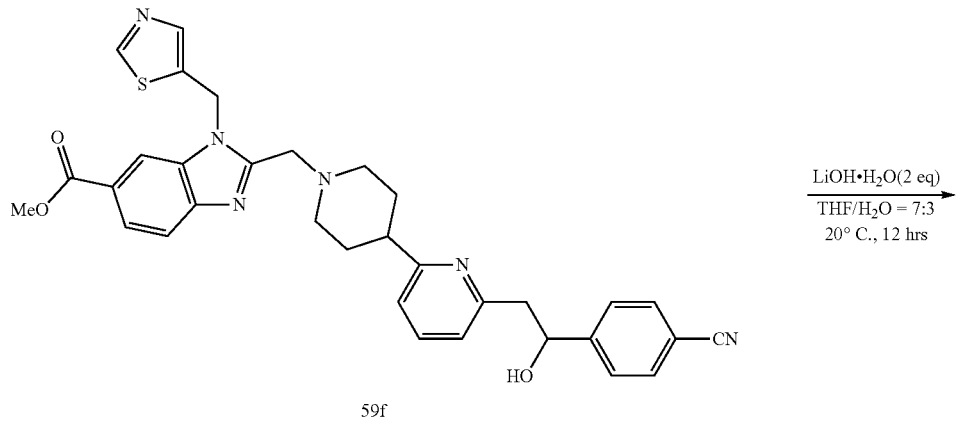

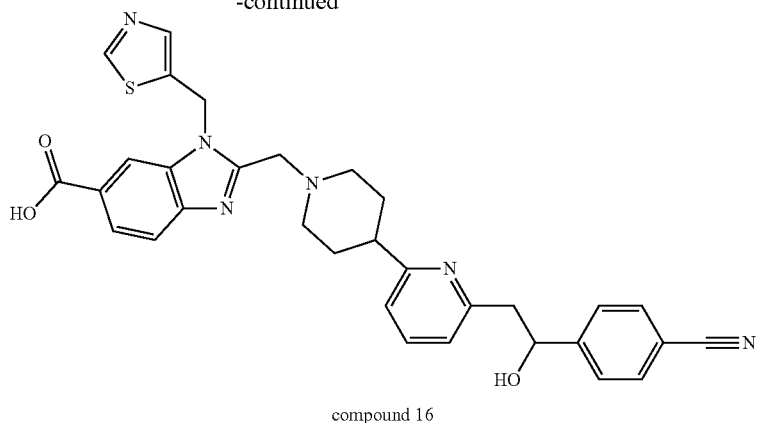

compound 16

A mixture of intermediate 59f (80 mg, 134.97 mol, 1 eq), LiOH H$_2$O (11.33 mg, 269.95 mol, 2 eq) in THF (1.4 mL), and H$_2$O (0.6 mL) was degassed and purged with N$_2$ for 3 times, and then the mixture was stirred at 20° C. for 12 hrs under N$_2$ atmosphere. The reaction mixture was filtered and the filtrate was concentrated. The crude product was purified by reversed-phase HPLC (column: Waters Xbridge Prep OBD C18 150*40 mm*10 um; mobile phase: [water (NH$_4$HCO$_3$)-ACN]; B %: 12%-42%, 8 min). Compound 16 (26.98 mg, 46.32 mol, 34.31% yield, 99.34% purity) was obtained as a white solid. LCMS: RT=2.284 min, MS cal.:578.68, [M+H]$^+$=579.3 $^1$H NMR (400 MHz, methanol-d$_4$) δ=ppm 8.96 (d, J=0.75 Hz, 1H) 8.23 (d, J=1.00 Hz, 1H) 7.96-8.01 (m, 2H) 7.70 (d, J=8.50 Hz, 1H) 7.58-7.66 (m, 3H) 7.50 (d, J=8.13 Hz, 2H) 7.10 (d, J=7.75 Hz, 1H) 7.02 (d, J=7.25 Hz, 1H) 6.01 (s, 2H) 5.16 (dd, J=7.38, 5.75 Hz, 1H) 3.96 (s, 2H) 3.09-3.15 (m, 2H) 3.05 (brd, J=11.38 Hz, 2H) 2.64-2.77 (m, 1H) 2.28-2.40 (m, 2H) 1.69-1.89 (m, 4H).

Example 9: Preparation of Compound 20

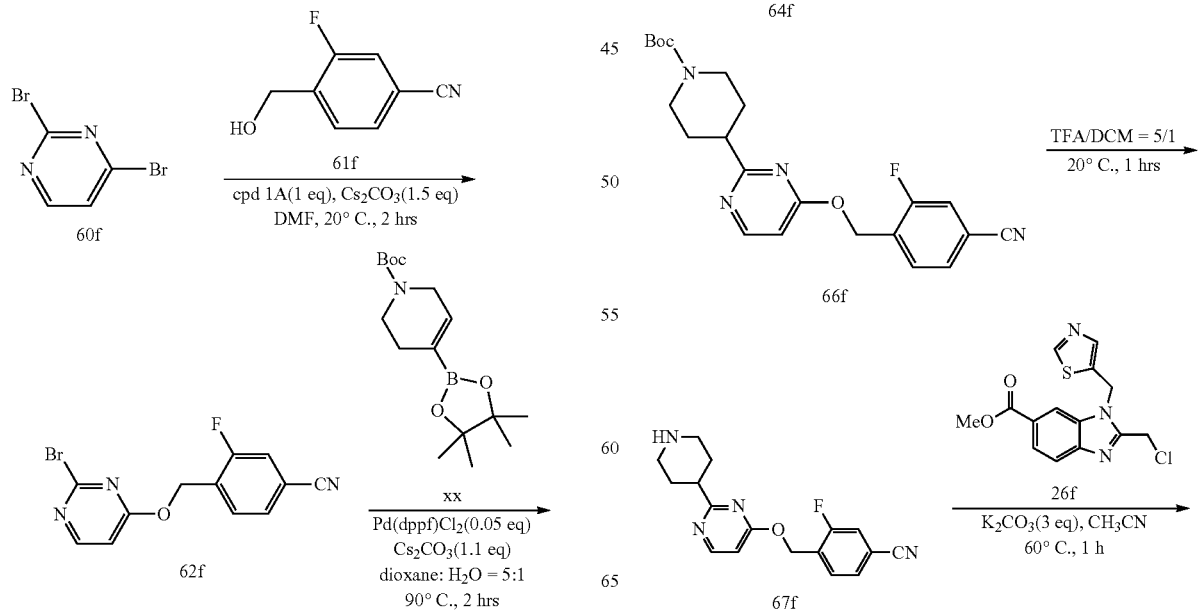

165
-continued

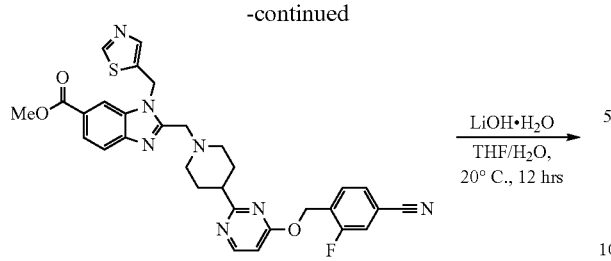

compound 20

Step 1: Preparation of Intermediate 62f

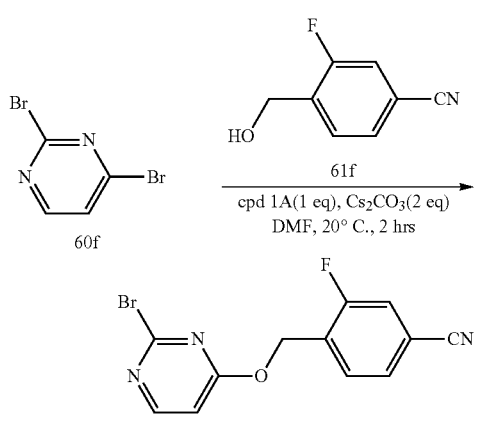

To a solution of intermediate 60f (3.18 g, 21.02 mmol, 1 eq) in DMF (40 mL) was added Cs₂CO₃ (13.70 g, 42.04 mmol, 2 eq) and intermediate 61f (5 g, 21.02 mmol, 1 eq). The mixture was stirred at 20° C. for 2 hrs. The residue was diluted with H₂O (30 mL) and extracted with EtOAc (30 mL*3). The combined organic layers were dried over Na₂SO₄, filtered and concentrated under reduced pressure to give a residue. The residue was purified by column chromatography (SiO₂, Petroleum ether/Ethyl acetate=50/1 to 5/1). Intermediate 62f (2 g, 6.49 mmol, 30.88% yield) was obtained as a white solid. ¹H NMR (400 MHz, DMSO-d₆) δ=3.32 (s, 1H) 5.53 (s, 2H) 7.10-7.20 (m, 1H) 7.53 (s, 1H) 7.77 (d, J=3.42 Hz, 2H) 7.94 (d, J=9.90 Hz, 1H) 8.45 (d, J=5.75 Hz, 1H).

166
Step 2: Preparation of Intermediate 63f

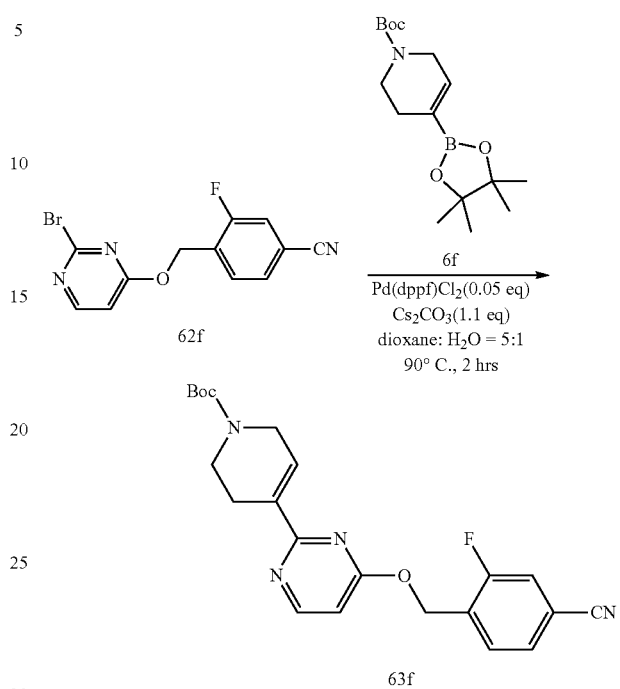

A mixture of intermediate 62f (1.5 g, 4.87 mmol, 1 eq), intermediate 6f (1.51 g, 4.87 mmol, 1 eq), Pd(dppf)Cl₂ (178.11 mg, 243.42 mol, 0.05 eq), K₂CO₃ (2.02 g, 14.61 mmol, 3 eq) in dioxane (10 mL), and H₂O (2 mL) was degassed and purged with N₂ for 3 times, and then the mixture was stirred at 90° C. for 2 hrs under N₂ atmosphere. The reaction mixture was diluted with H₂O (30 mL) and extracted with EtOAc (30 mL*3). The combined organic layers were washed with NaCl a.q. (30 mL), dried over Na₂SO₄, filtered and concentrated under reduced pressure to give a residue. The residue was purified by column chromatography (SiO₂, Petroleum ether/Ethyl acetate=10/1 to 0/1). Intermediate 63f (1.2 g, 2.92 mmol, 60.05% yield) was obtained as a white solid. LCMS: Rt=0.971 min, MS cal.: 410.2, [M+H]⁺=411.2 ¹H NMR (400 MHz, chloroform-d) δ=1.25 (s, 3H) 1.50 (s, 10H) 1.95 (s, 1H) 2.68 (br s, 2H) 3.63 (br t, J=5.38 Hz, 2H) 4.17 (br d, J=2.00 Hz, 2H) 5.58 (s, 2H) 6.66 (d, J=5.75 Hz, 1H) 7.17 (br s, 1H) 7.42 (dd, J=9.26, 1.25 Hz, 1H) 7.48 (dd, J=8.00, 1.00 Hz, 1H) 7.57-7.65 (m, 1H) 8.45-8.49 (m, 1H).

Step 3: Preparation of Intermediate 64f

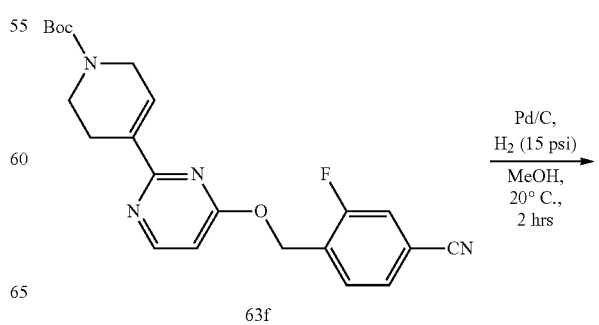

800.08 mol, 74.50% yield) was obtained as a white solid. $^1$H NMR (400 MHz, chloroform-d) δ=1.49 (s, 10H) 1.77 (qd, J=12.41, 4.34 Hz, 2H) 1.95 (br d, J=12.23 Hz, 2H) 2.81-2.99 (m, 3H) 4.20 (br d, J=2.20 Hz, 2H) 5.55 (s, 2H) 6.66 (d, J=5.75 Hz, 1H) 7.41 (dd, J=9.17, 1.47 Hz, 1H) 7.48 (dd, J=7.83, 1.34 Hz, 1H) 7.58-7.64 (m, 1H) 8.40-8.44 (m, 1H).

Step 3: Preparation of Intermediate 67f

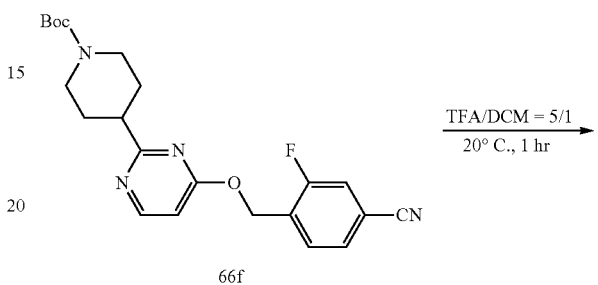

To a solution of intermediate 66f (0.3 g, 727.35 mol, 1 eq) in DCM (5 mL) was added TFA (3.08 g, 27.01 mmol, 2 mL, 37.14 eq). The mixture was stirred at 20° C. for 1 hr. The reaction was clean according to TLC. The reaction mixture was concentrated under reduced pressure to remove solvent. Intermediate 67f (220 mg, 704.36 mol, 96.84% yield) was obtained as a yellow oil.

Step 4: Preparation of Intermediate 68f

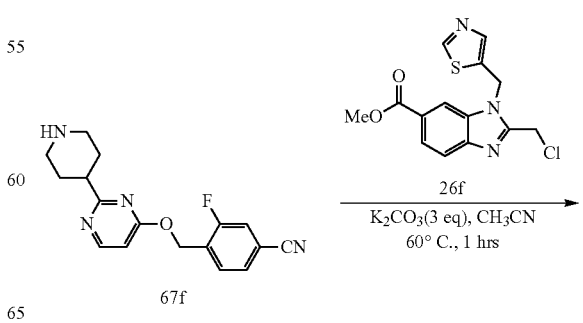

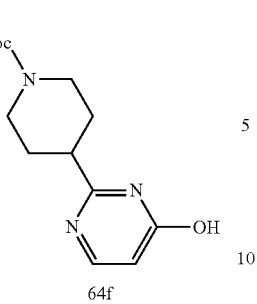

To a solution of intermediate 63f (500 mg, 1.22 mmol, 1 eq) in MeOH (8 mL) was added Pd/C (200 mg, 1.22 mmol, 10% purity, 1 eq) under N$_2$ atmosphere. The suspension was degassed and purged with H$_2$ for 3 times. The mixture was stirred under H$_2$ (15 Psi) at 20° C. for 2 hrs. The reaction mixture was filtered and concentrated under reduced pressure to give a residue. The residue was purified by column chromatography (SiO$_2$, Petroleum ether/Ethyl acetate=20/1 to 1/1). Intermediate 64f (330 mg, 1.18 mmol, 96.98% yield) was obtained as a white solid. LCMS: Rt=0.681 min, MS cal.: 279.16, [M−55]$^+$=224.2 $^1$H NMR (400 MHz, chloroform-d) δ=1.48 (s, 9H) 1.70-1.88 (m, 2H) 1.89-2.00 (m, 2H) 2.69-2.82 (m, 1H) 2.82-2.95 (m, 2H) 4.16-4.33 (m, 2H) 6.35 (d, J=6.60 Hz, 1H) 7.97-8.02 (m, 1H)

Step 3: Preparation of Intermediate 65f

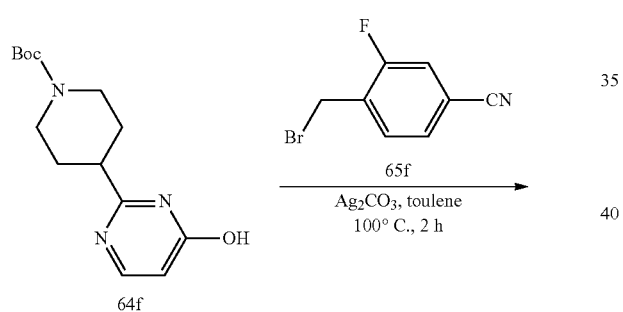

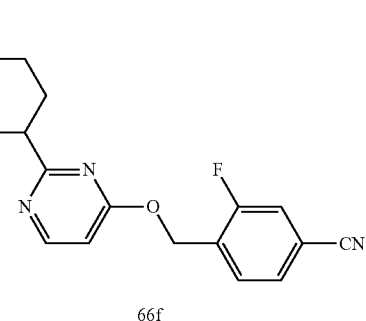

To a solution of intermediate 64f (0.3 g, 1.07 mmol, 1 eq) in toluene (5 mL) was added Ag$_2$CO$_3$ (592.29 mg, 2.15 mmol, 2 eq) and intermediate 65f (252.86 mg, 1.18 mmol, 1.1 eq). The mixture was stirred at 100° C. for 2 h. The reaction mixture was diluted with H$_2$O (20 mL) and extracted with EtOAc (20 mL*3). The combined organic layers were dried over Na$_2$SO$_4$, filtered and concentrated under reduced pressure to give a residue. The residue was purified by column chromatography (SiO$_2$, Petroleum ether/Ethyl acetate=10/1 to 1/1). Intermediate 66f (330 mg, -continued

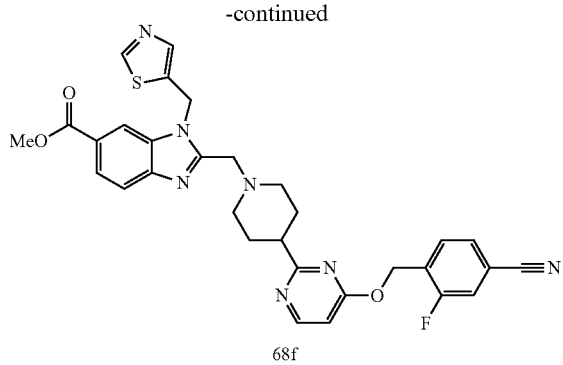

68f

To a solution of intermediate 67f (220 mg, 683.69 mol, 1 eq) in ACN (10 mL) was added K$_2$CO$_3$ (283.47 mg, 2.05 mmol, 3 eq) and intermediate 26f (213.55 mg, 683.69 mol, 1 eq). The mixture was stirred at 60° C. for 1 hr. The reaction mixture was concentrated under reduced pressure to remove solvent. The residue was diluted with H$_2$O (30 mL) and extracted with EtOAc (30 mL*3). The combined organic layers were washed with NaCl a.q. (20 mL), dried over Na$_2$SO$_4$, filtered and concentrated under reduced pressure to give a residue. The residue was purified by column chromatography (SiO$_2$, Petroleum ether/Ethyl acetate=10/1 to 0/1). Intermediate 68f (200 mg, 334.64 mol, 48.95% yield) was obtained as a white solid. LCMS: Rt=1.230 min, MS cal.: 597.2, [M+H]$^+$=598.4 $^1$H NMR (400 MHz, chloroform-d) δ=1.90 (br d, J=11.26 Hz, 2H) 1.97-2.14 (m, 6H) 2.35 (br d, J=8.25 Hz, 2H) 2.78-2.90 (m, 1H) 3.01 (br d, J=9.51 Hz, 2H) 3.91 (s, 2H) 3.96 (s, 3H) 5.56 (s, 2H) 5.94 (s, 2H) 6.66 (d, J=5.75 Hz, 1H) 7.35-7.45 (m, 1H) 7.48 (d, J=8.00 Hz, 1H) 7.60-7.68 (m, 1H) 7.77 (d, J=8.50 Hz, 1H) 7.87 (s, 1H) 8.01 (dd, J=8.57, 1.06 Hz, 1H) 8.14 (s, 1H) 8.39-8.45 (m, 1H) 8.73-8.76 (m, 1H).

Step 5: Preparation of Compound 20

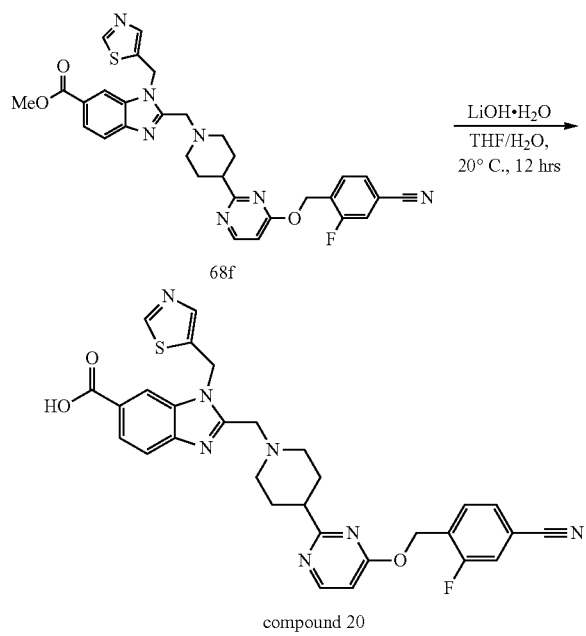

To a solution of intermediate 68f (0.1 g, 167.32 mol, 1 eq) in THF (1.5 mL) was added LiOH H$_2$O (10.53 mg, 250.98 mol, 1.5 eq) in H$_2$O (0.5 mL). The mixture was stirred at 20° C. for 12 hrs. The reaction was added citric acid to adjust to pH=8, then the mixture was purified directly. The residue was purified by prep-HPLC (neutral condition; column: Waters Xbridge BEH C18 100*30 mm*10 um; mobile phase: [water (NH$_4$HCO$_3$)-ACN]; B %: 30%-50%, 8 min). Compound 20 (43.79 mg, 75.03 mol, 44.84% yield) was obtained as a white solid. LCMS: Rt=2.003 min, MS cal.: 583.1, [M+H]$^+$=584.1 $^1$H NMR (400 MHz, methanol-d$_4$) δ=1.82-1.96 (m, 4H) 2.33 (td, J=11.07, 4.03 Hz, 2H) 2.80 (dt, J=10.30, 5.18 Hz, 1H) 3.02 (br d, J=11.37 Hz, 2H) 3.94 (s, 2H) 5.60 (s, 2H) 6.01 (s, 2H) 6.78 (d, J=5.87 Hz, 1H) 7.55-7.62 (m, 2H) 7.67-7.72 (m, 2H) 7.96-8.01 (m, 2H) 8.22 (d, J=0.98 Hz, 1H) 8.40 (d, J=5.87 Hz, 1H) 8.91-8.93 (m, 1H).

Compound 31 can be prepared according to synthetic methods described herein, optionally with guidance from WO2019/239319.

Biological Assays

Example B1: GLP-1R Cell Assay

Stable cell lines expressing high and low GLP-1R surface expression were generated in CHO-K1 cells transfected (Fugene 6) with a puromycin selectable DNA plasmid encoding human GLP-1R receptor (accession number: NM_002062.5) under control of an EF1A promoter. Transfected cells were seeded into 24-well plates (9,000 cells/well) containing complete medium and incubated in a humidified incubator at 37° C. with 5% carbon dioxide. After overnight incubation, medium was replaced with complete medium supplemented with puromycin (6 μg/mL) and refreshed every 2-3 days to select for stably transfected cells. Individual pools of selected cells were expanded prior to analysis for responsiveness to GLP-1 control peptide using a TR-FRET assay to detect cAMP (LANCE Ultra cAMP Assay, Perkin Elmer). Briefly, cells were collected in Versene solution, plated in 384-well plates (1,000 cells/well) and combined with serially diluted GLP-1R control peptide (10 nL) using an acoustic dispenser (ECHO). Plates were incubated for 30 minutes at 25° C. prior to the addition of EU-cAMP tracer (5 μL) and Ulight-anti-cAMP (5 μL) reagents to each well, followed by 15 minutes incubation at 25° C. TR-FRET signal was detected using an EnVision Multimode Plate Reader (excitation=320 nm; emission=615 and 655 nm). Dose-response curves were used to generate EC$_{50}$ values as a measure of responsiveness to the GLP-1R control peptide. Selected cell lines were monitored for responsiveness over multiple passages to ensure stability. CHO-K1_hGLP-1Rhigh_clone16 and CHO-K1_hGLP-1Rlow_clone10 showed consistently high and low responsiveness to GLP-1R control peptide, respectively, and were chosen for further analysis to determine relative levels of GLP-1R surface expression. Briefly, GLP-1R expression was analyzed by flow cytometry using a fluorescein-labeled Exendin-4 peptide fluorescent probe (FLEX). Cells were harvested in Versene solution and washed 3-times with PBS+0.5% BSA before incubation with FLEX reagent (10 μM) for 2 hours at room temperature. After incubation, cells were washed 3-times in PBS+0.5% BSA before final resuspension in PBS prior to analysis by flow cytometry to measure FLEX mean fluorescence intensity (MFI) as a measure of GLP-1R expression on the cell surface. Both cell lines showed higher MFI values relative to control CHO-K1 cells, confirming GLP-1R surface expression; CHO-K1_hGLP-1Rhigh_clone16 cells showed significantly higher MFI levels relative to CHO-K1-hGLP-1low_clone10 cells.

For compound testing in the CHO-K1_hGLP-1Rlow_clone10 cell line, cells were seeded in 384-well plates (1,000 cells/well). Test compounds were serially diluted in DMSO (10-point, 3-fold dilution), added to wells using an ECHO dispenser (10 nL/well) and plates were centrifuged for 1 min and agitated for 2 min at room temperature prior to 30-minute incubation at 25° C. After incubation, Eu-cAMP (5 μL) and Ulight-anti-cAMP (5 μL) reagents were added to each well, followed by centrifugation for 1 minute, agitation for 2 minutes at room temperature, and final incubation of the plates at 25° C. for 15 minutes. Plates were read using an EnVision microplate reader (excitation=320 nm; emission=615 and 655 nm). Dose-response curves were generated from duplicate wells based on percent activation calculated relative to a control GLP-1 peptide agonist that was run in parallel. $EC_{50}$ values were determined by fitting percent activation as a function of compound concentration using the Hill equation (XLfit).

The $EC_{50}$ values of exemplary compounds in the low expression assay are shown in Table 2 below. The compounds tested were compound samples prepared according to the General Procedures described in the Examples section.

TABLE 2

| Cmpd No. | GLP-1R Low Expression Cell Assay EC50 (nM) |
|---|---|
| Ref. Compd. A | 1.4 |
| 1 | 50.1 |
| 2 | 3.1 |
| 3 | 44.2 |
| 4 | 2.5 |
| 5 | 5.4 |
| 6 | 135.2 |
| 7 | 90.6 |
| 8 | 360.5 |
| 9 | 16.6 |
| 10 | 392.7 |
| 11 | 292.5 |
| 12 | 231.5 |
| 13 | 724.2 |
| 14 | 30.1 |
| 15 | 25.81 |
| 16 | >10000 |
| 18 | 9.9 |
| 19 | 161.3 |
| 20 | 9.4 |
| 21 | 6.6 |
| 22 | 87.5 |
| 23 | 3.3 |
| 24 | 15.1 |
| 25 | 24.4 |
| 26 | 4.0 |
| 27 | 8.6 |
| 29 | 27.8 |
| 30 | 1.7 |
| 31 | 0.6 |

Example B2: Rat Pharmacokinetics

Intravenous dosing: Compounds were formulated at 0.5 mg/mL in a solution comprising 500 polyethylene glycol 400 and 95% (12% (w/v) sulfobutyl-β-cyclodextrin in water) (v/v). Formulated compounds were sterile filtered through a 0.22 micron filter before dosing. Compounds were administered to male, 7-11-week-old Sprague-Dawley rats by jugular vein cannula infusion over 30 minutes at a dose of 1 mg/kg.

Oral dosing: Compounds were formulated at 0.3 mg/mL or 0.6 mg/mL in a solution comprising 5% polyethylene glycol 400 and 95% (12% (w/v) sulfobutyl-β-cyclodextrin in water) (v/v). Formulated compounds were administered to male, 7-11 week old Sprague-Dawley rats by oral gavage at a dose of 3 mg/kg.

Sample collection: Blood collections of about 0.2 mL per time point were performed from jugular vein or other suitable site of each animal, into pre-chilled commercial EDTA-K2 tubes and placed on wet ice until centrifugation. Blood samples were processed for plasma by centrifugation at approximately 4° C., 3,200 g for 10 min. Plasma was collected and transferred into pre-labeled 96 well plate or polypropylene tubes, quick frozen over dry ice and kept at −60° C. or lower until LC-MS/MS analysis.

Data analysis: Plasma concentration versus time data was plotted in graph and analyzed by non-compartmental approaches using the Phoenix WinNonlin 6.3 software program. Related PK parameters were calculated according to dosing route, e.g., CL, $V_{dss}$ and $C_0$ for intravenous administration, $C_{max}$, $T_{max}$ or % F for extravascular administration, and $T_{1/2}$, $AUC_{(0-t)}$, $AUC_{(0-inf)}$, $MRT_{(0-t)}$, $MRT_{(0-inf)}$ for all routes.

Figure 2:
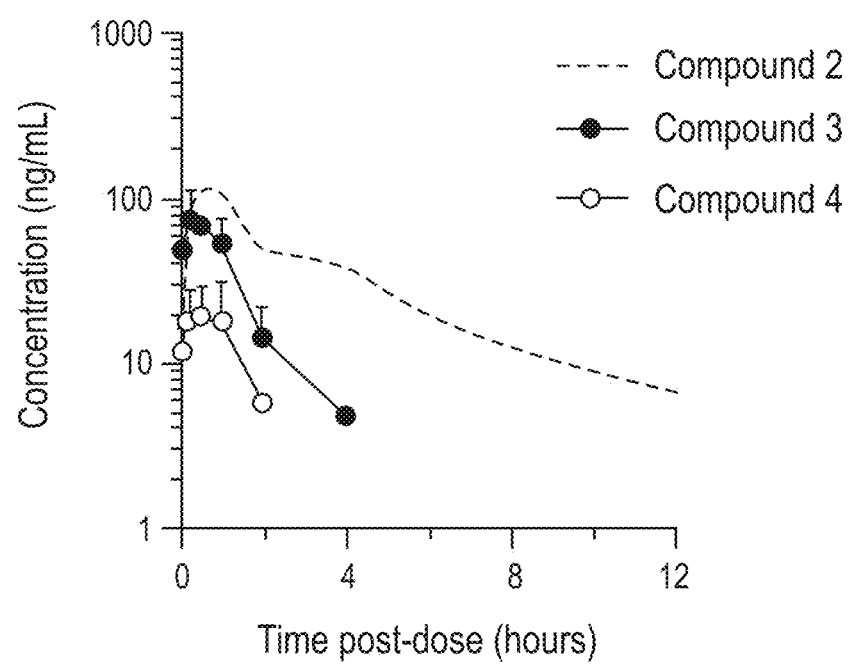
FIG. 2 shows plasma concentrations of compounds 2, 3, and 4 after oral (PO) administration to rats (0.3 mg/mL, 3 mg/kg).
Figure 3:
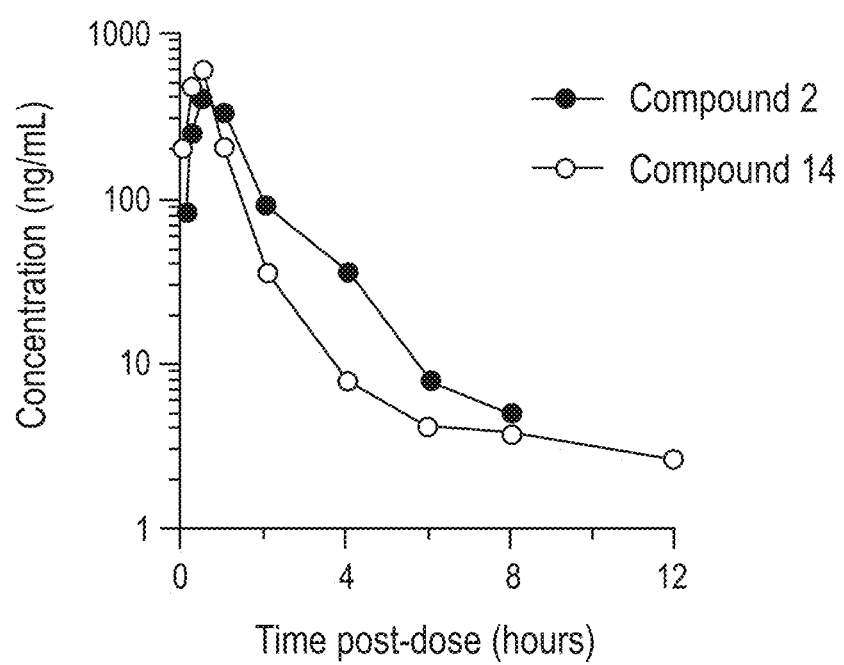
FIG. 3 shows plasma concentrations of compounds 2 and 14 after oral (PO) administration to rats (0.6 mg/mL, 3 mg/kg).

Results: PK parameters in plasma after intravenous dosing are shown in Table 3. PK parameters in plasma after oral dosing are shown in Tables 4 and 5. Plasma concentrations of Compound 2 and Reference Compound A after oral dosing with 3 mg/kg are shown in FIG. 1. Plasma concentrations of Compounds 2, 3, and 4 after oral dosing with 0.3 mg/mL, 3 mg/kg are shown in FIG. 2. Plasma concentrations for compounds 2 and 14 after oral dosing with 0.6 mg/mL, 3 mg/kg are shown in FIG. 3.

TABLE 3

| Compound No. | $C_{max}$ (ng/mL) | $t_{1/2}$ (h) | CL (mL/min/kg) | $AUC_{0-last}$ |
|---|---|---|---|---|
| Reference Compound A (PF-006882961) | 486 ± 37.9 | 0.613 ± 0.344 | 51.2 ± 2.59 | 325 ± 16.8 |
| 2 | 596 ± 42.3 | 1.57 ± 0.583 | 38.8 ± 2.55 | 427 ± 27.7 |

1 mg/kg IV (0.5 mg/mL in a solution comprising 5% polyethylene glycol 400 and 95% (12% (w/v) sulfobutyl-β-cyclodextrin in water) (v/v))

TABLE 4

| Compound No. | $C_{max}$ (ng/mL) | $t_{1/2}$ (h) | $AUC_{0-last}$ |
|---|---|---|---|
| Reference Compound A (PF-006882961) | 37.7 ± 8.09 | 2.00 ± 1.07 | 60.6 ± 9.01 |
| 2 | 117 ± 61 | 3.3 ± 0.44 | 384 ± 182 |
| 3 | 79.8 ± 24.4 | 1.1 ± 0.29 | 116 ± 23.2 |
| 4 | 21.6 ± 9.8 | 0.96 ± 0.33 | 28.3 ± 21.7 |

3 mg/kg PO (0.3 mg/mL in: 5% polyethylene glycol 400, 95% (12% (w/v) sulfobutyl-β-cyclodextrin in water) (v/v))

TABLE 5

| Compound No. | $C_{max}$ (ng/mL) | $t_{1/2}$ (h) | $AUC_{0-last}$ |
|---|---|---|---|
| Reference Compound A (PF-006882961) | 102 ± 57.0 | 1.68 ± 0.44 | 121 ± 36.9 |
| 2 | 491 ± 256 | 2.66 ± 1.74 | 525 ± 138 |

TABLE 5-continued

| Compound No. | $C_{max}$ (ng/mL) | $t_{1/2}$ (h) | $AUC_{0-last}$ |
|---|---|---|---|
| 14 | 581 ± 100 | 3.14 ± 1.88 | 582 ± 45 |
| 25 | 412 ± 98.3 | 1.52 ± 0.21 | 558 ± 100 |
| 27 | 478 ± 186 | 1.37 ± 0.18 | 617 ± 248 |
| 29 | 299 ± 62.9 | 1.54 ± 0.46 | 411 ± 32 |

3 mg/kg PO (0.6 mg/mL in: 5% polyethylene glycol 400, 95% (12% (w/v) sulfobutyl-β-cyclodextrin in water) (v/v))

Under various routes and methods of administration, Compound 2, and compounds similar to it (i.e., Compound 14) exhibit consistently improved in vivo pharmacokinetic performance as compared with Reference Compound A. After intravenous administration, Compound 2 exhibited greater exposure, ~2-fold longer $t_{1/2}$, and 30% lower clearance as compared with Reference Compound A (Table 3). Compound 2 also exhibited significantly enhanced PK properties relative to Reference Compound A after oral administration (Table 4, Table 5), with improved $t_{1/2}$, and 4-6-fold higher AUC. Compounds 14, 25, 27, and 29 exhibited similarly improved PK properties relative to Reference Compound A when dosed orally under identical conditions.

Example B3. Food Intake in Humanized Mouse Model

The ability of compounds disclosed herein to modify the food intake of C57BL/6 mice expressing human GLP-1R (hGLP-1R) was evaluated.

Vehicle: 5% polyethylene glycol 400: 95% (12% (w/v) sulfobutyl-β-cyclodextrin in water), (v/v).

Preparation of Vehicle: Sulfobutyl-β-cyclodextrin (12,000.0 mg) was added to a 100 mL volumetric flask and QC with water to 100 mL, and vortexed until fully dissolved; 95 mL was transferred to a new 100 mL flask/cylinder and 5 mL polyethylene glycol 400 was added, the mixture was vortexed until fully dissolved to achieve a clear solution.

Formulation Preparation: The formulation was used within 24 hours after preparation. The formulation was stirred continuously at room temperature if a suspension resulted.

Preparation of Reference Compound A (30 mg/kg, 10 mL/kg) PO Dosing: Reference Compound A (11.70 mg) was dissolved in 3.900 mL vehicle, vortex until fully dissolved to achieve a final concentration of 3.0000 mg/mL clear solution.

Preparation of Reference Compound A (10 mg/kg, 10 mL/kg) PO Dosing: Reference Compound A (12.000.0 mg) was dissolved (30 mg/kg) in 2.600 mL vehicle, vortexed until fully dissolved to achieve a final concentration of 1.0000 mg/mL, clear solution.

Preparation of Liraglutide (0.3 mg/kg, 2 mL/kg) SC Dosing: Liraglutide solution (0.05 mL) was diluted (6 mg/mL) in 1.950 mL saline and vortexed to achieve a final concentration of 0.150 mg/mL, clear solution.

Preparation of Compound 2 (60 mg/kg, 10 mL/kg) PO Dosing: Compound 2 (32.76 mg) as the meglumine salt was dissolved in 3.900 mL of vehicle and vortexed until fully dissolved to achieve a final concentration of 8.4000 mg/mL, suspension (~6.0 mg/mL active pharmaceutical ingredient [API]).

Preparation of Preparation of Compound 2 (30 mg/kg, 10 mL/kg) PO Dosing: Compound 2 (2.600 mL) (60 mg/kg) was diluted in 2.600 mL of vehicle, vortex until fully dissolved to achieve a final concentration at 4.2000 mg/mL, suspension (~3.0 mg/mL API).

Preparation of Preparation of Compound 2 (10 mg/kg, 10 mL/kg) PO Dosing: Compound 2 (1.300 mL) (30 mg/kg) was diluted in 2.600 mL of vehicle, vortex until fully dissolved to achieve a final concentration of 1.4000 mg/mL, suspension (~1.0 mg/mL API).

Animal Housing: The animal room environment was controlled for temperature (21-25° C.) and relative humidity (40-70%). Temperature and relative humidity were monitored and recorded twice daily. An electronic time-controlled lighting system was used to provide a 12 h light/12 h dark cycle, 7:00 pm-7:00 am, lights out. The mice were fed normal diet and fresh water during acclimation, animals were acclimated in the testing facility for one week prior to study start.

The dose protocol used in this study is described in Table 6.

TABLE 6

Dose Protocol

| Group ID | Treatment | Mice | Number | Dose level (mg/kg) | Dose volume (mL/kg) | Dose Method |
|---|---|---|---|---|---|---|
| 1 | Vehicle | hGLP1r | 10 | — | 10 | PO |
| 3 | Liraglutide | hGLP1r | 10 | 0.3 | 2 | SC |
| 4 | Reference Compound A | hGLP1r | 10 | 10 | 10 | PO |
| 5 | Reference Compound A | hGLP1r | 10 | 30 | 10 | PO |
| 6 | Compound 2 | hGLP1r | 10 | 10 | 10 | PO |
| 7 | Compound 2 | hGLP1r | 10 | 30 | 10 | PO |
| 8 | Compound 2 | hGLP1r | 10 | 60 | 10 | PO |

Food Intake Study Procedure:

Acclimation and grouping: Mice were acclimated for QD P dosing with vehicle for 4 days, baseline body weight and food intake were measured for 4 consecutive days. Animals were allocated into 8 groups based on body weight and $3^{rd}$ day's food intake.

Figure 4:
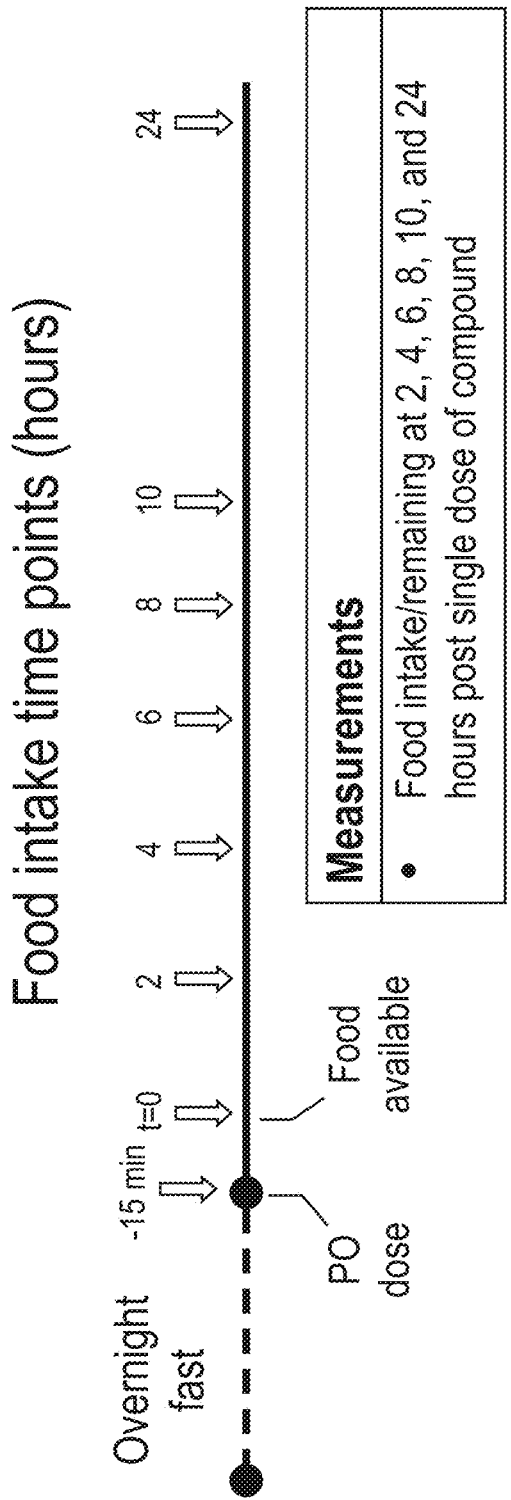
FIG. 4 is a timeline that shows the experimental design of the C57BL/6 mouse food intake study.

Dose body weight and food intake measurement: All animals were placed in clean cages with sawdust bedding and fasted overnight, mice were dosed with vehicle or test compound in the morning. All group's food was added 15 minutes post dosing, food remaining was recorded at 2—, 4-, 6-, 8-, 10- and 24-h post dosing. (FIG. 4) Body weight was determined on a daily basis during the study.

The time protocol for this study is described in Table 7.

TABLE 7

Time schedule

| Experiment Day | Experiment |
|---|---|
| Day −3 | BW, FI PO acclimation |
| Day −2 | BW, FI, PO acclimation |
| Day −1 | BW, FI, PO acclimation |

TABLE 7-continued

| | Time schedule | |
|---|---|---|
| Experiment Day | Experiment | |
| Day 0 | BW, FR, PO acclimation, group, change cages and fasting overnight | |
| Day 1 | BW, Dose, 2, 4, 6, 8, 10 hr FI | |
| Day 2 | BW, 24 hr FI | |

BW = Body Weight; FI = Food Intake; FR = Food Remaining; PO = Per Os (by mouth)

Figure 5:
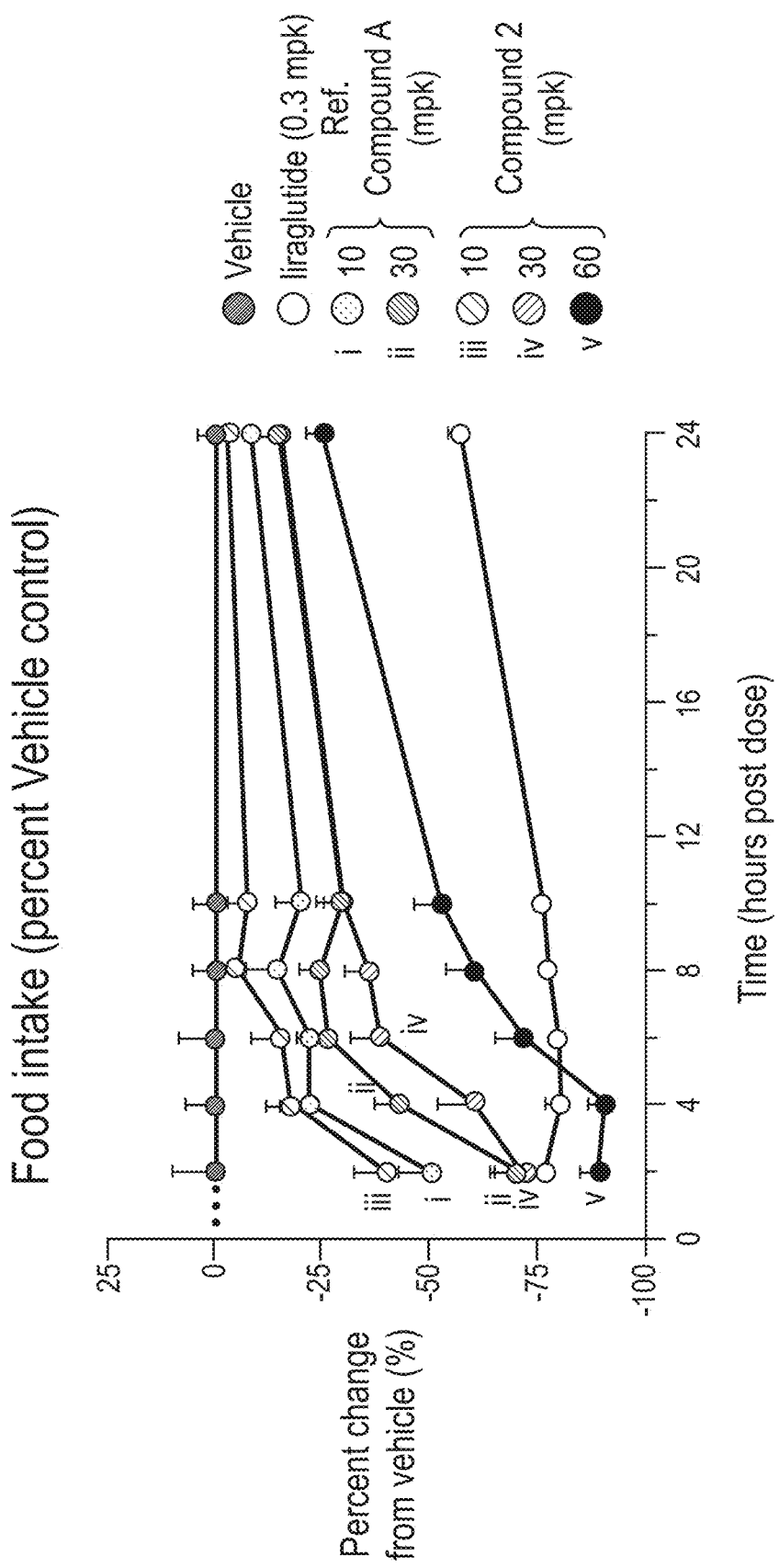
FIG. 5 shows the reduction in food intake caused by Compound 2, Reference Compound A, and liraglutide in C57BL/6 mice that express human GLP-1R.

Compound 2 significantly suppressed food intake in humanized mice relative to vehicle control (FIG. 5).

Data processing and analysis: Manual data were transferred into an excel spreadsheet. All values were expressed as mean±S.E.M. The significances of the differences among groups and within groups are evaluated by one-way or two-way ANOVA using Graph Pad statistic software. A p-value of less than 0.05 was considered statistically significant.

Example B4: Glucose Tolerance

The ability of compounds disclosed herein to modify the glucose tolerance of C57BL/6 mice expressing human GLP-1R (hGLP-1R), was evaluated.

Vehicle: 5% polyethylene glycol 400:95% (12% (w/v) sulfobutyl-β-cyclodextrin in water), (v/v)

Preparation of Vehicle: Sulfobutyl-β-cyclodextrin (12,000.0 mg) was added to a 100 mL volumetric flask and QC with water to 100 mL, vortexed until fully dissolved, transferred 95 mL to a new 100 mL flask/cylinder. 5 mL polyethylene glycol 400 was added to the mixture and vortexed until fully dissolved to achieve a clear solution.

Formulation preparation: The formulation was used within 24 hours after preparation. The formulation was stirred continuously at room temperature if a suspension resulted.

Preparation of Liraglutide (0.3 mg/kg, 2 mL/kg) SC Dosing: 0.05 mL of Liraglutide solution (6 mg/mL) was diluted in 1.950 mL saline and vortexed to achieve a final concentration of 0.150 mg/mL, clear solution.

Preparation of Reference Compound A (1 mg/kg, 10 mL/kg) PO Dosing: 1 mg of Reference Compound A was dissolved in in 10.000 mL vehicle and vortexed until fully dissolved to achieve a final concentration of 0.1000 mg/mL, clear solution.

Preparation of Reference Compound A (0.3 mg/kg, 10 mL/kg) PO Dosing: 1.050 mL of Reference Compound A (1 mg/kg) was diluted in 2.450 mL of vehicle and vortexed until fully dissolved to achieve a final concentration of 0.0300 mg/mL, clear solution.

Preparation of Compound 2 (3 mg/kg, 10 mL/kg) PO Dosing: 2 mg of compound 2 as the meglumine salt was dissolved in 4.762 mL of vehicle and vortexed until fully dissolved to achieve a final concentration of 0.4200 mg/mL, suspension solution (~0.3 mg/mL active pharmaceutical ingredient [API]).

Preparation of Preparation of Compound 2 (1 mg/kg, 10 mL/kg) PO Dosing: 1.520 mL of Compound 2 (3 mg/kg) as the meglumine salt was diluted in 3.040 mL vehicle and vortexed until fully dissolved to achieve a final concentration of 0.1400 mg/mL, clear solution (~0.1 mg/mL API).

Preparation of Preparation of Compound 2 (0.3 mg/kg, 10 mL/kg) PO Dosing: 1.050 mL of Compound 2 (1 mg/kg) as the meglumine salt was diluted in 2.450 mL vehicle and vortexed until fully dissolved to achieve a final concentration of 0.0420 mg/mL, clear solution (~0.03 mg/mL API).

Animal Housing: The animal room environment was controlled for temperature (21-25° C.) and relative humidity (40-70%). Temperature and relative humidity were monitored and recorded twice daily. An electronic time-controlled lighting system was used to provide a 12 h light/12 h dark cycle, 7:00 am-7:00 pm, lights out. The mice were fed normal diet and fresh water during acclimation, animals were acclimated in the testing facility for one week prior to study start.

Study Procedure: Intraperitoneal Glucose Tolerance Test:

The group design used in this study is described in Table 8.

TABLE 8

Dose protocol- IPGTT

| Group ID | Mice | Treatment | Number | Dose level (mg/kg) | Dose volume (mL/kg) | Dose Method |
|---|---|---|---|---|---|---|
| 1 | hGLP-1R | Vehicle | 7 | — | 10 | PO |
| 3 | hGLP-1R | Liraglutide | 7 | 0.3 | 2 | SC |
| 4 | hGLP-1R | Reference Compound A | 7 | 0.3 | 10 | PO |
| 5 | hGLP-1R | Reference Compound A | 7 | 1 | 10 | PO |
| 6 | hGLP-1R | Compound 2 | 7 | 0.3 | 10 | PO |
| 7 | hGLP-1R | Compound 2 | 7 | 1 | 10 | PO |

Acclimation and grouping: Following a one-wee washout period a ter in-life completion of the food intake study, mice were utilized to conduct an intraperitoneal Glucose Tolerance Test (IPGTT); mice remained in their treatment groups from study the food intake study. Baseline fasting glucose levels were used to balance treatment groups (final n=7 per treatment group); outlier mice (n=3), based on abnormal fasting blood glucose and body weight, were used for PK assessment.

Figure 6:
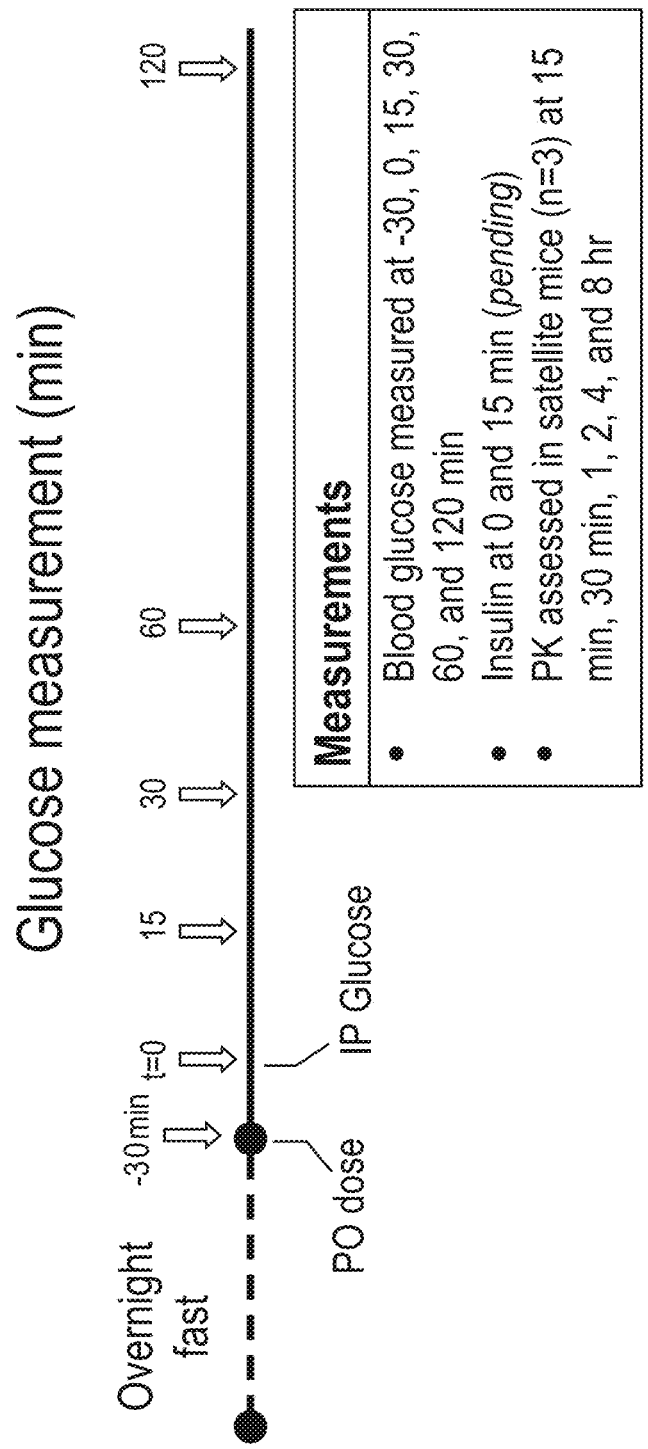
FIG. 6 is a timeline that shows the experimental design of the C57BL/6 mouse glucose tolerance study.

Intraperitoneal Glucose Tolerance Test (IPGTT): The mice were placed clean cages with sawdust bedding and fasted overnight. Basal fasting glucose was measured by tail vein nick before dosing in the morning, 3 mice per group of abnormal fasting blood glucose and body weight were used for PK assessment. Mice were administered with vehicle or test compounds according to dose protocol (Table 8) at 9:30 am. 0.5 h later after vehicle or test compounds dosing, glucose was intraperitoneal injected with 2 g/kg at a dose volume of 10 mL/kg at 10:00 am. Blood glucose levels were measured at 0 (pre-dose), 15-, 30-, 60-, and 120-min post glucose dosing. (FIG. 6) In addition, ~30 μL blood was collected by tail vein into pre-chilled EDTA-2K tubes and placed on ice following glucose measurement at 0 min and 15 min. Blood samples were processed for plasma as soon as possible by centrifugation at 4° C., 3200×g for 10 min and plasma was stored at −80° C. for insulin assay.

IPGTT (120 min)—PK bleeding: 40 µL blood samples (all treatment groups) were collected from mice under the jaw at IPGTT-120 min after blood glucose measurement into pre-chilled EDTA-2K tubes. Blood samples were processed for plasma by centrifugation at 4° C., 3200×g for 10 min. 15 µL plasma was stored at −80° C. for PK analysis. From 4 mice in Group 7 of the PD cohort, whole brain was collected after blood is harvested at 120 min post dose, rinsed with saline and patted dry and placed into a pre-weighed tube and stored at −80° C. collected for PK analysis.

PK bleeding group design is described in Table 9.

TABLE 9

Dose protocol- PK

| Group ID | Treatment | Number | Dose level (mg/kg) | Dose volume (mL/kg) | Dose Method | Dose Frequency |
|---|---|---|---|---|---|---|
| 4 | Reference Compound A | 3 | 1 | 10 | PO | Single |
| 5 | Reference Compound A | 3 | 0.3 | 10 | PO | Single |
| 6 | Compound 2 | 3 | 0.3 | 10 | PO | Single |
| 7 | Compound 2 | 3 | 1 | 10 | PO | Single |
| 8 | Compound 2 | 3 | 3 | 10 | PO | Single |

PK bleeding: 30 µL blood was collected at 0.25, 0.5, 1, 2, 4, and 8 h. Blood samples were processed for plasma by centrifugation at 4° C., 3200×g for 10 min. 12 µL plasma was collected at −80° C. for further analysis. From 3 mice in Group 7 of the PK cohort, whole brain was collected after blood is harvested at 8 hr post dose, rinsed with saline and patted dry and placed into a pre-weighed tube and stored at −80° C. collected for PK analysis. The PK time points are summarized in Table 10.

TABLE 10

PK time-points

| Group ID | Treatment/analyte | Dose, mg/kg (route) | Formulation | Sex | N | Blood time-points post dose (0.030 mL) |
|---|---|---|---|---|---|---|
| 4 | Reference Compound A | 0.3 (PO) | Vehicle | M | 3 | 0.25, 0.5, 1, 2, 4, and 8 |
| 5 | Reference Compound A | 1 (PO) | Vehicle | M | 3 | 0.25, 0.5, 1, 2, 4, and 8 |
| 6 | Compound 2 | 0.3 (PO) | Vehicle | M | 3 | 0.25, 0.5, 1, 2, 4, and 8 |
| 7 | Compound 2 | 1 (PO) | Vehicle | M | 3 | 0.25, 0.5, 1, 2, 4, and 8 |
| 8 | Compound 2 | 3 (PO) | Vehicle | M | 3 | 0.25, 0.5, 1, 2, 4, and 8 |

Data Processing and analysis: Manua data were transferred into an excel spreadsheet. All values are expressed as mean S.E.M. The significances of the differences among groups and within groups were evaluated by one-way or two-way ANOVA using Graph Pad statistic software. A p-value of less than 0.05 were considered statistically significant.

Figure 7:
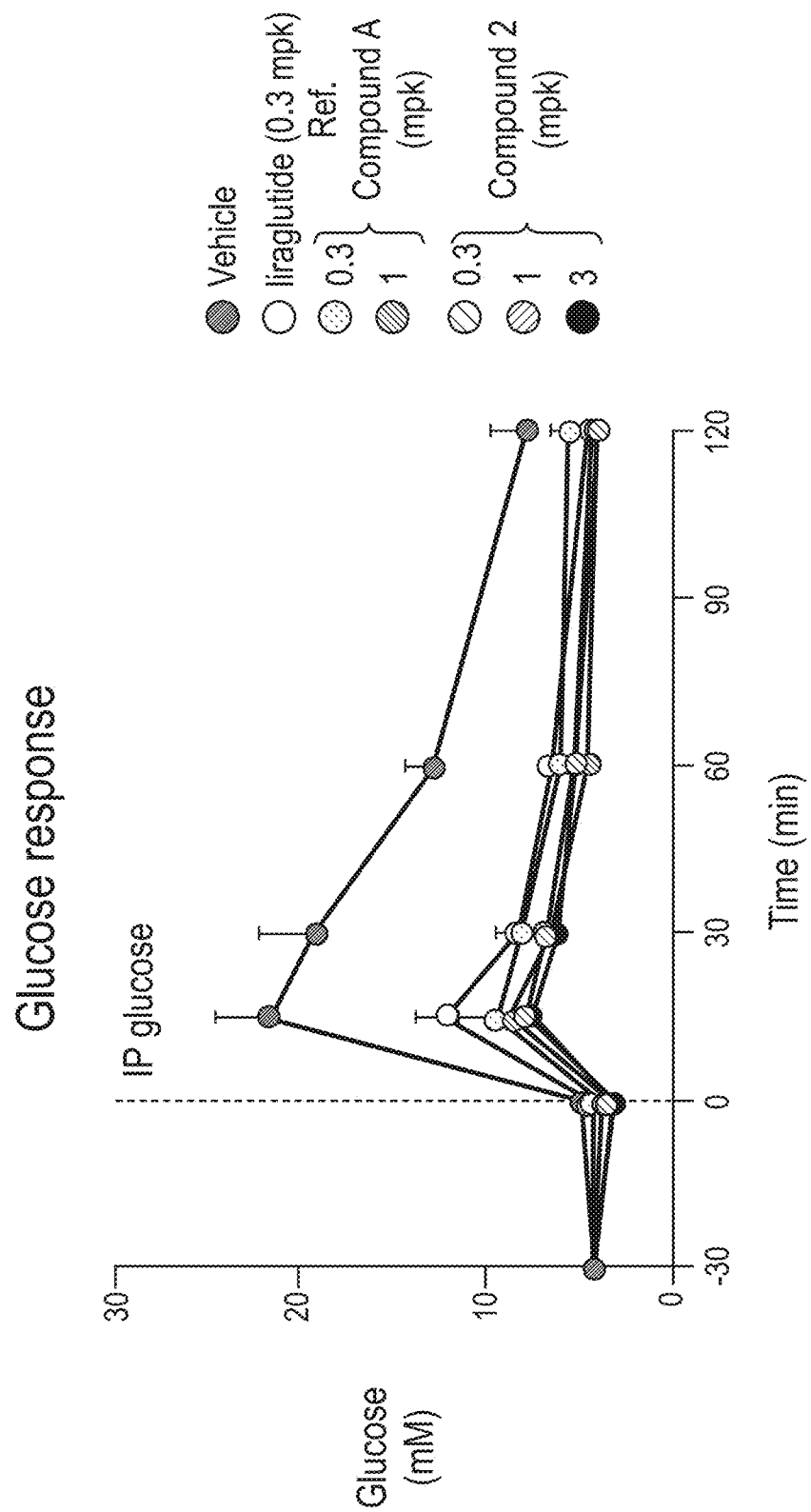
FIG. 7 shows the concentration of glucose over time in the blood of C57BL/6 mice that express human GLP-1R following an IP glucose bolus and the administration of Compound 2, Reference Compound A, and liraglutide.
Figure 8:
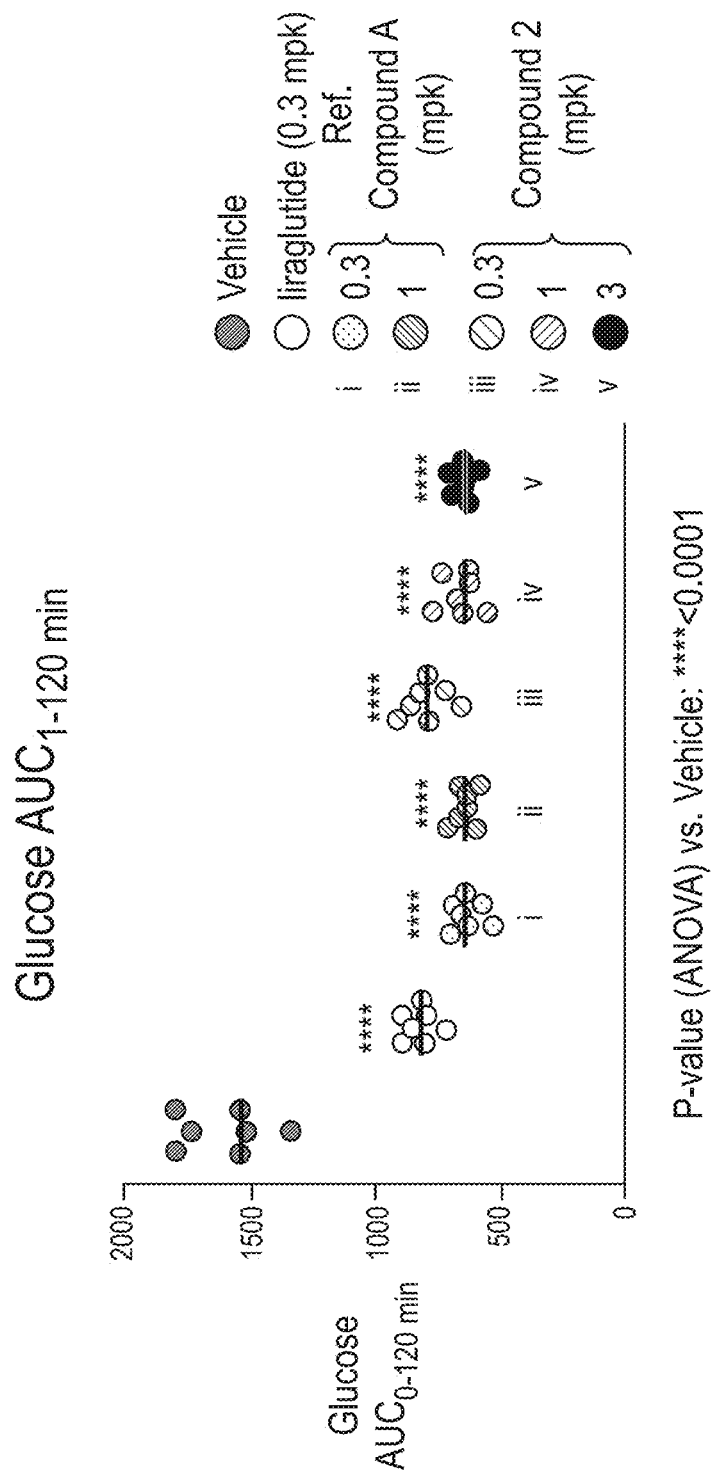
FIG. 8 shows the area under the glucose concentration vs time curve shown in FIG. 7.

Compound 2 significantly enhanced the glucose tolerance of the mice relative to the vehicle control (FIGS. 7 and 8).

Figure 9:
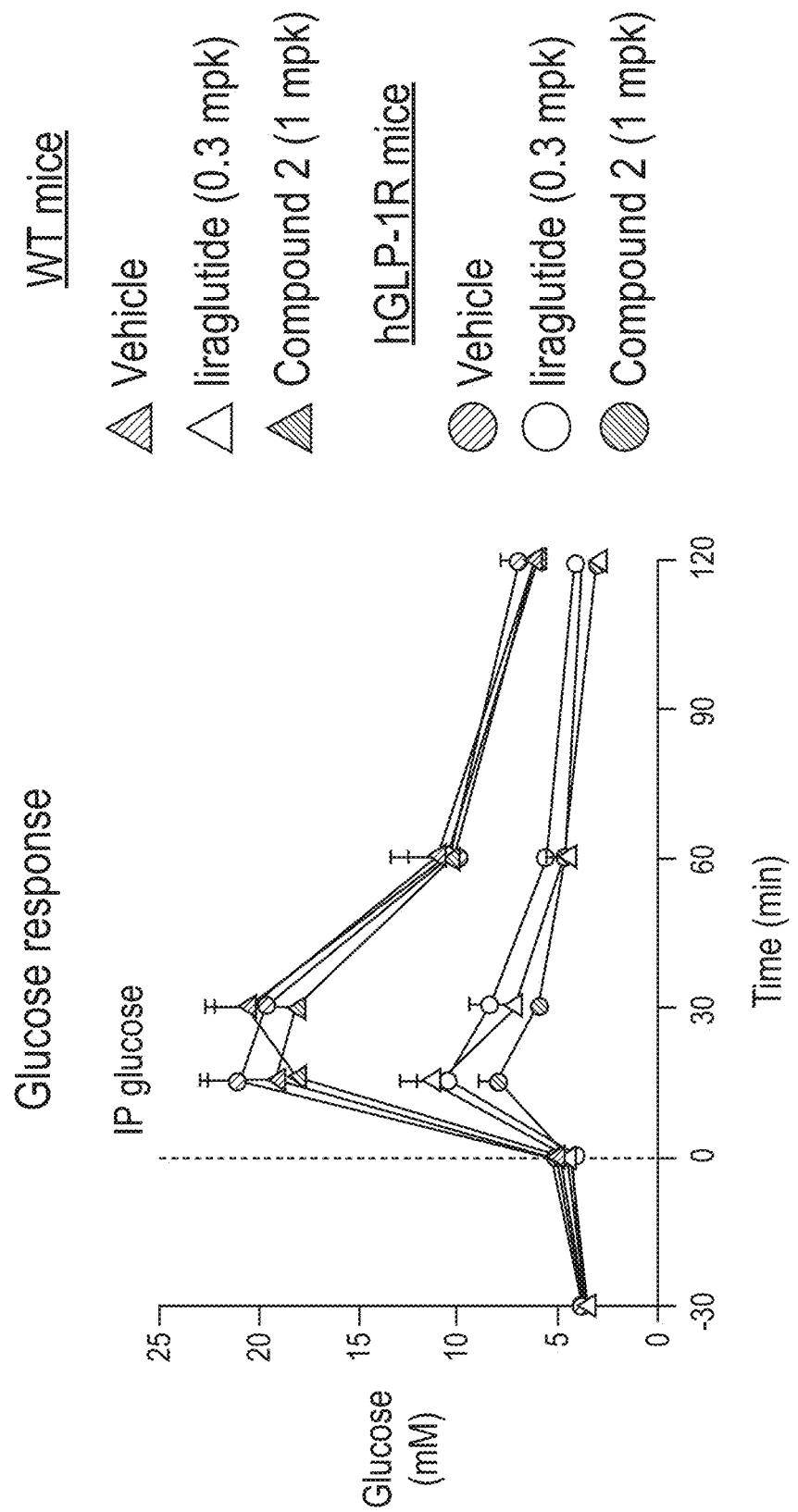
FIG. 9 shows the concentration of glucose in the blood of C57BL/6 mice expressing wild type mouse GLP-1R (triangles) and humanized GLP-1R (circles) following IP glucose bolus and administration of Compound 2 or liraglutide.
Figure 10:
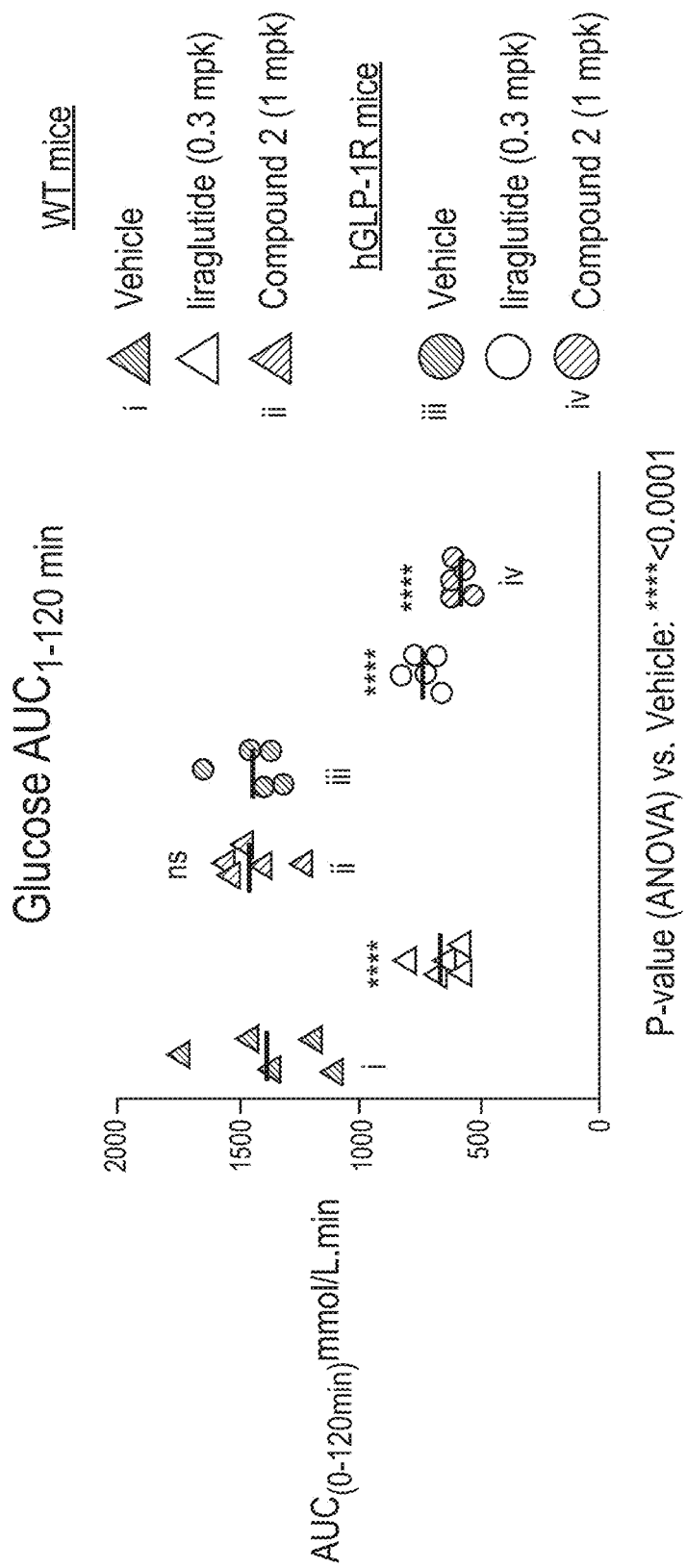
FIG. 10 shows the area under the glucose concentration vs. time curve shown in FIG. 9.
Figure 11A:
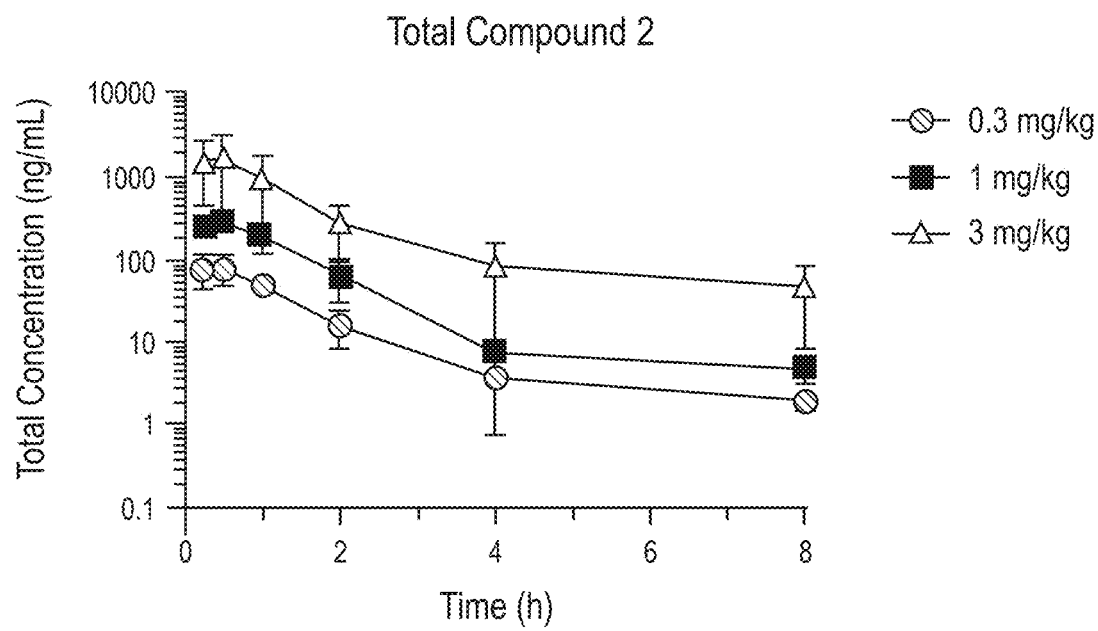
FIG. 11A and 11B depicts total (11A) and unbound (11B) Compound 2 in hGLP-1R mice from IPGTT evaluation at various amounts of Compound 2.
Figure 11B:
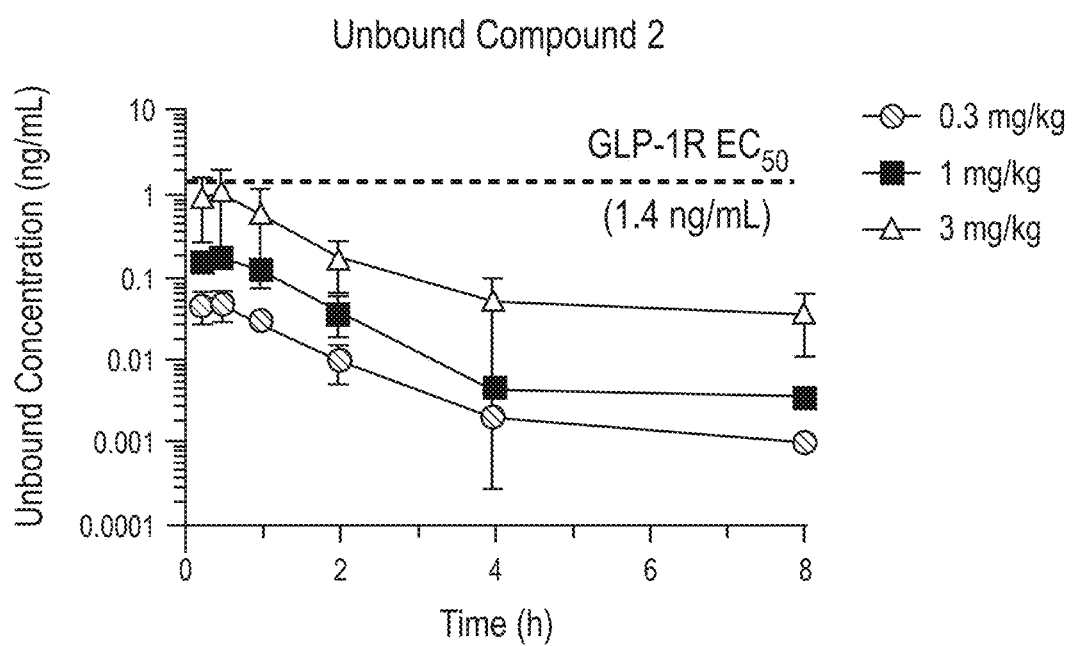
Figure 12A:
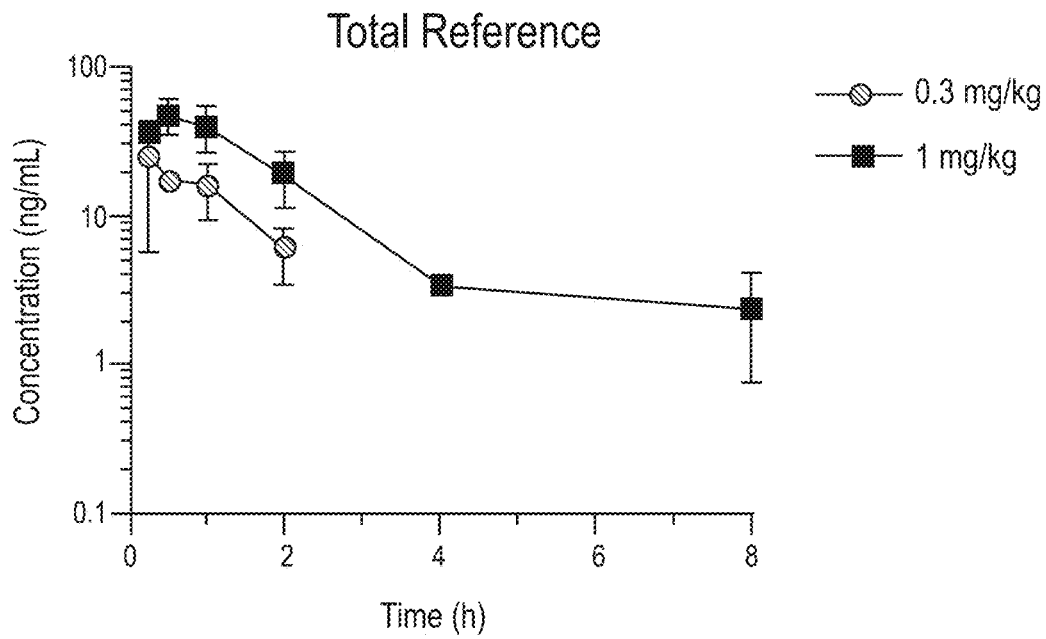
FIGS. 12A and 12B depicts total (12A) and unbound (12B) Reference Compound A in hGLP-1R mice from IPGTT evaluation at various amounts of Reference Compound A.
Figure 12B:
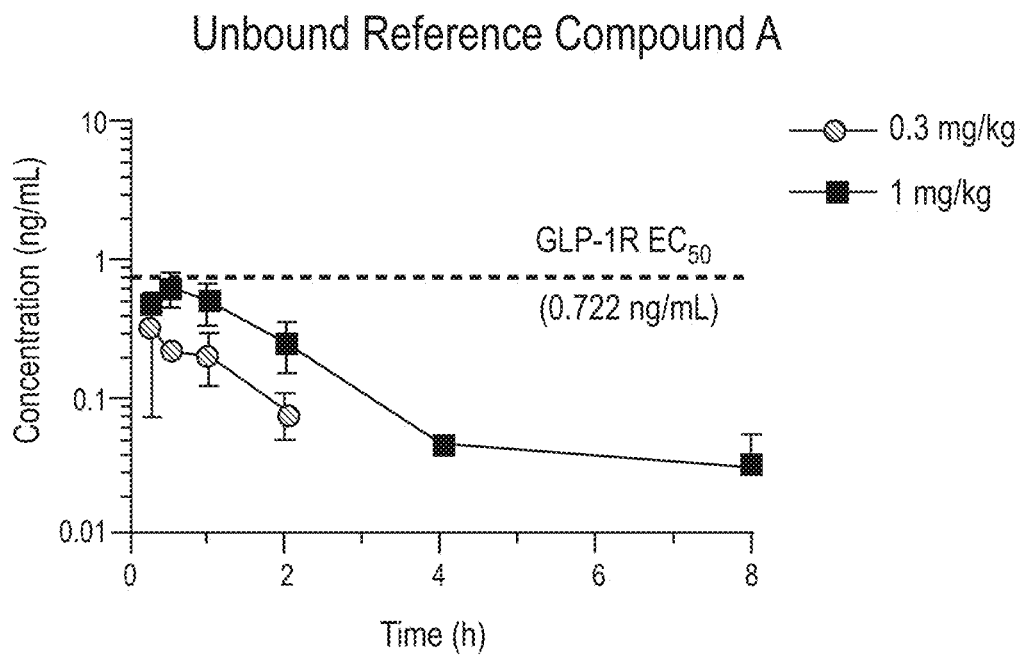

The glucose tolerance of mice expressing wildtype (WT) mouse GLP-1R was also evaluated after the administration of compound 2 using methods analogous to those described above. The glucose tolerance of mice expressing WT mouse GLP-1R was not affected by Compound 2, whereas the glucose tolerance of mice expressing human GLP-1R was improved by Compound 2 (FIGS. 9 and 10).

The results of the PK experiments are shown in FIGS. 11A, 11B, 12A, and 12B, and are summarized in Tables 11 and 12:

TABLE 11

Compound 2 PK data in hGLP-1R mice

| Total Compound 2 Dose mg/kg | $T_{1/2}$ h | $T_{max}$ Median h | $C_{max}$ Mean ng/mL | $C_{max}$ % CV % | $AUC_{last}$ Mean h · ng/mL | $AUC_{last}$ % CV % |
|---|---|---|---|---|---|---|
| 0.3 | 1.40 | 0.5 (0.25-0.5) | 82.7 | 37.0 | 107 | 16.2 |
| 1.0 | 1.42 | 0.5 | 283 | 14.0 | 390 | 24.3 |
| 3.0 | 2.03 | 0.5 (0.25-0.5) | 1821 | 77.5 | 2441 | 79.5 |

TABLE 12

Reference Compound A PK data in hGLP-1R mice

| Total Reference Compound A Dose mg/kg | $T_{1/2}$ h | $T_{max}$ Median h | $C_{max}$ Mean ng/mL | $C_{max}$ % CV % | $AUC_{last}$ Mean h · ng/mL | $AUC_{last}$ % CV % |
|---|---|---|---|---|---|---|
| 0.3 | 0.604 | 0.5 (0.25-0.5) | 27.0 | 64.2 | 24.5 | 39.3 |
| 1.0 | 2.0 | 0.5 (0.5-1.0) | 49.7 | 23.6 | 85.5 | 18.9 |

As shown above, Compound 2 achieved higher plasma concentrations than Reference Compound A. For example, when administered at 0.3 mg/kg, Compound 2 effectuated approximately a three-fold higher $C_{max}$ and a four-fold higher $AUC_{last}$ than Reference Compound A. When administered at 1.0 mg/kg, Compound 2 effectuated an approximately 5.7-fold higher $C_{max}$ than Reference Compound A and an approximately 4.6-fold higher $AUC_{last}$ than Reference Compound A.

Sample Processing

For plasma: An aliquot of 3 µL sample was protein precipitated with 60 µL internal standard (100 ng/mL Labetalol & 100 ng/mL Dexamethasone & 100 ng/mL Tolbutamide & 100 ng/mL Verapamil & 100 ng/mL Glyburide & 100 ng/mL Celecoxib in ACN) and then the mixture was vortex-mixed for 10 min at 800 rpm and centrifuged for 15 min at 3220×g, 4° C. An aliquot of 55 µL supernatant was transferred to another clean 96-well plate and centrifuged for 5 min at 3220×g, 4° C., 4 µL (Reference Compound A) or 6 µL (Compound 2 and retest) sample was injected for LC-MS/MS analysis.

Dilution procedure description: (for retest) Dilution factor as 10: An aliquot of 2 µL sample was mixed with 18 µL blank matrix.

Data Processing: Retention time, plotting of the chromatograms and peak area integrations and calculations were carried out by using Analyst® 1.6.3 Software (SCIEX, MA, USA).

Study Samples

Sample storage: During analysis, the study samples were stored at temperature of −20° C. After analysis, the study samples were stored in a freezer at a nominal temperature of −80° C.

Pharmacokinetic Data Analysis: The individual plasma concentrations of Reference Compound A and Compound 2 in study animals was subjected to non-compartmental pharmacokinetic analysis using the Phoenix WinNonlin software (version 6.3 or above, Certara) with extravascular input and uniform weighting. The linear/log trapezoidal rule was applied in obtaining the PK parameters. Individual plasma concentration values that were below the lower limit of quantitation (LOQ) were excluded from the PK parameter calculation. The nominal dose levels and nominal sampling times were used in the calculation of all pharmacokinetic parameters.

Analytical Results

Linearity: The calibration curve of Reference Compound A and Compound 2 was constructed using eight non-zero standards ranging from 1.00 to 3000 ng/mL for plasma. The regression analysis of Reference Compound A and Compound 2 was performed by plotting the peak area ratio of Reference Compound A and Compound 2 over IS (Y) against their concentration (X) in ng/mL, respectively. The fit equation of calibration curve Reference Compound A was linear regression with 1/×2 as weighting factor. The fit equation of calibration curve Compound 2 was quadratic regression with 1/×2 as weighting factor for plasma. The correlation coefficient (R) of the linear regression of Reference Compound A in plasma is >0.9875. The correlation coefficient (R) of the quadratic regression of Compound 2 in plasma is >0.996.

Calibration Standards: At least 75% of the calibration standards or at least 6 calibration standards, when back-calculated, should fall within ±20% of the nominal values for plasma.

QC Samples: For plasma samples, at least two thirds of all QC samples and 50% of the QC samples at each concentration level, when back-calculated, should fall within ±20% of the nominal value for plasma samples.

Study Sample Concentrations: All bioanalytical runs were completed successfully and accepted.

The concentrations of Reference Compound A in male C57BL/6J hGLP-1R mouse plasma after PO (0.300 and 1.00 mg/kg) administrations of Reference Compound A were determined. Bioanalytical concentration of Reference Compound A in male C57BL/6J hGLP-1R mouse plasma was listed in Table 13 and Table 14.

The concentrations of Compound 2 in male C57BL/6J hGLP-1R mouse plasma after PO (0.300, 1.00 and 3.00 mg/kg) administrations of compound 2 were determined. Bioanalytical concentration of Compound 2 in male C57BL/6J hGLP-1R mouse plasma are listed in Table 15 and Table 16.

Pharmacokinetic Analysis Results: In general, all animals were exposed to either Reference Compound A or Compound 2 following oral dosing to C57BL/6 hGLP-1R mice. PK parameters for Reference Compound A are shown in Table 17 and Table 18, and PK parameters for Compound 2 are shown in Table 19, Table 20, and Table 21.

Following oral administration of Reference Compound A at 0.3 and 1 mg/kg in mice, the observed maximum plasma concentrations were reach by a median Tmax of 0.5 hours post administration and then declined with a terminal elimination t1/2 of 0.604 hours following 0.3 mg/kg, and 1.99 hours following 1 mg/kg. By 4 hours post administration at 0.3 mg/kg, all concentrations were below the limit of quantitation (<1 ng/mL), resulting in mean AUC0-last of 24.5 ng·h/mL. In general, plasma concentrations were measurable out to 8 hours post administration at 1 mg/kg, resulting in mean AUC0- last of 85.5 ng·h/mL. Overall, exposure to Reference Compound A increased with dose in an approximately proportional manner.

Following oral administration of Compound 2 at 0.3, 1, and 3 mg/kg in mice, the observed maximum plasma concentrations were reach by a median Tmax of 0.5 hours post administration, and then declined with a terminal elimination t1/2 of 1.40 hours, 1.42 hours, and 2.03 following 0.3 mg/kg, 1 mg/kg, and 3 mg/kg, respectively. In general, plasma concentrations were measurable out to 8 hours post administration across all doses, resulting in mean AUC0-last of 107 ng·h/mL, 390 ng·h/mL, and 2441 ng·h/mL at 0.3 mg/kg, 1 mg/kg, and 3 mg/kg, respectively.

Overall, exposure to Compound 2 increase with dose in a greater than proportional manner, with a 22-fold increase in exposure values over a ten-fold increase in dose. Comparatively, exposures to Compound 2 in the plasma were about 4-fold greater than the exposures to Reference Compound A at 0.3 and 1 mg/kg in the mouse.

Absorption in C57BL/6 hGLP-1R male mice was rapid, with median Tmax of 0.5 hour for both Reference Compound A and Compound 2, where plasma concentrations then declined with a terminal T1/2 of less than 2 hours for both test articles. Exposure to Reference Compound A increased from 0.3 mg/kg to 1 mg/kg in an approximately dose proportional manner, while exposure to compound 2 increased from 0.3 mg/kg to 3 mg/kg in a greater than proportional manner. Comparatively, plasma exposures to Compound 2 were 4-fold greater than the exposures to Reference Compound A at both 0.3 mg/kg and 1 mg/kg.

TABLE 13

Individual and mean plasma concentrations of Reference Compound A in male C57BL/6J hGLP-1R mouse following single oral administration of Reference Compound A at 0.3 and 1 mg/kg

| Group | Sample time | Animal ID | Concentration (ng/mL) | Mean Concentration (ng/mL) | SD |
|---|---|---|---|---|---|
| Reference Compound A 0.3 mpk | 0.25 h | 8 | 16.7 | 24.9 | 19.2 |
| | | 80 | 46.8 | | |
| | | 89 | 11.2 | | |
| | 0.5 h | 8 | 19.6 | 17.3 | 2.52 |
| | | 80 | 17.6 | | |
| | | 89 | 14.6 | | |
| | 1 h | 8 | 13.4 | 16.0 | 6.60 |
| | | 80 | 23.5 | | |
| | | 89 | 11.1 | | |
| | 2 h | 8 | 2.43 | 3.37 | 1.35 |
| | | 80 | 4.91 | | |
| | | 89 | 2.76 | | |
| | 4 h | 8 | BQL | ND | ND |
| | | 80 | BQL | | |
| | | 89 | BQL | | |
| | 8 h | 8 | BQL | ND | ND |
| | | 80 | BQL | | |
| | | 89 | BQL | | |
| Reference Compound A 1 mpk | 0.25 h | 36 | 43.5 | 35.7 | 6.73 |
| | | 56 | 31.9 | | |
| | | 69 | 31.8 | | |
| | 0.5 h | 36 | 62.8 | 48.1 | 12.8 |
| | | 56 | 40.2 | | |
| | | 69 | 41.2 | | |
| | 1 h | 36 | 48.7 | 39.5 | 13.7 |
| | | 56 | 23.7 | | |
| | | 69 | 46.0 | | |
| | 2 h | 36 | 22.4 | 14.5 | 8.38 |
| | | 56 | 5.72 | | |
| | | 69 | 15.4 | | |
| | 4 h | 36 | 3.59 | 3.40 | ND |
| | | 56 | BQL | | |
| | | 69 | 3.21 | | |
| | 8 h | 36 | BQL | 2.42 | ND |

TABLE 14

Individual and mean plasma concentrations of Reference Compound A in male C57BL/6J hGLP-1R mouse collected at 120 min following single oral administration of Reference Compound A at 0.3 and 1 mg/kg

| Group | Sample time | Animal ID | Concentration (ng/mL) | Mean Concentration (ng/mL) | SD |
|---|---|---|---|---|---|
| Reference Compound A 0.3 mpk, PO, 10 mL/kg Vehicle: 5% polyethylene glycol 400: 95% (12% (w/v) sulfobutyl-β-cyclodextrin in water), (v/v) | 120 min | 2 | 6.14 | 7.16 | 1.12 |
| | | 19 | 7.91 | | |
| | | 20 | 8.61 | | |
| | | 40 | 8.10 | | |
| | | 57 | 5.55 | | |
| | | 68 | 7.19 | | |
| | | 83 | 6.60 | | |
| Reference Compound A 1 mpk, PO, 10 mL/kg Vehicle: 5% polyethylene glycol 400: 95% (12% (w/v) sulfobutyl-β-cyclodextrin in water), (v/v) | 120 min | 25 | 29.7 | 21.4 | 7.34 |
| | | 29 | 31.0 | | |
| | | 50 | 17.9 | | |
| | | 61 | 14.2 | | |
| | | 65 | 15.9 | | |
| | | 66 | 14.9 | | |
| | | 74 | 26.5 | | |

TABLE 15

Individual and mean plasma concentrations of Compound 2 in male C57BL/6J hGLP-1R mouse following single oral administration of compound 2 at 0.3, 1 and 3 mg/kg

| Group | Sample time | Animal ID | Concentration (ng/mL) | Mean Concentration (ng/mL) | SD |
|---|---|---|---|---|---|
| Compound 2 0.3 mpk | 0.25 h | 39 | 52.2 | 78.3 | 33.4 |
| | | 67 | 66.8 | | |
| | | 88 | 116 | | |
| | 0.5 h | 39 | 63.4 | 80.6 | 32.5 |
| | | 67 | 60.3 | | |
| | | 88 | 118 | | |
| | 1 h | 39 | 43.3 | 49.4 | 6.25 |
| | | 67 | 49.2 | | |
| | | 88 | 55.8 | | |
| | 2 h | 39 | 18.2 | 10.6 | 6.57 |
| | | 67 | 6.53 | | |
| | | 88 | 7.14 | | |
| | 4 h | 39 | 7.15 | 3.74 | 2.96 |
| | | 67 | 1.84 | | |
| | | 88 | 2.23 | | |
| | 8 h | 39 | 2.34 | 1.99 | ND |
| | | 67 | 1.64 | | |
| | | 88 | BQL | | |
| Compound 2 1 mpk | 0.25 h | 27 | 320 | 251 | 60.6 |
| | | 53 | 208 | | |
| | | 85 | 224 | | |
| | 0.5 h | 27 | 329 | 283 | 39.8 |
| | | 53 | 256 | | |
| | | 85 | 265 | | |
| | 1 h | 27 | 252 | 197 | 49.5 |
| | | 53 | 183 | | |
| | | 85 | 156 | | |
| | 2 h | 27 | 77.6 | 48.6 | 25.2 |
| | | 53 | 36.6 | | |
| | | 85 | 31.7 | | |
| | 4 h | 27 | 7.58 | 7.51 | 1.12 |
| | | 53 | 8.59 | | |
| | | 85 | 6.36 | | |
| | 8 h | 27 | 4.90 | 4.73 | 1.59 |
| | | 53 | 6.23 | | |
| | | 85 | 3.07 | | |
| Compound 2 3 mpk | 0.25 h | 26 | 823 | 1574 | 1127 |
| | | 33 | 1030 | | |
| | | 55 | 2870 | | |
| | 0.5 h | 26 | 982 | 1790 | 1438 |
| | | 33 | 937 | | |
| | | 55 | 3450 | | |
| | 1 h | 26 | 592 | 990 | 872 |
| | | 33 | 387 | | |
| | | 55 | 1990 | | |

TABLE 15-continued

Individual and mean plasma concentrations of Compound 2 in male
C57BL/6J hGLP-1R mouse following single oral administration of compound 2 at
0.3, 1 and 3 mg/kg

| Group | Sample time | Animal ID | Concentration (ng/mL) | Mean Concentration (ng/mL) | SD |
|---|---|---|---|---|---|
| | 2 h | 26 | 157 | 304 | 305 |
| | | 33 | 100 | | |
| | | 55 | 655 | | |
| | 4 h | 26 | 48.1 | 84.4 | 74.4 |
| | | 33 | 35.1 | | |
| | | 55 | 170 | | |
| | 8 h | 26 | 92.1 | 47.5 | 39.1 |

TABLE 16

Individual and mean plasma concentrations of Compound 2 in male
C57BL/6J hGLP-1R mouse collected at 120 min following single oral
administration of Compound 2 at 0.3, 1 and 3 mg/kg

| Group | Animal ID | Conc. (ng/mL) | Mean Concentration (ng/mL) | SD |
|---|---|---|---|---|
| Compound 2 0.3 mpk, PO, 10 mL/kg Vehicle: 5% polyethylene glycol 400: 95% (12% (w/v) sulfobutyl-β-cyclodextrin in water), (v/v) | 6 | 13.1 | 18.8 | 7.27 |
| | 15 | 26.1 | | |
| | 28 | 11.5 | | |
| | 37 | 15.0 | | |
| | 43 | 31.4 | | |
| | 52 | 17.3 | | |
| | 78 | 17.2 | | |
| Compound 2 1 mpk, PO, 10 mL/kg Vehicle: 5% polyethylene glycol 400: 95% (12%(w/v) sulfobutyl-β-cyclodextrin in water), | 13 | 61.2 | 69.8 | 34.8 |
| | 21 | 53.6 | | |
| | 30 | 148 | | |
| | 49 | 60.4 | | |
| | 59 | 60.3 | | |
| | 60 | 48.9 | | |
| | 86 | 56.3 | | |
| Compound 2 3 mpk, PO, 10 mL/kg Vehicle: 5% polyethylene glycol 400: | 5 | 159 | 277 | 129 |
| | 12 | 227 | | |
| | 14 | 555 | | |
| | 32 | 301 | | |
| | 63 | 239 | | |
| | 71 | 229 | | |
| | 76 | 231 | | |

TABLE 17

PK parameters of Reference Compound A in male C57BL/6J hGLP-1R
Mouse plasma following oral administration at 0.3 mg/kg

| PK Parameters | Mouse 8 | Mouse 80 | Mouse 89 | Mean | SD | CV (%) |
|---|---|---|---|---|---|---|
| Rsq_adj | 0.948 | 0.527 | 0.936 | — | — | — |
| No. points used for $T_{1/2}$ | 3.00 | 3.00 | 3.00 | 3.00 | — | — |
| $C_{max}$ (ng/mL) | 19.6 | 46.8 | 14.6 | 27.0 | 17.3 | 64.2 |
| $T_{max}$ (h) | 0.500 | 0.250 | 0.500 | 0.417 | 0.144 | 34.6 |
| $T_{1/2}$ (h) | 0.482 | 0.727* | 0.602 | 0.604 | 0.123 | 20.3 |
| $T_{last}$ (h) | 2.00 | 2.00 | 2.00 | 2.00 | — | — |
| $AUC_{0-last}$ (ng · h/mL) | 21.2 | 35.4 | 17.0 | 24.5 | 9.64 | 39.3 |
| $AUC_{0-inf}$ (ng · h/mL) | 22.9 | 40.5 | 19.4 | 27.6 | 11.3 | 41.0 |
| $MRT_{0-last}$ (h) | 0.803 | 0.797 | 0.861 | 0.820 | 0.0353 | 4.31 |
| $MRT_{0-inf}$ (h) | 0.943 | 1.08 | 1.11 | 1.04 | 0.0890 | 8.53 |
| $AUC_{Extra}$ (%) | 7.39 | 12.7 | 12.4 | 10.8 | 2.98 | 27.5 |
| $AUMC_{Extra}$ (%) | 21.1 | 35.8 | 32.0 | 29.6 | 7.63 | 25.7 |

If the % $AUC_{Extra}$ > 20%, $AUC_{0-inf}$, CL, $MRT_{0-inf}$ and $V_{dss}$ might not be accurately estimated. If the % $AUMC_{Extra}$ > 20%, $MRT_{0-inf}$ and $V_{dss}$ might not be accurately estimated.
*The adjusted linear regression coefficient of the concentration value on the terminal phase is less than 0.9, $T_{1/2}$ might not be accurately estimated.

TABLE 18

PK parameters of Reference Compound A in male C57BL/6J hGLP-1R
mouse plasma following oral administration at 1 mg/kg

| PK Parameters | Mouse 36 | Mouse 56 | Mouse 69 | Mean | SD | CV (%) |
|---|---|---|---|---|---|---|
| Rsq_adj | 0.997 | 0.218 | 0.787 | — | — | — |
| No. points used for $T_{1/2}$ | 3.00 | 3.00 | 3.00 | 3.00 | — | — |
| $C_{max}$ (ng/mL) | 62.8 | 40.2 | 46.0 | 49.7 | 11.7 | 23.6 |

TABLE 18-continued

PK parameters of Reference Compound A in male C57BL/6J hGLP-1R mouse plasma following oral administration at 1 mg/kg

| PK Parameters | Mouse 36 | Mouse 56 | Mouse 69 | Mean | SD | CV (%) |
|---|---|---|---|---|---|---|
| $T_{max}$ (h) | 0.500 | 0.500 | 1.00 | 0.667 | 0.289 | 43.3 |
| $T_{1/2}$ (h) | 0.791 | 3.42* | 1.77* | 1.99 | 1.33 | 66.6 |
| $T_{last}$ (h) | 4.00 | 8.00 | 8.00 | ND | — | — |
| $AUC_{0-last}$ (ng · h/mL) | 101 | 68.7 | 86.7 | 85.5 | 16.2 | 18.9 |
| $AUC_{0-inf}$ (ng · h/mL) | 105 | 86.4 | 89.9 | 93.8 | 9.88 | 10.5 |
| $MRT_{0-last}$ (h) | 1.30 | 2.39 | 1.74 | 1.81 | 0.548 | 30.3 |
| $MRT_{0-inf}$ (h) | 1.45 | 4.55 | 2.05 | 2.68 | 1.64 | 61.3 |
| $AUC_{Extra}$ (%) | 3.91 | 20.5 | 3.54 | 9.32 | 9.69 | 104 |
| $AUMC_{Extra}$ (%) | 13.8 | 58.3 | 18.2 | 30.1 | 24.5 | 81.5 |

ND = Not determined

If the % $AUC_{Extra}$ > 20%, $AUC_{0-inf}$, CL, $MRT_{0-inf}$ and $V_{dss}$ might not be accurately estimated. If the % $AUMC_{Extra}$ > 20%, $MRT_{0-inf}$ and $V_{dss}$ might not be accurately estimated.
*The adjusted linear regression coefficient of the concentration value on the terminal phase is less than 0.9, $T_{1/2}$ might not be accurately estimated.

TABLE 19

PK parameters of Compound 2 in male C57BL/6J hGLP-1R mouse plasma following oral administration at 0.3 mg/kg

| PK Parameters | Mouse 39 | Mouse 67 | Mouse 88 | Mean | SD | CV (%) |
|---|---|---|---|---|---|---|
| Rsq_adj | 0.962 | 0.625 | 0.766 | — | — | — |
| No. points used for $T_{1/2}$ | 3.00 | 5.00 | 3.00 | ND | — | — |
| $C_{max}$ (ng/mL) | 63.4 | 66.8 | 118 | 82.7 | 30.6 | 37.0 |
| $T_{max}$ (h) | 0.500 | 0.250 | 0.500 | 0.417 | 0.144 | 34.6 |
| $T_{1/2}$ (h) | 2.08 | 1.44* | 0.691* | 1.40 | 0.695 | 49.5 |
| $T_{last}$ (h) | 8.00 | 8.00 | 4.00 | ND | — | — |
| $AUC_{0-last}$ (ng · h/mL) | 117 | 87.0 | 117 | 107 | 17.3 | 16.2 |
| $AUC_{0-inf}$ (ng · h/mL) | 124 | 90.4 | 120 | 111 | 18.4 | 16.5 |
| $MRT_{0-last}$ (h) | 1.98 | 1.36 | 0.851 | 1.40 | 0.565 | 40.5 |
| $MRT_{0-inf}$ (h) | 2.49 | 1.69 | 0.928 | 1.70 | 0.781 | 45.9 |
| $AUC_{Extra}$ (%) | 5.66 | 3.76 | 1.86 | 3.76 | 1.90 | 50.5 |
| $AUMC_{Extra}$ (%) | 25.0 | 22.4 | 10.0 | 19.1 | 8.02 | 41.9 |

ND = Not determined

If the % $AUC_{Extra}$ > 20%, $AUC_{0-inf}$, CL, $MRT_{0-inf}$ and $V_{dss}$ might not be accurately estimated. If the % $AUMC_{Extra}$ > 20%, $MRT_{0-inf}$ and $V_{dss}$ might not be accurately estimated.
*The adjusted linear regression coefficient of the concentration value on the terminal phase is less than 0.9, $T_{1/2}$ might not be accurately estimated

TABLE 20

PK parameters of Compound 2 in male C57BL/6J hGLP-1R mouse plasma following oral administration at 1 mg/kg

| PK Parameters | Mouse 27 | Mouse 53 | Mouse 85 | Mean | SD | CV (%) |
|---|---|---|---|---|---|---|
| Rsq_adj | 0.691 | 0.602 | 0.727 | — | — | — |
| No. points used for $T_{1/2}$ | 4.00 | 4.00 | 4.00 | 4.00 | — | — |
| $C_{max}$ (ng/mL) | 329 | 256 | 265 | 283 | 39.8 | 14.0 |
| $T_{max}$ (h) | 0.500 | 0.500 | 0.500 | 0.500 | 0.00 | 0.00 |
| $T_{1/2}$ (h) | 1.28* | 1.62* | 1.36* | 1.42 | 0.178 | 12.5 |
| $T_{last}$ (h) | 8.00 | 8.00 | 8.00 | 8.00 | — | — |
| $AUC_{0-last}$ (ng · h/mL) | 498 | 352 | 320 | 390 | 94.9 | 24.3 |
| $AUC_{0-inf}$ (ng · h/mL) | 507 | 366 | 326 | 400 | 95.1 | 23.8 |
| $MRT_{0-last}$ (h) | 1.32 | 1.46 | 1.26 | 1.35 | 0.103 | 7.62 |
| $MRT_{0-inf}$ (h) | 1.47 | 1.81 | 1.42 | 1.57 | 0.212 | 13.5 |
| $AUC_{Extra}$ (%) | 1.78 | 3.97 | 1.84 | 2.53 | 1.25 | 49.3 |
| $AUMC_{Extra}$ (%) | 11.9 | 22.6 | 12.9 | 15.8 | 5.91 | 37.4 |

If the % $AUC_{Extra}$ > 20%, $AUC_{0-inf}$, CL, $MRT_{0-inf}$ and $V_{dss}$ might not be accurately estimated. If the % $AUMC_{Extra}$ > 20%, $MRT_{0-inf}$ and $V_{dss}$ might not be accurately estimated.
*The adjusted linear regression coefficient of the concentration value on the terminal phase is less than 0.9, $T_{1/2}$ might not be accurately estimated.

TABLE 21

PK parameters of Compound 2 in male C57BL/6J hGLP-1R
mouse plasma following oral administration at 3 mg/kg

| PK Parameters | 26 | 33 | 55 | Mean | SD | CV (%) |
|---|---|---|---|---|---|---|
| Rsq_adj | 0.0909 | 0.611 | 0.994 | — | — | — |
| No. points used for $T_{1/2}$ | 4.00 | 5.00 | 3.00 | ND | — | — |
| $C_{max}$ (ng/mL) | 982 | 1030 | 3450 | 1821 | 1411 | 77.5 |
| $T_{max}$ (h) | 0.500 | 0.250 | 0.500 | 0.417 | 0.144 | 34.6 |
| $T_{1/2}$ (h) | 3.21* | 1.68* | 1.19 | 2.03 | 1.05 | 52.0 |
| $T_{last}$ (h) | 8.00 | 8.00 | 8.00 | 8.00 | — | — |
| $AUC_{0\text{-}last}$ (ng · h/mL) | 1497 | 1154 | 4673 | 2441 | 1940 | 79.5 |
| $AUC_{0\text{-}inf}$ (ng · h/mL) | 1923 | 1229 | 4707 | 2620 | 1841 | 70.3 |
| $MRT_{0\text{-}last}$ (h) | 2.04 | 1.54 | 1.40 | 1.66 | 0.336 | 20.3 |
| $MRT_{0\text{-}inf}$ (h) | 4.39 | 2.08 | 1.46 | 2.64 | 1.54 | 58.4 |
| $AUC_{Extra}$ (%) | 22.2 | 6.12 | 0.710 | 9.68 | 11.2 | 116 |
| $AUMC_{Extra}$ (%) | 63.8 | 30.6 | 4.74 | 33.0 | 29.6 | 89.6 |

Example B5. Metabolic Stability in Hepatocytes

Test compounds were incubated in rat and human hepatocytes and stability was assessed from the substrate depilation approach. Test compounds were dissolved in dimethyl sulfoxide (DMS0) to create a 10 mM Stock, and then further diluted to create a 1000× Working Stock of 1 mM with DMS0 in 96-well plates for test compounds and the positive control (midazolam). Vials containing cryopreserved hepatocytes were removed from the liquid nitrogen tank and immediately immersed in a 37° C. water bath. The vials were shaken gently until the contents had thawed and were then immediately emptied into 48 mL of pre-warmed HT Medium in a 50 mL conical tube. Cells remaining in the vial were resuspended with 1.0 mL of pre-warmed HT Medium and added to the conical tube. The tube was capped and then gently inverted several times to resuspend the hepatocytes. The cell suspension was centrifuged at 50×g at room temperature for 5 minutes and the supernatant discarded. The cell pellet was loosened by gently swirling the centrifuge tube and was re-suspended in 4 mL of warm Dulbecco's Modified Eagle medium (DMEM). Cell density was determined by a cell counter by Nexcelom, and DMVEM medium was added to obtain a target density of 1×106 cells/mL. The assay was carried out in 96-well microtiter plates. Test Compounds were incubated at 1 µM with 1×10$^6$ cells/mL hepatocytes in DMEM for 0, 30, 60, 120 and 240 minutes. The incubation was carried out with gentle shaking at 37° C. under a humid atmosphere of 95% air/5% $CO_2$. The volume of the incubation mixture was 37 µL with a final 0.1% DMSO. At each of the time points, the incubation was stopped by adding 150 µL quenching solution (100% acetonitrile, 0.1% formic acid containing bucetin as an internal standard for positive ESI mode). Subsequently, the mixtures were vortexed for 20 min and centrifuged at 4,000 RPM at 10° C. The supernatant (80 µL) was transferred to a clean 96-well plate and analyzed by LC-MS/MS. Midazolam at 1 µM with a final 0.1% DMSO was included as a positive control to verify assay performance. The percent parent remaining, intrinsic and predicted hepatic clearance and $t_{1/2}$ were calculated. All samples were analyzed by LC-MS/MS using an AB Sciex API 4000 instrument, coupled to a Shimadzu LC-20AD LC Pump system. Separation was achieved using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B). Elution conditions are detailed below.

| Time (min) | Flow (µL/min) | % A | % B |
|---|---|---|---|
| 0 | 500 | 98 | 2 |
| 0.30 | 500 | 98 | 2 |
| 1.40 | 500 | 2 | 98 |
| 2.20 | 500 | 2 | 98 |
| 2.21 | 500 | 98 | 2 |
| 3.00 | 500 | 98 | 2 |

The ion optics of each test compound were optimized for their declustering potential (DP), collection energy (CE), collision-cell exit potential (CXP) and used in a selected ion monitoring experiment in the positive ion mode. The peak area ratio of each test compound to internal standard was then evaluated for stability. The extent of metabolism was calculated based on the disappearance of the test compound, compared to its initial concentration. The initial rates of clearance of the test compound were calculated using the linear regression plot of semi-log % remaining of the compound versus time. The elimination rate constant (k) of the linear regression plot was then used to determine $t_{1/2}$ and the intrinsic clearance ($CL_{int}$) using the following formula, where $C_{hepatocyte}$ (million cells/mL) is the cell density of the incubation:

$$k = -\text{slope}$$

$$t_{1/2} = 0.693/k$$

$$CL_{int} = k/C_{hepatocyte}$$

This method of intrinsic clearance determination assumes that the test compound concentration is far below the Michaelis-Menten constant of the compound to its metabolizing enzymes.

The predicted hepatic clearance ($CL_{hep}$) was calculated using the well stirred method with the following formula with $CL_{int(in\ vivo)}$ normalized based on liver weight:

$$CL_{int(in\ vivo)} = CL_{int} \times \text{Hepatocellularity} \times \text{liver weight}$$

$$CL_{hep\ predicted} = (CL_{int(in\ vivo)} \times Q_{liver})/(CL_{int(in\ vivo)} + Q_{liver})$$

Where $Q_{liver}$ ((ml/min/kg) is Liver Blood Flow

The relevant physiological parameters of liver weight, blood flow, and hepatocellularity for various species are listed below:

| Species | Liver Weight (g liver/kg body weight) | Hepatocellularity (106 cells/g liver) | Liver Blood Flow ($Q_{liver}$, mL/min/kg) |
|---|---|---|---|
| Human | 25.7 | 135 | 20.7 |
| Rat | 40 | 120 | 55.2 |

Results are presented in the Table below for the intrinsic clearance (mL/min/kg) and half-life (t1/2)

| | Rat | | Human | |
|---|---|---|---|---|
| Cmpd # | Clint (mL/min/kg) | t1/2 (min) | Clint (mL/min/kg) | t1/2 (min) |
| A | 48.16 ± 1.33 | 72.33 ± 2.55 | 7.18 ± 0.45 | 347.47 ± 22.71 |
| 2 | 42.6 ± 2.46 | 79.39 ± 4.98 | 15.51 ± 0.82 | 156.48 ± 9.23 |
| 4 | 35.97 ± 1.36 | 97.24 ± 2.86 | 24.26 ± 0.74 | 99.65 ± 3.05 |
| 12 | 91.73 ± 1.76 | 36.26 ± 0.7 | 26.83 ± 0.8 | 89.62 ± 2.67 |
| 14 | 92.83 ± 3.3 | 35.83 ± 1.27 | 20.13 ± 0.59 | 119.44 ± 3.5 |
| 20 | 38.93 ± 1.14 | 89.6 ± 2.64 | 10.59 ± 0.66 | 229.31 ± 14.45 |
| 26 | 24.13 ± 0.83 | 137.83 ± 4.75 | 20.86 ± 0.98 | 115.27 ± 5.43 |
| 27 | 28.99 ± 0.58 | 114.74 ± 2.3 | 15.57 ± 0.7 | 154.45 ± 6.99 |
| 29 | 35.83 ± 1.42 | 92.83 ± 3.69 | 15.33 ± 0.76 | 156.86 ± 7.79 |
| 23 | 57.94 ± 1.25 | 57.42 ± 1.23 | 42.28 ± 1.59 | 66.39 ± 3.14 |
| 31 | 30.24 ± 1.5 | 110 ± 5.44 | 17.48 ± 1.33 | 137.58 ± 10.46 |
| 30 | 32.45 ± 0.73 | 102.51 ± 2.3 | 7.18 ± 0.31 | 334.94 ± 14.66 |

Compounds 12, 14 and 23 gave significantly increased CLint values in rat hepatocytes relative to reference standard, while values for remaining compounds 4, 20, 2.6, 27, 29, 30 and 31 were significantly lower than reference. (lint for compound 2 was not significantly different from reference.

Half-life of compounds 4, 20, 26, 27, 29, 30, 31 in rat hepatocytes were significantly higher relative to reference, while values obtained for 12, 13 and 23 were significantly lower; Compounds showed no significant difference from reference.

CLint values calculated for humans were higher than reference for all compounds except compound 30, which showed no significant difference.

Calculated half-life of all compounds except compound 30 was significantly lower relative to standard; compound 30 showed no significant difference relative to reference.

All compounds except compound 30 showed improved CLint and half-live in human relative to reference standard.

Example B5. Passive Permeability and Efflux Ratio

Caco-2 cells (clone C2BBe1) were obtained from American Type Culture Collection (Manassas, VA). Cell monolayers were grown to confluence on collagen-coated, microporous membranes in 12-well assay plates. Details of the plates and their certification are shown below. The permeability assay buffer was Hanks' balanced salt solution containing 10 mM HEPES and 15 mM glucose at a pH of 7.4. The buffer in the receiver chamber also contained 1% bovine serum albumin. The dosing solution concentration was 5 µM of test article in the assay buffer. Cell monolayers were dosed on the apical side (A-to-B) or basolateral side (B-to-A) and incubated at 37° C. with 5% $CO_2$ in a humidified incubator. Samples were taken from the donor and receiver chambers at 120 minutes. Each determination was performed in duplicate. The flux of lucifer yellow was also measured post-experimentally for each monolayer to ensure no damage was inflicted to the cell monolayers during the flux period. All samples were assayed by LC-MS/MS using electrospray ionization. The apparent permeability ($P_{app}$) and percent recovery were calculated as follows:

$$P_{app} = (dC_r/dt) \times V_r / (A \times C_A) \quad (1)$$

$$\text{Percent Recovery} = 100 \times \left( \left( V_r \times C_r^{final} \right) + \left( V_d \times C_d^{final} \right) \right) / (V_d \times C_N), \quad (2)$$

where, $dC_r/dt$ is the slope of the cumulative receiver concentration versus time in µM s$^{-1}$; $V_r$ is the volume of the receiver compartment in cm$^3$; $V_d$ is the volume of the donor compartment in cm$^3$; A is the area of the insert (1.13 cm$^2$ for 12-well); $C_A$ is the average of the nominal dosing concentration and the measured 120-minute donor concentration in µM; $C_N$ is the nominal concentration of the dosing solution in µM; $C_r^{final}$ is the cumulative receiver concentration in µM at the end of the incubation period; $C_d^{final}$ is the concentration of the donor in µM at the end of the incubation period. Efflux ratio (ER) is defined as $P_{app}$ (B-to-A)/$P_{app}$(A-to-B).

| Compound ID | Mean Passive Permeability (Papp) | Efflux Ratio (ER) |
|---|---|---|
| Reference Compound A | 15.5 | 2.89 |
| 2 | 31.5 | 1.66 |
| 4 | 49.9 | 0.975 |
| 20 | 2.82 | 9.77 |
| 30 | 9.41 | 2.14 |
| 31 | 16.8 | 1.31 |

Passive permeability and efflux ratio are meant to serve as a proxies to evaluate the potential of molecules' oral bioavailability. Here, high passive permeability (Papp) and low efflux ratio (ER) are preferable and indicate a higher likelihood of orally bioavailable compound. These data demonstrate superior Papp and ER relative to benchmark molecules.

All publications, including patents, patent applications, and scientific articles, mentioned in this specification are herein incorporated by reference in their entirety for all purposes to the same extent as if each individual publication, including patent, patent application, or scientific article, were specifically and individually indicated to be incorporated by reference.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed is:
1. A compound selected from
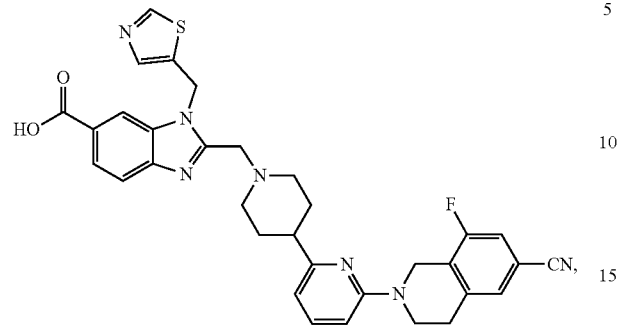
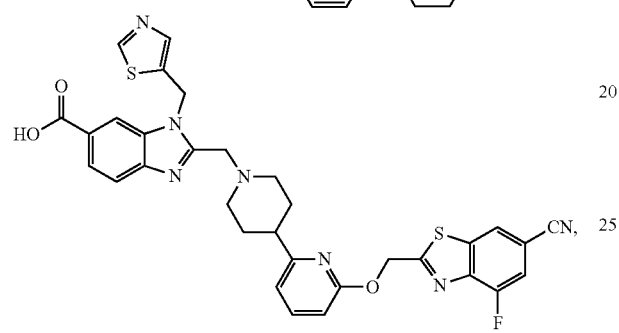
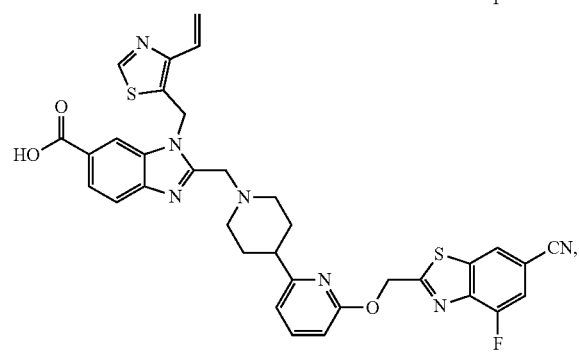
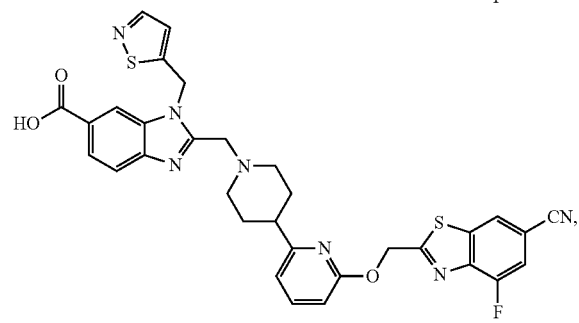
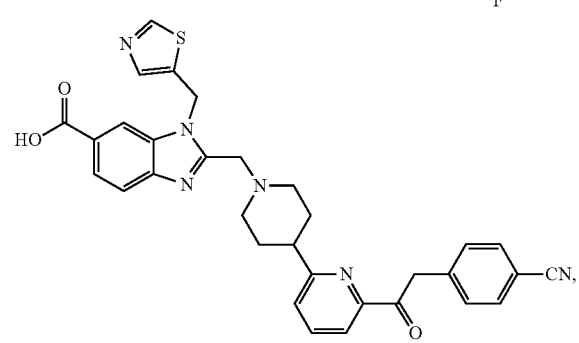
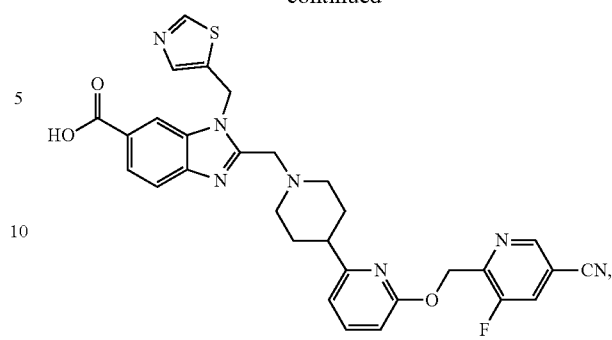
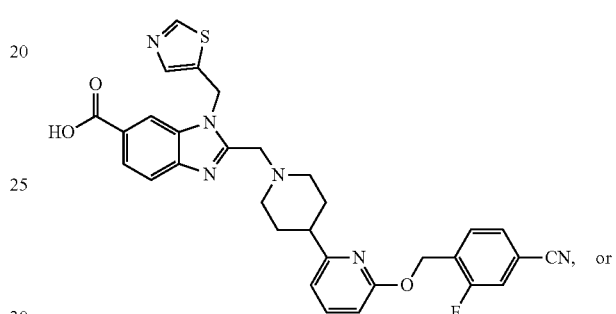
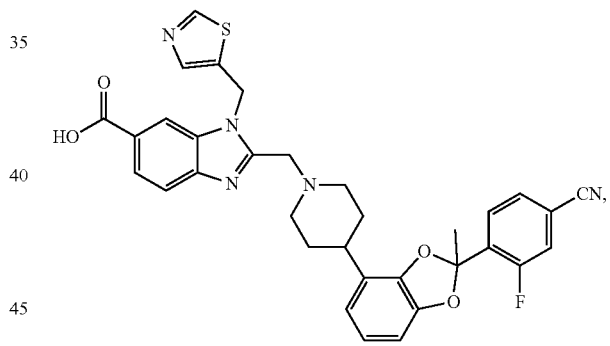
or a pharmaceutically acceptable salt thereof.
2. The compound of claim 1, wherein the compound is
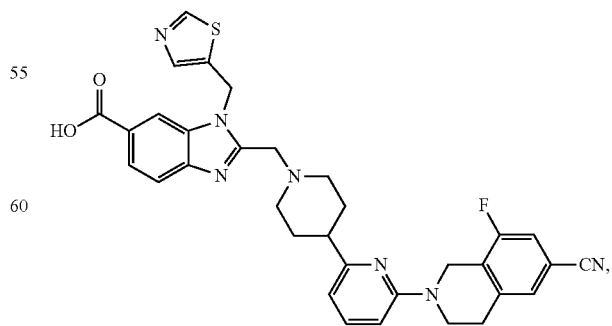
or a pharmaceutically acceptable salt thereof.

3. The compound of claim 1, wherein the compound is

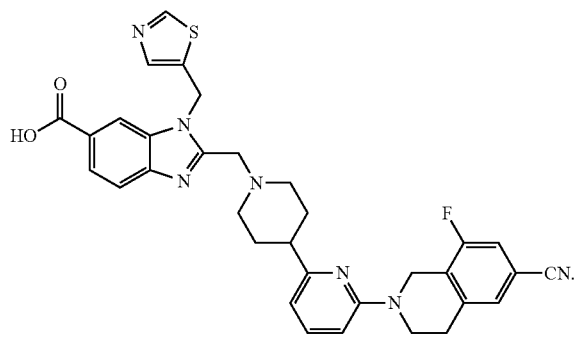 [SMILES: N#Cc1cc(F)c2c(c1)CCN(c1cccc(C3CCN(Cc4nc5ccc(C(=O)O)cc5n4Cc4cncs4)CC3)n1)C2]

4. The compound of claim 1, wherein the compound is

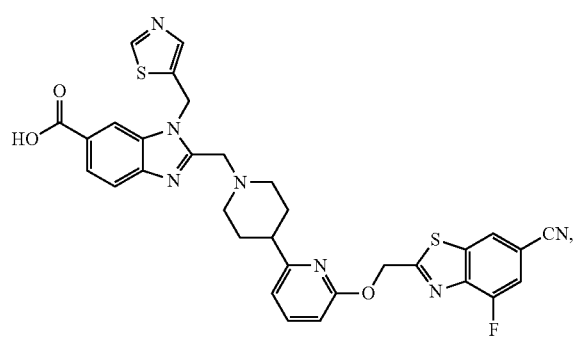 [SMILES: N#Cc1cc(F)c2nc(COc3cccc(C4CCN(Cc5nc6ccc(C(=O)O)cc6n5Cc5cncs5)CC4)n3)sc2c1]

or a pharmaceutically acceptable salt thereof.

5. The compound of claim 1, wherein the compound is

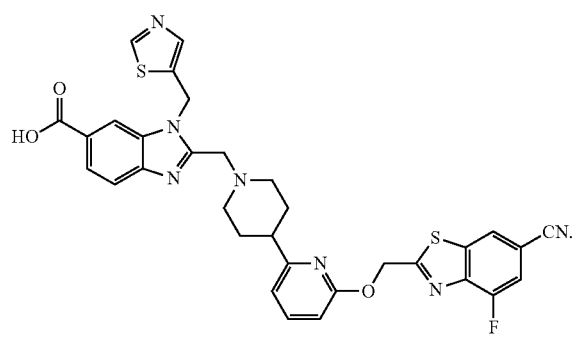 [SMILES: N#Cc1cc(F)c2nc(COc3cccc(C4CCN(Cc5nc6ccc(C(=O)O)cc6n5Cc5cncs5)CC4)n3)sc2c1]

6. The compound of claim 1, wherein the compound is

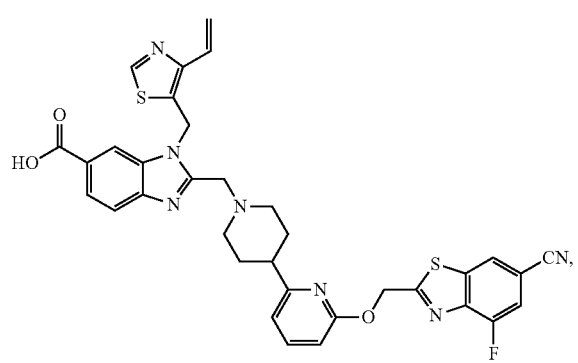 [SMILES: C=Cc1ncsc1Cn1c(CN2CCC(c3cccc(OCc4nc5c(F)cc(C#N)cc5s4)n3)CC2)nc2ccc(C(=O)O)cc21]

or a pharmaceutically acceptable salt thereof.

7. The compound of claim 1, wherein the compound is

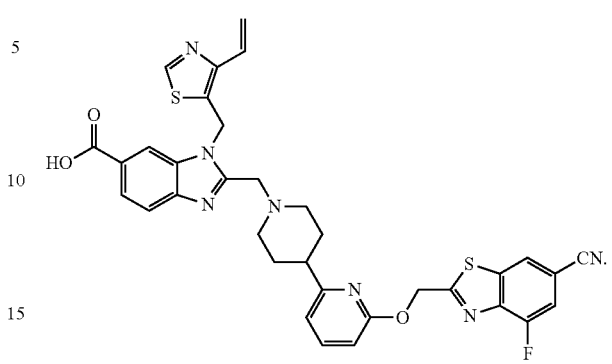

8. The compound of claim 1, wherein the compound is

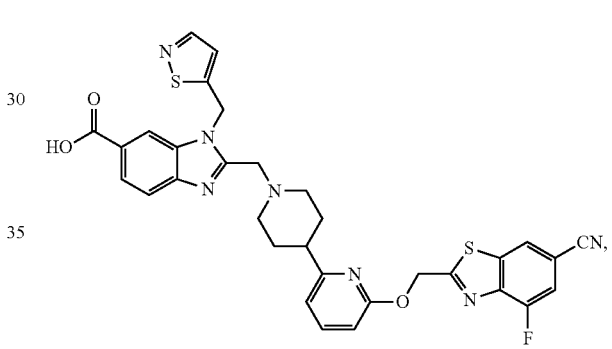

or a pharmaceutically acceptable salt thereof.

9. The compound of claim 1, wherein the compound is

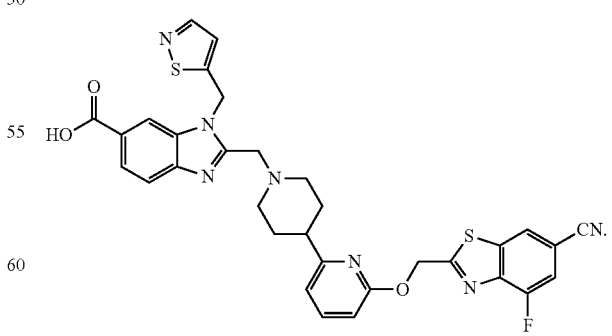

10. The compound of claim 1, wherein the compound is

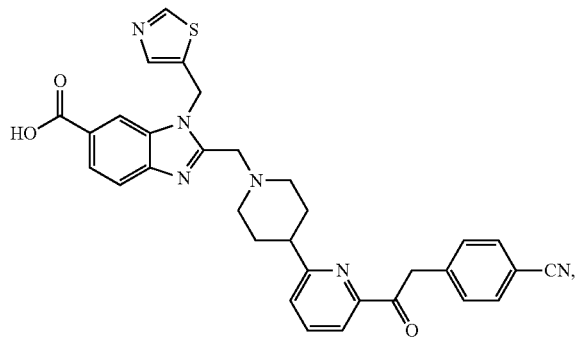 [SMILES: N#Cc1ccc(CC(=O)c2cccc(C3CCN(Cc4nc5ccc(C(=O)O)cc5n4Cc4cncs4)CC3)n2)cc1]

or a pharmaceutically acceptable salt thereof.

11. The compound of claim 1, wherein the compound is

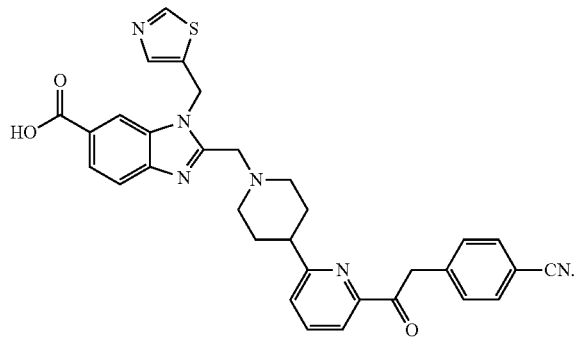 [SMILES: N#Cc1ccc(CC(=O)c2cccc(C3CCN(Cc4nc5ccc(C(=O)O)cc5n4Cc4cncs4)CC3)n2)cc1]

or a pharmaceutically acceptable salt thereof.

12. The compound of claim 1, wherein the compound is

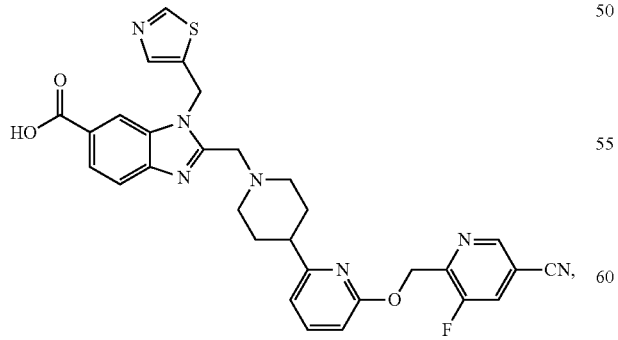

or a pharmaceutically acceptable salt thereof.

13. The compound of claim 1, wherein the compound is

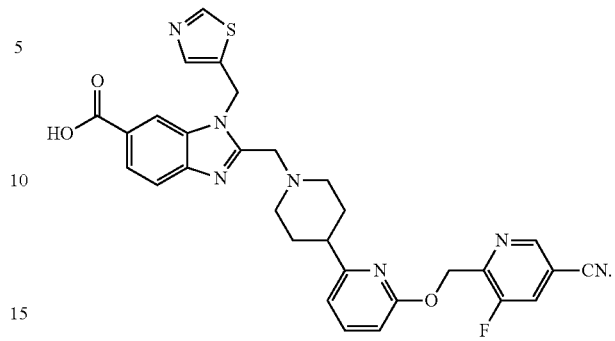

14. The compound of claim 1, wherein the compound is

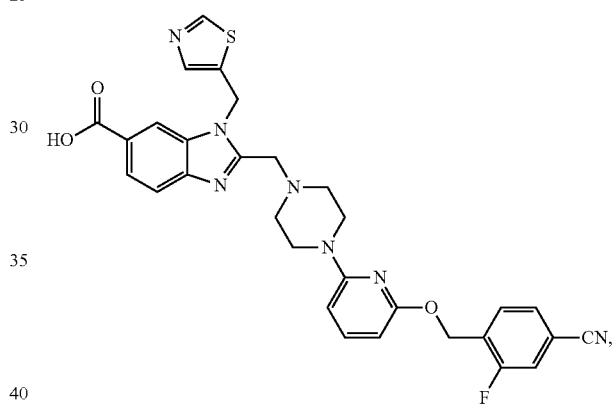

or a pharmaceutically acceptable salt thereof.

15. The compound of claim 1, wherein the compound is

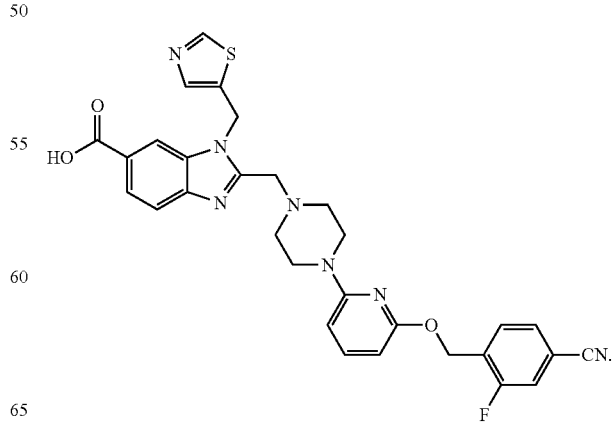

16. The compound of claim 1, wherein the compound is

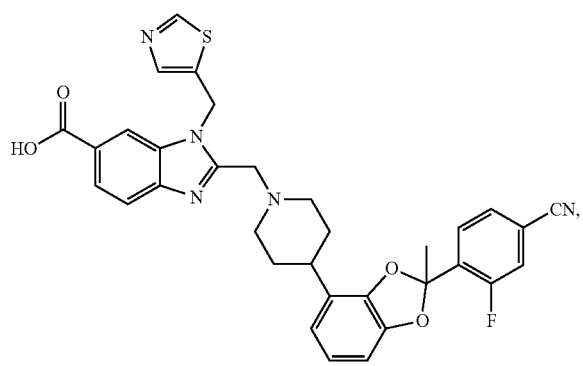 [SMILES: CC1(c2ccc(C#N)cc2F)Oc2cccc(C3CCN(Cc4nc5ccc(C(=O)O)cc5n4Cc4cncs4)CC3)c2O1]

or a pharmaceutically acceptable salt thereof.

17. The compound of claim 1, wherein the compound is

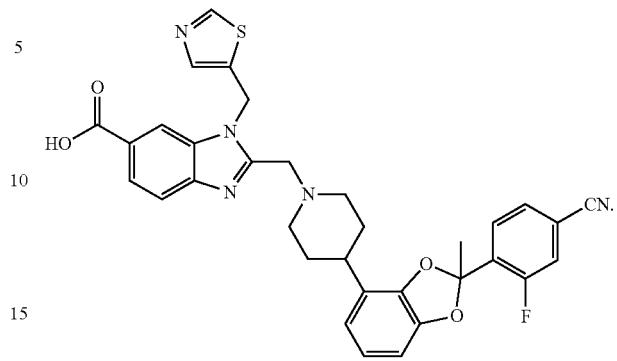

18. The compound of claim 14, wherein the compound is a meglumine salt of the compound.

19. A pharmaceutical composition comprising the compound of claim 18 and a pharmaceutically acceptable excipient.

20. A method of treating a disease mediated by glucagon-like peptide-1 receptor (GLP-1R) in an individual in need thereof, comprising administering to the individual a therapeutically effective amount of the compound of claim 14, or a pharmaceutically acceptable salt thereof.

* * * * *